US012582644B2

(12) United States Patent
Kahne et al.

(10) Patent No.: US 12,582,644 B2
(45) Date of Patent: Mar. 24, 2026

(54) O-GlcNAc TRANSFERASE INHIBITORS AND USES THEREOF

(71) Applicants: President and Fellows of Harvard College, Cambridge, MA (US); The United States of America, as represented by the Secretary, Department of Health and Human Services, Bethesda, MD (US)

(72) Inventors: Suzanne Walker Kahne, Cambridge, MA (US); Sara Evelyn Schwanger Martin, Cambridge, MA (US); Craig Joseph Thomas, Gaithersburg, MD (US); Damien Yves Duveau, Germantown, MD (US)

(73) Assignees: President and Fellows of Harvard College, Cambridge, MA (US); The United States of America, as represented by the Secretary, Department of Health and Human Services, Bethesda, MD (US)

( * ) Notice: Subject to any disclaimer, the term of this patent is extended or adjusted under 35 U.S.C. 154(b) by 1129 days.

Patent file contains an affidavit/declaration under 37 CFR 1.130(b).

(21) Appl. No.: 17/271,793

(22) PCT Filed: Aug. 29, 2019

(86) PCT No.: PCT/US2019/048805

§ 371 (c)(1),
(2) Date: Feb. 26, 2021

(87) PCT Pub. No.: WO2020/047251

PCT Pub. Date: Mar. 5, 2020

(65) Prior Publication Data

US 2021/0346367 A1 Nov. 11, 2021

Related U.S. Application Data

(60) Provisional application No. 62/724,479, filed on Aug. 29, 2018.

(51) Int. Cl.

| | |
|---|---|
| ***A61K 31/4709*** | (2006.01) |
| ***A61K 45/06*** | (2006.01) |
| ***C07D 409/12*** | (2006.01) |

(52) U.S. Cl.

CPC .......... *A61K 31/4709* (2013.01); *A61K 45/06* (2013.01); *C07D 409/12* (2013.01)

(58) Field of Classification Search

None

See application file for complete search history.

(56) References Cited

U.S. PATENT DOCUMENTS

| | | | |
|---|---|---|---|
| 3,854,480 | A | 12/1974 | Zaffaroni |
| 4,270,537 | A | 6/1981 | Romaine |
| 4,420,486 | A | 12/1983 | Ohyama et al. |
| 4,452,775 | A | 6/1984 | Kent |

(Continued)

FOREIGN PATENT DOCUMENTS

| | | | |
|---|---|---|---|
| CH | 570990 | A | 12/1975 |
| CH | 572305 | A | 2/1976 |

(Continued)

OTHER PUBLICATIONS

National Center for Biotechnology Information. PubChem Substance Database. SID 382086181. Retrieved from the Internet: Apr. 17, 2024. <https://pubchem.ncbi.nlm.nih.gov/substance/382086181>. pp. 1-5. (Year: 2024).*

(Continued)

*Primary Examiner* — Leslie A. Royds Draper

(74) *Attorney, Agent, or Firm* — Wolf, Greenfield & Sacks, P.C.

(57) ABSTRACT

Provided herein are O-GlcNAc transferase (OGT) inhibitor compounds of Formula (I), and pharmaceutically acceptable salts, solvates, hydrates, polymorphs, co-crystals, tautomers, stereoisomers, isotopically labeled derivatives, prodrugs, and compositions thereof. Also provided are methods and kits involving the inventive compounds or compositions for treating and/or preventing diseases (e.g., diabetes and complications thereof, neurodegenerative diseases, proliferative diseases such as cancers, autoimmune diseases, and inflammatory diseases) in a subject. Provided are methods of inhibiting OGT in a subject or biological sample.

(I')

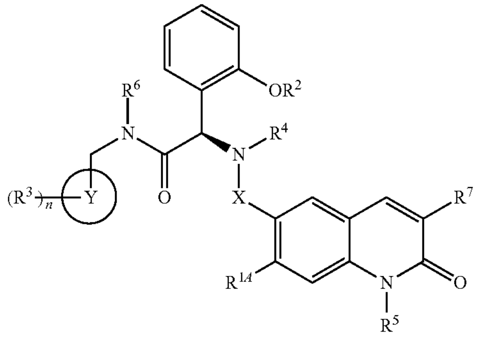

12 Claims, 33 Drawing Sheets

Specification includes a Sequence Listing.

(56) References Cited

U.S. PATENT DOCUMENTS

| | | | |
|---|---|---|---|
| 4,596,556 | A | 6/1986 | Morrow et al. |
| 4,675,189 | A | 6/1987 | Kent et al. |
| 4,790,824 | A | 12/1988 | Morrow et al. |
| 4,886,499 | A | 12/1989 | Cirelli et al. |
| 4,940,460 | A | 7/1990 | Casey, I et al. |
| 4,941,880 | A | 7/1990 | Burns |
| 5,015,235 | A | 5/1991 | Crossman |
| 5,064,413 | A | 11/1991 | McKinnon et al. |
| 5,133,974 | A | 7/1992 | Paradissis et al. |
| 5,141,496 | A | 8/1992 | Dalto et al. |
| 5,190,521 | A | 3/1993 | Hubbard et al. |
| 5,312,335 | A | 5/1994 | McKinnon et al. |
| 5,328,483 | A | 7/1994 | Jacoby |
| 5,334,144 | A | 8/1994 | Alchas et al. |
| 5,339,163 | A | 8/1994 | Homma et al. |
| 5,383,851 | A | 1/1995 | McKinnon, Jr. et al. |
| 5,407,686 | A | 4/1995 | Patel et al. |
| 5,417,662 | A | 5/1995 | Hjertman et al. |
| 5,466,220 | A | 11/1995 | Brenneman |
| 5,480,381 | A | 1/1996 | Weston |
| 5,503,627 | A | 4/1996 | McKinnon et al. |
| 5,520,639 | A | 5/1996 | Peterson et al. |
| 5,527,288 | A | 6/1996 | Gross et al. |
| 5,569,189 | A | 10/1996 | Parsons |
| 5,599,302 | A | 2/1997 | Lilley et al. |
| 5,649,912 | A | 7/1997 | Peterson |
| 5,704,911 | A | 1/1998 | Parsons |
| 5,736,152 | A | 4/1998 | Dunn |
| 5,893,397 | A | 4/1999 | Peterson et al. |
| 5,993,412 | A | 11/1999 | Deily et al. |
| 6,388,063 | B1 | 5/2002 | Plowman et al. |
| 6,476,187 | B1 | 11/2002 | Cone et al. |
| 6,852,838 | B2 | 2/2005 | Valenzuela et al. |
| 6,905,681 | B1 | 6/2005 | June et al. |
| 6,916,636 | B2 | 7/2005 | Marx et al. |
| 6,924,356 | B2 | 8/2005 | Ruben et al. |
| 6,955,894 | B1 | 10/2005 | Gatanaga et al. |
| 6,969,758 | B2 | 11/2005 | Ferrara et al. |
| 8,524,444 | B2 | 9/2013 | Gross et al. |
| 8,957,075 | B2 | 2/2015 | Kahne et al. |
| 8,993,718 | B2 | 3/2015 | Gross et al. |
| 9,573,911 | B2 | 2/2017 | Kahne et al. |
| 2002/0128235 | A1 | 9/2002 | Konrad et al. |
| 2003/0032054 | A1 | 2/2003 | Colyer et al. |
| 2003/0087328 | A1 | 5/2003 | Pollok et al. |
| 2003/0186948 | A1 | 10/2003 | Kudlow et al. |
| 2004/0191811 | A1 | 9/2004 | Burghardt et al. |
| 2004/0259910 | A1 | 12/2004 | Bolin et al. |
| 2005/0026266 | A1 | 2/2005 | Clausen et al. |
| 2005/0032145 | A1 | 2/2005 | Burghardt et al. |
| 2005/0113407 | A1 | 5/2005 | Bolin et al. |
| 2005/0113436 | A1 | 5/2005 | Elokdah et al. |
| 2005/0250678 | A1 | 11/2005 | DeFrees et al. |
| 2006/0099150 | A1 | 5/2006 | Houston et al. |
| 2006/0099688 | A1 | 5/2006 | Clausen et al. |
| 2007/0027068 | A1 | 2/2007 | DeFrees et al. |
| 2009/0163545 | A1 | 6/2009 | Goldfarb |
| 2009/0325944 | A1 | 12/2009 | Kahne et al. |
| 2010/0290987 | A1 | 11/2010 | Gross et al. |
| 2012/0108605 | A1 | 5/2012 | Kahne et al. |
| 2014/0163079 | A1 | 6/2014 | Kahne et al. |
| 2014/0187444 | A1 | 7/2014 | Gross et al. |
| 2017/0166558 | A1 | 6/2017 | Kahne et al. |

FOREIGN PATENT DOCUMENTS

| | | | |
|---|---|---|---|
| DE | 2210419 | A1 | 9/1973 |
| FR | 2179293 | A5 | 11/1973 |
| GB | 1330611 | A | 9/1973 |
| WO | WO 95/24929 | A2 | 9/1995 |
| WO | WO 97/13537 | A1 | 4/1997 |
| WO | WO 97/37705 | A1 | 10/1997 |
| WO | WO 99/34850 | A1 | 7/1999 |
| WO | WO 2007/120638 | A2 | 10/2007 |
| WO | WO 2008/057933 | A2 | 5/2008 |
| WO | WO 2008/156676 | A1 | 12/2008 |
| WO | WO 2009/036341 | A2 | 3/2009 |
| WO | WO 2009/086952 | A2 | 7/2009 |
| WO | WO 2010/141074 | A2 | 12/2010 |
| WO | WO 2013/006758 | A1 | 1/2013 |
| WO | WO 2013/027168 | A1 | 2/2013 |

OTHER PUBLICATIONS

Gross et al., Discovery of O-GlcNAc Transferase Inhibitors. J Am Chem Soc. Oct. 26, 2005;127(42):14588-9. doi: 10.1021/ja0555217.

Guo et al., O-GlcNAc-modification of SNAP-29 regulates autophagosome maturation. Nat Cell Biol. Dec. 2014;16(12):1215-26. doi: 10.1038/ncb3066. Epub Nov. 24, 2014.

Suh et al., Glucosamine-induced Sp1 O-GlcNAcylation ameliorates hypoxia-induced SGLT dysfunction in primary cultured renal proximal tubule cells. J Cell Physiol. Oct. 2014;229(10):1557-68. doi: 10.1002/jcp.24599.

Extended European Search Report for EP 10783701.5 mailed Mar. 20, 2013.

International Search Report and Written Opinion for PCT/US2010/001596, mailed Jan. 31, 2011.

International Preliminary Report on Patentability for PCT/US2010/001596, mailed Dec. 15, 2011.

International Search Report and Written Opinion for PCT/US2007/008806 mailed Jun. 6, 2008.

International Preliminary Report on Patentability for PCT/US2007/008806 mailed Oct. 23, 2008.

International Search Report and Written Opinion for PCT/US2008/007410, mailed Sep. 16, 2008.

International Preliminary Report on Patentability for PCT/US2008/007410, mailed Dec. 30, 2009.

International Search Report and Written Opinion for PCT/US2011/051431, mailed Feb. 29, 2012.

International Preliminary Report on Patentability for PCT/US2011/051431, mailed Mar. 28, 2013.

International Search Report and Written Opinion for PCT/US2012/045675, mailed Nov. 22, 2012.

International Preliminary Report on Patentability for PCT/US2012/045675, mailed Jan. 16, 2014.

International Search Report and Written Opinion for PCT/US2015/038792, mailed Oct. 1, 2015.

International Preliminary Report on Patentability for PCT/US2015/038792, mailed Jan. 12, 2017.

Invitation to Pay Additional Fees for PCT/US2019/048805, mailed Oct. 11, 2019.

International Search Report and Written Opinion for PCT/US2019/048805, mailed Dec. 27, 2019.

International Preliminary Report on Patentability for PCT/US2019/048805, mailed Mar. 11, 2021.

PubChem Compound submission: NIH/NCBI; Accession No. 1352610; Jul. 11, 2005.

PubChem Compound submission: NIH/NCBI; Accession No. 2816723; Sep. 9, 2005.

PubChem Compound submission: NIH/NCBI; Accession No. 3531968; Sep. 9, 2005.

PubChem Compound submission: NIH/NCBI; Accession No. 3655724; Sep. 10, 2005.

PubChem Compound submission: NIH/NCBI; Accession No. 4048808; Sep. 13, 2005.

PubChem Compound submission: NIH/NCBI; Accession No. 4247320; Sep. 14, 2005.

PubChem Compound submission: NIH/NCBI; Accession No. 5309478; Dec. 9, 2005.

PubChem Compound submission: NIH/NCBI; Accession No. 6619624; Jun. 5, 2006.

PubChem Compound submission: NIH/NCBI; Accession No. 6619906; Jun. 5, 2006.

PubChem Compound submission: NIH/NCBI; Accession No. 6619938; Jun. 5, 2006.

(56) References Cited

OTHER PUBLICATIONS

PubChem Compound submission: NIH/NCBI; Accession No. 6619971; Jun. 5, 2006.
PubChem Compound submission: NIH/NCBI; Accession No. 6620110; Jun. 5, 2006.
PubChem Compound submission: NIH/NCBI; Accession No. 6624064; Jun. 5, 2006.
PubChem Compound submission: NIH/NCBI; Accession No. 6624183; Jun. 5, 2006.
[No Author Listed] The CCP4 suite: programs for protein crystallography. Acta Crystallogr D Biol Crystallogr. Collaborative Computational Project, No. 4. Sep. 1, 1994;50(Pt 5):760-3.
Adams et al., PHENIX: a comprehensive Python-based system for macromolecular structure solution. Acta Crystallogr D Biol Crystallogr. Feb. 2010;66(Pt 2):213-21. Epub Jan. 22, 2010.
Akimoto et al., Elevated expression of O-GlcNAc-modified proteins and O-GlcNAc transferase in corneas of diabetic Goto-Kakizaki rats. Invest Ophthalmol Vis Sci. Sep. 2003;44(9):3802-9.
Akimoto et al., Hyperglycemia and the O-GlcNAc transferase in rat aortic smooth muscle cells: elevated expression and altered patterns of O-GlcNAcylation. Arch Biochem Biophys. May 15, 2001;389(2):166-75.
Akimoto et al., Increased O-GlcNAc transferase in pancreas of rats with streptozotocin-induced diabetes. Diabetologia. Oct. 2000;43(10):1239-47.
Alexander et al., Mechanism of carbamate inactivation of FAAH: implications for the design of covalent inhibitors and in vivo functional probes for enzymes. Chem Biol. Nov. 2005;12(11):1179-87.
Almerico et al., In-silico screening of new potential Bcl-2/Bcl-xl inhibitors as apoptosis modulators. J Mol Model. Apr. 2009;15(4):349-55. Epub Dec. 6, 2008.
Andres et al., 4-Thiazolidinones: novel inhibitors of the bacterial enzyme MurB. Bioorg Med Chem Lett. Apr. 17, 2000;10(8):715-7.
Arias et al., Prolonged incubation in PUGNAc results in increased protein O-Linked glycosylation and insulin resistance in rat skeletal muscle. Diabetes. Apr. 2004;53(4):921-30.
Arnold et al., The microtubule-associated protein tau is extensively modified with O-linked N-acetylglucosamine. J Biol Chem. Nov. 15, 1996;271(46):28741-4.
Arnold et al., The Swiss-Model workspace: a web-based environment for protein structure homology modelling. Bioinformatics. Jan. 15, 2006;22(2):195-201. Epub Nov. 13, 2005.
Bartlett et al., CAVEAT: A Program to Facilitate the Structure-derived Design of Biologically Active Molecules. Molecular Recognition in Chemical and Biological Problems. Special Pub. Royal Chem Soc. 1989;78:182-196.
Beasley et al., Miniaturized, ultra-high throughput screening of tyrosine kinases using homogeneous, competitive fluorescence immunoassays. Assay Drug Dev Technol. Apr. 2004;2(2):141-51.
Berge et al., Pharmaceutical salts. J Pharm Sci. Jan. 1977;66(1):1-19.
Boehmelt et al., Decreased UDP-GlcNAc levels abrogate proliferation control in EMeg32- deficient cells. EMBO J. Oct. 2, 2000;19(19):5092-104.
Boggon et al., Screening for phasing atoms in protein crystallography. Structure. Jul. 15, 2000;8(7):R143-9.
Bohm, The computer program LUDI: a new method for the de novo design of enzyme inhibitors. J Comput Aided Mol Des. Feb. 1992;6(1):61-78.
Bond et al., O-GlcNAc cycling: a link between metabolism and chronic disease. Annu Rev Nutr. 2013;33:205-29. doi: 10.1146/annurev-nutr-071812-161240. Epub Apr. 29, 2013.
Borodkin et al., Bisubstrate UDP-peptide conjugates as human O-GlcNAc transferase inhibitors. Biochem J. Feb. 1, 2014; 457(Pt 3): 497-502.
Botella et al., Aminolyse de carbamates cycliques analogues de la carboxybiotine ; catalyse métallique et modélisation de transfert de carboxyle. Tetrahedron. 1992;48(24):5111-22. French. Retrieved from DD ACS on STN CA: 117:110975, compound with RN 27087-39-4.
Bowman et al., Small molecule inhibitors of the MDM2-p53 interaction discovered by ensemble-based receptor models. J Am Chem Soc. Oct. 24, 2007;129(42):12809-14. Epub Sep. 29, 2007.
Brown et al., Glycan antagonists and inhibitors: a fount for drug discovery. Crit Rev Biochem Mol Biol. Nov.-Dec. 2007;42(6):481-515.
Brownlee, Biochemistry and molecular cell biology of diabetic complications. Nature. Dec. 13, 2001;414(6865):813-20.
Brünger et al., Crystallography & NMR system: A new software suite for macromolecular structure determination. Acta Crystallogr D Biol Crystallogr. Sep. 1, 1998;54(Pt 5):905-21.
Buchan et al., tRNA properties help shape codon pair preferences in open reading frames. Nucleic Acids Res. Feb. 9, 2006;34(3):1015-27. Print 2006.
Burns et al., Silencing of the novel p53 target gene Snk/Plk2 leads to mitotic catastrophe in paclitaxel (taxol)-exposed cells. Mol Cell Biol. Aug. 2003;23(16):5556-71.
Caldwell et al., Nutrient sensor O-GlcNAc transferase regulates breast cancer tumorigenesis through targeting of the oncogenic transcription factor FoxM1. Oncogene. May 13, 2010;29(19):2831-42. Epub Mar. 1, 2010.
Campbell et al., A homogeneous immunoassay for cyclic nucleotides based on chemiluminescence energy transfer. Biochem J. Oct. 15, 1983;216(1):185-94.
Chen et al., Alternative O-GlcNAcylation/O-phosphorylation of Ser16 induce different conformational disturbances to the N terminus of murine estrogen receptor beta. Chem Biol. Sep. 2006;13(9):937-44.
Chen et al., Identification of secret agent as the O-GlcNAc transferase that participates in Plum pox virus infection. J Virol. Aug. 2005;79(15):9381-7.
Cheng et al., Alternative O-glycosylation/O-phosphorylation of the murine estrogen receptor beta. Biochemistry. Sep. 26, 2000;39(38):11609-20.
Chou et al., Characterization and dynamics of O-linked glycosylation of human cytokeratin 8 and 18. J Biol Chem. Feb. 25, 1992;267(6):3901-6.
Chou et al., c-Myc is glycosylated at threonine 58, a known phosphorylation site and a mutational hot spot in lymphomas. J Biol Chem. Aug. 11, 1995;270(32):18961-5.
Chou et al., Glycosylation of the c-Myc transactivation domain. Proc Natl Acad Sci U S A. May 9, 1995;92(10):4417-21.
Cieniewski-Bernard et al., Identification of O-linked N-acetylglucosamine proteins in rat skeletal muscle using two-dimensional gel electrophoresis and mass spectrometry. Mol Cell Proteomics. Jun. 2004;3(6):577-85. Epub Feb. 24, 2004.
Clark et al., Diabetes and the accompanying hyperglycemia impairs cardiomyocyte calcium cycling through increased nuclear O-GlcNAcylation. J Biol Chem. Nov. 7, 2003;278(45):44230-7. Epub Aug. 26, 2003.
Clarke et al., Structural insights into mechanism and specificity of O-GlcNAc transferase. EMBO J. Oct. 22, 2008;27(20):2780-8. Epub Sep. 25, 2008.
Cline et al., Effects of a novel glycogen synthase kinase-3 inhibitor on insulin-stimulated glucose metabolism in Zucker diabetic fatty (fa/fa) rats. Diabetes. Oct. 2002;51(10):2903-10.
Cohen et al., Molecular modeling software and methods for medicinal chemistry. J Med Chem. Mar. 1990;33(3):883-94.
Cole et al., Cytosolic O-glycosylation is abundant in nerve terminals. J Neurochem. Dec. 2001;79(5):1080-9.
Cole et al., Glycosylation sites flank phosphorylation sites on synapsin I: O-linked N-acetylglucosamine residues are localized within domains mediating synapsin I interactions. J Neurochem. Jul. 1999;73(1):418-28.
Comer et al., Characterization of a mouse monoclonal antibody specific for O-linked N-acetylglucosamine. Anal Biochem. Jun. 15, 2001;293(2):169-77.
Comer et al., O-Glycosylation of nuclear and cytosolic proteins. Dynamic interplay between O-GlcNAc and O-phosphate. J Biol Chem. Sep. 22, 2000;275(38):29179-82.

(56) References Cited

OTHER PUBLICATIONS

Comer et al., Reciprocity between O-GlcNAc and O-phosphate on the carboxyl terminal domain of RNA polymerase II. Biochemistry. Jul. 3, 2001;40(26):7845-52.
Comess et al., Affinity-based screening techniques for enhancing lead discovery. Curr Opin Drug Discov Devel. Jul. 2004;7(4):411-6.
Compain et al., Carbohydrate mimetics-based glycosyltransferase inhibitors. Bioorg Med Chem. Dec. 2001;9(12):3077-92.
Compain et al., Design, synthesis and biological evaluation of iminosugar-based glycosyltransferase inhibitors. Curr Top Med Chem. 2003;3(5):541-60.
Copeland et al., Cross-talk between GlcNAcylation and phosphorylation: roles in insulin resistance and glucose toxicity. Am J Physiol Endocrinol Metab. Jul. 2008;295(1):E17-28. Epub Apr. 29, 2008.
Database Registry [Online] Chemical Abstracts Service, Columbus, Ohio, US; Database accession No. 1094798-35-2; Jan. 21, 2009.
De La Fortelle et al., SHARP: A Maximum-Likelihood Heavy-Atom Parameter Refinement Program for the MIR and MAD Mehtods. Methods Enzymol. 1997;276:472-94.
Defronzo, Insulin resistance, hyperinsulinemia, and coronary artery disease: a complex metabolic web. J Cardiovasc Pharmacol. 1992;20 Suppl 11:S1-16.
Dehennaut et al., O-linked N-acetylglucosaminyltransferase inhibition prevents G2/M transition in Xenopus laevis oocytes. J Biol Chem. Apr. 27, 2007;282(17):12527-36. Epub Feb. 28, 2007.
Dentin et al., Hepatic glucose sensing via the CREB coactivator CRTC2. Science. Mar. 7, 2008;319(5868):1402-5.
Dias et al., Regulation of calcium/calmodulin-dependent kinase IV by O-GlcNAc modification. J Biol Chem. Aug. 7, 2009;284(32):21327-37. Epub Jun. 8, 2009.
Dong et al., Cytoplasmic O-GlcNAc modification of the head domain and the KSP repeat motif of the neurofilament protein neurofilament-H. J Biol Chem. Aug. 23, 1996;271(34):20845-52.
Dong et al., Glycosylation of mammalian neurofilaments. Localization of multiple O-linked N-acetylglucosamine moieties on neurofilament polypeptides L and M. J Biol Chem. Aug. 5, 1993;268(22):16679-87.
Dong et al., Purification and characterization of an O-GlcNAc selective N-acetyl-beta-D-glucosaminidase from rat spleen cytosol. J Biol Chem. Jul. 29, 1994;269(30):19321-30.
Donovan et al., A solid-phase glycosyltransferase assay for high-throughput screening in drug discovery research. Glycoconj J. 1999;16(10):607-15.
Dorfmueller et al., Cell-penetrant, nanomolar O-GlcNAcase inhibitors selective against lysosomal hexosaminidases. Chem Biol. Nov. 24, 2010;17(11):1250-5.
Dorfmueller et al., GlcNAcstatin: a picomolar, selective O-GlcNAcase inhibitor that modulates intracellular O-glcNAcylation levels. J Am Chem Soc. Dec. 27, 2006;128(51):16484-5.
Dorfmueller et al., Substrate and product analogues as human O-GlcNAc transferase inhibitors. Amino Acids. Mar. 2011;40(3):781-92. Epub Jul. 17, 2010.
Du et al., Hyperglycemia inhibits endothelial nitric oxide synthase activity by posttranslational modification at the Akt site. J Clin Invest. Nov. 2001;108(9):1341-8.
Emsley et al., Coot: model-building tools for molecular graphics. Acta Crystallogr D Biol Crystallogr. Dec. 2004;60(Pt 12 Pt 1):2126-32. Epub Nov. 26, 2004.
Emsley et al., Features and development of Coot. Acta Crystallogr D Biol Crystallogr. Apr. 2010;66(Pt 4):486-501. Epub Mar. 24, 2010.
Evans, Scaling and assessment of data quality. Acta Crystallogr D Biol Crystallogr. Jan. 2006;62(Pt 1):72-82. Epub Dec. 14, 2005.
Fan et al., Apoptosis induction with polo-like kinase-1 antisense phosphorothioate oligodeoxynucleotide of colon cancer cell line SW480. World J Gastroenterol. Aug. 7, 2005;11(29):4596-9.
Feng et al., A detergent-based assay for the detection of promiscuous inhibitors. Nat Protoc. 2006;1(2):550-3.
Feng et al., High-throughput assays for promiscuous inhibitors. Nat Chem Biol. Aug. 2005;1(3):146-8. Epub Jul. 3, 2005.
Frantom et al., UDP-(5F)-GlcNAc acts as a slow-binding inhibitor of MshA, a retaining glycosyltransferase. J Am Chem Soc. May 19, 2010;132(19):6626-7.
Friesner et al., Extra precision glide: docking and scoring incorporating a model of hydrophobic enclosure for protein-ligand complexes. J Med Chem. Oct. 19, 2006;49(21):6177-96.
Friesner et al., Glide: a new approach for rapid, accurate docking and scoring. 1. Method and assessment of docking accuracy. J Med Chem. Mar. 25, 2004;47(7):1739-49.
Fujiki et al., GlcNAcylation of a histone methyltransferase in retinoic-acid-induced granulopoiesis. Nature. May 21, 2009;459(7245):455-9. Epub Apr. 19, 2009.
Gambetta et al., Essential role of the glycosyltransferase sxc/Ogt in polycomb repression. Science. Jul. 3, 2009;325(5936):93-6. Epub May 28, 2009.
Gao et al., Dynamic O-glycosylation of nuclear and cytosolic proteins: cloning and characterization of a neutral, cytosolic beta-N-acetylglucosaminidase from human brain. J Biol Chem. Mar. 30, 2001;276(13):9838-45. Epub Jan. 8, 2001.
Gloster et al., Glycosidase inhibition: assessing mimicry of the transition state. Org Biomol Chem. Jan. 21, 2010;8(2):305-20. Epub Nov. 5, 2009.
Gloster et al., Hijacking a biosynthetic pathway yields a glycosyltransferase inhibitor within cells. Nat Chem Biol. Mar. 2011;7(3):174-81. Epub Jan. 23, 2011.
Goldberg et al., Posttranslational, reversible O-glycosylation is stimulated by high glucose and mediates plasminogen activator inhibitor-1 gene expression and Sp1 transcriptional activity in glomerular mesangial cells. Endocrinology. Jan. 2006;147(1):222-31.
Golks et al., Requirement for O-linked N-acetylglucosaminyltransferase in lymphocytes activation. EMBO J. Oct. 17, 2007;26(20):4368-79. Epub Sep. 20, 2007.
Golks et al., The O-linked N-acetylglucosamine modification in cellular signalling and the immune system. 'Protein modifications: beyond the usual suspects' review series. EMBO Rep. Aug. 2008;9(8):748-53. Epub Jul. 11, 2008.
Good et al., Hydrogen ion buffers for biological research. Biochemistry. Feb. 1966;5(2):467-77.
Goodford, A computational procedure for determining energetically favorable binding sites on biologically important macromolecules. J Med Chem. Jul. 1985;28(7):849-57.
Goodsell et al., Automated docking of substrates to proteins by simulated annealing. Proteins. 1990;8(3):195-202.
Gorodkin et al., Displaying the information contents of structural RNA alignments: the structure logos. Comput Appl Biosci. Dec. 1997;13(6):583-6.
Gosselin et al., A continuous spectrophotometric assay for glycosyltransferases. Anal Biochem. Jul. 1994;220(1):92-7.
Gould et al., Glycogen synthase kinase-3: a putative molecular target for lithium mimetic drugs. Neuropsychopharmacology. Jul. 2005;30(7):1223-37.
Griffith et al., O-linked N-acetylglucosamine levels in cerebellar neurons respond reciprocally to pertubations of phosphorylation. Eur J Biochem. Jun. 1999;262(3):824-31.
Gross et al., A strategy to discover inhibitors of O-linked glycosylation. J Am Chem Soc. Jan. 16, 2008;130(2):440-1. Epub Dec. 20, 2007.
Gross et al., Discovery of O-GlcNAc transferase inhibitors. J Am Chem Soc. Oct. 26, 2005;127(42):14588-9.
Guan et al., Small interfering RNA-mediated Polo-like kinase 1 depletion preferentially reduces the survival of p53-defective, oncogenic transformed cells and inhibits tumor growth in animals. Cancer Res. Apr. 1, 2005;65(7):2698-704.
Ha et al., The 1.9 A crystal structure of *Escherichia coli* MurG, a membrane-associated glycosyltransferase involved in peptidoglycan biosynthesis. Protein Sci. Jun. 2000;9(6):1045-52.
Hadjuch et al., A convenient synthesis of the C-1-phosphonate analogue of UDP-GlcNAc and its evaluation as an inhibitor of O-linked GlcNAc transferase (OGT). Carbohydr Res. Feb. 4, 2008;343(2):189-95. Epub Nov. 1, 2007.
Hagen et al., All in the family: the UDP-GalNAc:polypeptide N-acetylgalactosaminyltransferases. Glycobiology. 2003;13(1):1R-16R.

(56) References Cited

OTHER PUBLICATIONS

Halgren et al., Glide: a new approach for rapid, accurate docking and scoring. 2. Enrichment factors in database screening. J Med Chem. Mar. 25, 2004;47(7):1750-9.
Haltiwanger et al., Enzymatic addition of O-GlcNAc to nuclear and cytoplasmic proteins. Identification of a uridine diphospho-N-acetylglucosamine:peptide beta-N-acetylglucosaminyltransferase. J Biol Chem. Feb. 15, 1990;265(5):2563-8.
Haltiwanger et al., Glycosylation of nuclear and cytoplasmic proteins. Purification and characterization of a uridine diphospho-N-acetylglucosamine:polypeptide beta-N-acetylglucosaminyltransferase. J Biol Chem. May 5, 1992;267(13):9005-13.
Haltiwanger et al., Modulation of O-linked N-acetylglucosamine levels on nuclear and cytoplasmic proteins in vivo using the peptide O-GlcNAc-beta-N-acetylglucosaminidase inhibitor O-(2-acetamido-2-deoxy-D-glucopyranosylidene)amino-N-phenylcarbamate. J Biol Chem. Feb. 6, 1998;273(6):3611-7.
Hamanaka et al., Polo-like kinase is a cell cycle-regulated kinase activated during mitosis. J Biol Chem. Sep. 8, 1995;270(36):21086-91.
Hang et al., Small molecule inhibitors of mucin-type O-linked glycosylation from a uridine-based library. Chem Biol. Mar. 2004;11(3):337-45.
Hanover et al., A Caenorhabditis elegans model of insulin resistance: altered macronutrient storage and dauer formation in an OGT-1 knockout. Proc Natl Acad Sci U S A. Aug. 9, 2005;102(32):11266-71. Epub Jul. 28, 2005.
Hanover et al., Mitochondrial and nucleocytoplasmic isoforms of O-linked GlcNAc transferase encoded by a single mammalian gene. Arch Biochem Biophys. Jan. 15, 2003;409(2):287-97.
Hanover, Glycan-dependent signaling: O-linked N-acetylglucosamine. FASEB J. Sep. 2001;15(11):1865-76.
Hart et al., Chapter 18. The O-GlcNAc modification. In: Essentials of glycobiology. Varki et al., eds. Cold Spring Harbor Laboratory Press, Cold Spring Harbor, NY. 2009. 21 pages.
Hart et al., Cross talk between O-GlcNAcylation and phosphorylation: roles in signaling, transcription, and chronic disease. Annu Rev Biochem. 2011;80:825-58. doi: 10.1146/annurev-biochem-060608-102511.
Hart et al., Cycling of O-linked beta-N-acetylglucosamine on nucleocytoplasmic proteins. Nature. Apr. 26, 2007;446(7139):1017-22.
Hart et al., O-GlcNAcylation of key nuclear and cytoskeletal proteins: reciprocity with O-phosphorylation and putative roles in protein multimerization. Glycobiology. Oct. 1996;6(7):711-6.
Hart et al., O-linked N-acetylglucosamine: the "yin-yang" of Ser/Thr phosphorylation? Nuclear and cytoplasmic glycosylation. Glycoimmunology. 1995:115-23.
Hartweck et al., Two O-linked N-acetylglucosamine transferase genes of *Arabidopsis thaliana* L. Heynh. have overlapping functions necessary for gamete and seed development. Genetics. Jul. 2002;161(3):1279-91.
Helm et al., Identification of active-site inhibitors of MurG using a generalizable, high-throughput glycosyltransferase screen. J Am Chem Soc. Sep. 17, 2003;125(37):11168-9.
Hinou et al., Systematic syntheses and inhibitory activities of bisubstrate-type inhibitors of sialyltransferases. J Org Chem. Jul. 11, 2003;68(14):5602-13.
Holt et al., Erythrocytes contain cytoplasmic glycoproteins. O-linked GlcNAc on Band 4.1. J Biol Chem. Nov. 5, 1987;262(31):14847-50.
Hooper et al., The GSK3 hypothesis of Alzheimer's disease. J Neurochem. Mar. 2008;104(6):1433-9. Epub Dec. 18, 2007.
Housley et al., A PGC-1alpha-O-GlcNAc transferase complex regulates FoxO transcription factor activity in response to glucose. J Biol Chem. Feb. 20, 2009;284(8):5148-57. Epub Dec. 22, 2008.
Housley et al., O-GlcNAc regulates FoxO activation in response to glucose. J Biol Chem. Jun. 13, 2008;283(24):16283-92. Epub Apr. 17, 2008.
Hu et al., Adenovirus-mediated overexpression of O-GlcNAcase improves contractile function in the diabetic heart. Circ Res. May 13, 2005;96(9):1006-13. Epub Apr. 7, 2005.
Hu et al., Crystal structure of the MurG:UDP-GlcNAc complex reveals common structural principles of a superfamily of glycosyltransferases. Proc Natl Acad Sci U S A. Feb. 4, 2003;100(3):845-9. Epub Jan. 21, 2003.
Hu et al., Identification of selective inhibitors for the glycosyltransferase MurG via high-throughput screening. Chem Biol. May 2004;11(5):703-11.
Huang et al., A Continuous Method for Enzymatic Assay of Sucrose Synthase in the Synthetic Direction. J Agric Food Chem. 1999;47:2746-50.
Hudson et al., Late mitotic failure in mice lacking Sak, a polo-like kinase. Curr Biol. Mar. 20, 2001;11(6):441-6.
Hurtado-Guerrero et al., Molecular mechanisms of O-GlcNAcylation. Curr Opin Struct Biol. Oct. 2008;18(5):551-7. Epub Oct. 6, 2008.
Itkonen et al., O-GlcNAc transferase integrates metabolic pathways to regulate the stability of c-MYC in human prostate cancer cells. Cancer Res. Aug. 15, 2013;73(16):5277-87. doi: 10.1158/0008-5472.CAN-13-0549. Epub May 29, 2013.
Izumi et al., Bisubstrate analogues as glycosyltransferase inhibitors. Curr Top Med Chem. 2009;9(1):87-105.
Izumi et al., Neutral beta-N-acetylhexosaminidases of rat brain. Purification and enzymatic and immunological characterization. J Biol Chem. Jun. 10, 1983;258(11):6991-9.
Jackson et al., O-glycosylation of eukaryotic transcription factors: implications for mechanisms of transcriptional regulation. Cell. Oct. 7, 1988;55(1):125-33.
James et al., Flux through the hexosamine pathway is a determinant of nuclear factor kappaB-dependent promoter activation. Diabetes. Apr. 2002;51(4):1146-56.
Janetzko et al., The making of a sweet modification: structure and function of O-GlcNAc transferase. J Biol Chem. Dec. 12, 2014;289(50):34424-32. doi: 10.1074/jbc.R114.604405. Epub Oct. 21, 2014.
Jiang et al., A neutral diphosphate mimic crosslinks the active site of human O-GlcNAc transferase. Nat Chem Biol. Nov. 13, 2011;8(1):72-7. doi: 10.1038/nchembio.711. Supplementary Information included.
Jiang et al., A subpopulation of estrogen receptors are modified by O-linked N-acetylglucosamine. J Biol Chem. Jan. 24, 1997;272(4):2421-8.
Jinek et al., The superhelical TPR-repeat domain of O-linked GlcNAc transferase exhibits structural similarities to importin alpha. Nat Struct Mol Biol. Oct. 2004;11(10):1001-7. Epub Sep. 12, 2004.
Jones, A bittersweet modification: O-GlcNAc and cardiac dysfunction. Circ Res. May 13, 2005;96(9):925-6.
Jope et al., Glycogen synthase kinase-3 (GSK3): inflammation, diseases, and therapeutics. Neurochem Res. Apr.-May 2007;32(4-5):577-95. Epub Aug. 30, 2006.
Juang et al., Phosphorylation and O-linked glycosylation of Elf-1 leads to its translocation to the nucleus and binding to the promoter of the TCR zeta-chain. J Immunol. Mar. 15, 2002;168(6):2865-71.
Kamemura et al., Dynamic interplay between O-glycosylation and O-phosphorylation of nucleocytoplasmic proteins: alternative glycosylation/phosphorylation of THR-58, a known mutational hot spot of c-Myc in lymphomas, is regulated by mitogens. J Biol Chem. May 24, 2002;277(21):19229-35. Epub Mar. 19, 2002.
Kang et al., O-GlcNAc modulation at Akt1 Ser473 correlates with apoptosis of murine pancreatic beta cells. Exp Cell Res. Jul. 1, 2008;314(11-12):2238-48. doi: 10.1016/j.yexcr.2008.04.014. Epub May 9, 2008.
Kannoji et al., GSK3beta: a master switch and a promising target. Expert Opin Ther Targets. Nov. 2008;12(11):1443-55. doi: 10.1517/14728222.12.11.1443.
Kazemi et al., O-linked beta-N-acetylglucosamine (O-GlcNAc) regulates stress-induced heat shock protein expression in a GSK-3beta-dependent manner. J Biol Chem. Dec. 10, 2010;285(50):39096-107. doi: 10.1074/jbc.M110.131102. Epub Oct. 6, 2010.
Kelly et al., RNA polymerase II is a glycoprotein. Modification of the COOH-terminal domain by O-GlcNAc. J Biol Chem. May 15, 1993;268(14):10416-24.

(56) References Cited

OTHER PUBLICATIONS

Khidekel et al., Probing the dynamics of O-GlcNAc glycosylation in the brain using quantitative proteomics. Nat Chem Biol. Jun. 2007;3(6):339-48. Epub May 13, 2007.
Khraltsova et al., An enzyme-linked lectin assay for alpha1,3-galactosyltransferase. Anal Biochem. May 1, 2000;280(2):250-7.
Kiefer et al., The Swiss-Model Repository and associated resources. Nucleic Acids Res. Jan. 2009;37(Database issue): D387-92. Epub Oct. 18, 2008.
Kiessling et al., Chemical approaches to glycobiology. Annu Rev Biochem. 2010;79:619-53.
Kim et al., An O-GlcNAcase-specific inhibitor and substrate engineered by the extension of the N-acetyl moiety. J Am Chem Soc. Apr. 5, 2006;128(13):4234-5.
Kim, Chemical arsenal for the study of O-GlcNAc. Molecules. Feb. 28, 2011;16(3):1987-2022. doi: 10.3390/molecules16031987.
King et al., Cytokeratin 13 contains O-glycosidically linked N-acetylglucosamine residues. J Biol Chem. Aug. 25, 1989;264(24):14022-8.
Klein et al., O-linked N-acetylglucosamine modification of insulin receptor substrate-1 occurs in close proximity to multiple SH2 domain binding motifs. Mol Cell Proteomics. Dec. 2009;8(12):2733-45. Epub Aug. 11, 2009.
Koh et al., Inhibition of GSK-3 reduces infarct volume and improves neurobehavioral functions. Biochem Biophys Res Commun. Jul. 11, 2008;371(4):894-9. doi: 10.1016/j.bbrc.2008.05.006. Epub May 12, 2008.
Konrad et al., Alloxan is an inhibitor of the enzyme O-linked N-acetylglucosamine transferase. Biochem Biophys Res Commun. Apr. 26, 2002;293(1):207-12.
Konrad et al., The role of O-linked protein glycosylation in beta-cell dysfunction. Int J Mol Med. Nov. 2002;10(5):535-9.
Koresawa et al., High-throughput screening with quantitation of ATP consumption: a universal non-radioisotope, homogeneous assay for protein kinase. Assay Drug Dev Technol. Apr. 2004;2(2):153-60.
Kozarsky et al., Use of a mutant cell line to study the kinetics and function of O-linked glycosylation of low density lipoprotein receptors. Proc Natl Acad Sci U S A. Jun. 1988;85(12):4335-9.
Kreppel et al., Dynamic glycosylation of nuclear and cytosolic proteins. Cloning and characterization of a unique O-GlcNAc transferase with multiple tetratricopeptide repeats. J Biol Chem. Apr. 4, 1997;272(14):9308-15.
Kreppel et al., Regulation of a cytosolic and nuclear O-GlcNAc transferase. Role of the tetratricopeptide repeats. J Biol Chem. Nov. 5, 1999;274(45):32015-22.
Kuntz et al., A geometric approach to macromolecule-ligand interactions. J Mol Biol. Oct. 25, 1982;161(2):269-88.
Lairson et al., Glycosyltransferases: structures, functions, and mechanisms. Annu Rev Biochem. 2008;77:521-55.
Lamarre-Vincent et al., Dynamic glycosylation of the transcription factor CREB: a potential role in gene regulation. J Am Chem Soc. Jun. 4, 2003;125(22):6612-3.
Lane et al., Antibody microinjection reveals an essential role for human polo-like kinase 1 (Plk1) in the functional maturation of mitotic centrosomes. J Cell Biol. Dec. 1996;135(6 Pt 2):1701-13.
Lazarus et al., Mutational analysis of the catalytic domain of O-linked N-acetylglucosaminyl transferase. J Biol Chem. Oct. 21, 2005;280(42):35537-44. Epub Aug. 16, 2005.
Lazarus et al., Structure of human O-GlcNAc transferase and its complex with a peptide substrate. Nature. Jan. 27, 2011;469(7331):564-7. Epub Jan. 16, 2011.
Leavy et al., A high-throughput assay for O-GlcNAc transferase detects primary sequence preferences in peptide substrates. Bioorg Med Chem Lett. Jul. 15, 2007;17(14):3851-4. Epub May 10, 2007.
Lee et al., A potent and highly selective inhibitor of human alpha-1,3-fucosyltransferase via click chemistry. J Am Chem Soc. Aug. 13, 2003;125(32):9588-9.
Lee et al., Alloxan is an inhibitor of O-GlcNAc-selective N-acetyl-beta-D-glucosaminidase. Biochem Biophys Res Commun. Dec. 1, 2006;350(4):1038-43. Epub Oct. 6, 2006.
Lefebvre et al., Effect of okadaic acid on O-linked N-acetylglucosamine levels in a neuroblastoma cell line. Biochim Biophys Acta. Oct. 18, 1999;1472(1-2):71-81.
Lefebvre et al., Evidence of a balance between phosphorylation and O-GlcNAc glycosylation of Tau proteins—a role in nuclear localization. Biochim Biophys Acta. Jan. 20, 2003;1619(2):167-76.
Lefebvre et al., Identification of N-acetyl-d-glucosamine-specific lectins from rat liver cytosolic and nuclear compartments as heat-shock proteins. Biochem J. Nov. 15, 2001;360(Pt 1):179-88.
Lefebvre et al., The tumor suppressor HIC1 (hypermethylated in cancer 1) is O-GlcNAc glycosylated. Eur J Biochem. Oct. 2004;271(19):3843-54.
Lehman et al., A single nucleotide polymorphism in MGEA5 encoding O-GlcNAc-selective N-acetyl-beta-D glucosaminidase is associated with type 2 diabetes in Mexican Americans. Diabetes. Apr. 2005;54(4):1214-21.
Lenzen et al., Alloxan: history and mechanism of action. Diabetologia. Jun. 1988;31(6):337-42.
Li et al., Function of polo-like kinase 3 in NF-kappaB-mediated proapoptotic response. J Biol Chem. Apr. 29, 2005;280(17):16843-50. Epub Jan. 25, 2005.
Li et al., Regulation of mouse brain glycogen synthase kinase-3 by atypical antipsychotics. Int J Neuropsychopharmacol. 2007;10:7-19.
Li et al., SAK, a new polo-like kinase, is transcriptionally repressed by p53 and induces apoptosis upon RNAi silencing. Neoplasia. Apr. 2005;7(4):312-23.
Lima et al., O-GlcNAcylation contributes to the vascular effects of ET-1 via activation of the RhoA/Rho-kinase pathway. Cardiovasc Res. Feb. 15, 2011;89(3):614-22. doi: 10.1093/cvr/cvq338. Epub Oct. 26, 2010.
Lima et al., Vascular O-GlcNAcylation augments reactivity to constrictor stimuli by prolonging phosphorylated levels of the myosin light chain. Braz J Med Biol Res. Oct. 2014;47(10):826-33. Epub Aug. 15, 2014.
Liu et al., Glucose stimulates protein modification by O-linked GlcNAc in pancreatic beta cells: linkage of O-linked GlcNAc to beta cell death. Proc Natl Acad Sci U S A. Mar. 14, 2000;97(6):2820-5.
Liu et al., O-GlcNAcylation regulates phosphorylation of tau: a mechanism involved in Alzheimer's disease. Proc Natl Acad Sci U S A. Jul. 20, 2004;101(29):10804-9. Epub Jul. 12, 2004.
Liu et al., Polo-like kinase (Plk)1 depletion induces apoptosis in cancer cells. Proc Natl Acad Sci U S A. May 13, 2003;100(10):5789-94. Epub May 5, 2003.
Liu et al., The Synthesis and Characterization of a Helical Miniature Protein Mimicking the OGT Active Domain. Int J Pept Res Ther. 2006;12(3):237-41.
Love et al., Dynamic O-GlcNAc cycling at promoters of Caenorhabditis elegans genes regulating longevity, stress, and immunity. Proc Natl Acad Sci U S A. Apr. 20, 2010;107(16):7413-8. Epub Apr. 5, 2010.
Love et al., Mitochondrial and nucleocytoplasmic targeting of O-linked GlcNAc transferase. J Cell Sci. Feb. 15, 2003;116(Pt 4):647-54.
Love et al., The hexosamine signaling pathway: deciphering the "O-GlcNAc code".Sci STKE. Nov. 29, 2005;2005(312):re13.
Lowery et al., Structure and function of Polo-like kinases. Oncogene. Jan. 10, 2005;24(2):248-59.
Lowery et al., Transcreener: screening enzymes involved in covalent regulation. Expert Opin Ther Targets. Feb. 2006;10(1):179-90.
Lubas et al., Analysis of nuclear pore protein p62 glycosylation. Biochemistry. Feb. 7, 1995;34(5):1686-94.
Lubas et al., Functional expression of O-linked GlcNAc transferase. Domain structure and substrate specificity. J Biol Chem. Apr. 14, 2000;275(15):10983-8.
Lubas et al., O-Linked GlcNAc transferase is a conserved nucleocytoplasmic protein containing tetratricopeptide repeats. J Biol Chem. Apr. 4, 1997;272(14):9316-24.
Ma et al., Drug targeting *Mycobacterium tuberculosis* cell wall synthesis: genetics of dTDP-rhamnose synthetic enzymes and development of a microtiter plate-based screen for inhibitors of conversion of dTDP-glucose to dTDP-rhamnose. Antimicrob Agents Chemother. May 2001;45(5):1407-16.

(56) References Cited

OTHER PUBLICATIONS

Ma et al., Hyper-O-GlcNAcylation is anti-apoptotic and maintains constitutive NF-κB activity in pancreatic cancer cells. J Biol Chem. May 24, 2013;288(21):15121-30. doi: 10.1074/jbc.M113.470047. Epub Apr. 16, 2013.
Ma et al., Role of Plk2 (Snk) in mouse development and cell proliferation. Mol Cell Biol. Oct. 2003;23(19):6936-43.
Macauley et al., Increasing O-GlcNAc levels: An overview of small-molecule inhibitors of O-GlcNAcase. Biochim Biophys Acta. Feb. 2010;1800(2):107-21. Epub Aug. 4, 2009.
Macauley et al., O-GlcNAcase uses substrate-assisted catalysis: kinetic analysis and development of highly selective mechanism-inspired inhibitors. J Biol Chem. Jul. 8, 2005;280(27):25313-22. Epub Mar. 28, 2005.
Macmillan et al., Comparative expression of the mitotic regulators SAK and PLK in colorectal cancer. Ann Surg Oncol. Oct. 2001;8(9):729-40.
Majumdar et al., Insulin stimulates and diabetes inhibits O-linked N-acetylglucosamine transferase and O-glycosylation of Sp1. Diabetes. Dec. 2004;53(12):3184-92.
Malinka et al., 2-Substituted-3-oxoisothiazolo[5,4-b]pyridines as potential central nervous system and antimycobacterial agents. Farmaco. Jul. 30, 1998;53(7):504-12.
Marshall et al., Discovery of a metabolic pathway mediating glucose-induced desensitization of the glucose transport system. Role of hexosamine biosynthesis in the induction of insulin resistance. J Biol Chem. Mar. 15, 1991;266(8):4706-12.
Marshall et al., Enhanced expression of uridine diphosphate-N-acetylglucosaminyl transferase (OGT) in a stable, tetracycline-inducible HeLa cell line using histone deacetylase inhibitors: kinetics of cytosolic OGT accumulation and nuclear translocation. Anal Biochem. Aug. 15, 2003;319(2):304-13.
Marshall et al., Measurement of UDP-N-acetylglucosaminyl transferase (OGT) in brain cytosol and characterization of anti-OGT antibodies. Anal Biochem. Mar. 15, 2003;314(2):169-79.
Martin et al., 3D database searching in drug design. J Med Chem. Jun. 12, 1992;35(12):2145-54.
Martin et al., Developing New Tools for the Study of O-GlcNAc Transferase in Disease. Harvard Medical School. Poster. 1 page. Aug. 2017.
Martin et al., Structure-Based Evolution of Low Nanomolar O-GlcNAc Transferase Inhibitors. J Am Chem Soc. Oct. 24, 2018;140(42):13542-13545. doi: 10.1021/jacs.8b07328. Epub Oct. 4, 2018.
Martinez-Fleites et al., Structural analyses of enzymes involved in the O-GlcNAc modification. Biochim Biophys Acta. Feb. 2010;1800(2):122-33. Epub Jul. 30, 2009.
Martinez-Fleites et al., Structure of an O-GlcNAc transferase homolog provides insight into intracellular glycosylation. Nat Struct Mol Biol. Jul. 2008;15(7):764-5. Epub Jun. 8, 2008.
Martinez-Fleites et al., Structure of an O-GlcNAc transferase homolog provides insight into intracellular glycosylation. Nat Struct Mol Biol. Jul. 2008;15(7):764-5. Epub Jun. 8, 2008. Supplementary Information.
Mathis, Probing molecular interactions with homogeneous techniques based on rare earth cryptates and fluorescence energy transfer. Clin Chem. Sep. 1995;41(9):1391-7.
Mccoy et al., Phaser crystallographic software. J Appl Crystallogr. Aug. 1, 2007;40(Pt 4):658-674. Epub Jul. 13, 2007.
Mccoy, Solving structures of protein complexes by molecular replacement with Phaser. Acta Crystallogr D Biol Crystallogr. Jan. 2007;63(Pt 1):32-41. Epub Dec. 13, 2006.
Medina et al., SV40 large T antigen is modified with O-linked N-acetylglucosamine but not with other forms of glycosylation. Glycobiology. Apr. 1998;8(4):383-91.
Meikrantz et al., Nuclear localization of an O-glycosylated protein phosphotyrosine phosphatase from human cells. J Cell Sci. Mar. 1991;98 ( Pt 3):303-7.
Miranker et al., Functionality maps of binding sites: a multiple copy simultaneous search method. Proteins. 1991;11(1):29-34.
Mizanur et al., One-step synthesis of labeled sugar nucleotides for protein O-GlcNAc modification studies by chemical function analysis of an archaeal protein. J Am Chem Soc. Jan. 26, 2005;127(3):836-7.
Moura et al., Large scale comparative codon-pair context analysis unveils general rules that fine-tune evolution of mRNA primary structure. PLoS One. Sep. 5, 2007;2(9):e847.
Navaza et al., AmoRE: an Automated Package for Molecular Replacement. Acta Cryst. 1994; A50:157-63.
Navia et al., Use of structural information in drug design. Curr Opin Struct Biol. 1992;2:202-10.
Nikoulina et al., Potential role of glycogen synthase kinase-3 in skeletal muscle insulin resistance of type 2 diabetes. Diabetes. Feb. 2000;49(2):263-71.
Ninkovic et al., O-glycosylated human MUC1 repeats are processed in vitro by immunoproteasomes. J Immunol. Aug. 15, 2007;179(4):2380-8.
Nishibata et al., Automatic Creation of Drug Candidate Structures Based on Receptor Structure. Starting Point for Artificial Lead Generation. Tetrahedron. 1991;47(43):8985-90.
Nishikata et al., A phosphotyrosine-containing quenched fluorogenic peptide as a novel substrate for protein tyrosine phosphatases. Biochem J. 1999;343:385-91.
Nishikata et al., Continuous assay of protein tyrosine phosphatases based on fluorescence resonance energy transfer. Biochimie. Jul. 2006;88(7):879-86. Epub Feb. 28, 2006.
Nishio et al., Acylation and Alkoxycarbonylation of Benzoxazoline-2-thione and Benzothiazoline-2-thione. Heterocycles. 2004;62(1):313-324.
Nolte et al., Human O-GlcNAc transferase (OGT): genomic structure, analysis of splice variants, fine mapping in Xq13.1. Mamm Genome. Jan. 2002;13(1):62-4.
Novak et al., Heterogeneity of O-glycosylation in the hinge region of human IgA1. Mol Immunol. Dec. 2000;37(17):1047-56.
O'Donnell et al., Ogt-dependent X-chromosome-linked protein glycosylation is a requisite modification in somatic cell function and embryo viability. Mol Cell Biol. Feb. 2004;24(4):1680-90.
Ogawa et al., Profiling terminal N-acetyllactosamines of glycans on mammalian cells by an immuno-enzymatic assay. Glycoconj J. Dec. 2006;23(9):663-74. Epub Nov. 18, 2006.
Ohn et al., A functional RNAi screen links O-GlcNAc modification of ribosomal proteins to stress granule and processing body assembly. Nat Cell Biol. Oct. 2008;10(10):1224-31. Epub Sep. 14, 2008.
Olah et al., Strategies for compound selection. Curr Drug Discov Technol. Oct. 2004;1(3):211-20.
Ortiz-Meoz et al., Microarray discovery of new OGT substrates: the medulloblastoma oncogene OTX2 is O-GlcNAcylated. J Am Chem Soc. Apr. 2, 2014;136(13):4845-8. doi: 10.1021/ja500451w. Epub Mar. 17, 2014.
Ougolkov et al., Targeting GSK-3: a promising approach for cancer therapy? Future Oncol. Feb. 2006;2(1):91-100.
Painter et al., Optimal description of a protein structure in terms of multiple groups undergoing TLS motion. Acta Crystallogr D Biol Crystallogr. Apr. 2006;62(Pt 4):439-50. Epub Mar. 18, 2006.
Painter et al., TLSMD web server for the generation of multi-group TLS models. J Appl Cryst. 2006;39:109-11.
Palcic et al., Assays for Glycosyltransferases. Trends in Glycosci and Glycotechnol. 2001;13(72):361-70.
Pape et al., HKL2MAP: a graphical user interface for macromolecular phasing with SHELX programs. J Appl Cryst. 2004;37:843-44.
Parker et al., Insulin resistance of glycogen synthase mediated by o-linked N-acetylglucosamine. J Biol Chem. Mar. 21, 2003;278(12):10022-7. Epub Jan. 1, 2003.
Patti et al., Activation of the Hexosamine Pathway by Glucosamine in Vivo Induces Insulin Resistance of Early Postreceptor Insulin Signaling Events in Skeletal Muscle. Diabetes 1999 v48 p. 1562-71.
Peineau et al., LTP inhibits LTD in the hippocampus via regulation of GSK3beta. Neuron. Mar. 1, 2007;53(5):703-17.
Peitsch, Protein modeling by E-mail. Bio/Technol. 1995;13:658-60.
Pesnot et al., Structural and mechanistic basis for a new mode of glycosyltransferase inhibition. Nat Chem Biol. May 2010;6(5):321-3. Epub Apr. 4, 2010.

(56) References Cited

OTHER PUBLICATIONS

Phiel et al., GSK-3alpha regulates production of Alzheimer's disease amyloid-beta peptides. Nature. May 22, 2003;423(6938):435-9.
Potterton et al., Developments in the CCP4 molecular-graphics project. Acta Crystallogr D Biol Crystallogr. Dec. 2004;60(Pt 12 Pt 1):2288-94. Epub Nov. 26, 2004.
Poznanskaya et al., New derivatives of benzoxazolinones and benzoxazolinethiones. I. Synthesis and acylating activity of N-aryloxycarbony 1-2-benzoxazolinones. Khimiya Geterotsiklicheskikh Soedinenii. 1969;6:965-7. Russian. Retrieved from DB ACS on STN CA: 72:121409, compounds with RN 27087-35-0, 27087-36-1, 27087-37-2, 27087-38-3, 27087-39-4, 27087-40-7, 27087-41-8, 27087-42-9, 27087-43-0.
Pratt et al., Deconvoluting the functions of polypeptide N-alpha-acetylgalactosaminyltransferase family members by glycopeptide substrate profiling. Chem Biol. Jul. 2004;11(7):1009-16.
Qiu et al., Expressions of polypeptide: N-acetylgalactosaminyltransferase in leukemia cell lines during 1,25-dihydroxyvitamin D3 induced differentiation. Glycoconj J. Nov. 2006;23(7-8):575-84.
Reason et al., Localization of O-GlcNAc modification on the serum response transcription factor. J Biol Chem. Aug. 25, 1992;267(24):16911-21.
Reaven, Pathophysiology of insulin resistance in human disease. Physiol Rev. Jul. 1995;75(3):473-86.
Reeves et al., Characterization of the specificity of O-GlcNAc reactive antibodies under conditions of starvation and stress. Anal Biochem. Jul. 15, 2014;457:8-18. doi: 10.1016/j.ab.2014.04.008. Epub Apr. 18, 2014.
Rempel et al., Covalent inhibitors of glycosidases and their applications in biochemistry and biology. Glycobiology. Aug. 2008;18(8):570-86. Epub May 22, 2008.
Rex-Mathes et al., Immunological detection of O-GlcNAc. Methods Mol Biol. 2002;194:73-87.
Ring et al., Selective glycogen synthase kinase 3 inhibitors potentiate insulin activation of glucose transport and utilization in vitro and in vivo. Diabetes. Mar. 2003;52(3):588-95.
Rodems et al., A FRET-based assay platform for ultra-high density drug screening of protein kinases and phosphatases. Assay Drug Dev Technol. Nov. 2002;1(1 Pt 1):9-19.
Rogawski et al., The neuropharmacological basis for the use of memantine in the treatment of Alzheimer's disease. CNS Drug Rev. 2003 Fall;9(3):275-308.
Roquemore et al., Detection of O-linked N-acetylglucosamine (O-GlcNAc) on cytoplasmic and nuclear proteins. Methods Enzymol. 1994;230:443-60.
Roquemore et al., Dynamic O-GlcNAcylation of the small heat shock protein alpha B-crystallin. Biochemistry. Mar. 19, 1996;35(11):3578-86.
Saotome et al., Combinatorial library of five-membered iminocyclitol and the inhibitory activities against glyco-enzymes. Chem Biol. Nov. 2001;8(11):1061-70.
Sawhney et al., Bioerodible Hydrogels Based on Photopolymerized Poly(ethylene glycol)-co-poly($\alpha$-hydroxy acid) Diacrylate Macromers. Macromolecules. 1993;26:581-587.
Schneider et al., Sequence logos: a new way to display consensus sequences. Nucleic Acids Res. Oct. 25, 1990;18(20):6097-100.
Schüttelkopf et al., PRODRG: a tool for high-throughput crystallography of protein-ligand complexes. Acta Crystallogr D Biol Crystallogr. Aug. 2004;60(Pt 8):1355-63. Epub Jul. 21, 2004.
Seidler et al., Identification and prediction of promiscuous aggregating inhibitors among known drugs. J Med Chem. Oct. 9, 2003;46(21):4477-86.
Sereno et al., A novel GSK-3beta inhibitor reduces Alzheimer's pathology and rescues neuronal loss in vivo. Neurobiol Dis. Sep. 2009;35(3):359-67. doi: 10.1016/j.nbd.2009.05.025. Epub Jun. 10, 2009.
Shaw et al., Regulation of specific DNA binding by p53: evidence for a role for O-glycosylation and charged residues at the carboxy-terminus. Oncogene. Feb. 15, 1996;12(4):921-30.
Shi et al., Aberrant O-GlcNAcylation characterizes chronic lymphocytic leukemia. Leukemia. Sep. 2010;24(9):1588-98. doi: 10.1038/leu.2010.152. Epub Jul. 29, 2010.
Shi et al., Protein O-fucosyltransferase 1 is an essential component of Notch signaling pathways. Proc Natl Acad Sci U S A. Apr. 29, 2003;100(9):5234-9. Epub Apr. 15, 2003.
Sim et al., Benzylidene rhodanines as novel inhibitors of UDP-N-acetylmuramate/L-alanine ligase. Bioorg Med Chem Lett. Feb. 25, 2002;12(4):697-9.
Sinclair et al., *Drosophila* O-GlcNAc transferase (OGT) is encoded by the Polycomb group (PcG) gene, super sex combs (sxc). Proc Natl Acad Sci U S A. Aug. 11, 2009;106(32):13427-32. Epub Jul. 28, 2009.
Skropeta et al., Asymmetric synthesis and affinity of potent sialyltransferase inhibitors based on transition-state analogues. Glycoconj J. 2004;21(5):205-19.
Slawson et al., O-GlcNAc signalling: implications for cancer cell biology. Nat Rev Cancer. Aug. 18, 2011;11(9):678-84. doi: 10.1038/nrc3114.
Slawson et al., Perturbations in O-linked $\beta$-N-Acetylglucosamine Protein Modification Cause Severe Defects in Mitotic Progression and Cytokinesis. J. Biol. Chem., 2005;280:3244-56.
Smith et al., Malignant transformation of mammalian cells initiated by constitutive expression of the polo-like kinase. Biochem Biophys Res Commun. May 19, 1997;234(2):397-405.
Soltero-Higgin et al., Identification of inhibitors for UDP-galactopyranose mutase. J Am Chem Soc. Sep. 1, 2004;126(34):10532-3.
Stambolic et al., Lithium inhibits glycogen synthase kinase-3 activity and mimics wingless signalling in intact cells. Curr Biol. Dec. 1, 1996;6(12):1664-8.
Szczepankiewicz et al., Association analysis of the GSK-3beta T-50C gene polymorphism with schizophrenia and bipolar disorder. Neuropsychobiology. 2006;53(1):51-6. Epub Jan. 4, 2006.
Tai et al., Parallel identification of O-GlcNAc-modified proteins from cell lysates. J Am Chem Soc. Sep. 1, 2004;126(34):10500-1.
Tanabe et al., Genetic Deficiency of Glycogen Synthase Kinase-3$\beta$ Corrects Diabetes in Mouse Models of Insulin Resistance. PloS Biology. 2008;6(2):307-318.
Tarrant et al., Regulation of CK2 by phosphorylation and O-GlcNAcylation revealed by semisynthesis. Nature Chemical Biology, Jan. 2012;8:262-9.
Tats et al., Preferred and avoided codon pairs in three domains of life. BMC Genomics. Oct. 8, 2008;9:463.
Tenno et al., Initiation of protein O glycosylation by the polypeptide GalNAcT-1 in vascular biology and humoral immunity. Mol Cell Biol. Dec. 2007;27(24):8783-96. Epub Oct. 8, 2007.
Toleman et al., Characterization of the histone acetyltransferase (HAT) domain of a bifunctional protein with activable O-GlcNAcase and HAT activities. J Biol Chem. Dec. 17, 2004;279(51):53665-73. Epub Oct. 12, 2004.
Topaz et al., Absence of intraepidermal glycosyltransferase ppGalNac-T3 expression in familial tumoral calcinosis. Am J Dermatopathol. Jun. 2005;27(3):211-5.
Torres et al., Topography and polypeptide distribution of terminal N-acetylglucosamine residues on the surfaces of intact lymphocytes. Evidence for O-linked GlcNAc. J Biol Chem. Mar. 10, 1984;259(5):3308-17.
Trunkfield et al., Inhibition of Escherichia coli glycosyltransferase MurG and *Mycobacterium tuberculosis* Gal transferase by uridine-linked transition state mimics. Bioorg Med Chem. Apr. 1, 2010;18(7):2651-63. Epub Feb. 19, 2010.
Tsokos et al., Activation of the Ets transcription factor Elf-1 requires phosphorylation and glycosylation: defective expression of activated Elf-1 is involved in the decreased TCR zeta chain gene expression in patients with systemic lupus erythematosus. Ann N Y Acad Sci. Apr. 2003;987:240-5.
Turner et al., Cytologic assessment of nuclear and cytoplasmic O-linked N-acetylglucosamine distribution by using anti-streptococcal monoclonal antibodies. Proc Natl Acad Sci U S A. Aug. 1990;87(15):5608-12.

(56) References Cited

OTHER PUBLICATIONS

Vocadlo et al., A chemical approach for identifying O-GlcNAc-modified proteins in cells. Proc Natl Acad Sci U S A. Aug. 5, 2003;100(16):9116-21. Epub Jul. 21, 2003.
Vocadlo et al., Mechanistic insights into glycosidase chemistry. Curr Opin Chem Biol. Oct. 2008;12(5):539-55.
Von Ahsen et al., High-throughput screening for kinase inhibitors. Chembiochem. Mar. 2005;6(3):481-90.
Vosseller et al., Elevated nucleocytoplasmic glycosylation by O-GlcNAc results in insulin resistance associated with defects in Akt activation in 3T3-L1 adipocytes. Proc Natl Acad Sci U S A. Apr. 16, 2002;99(8):5313-8.
Vosseller et al., O-linked N-acetylglucosamine proteomics of post-synaptic density preparations using lectin weak affinity chromatography and mass spectrometry. Mol Cell Proteomics. May 2006;5(5):923-34. Epub Feb. 1, 2006.
Wagner et al., Glycosyltransferases and their assays. Chembiochem. Sep. 24, 2010;11(14):1939-49.
Walgren et al., High glucose and insulin promote O-GlcNAc modification of proteins, including alpha-tubulin. Am J Physiol Endocrinol Metab. Feb. 2003;284(2):E424-34. Epub Oct. 22, 2002.
Wang et al., A search for pyrophosphate mimics for the development of substrates and inhibitors of glycosyltransferases. Bioorg Med Chem. Apr. 1997;5(4):661-72.
Wang et al., Design of glycosyltransferase inhibitors targeting human O-GlcNAc transferase (OGT). Med. Chem. Commun., 2014;5:1172-8.
Wang et al., Enrichment and site mapping of O-linked N-acetylglucosamine by a combination of chemical/enzymatic tagging, photochemical cleavage, and electron transfer dissociation mass spectrometry. Mol Cell Proteomics. Jan. 2010;9(1):153-60. Epub Aug. 19, 2009.
Wang et al., Extensive crosstalk between O-GlcNAcylation and phosphorylation regulates cytokinesis. Sci Signal. Jan. 12, 2010;3(104):ra2.
Wang et al., Glycogen synthase kinase 3 in MLL leukaemia maintenance and targeted therapy. Nature. Oct. 30, 2008;455(7217):1205-9. doi: 10.1038/nature07284. Epub Sep. 17, 2008.
Watson et al., Cardiomyocyte Ogt is essential for postnatal viability. Am J Physiol Heart Circ Physiol. Jan. 1, 2014;306(1):H142-53. doi: 10.1152/ajpheart.00438.2013. Epub Nov. 1, 2013.
Weichert et al., Polo-like kinase isoform expression is a prognostic factor in ovarian carcinoma. Br J Cancer. Feb. 23, 2004;90(4):815-21.
Weichert et al., Polo-like kinase isoforms in breast cancer: expression patterns and prognostic implications. Virchows Arch. Apr. 2005;446(4):442-50. Epub Mar. 23, 2005.
Wells et al., A role for N-acetylglucosamine as a nutrient sensor and mediator of insulin resistance. Cell Mol Life Sci. Feb. 2003;60(2):222-8.
Wells et al., Dynamic O-glycosylation of nuclear and cytosolic proteins: further characterization of the nucleocytoplasmic beta-N-acetylglucosaminidase, O-GlcNAcase. J Biol Chem. Jan. 18, 2002;277(3):1755-61.
Wells et al., Glycosylation of nucleocytoplasmic proteins: signal transduction and O-GlcNAc. Science. Mar. 23, 2001;291(5512):2376-8.
Wells et al., Mapping sites of O-GlcNAc modification using affinity tags for serine and threonine post-translational modifications. Mol Cell Proteomics. Oct. 2002;1(10):791-804.
Wells et al., O-GlcNAc transferase is in a functional complex with protein phosphatase 1 catalytic subunits. J Biol Chem. Sep. 10, 2004;279(37):38466-70. Epub Jul. 7, 2004.
Wesche et al., High throughput screening for protein kinase inhibitors. Comb Chem High Throughput Screen. Mar. 2005;8(2):181-95.
Wilen et al., Strategies in Optical Resolutions. Tetrahedron. 1977;33:2725-35.
Wilen, Tables of Resolving Agents and Optical Resolutions. E.L. Eliel, ed. Universtify of Notre Dame Press, Notre Dame, IN. 1972:268-98.
Wongkongkatep et al., Label-free, real-time glycosyltransferase assay based on a fluorescent artificial chemosensor. Angew Chem Int Ed Engl. Jan. 16, 2006;45(4):665-8.
Wrabl et al., Homology between O-linked GlcNAc transferases and proteins of the glycogen phosphorylase superfamily. J Mol Biol. Nov. 30, 2001;314(3):365-74.
Xu et al., A bioluminescence resonance energy transfer (BRET) system: application to interacting circadian clock proteins. Proc Natl Acad Sci U S A. Jan. 5, 1999;96(1):151-6.
Yang et al., Modification of p53 with O-linked N-acetylglucosamine regulates p53 activity and stability. Nat Cell Biol. Oct. 2006;8(10):1074-83. Epub Sep. 10, 2006. Supplementary Information included.
Yang et al., O-linkage of N-acetylglucosamine to Sp1 activation domain inhibits its transcriptional capability. Proc Natl Acad Sci U S A. Jun. 5, 2001;98(12):6611-6. Epub May 22, 2001.
Yang et al., Phosphoinositide signalling links O-GlcNAc transferase to insulin resistance. Nature. Feb. 21, 2008;451(7181):964-9.
Yang et al., Recruitment of O-GlcNAc transferase to promoters by corepressor mSin3A: coupling protein O-GlcNAcylation to transcriptional repression. Cell. Jul. 12, 2002;110(1):69-80.
Zachara et al., O-GlcNAc a sensor of cellular state: the role of nucleocytoplasmic glycosylation in modulating cellular function in response to nutrition and stress. Biochim Biophys Acta. Jul. 6, 2004;1673(1-2):13-28.
Zachara et al., The emerging significance of O-GlcNAc in cellular regulation. Chem Rev. Feb. 2002;102(2):431-8.
Zhang et al., A Modified Coupled Enzyme Method for O-linked GlcNAc Transferase Activity Assay. Biol Proced Online. Dec. 3, 2009;11:170-83.
Zhang et al., O-GlcNAc modification is an endogenous inhibitor of the proteasome. Cell. Dec. 12, 2003;115(6):715-25.
Zhou et al., Growth control of multiple myeloma cells through inhibition of glycogen synthase kinase-3. Leukemia & Lymphoma, 2008;49(10):1945-1953.

* cited by examiner

2a/2b n=3, R=H/Et
3a/3b n=4, R=H/Me

1a/1b R=H/Me

4a/4b R=H/Et

Calculated Druggability with SiteMap

| Dscore[a] | size | hydrophilic | hydrophobic |
|---|---|---|---|
| 0.94 | 119 | 1.49 | 0.17 |

[a]Dscore < 1.0 sites belong to the difficult category

O-GlcNAc TRANSFERASE INHIBITORS AND USES THEREOF

RELATED APPLICATIONS

This application is a national stage filing under 35 U.S.C. § 371 of International Application No. PCT/US2019/048805, filed Aug. 29, 2019, which claims priority under 35 U.S.C. § 119 (e) to U.S. Provisional Application, U.S. Ser. No. 62/724,479, filed Aug. 29, 2018, each of which is incorporated herein by reference.

GOVERNMENT SUPPORT

This invention was made with government support under grant numbers GM094263 awarded by the National Institutes of Health (NIH). The government has certain rights in the invention.

BACKGROUND OF THE INVENTION

The hexosamine biosynthetic pathway (HSP) is a minor branch of the glycolytic pathway, diverting 3-5% of cellular glucose toward the synthesis of UDP-GlcNAc, which is either transported to the Golgi and used in the synthesis of complex glycans or remains in the cytoplasm where it is the substrate for O-GlcNAc transferase (OGT). OGT is the sole known enzyme to catalyze the glycosylation of serine and threonine residues on many nuclear and cytoplasmic proteins (termed O-GlcNAcylation). This post-translational modification is dynamic and is a general mechanism, like protein phosphorylation, of signal transduction. O-GlcNAc transferase (OGT) is an essential mammalian enzyme that modifies myriad nuclear and cytoplasmic proteins with O-linked N-acetylglucosamine (O-GlcNAc), affecting their stability, localization, activity, and interactions with other proteins.[1] Evidence points to a crucial role for O-GlcNAc in metabolic homeostasis and elevated O-GlcNAc levels have been linked to metabolic adaptations associated with several disease phenotypes, including the abnormal proliferative capacity of cancer cells.[2] To better understand OGT function, small molecule OGT inhibitors are required. OGT inhibitors with some cellular activity have been reported, but most are substrate analogs that offer limited opportunities for modifications to improve potency or selectivity.[3]

Excess flux through the HSP has been implicated in both the early (insulin resistance) and late (nephropathy, microvascular damage) stages of diabetes mellitus, both in vivo and in vitro. Diabetes involves a deficiency in the availability and/or utilization of insulin. Insulin is a hormone produced by the pancreas and is necessary for cells to utilize glucose. Insulin resistance is a condition in which muscle, fat, and liver cells do not use insulin properly. As a result, the pancreas produces more insulin, which is also not used properly. Eventually, the pancreas cannot keep up with the body's need for insulin, and excess glucose builds up in the bloodstream. Thus, in insulin resistance, there may be high levels of blood glucose and high levels of insulin circulating in the bloodstream at the same time.

Experiments have shown that insulin resistance due to increased hexosamine flux is caused by hyper O-GlcNAcylation. Diabetics have increased production of two adipokines directly responsible for vascular injury, plasminogen activator inhibitor-1 (PAI-1) and transforming growth factor β1 (TGF-β1). Transcription of both of these proteins is decreased in cell culture when levels of O-GlcNAcylation are decreased. The molecular mechanism for this is known; increased transcription is mediated by the O-GlcNAcylation state of the transcription factor Sp1.

OGT activity and O-GlcNAcylation have also been implicated in other disease states, such as neurodegenerative diseases, cancer, autoimmune diseases, and inflammatory diseases. Accordingly, there is a need to find OGT inhibitors useful as therapeutic agents.

SUMMARY OF THE INVENTION

Reversible glycosylation of nuclear and cytoplasmic proteins is an important regulatory mechanism across metazoans. One enzyme, O-linked N-acetylglucosamine transferase (OGT), is responsible for all nucleocytoplasmic glycosylation, and there is a need for potent, cell-permeable inhibitors to interrogate OGT function. The invention relates in part to compounds that inhibit O-GlcNAc transferase (OGT) activity. The inventive compounds are based on hits identified in a screen of over 1200 compounds for their ability to inhibit OGT. Described herein are OGT inhibitors based on a structure-based development of OGT inhibitors culminating in compounds with low nanomolar inhibitory potency and on-target cellular activity. In addition to disclosing useful OGT inhibitors, the structures disclosed herein provide insight into how to inhibit glycosyltransferases, a family of enzymes that has been notoriously refractory to inhibitor development. The active site of OGT is particularly challenging to inhibit. The nucleotide-sugar substrate, UDP-GlcNAc, lies in an extended conformation underneath the peptide substrate; filling the active site requires molecules that can mimic this stacked substrate geometry (FIG. 5).[4] Complicating matters, OGT's active site is hydrophilic and accommodates many peptide sequences, with substrate selection being determined not by specific contacts to OGT side chains, but by binding of proteins to the tetratricopeptide repeat (TPR) domain.[5] At a loss for how to design inhibitors for OGT's large, hydrophilic, and promiscuous active site, a high-throughput screen that led to a weakly active compound containing a quinolinone-6-sulfonamide (Q6S) was previously carried out.[3b,6] Here structures of OGT complexed with several cell-permeable Q6S-based inhibitors are reported, including two having low nanomolar $K_d$s. These are the first known structures of a nucleotide-sugar glycosyltransferase complexed with biologically active inhibitors that are not substrate mimics. Compounds of the invention inhibit O-GlcNAcylation by OGT. O-GlcNAcylation is the glycosylation of serine and/or threonine residues on nuclear and cytoplasmic proteins that is catalyzed by OGT. Compounds of the invention are useful for the treatment of diseases and disorders associated with hyper-O-GlcNAcylation (e.g., diabetes and complications thereof, cancers, neurodegenerative diseases, autoimmune diseases, and inflammatory diseases).

In one aspect, the present disclosure provides compounds of Formula (I'):

(I')

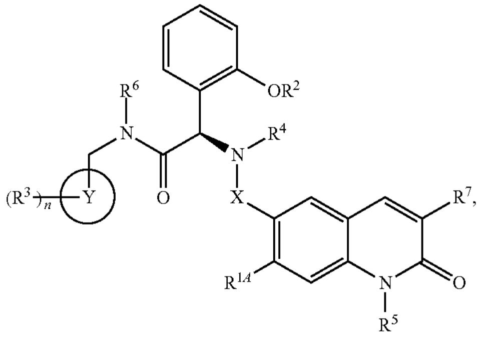

and pharmaceutically acceptable salts, solvates, hydrates, polymorphs, co-crystals, tautomers, stereoisomers, isotopically labeled derivatives, and prodrugs thereof, wherein X, Ring Y, $R^{1A}$, $R^2$, $R^3$, $R^4$, $R^5$, $R^6$, $R^7$, and n are as defined herein. In certain embodiments, a compound of Formula (I') is a compound of Formula (I-A) or (I). In certain embodiments, a compound of Formula (I') is a compound of Formula (I-A). In certain embodiments, $R^{1A}$ is $R^1$.

In certain embodiments, provided are compounds of Formula (I-A):

(I-A)

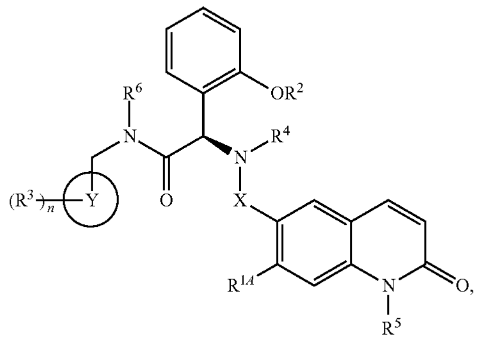

and pharmaceutically acceptable salts, solvates, hydrates, polymorphs, co-crystals, tautomers, stereoisomers, isotopically labeled derivatives, and prodrugs thereof, wherein X, Ring Y, $R^1$, $R^2$, $R^3$, $R^4$, $R^5$, $R^6$, and n are as defined herein.

In one aspect, the present disclosure provides compounds of Formula (I):

(I)

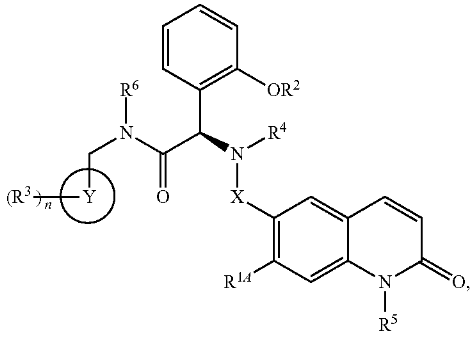

and pharmaceutically acceptable salts, solvates, hydrates, polymorphs, co-crystals, tautomers, stereoisomers, isotopically labeled derivatives, and prodrugs thereof, wherein X, Ring Y, $R^1$, $R^2$, $R^3$, $R^4$, $R^5$, $R^6$, and n are as defined herein.

Exemplary compounds of Formula (I') include, but are not limited to:

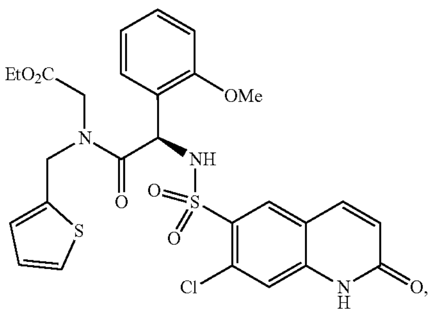

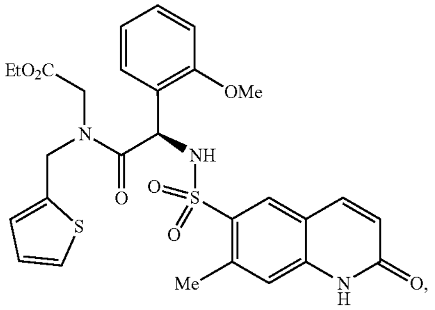

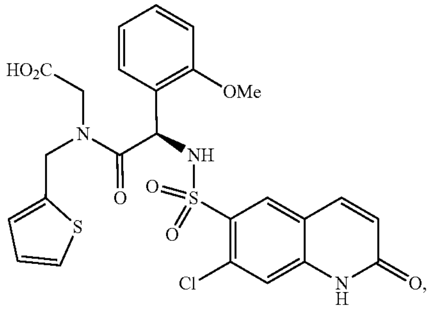

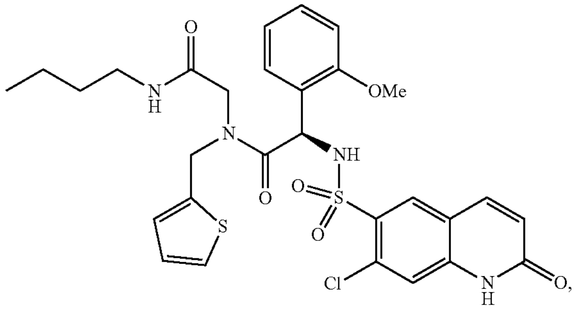

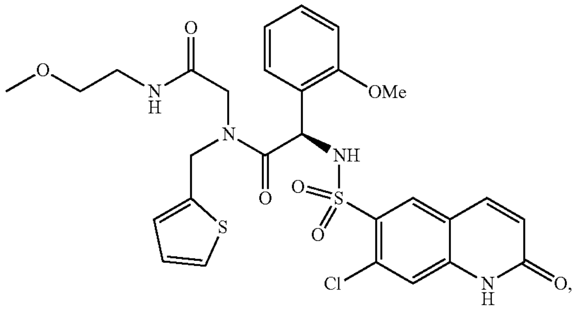

-continued
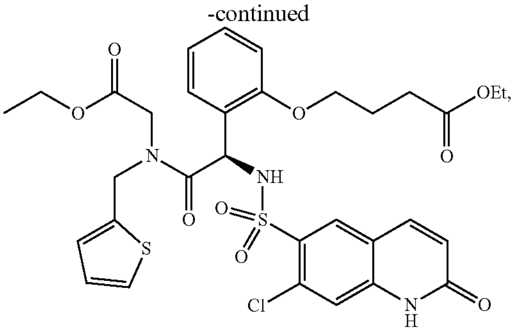
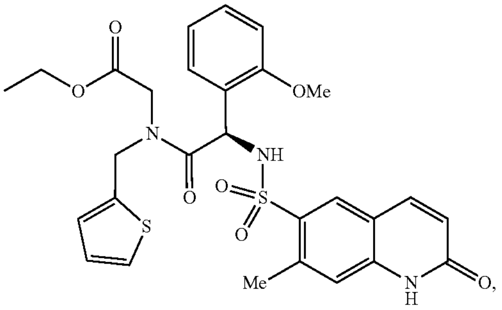
and pharmaceutically acceptable salts, solvates, hydrates, polymorphs, co-crystals, tautomers, stereoisomers, isotopically labeled derivatives, and prodrugs thereof.
Exemplary compounds of Formula (I') include, but are not limited to:
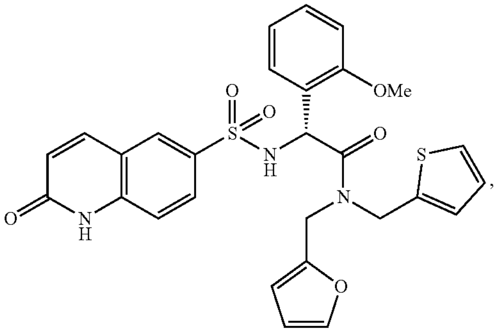
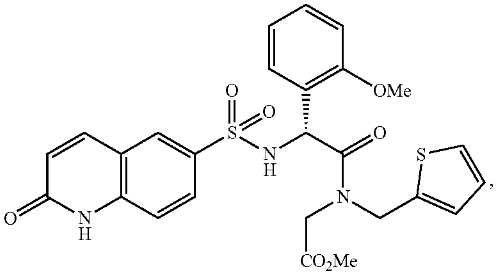
-continued
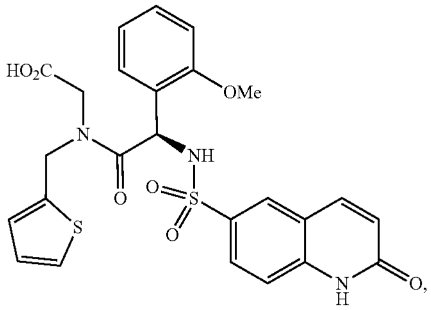
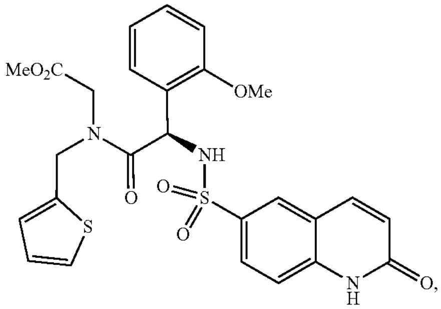
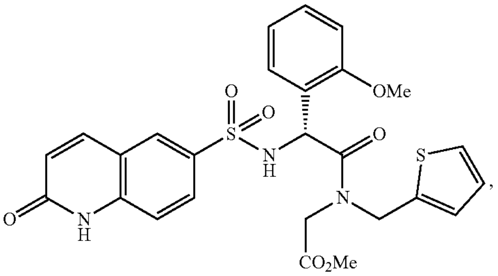
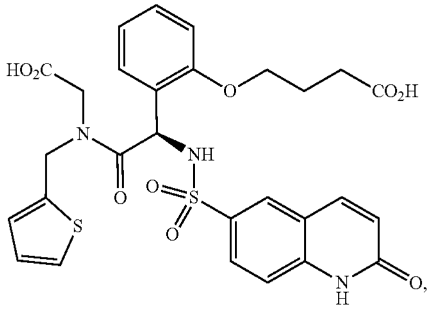
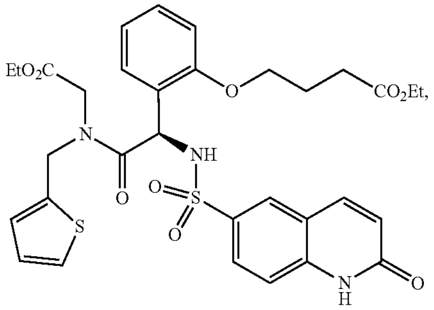

-continued
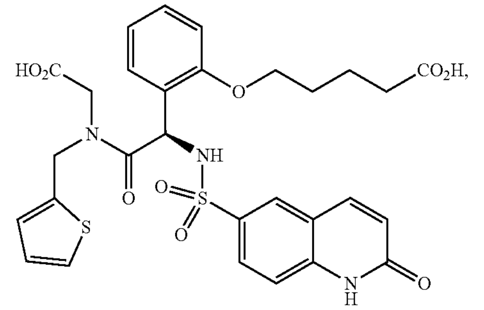
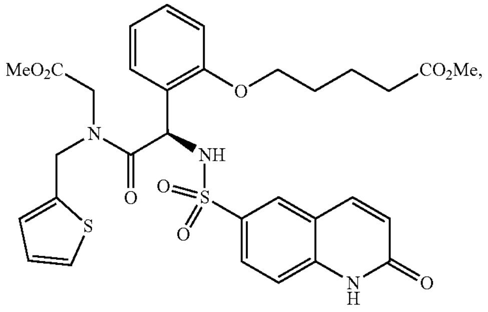
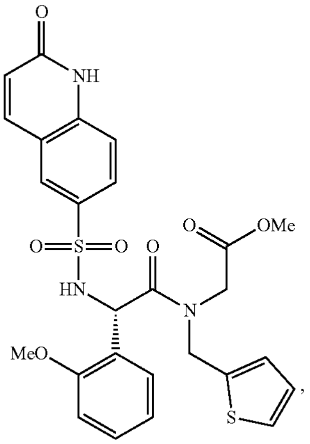
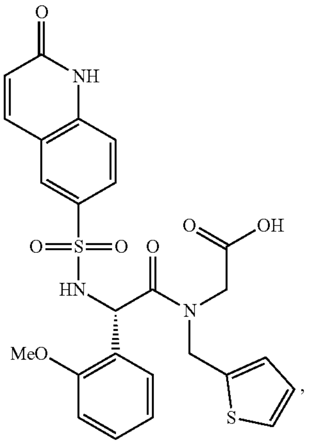
-continued
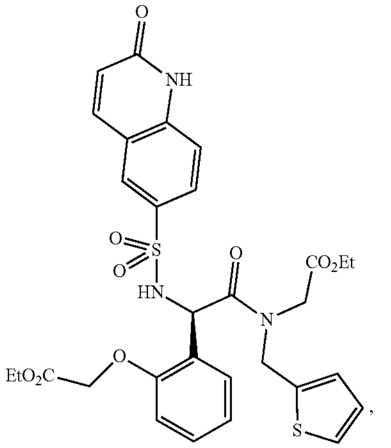
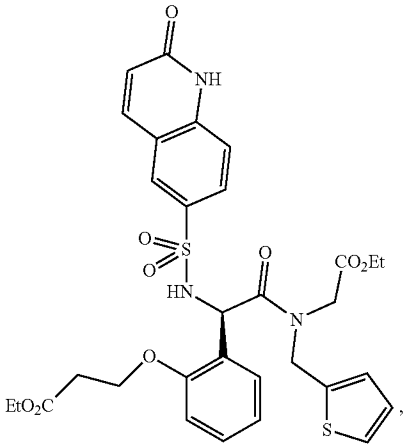
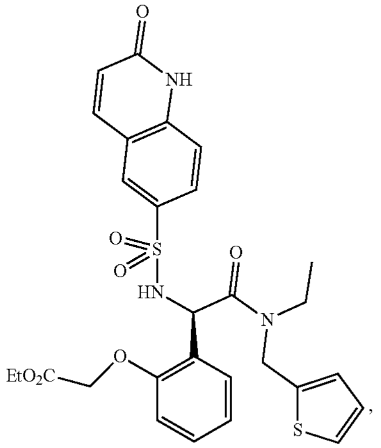

-continued
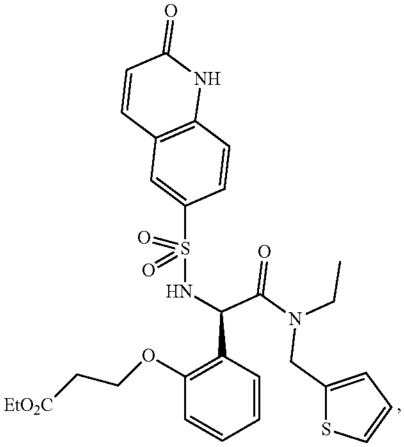
,
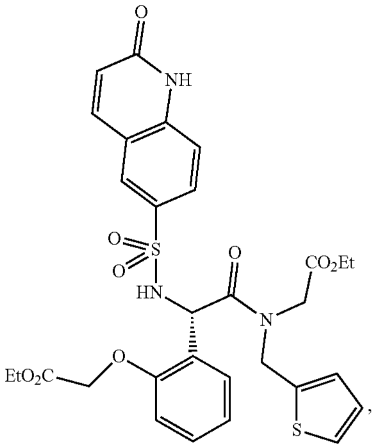
,
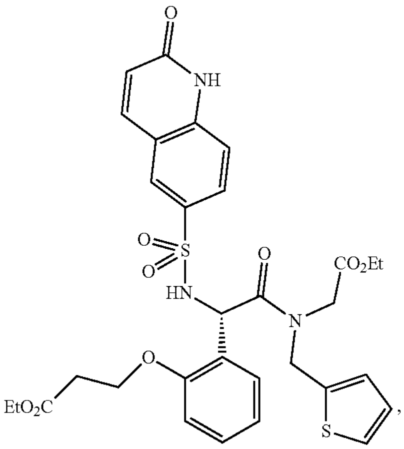
,
-continued
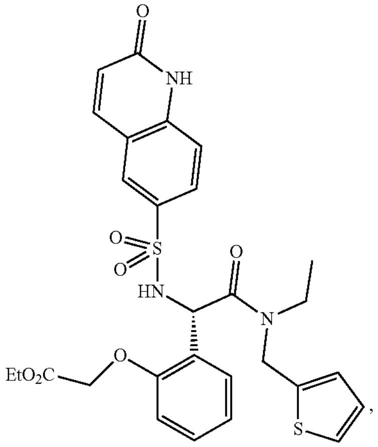
,
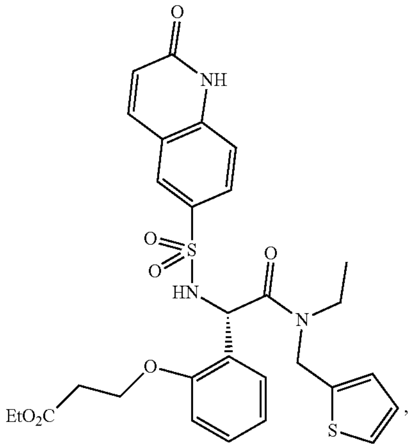
,
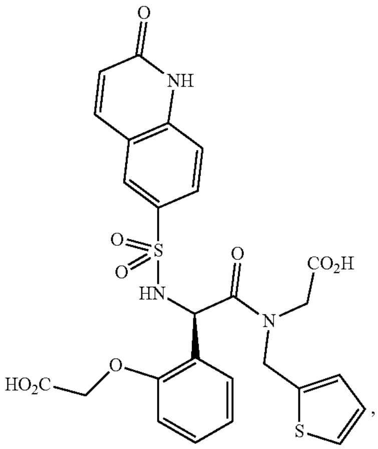
, -continued
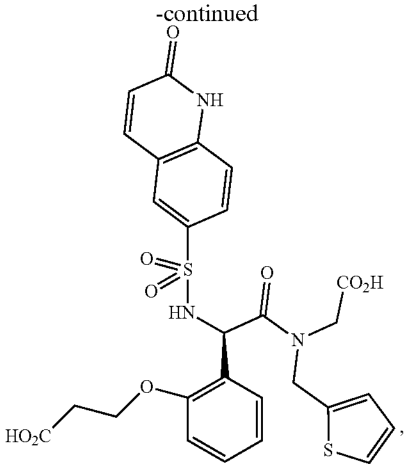
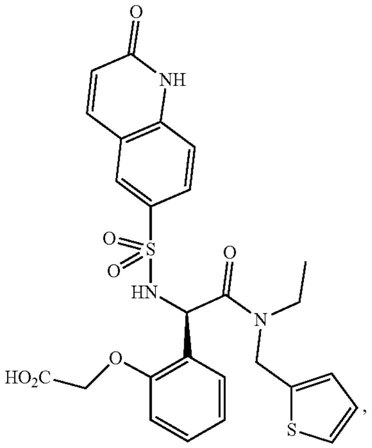
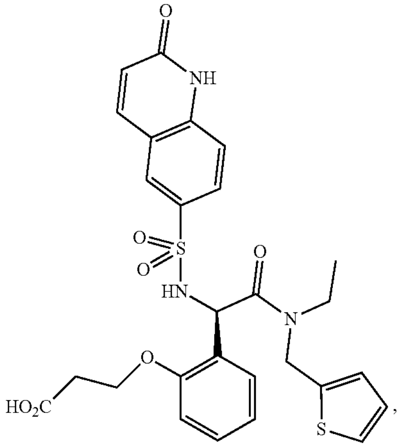
-continued
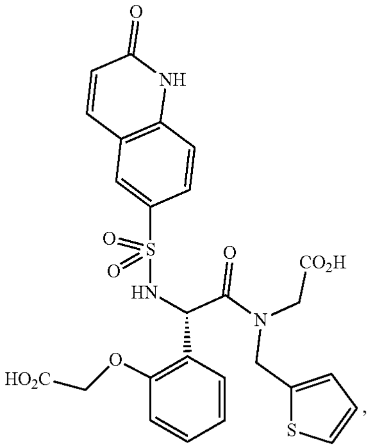
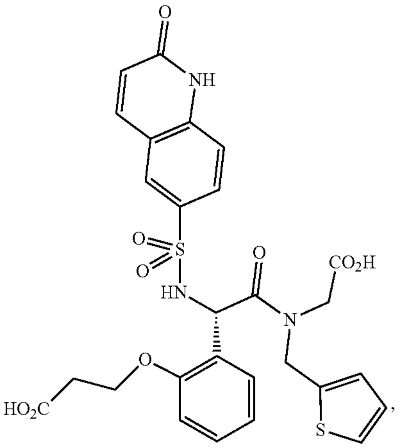
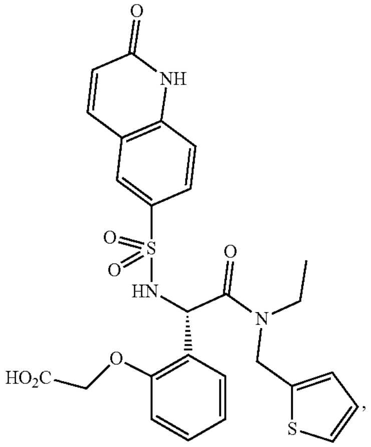 [SMILES: CCN(Cc1cccs1)C(=O)[C@@H](NS(=O)(=O)c1ccc2[nH]c(=O)ccc2c1)c1ccccc1OCC(=O)O]

-continued
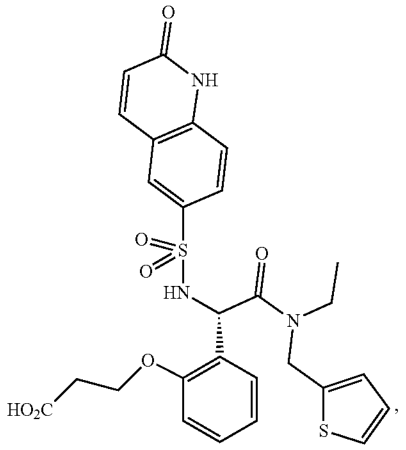
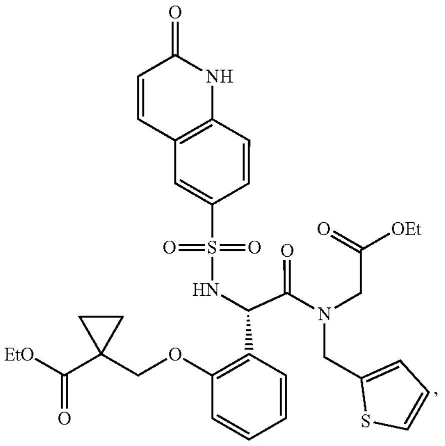
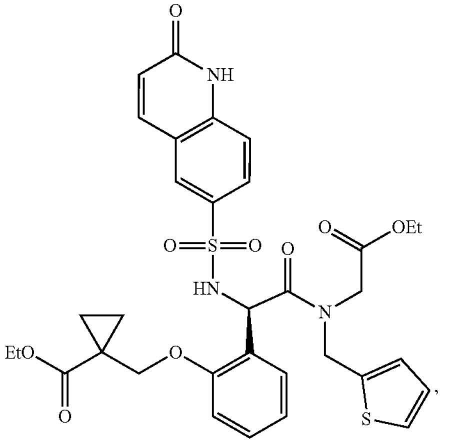
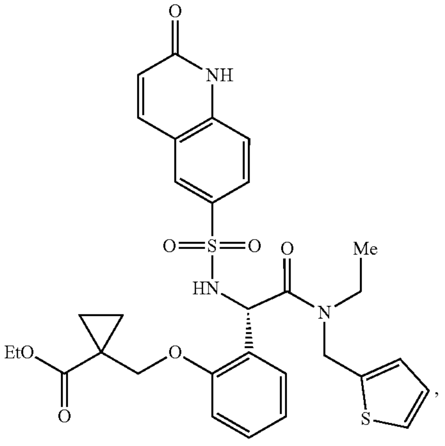
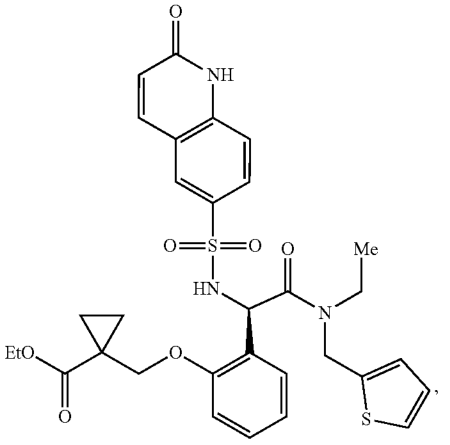
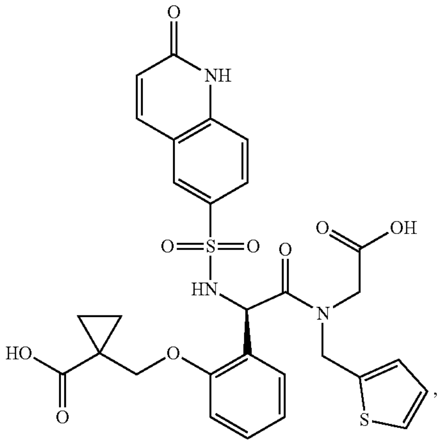

-continued

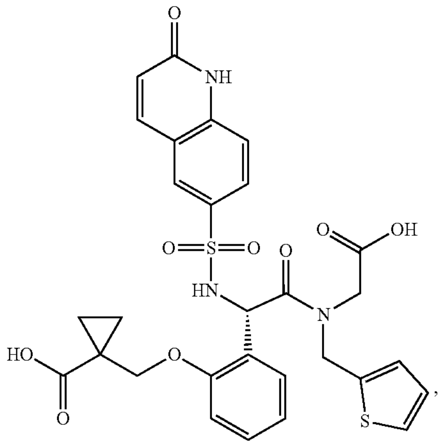

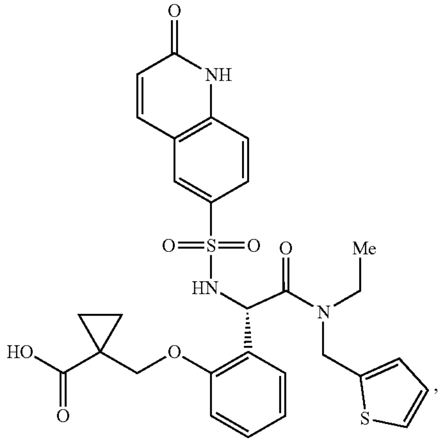

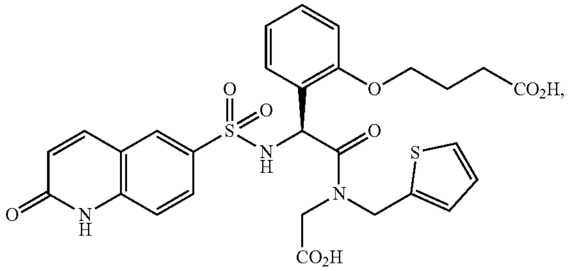

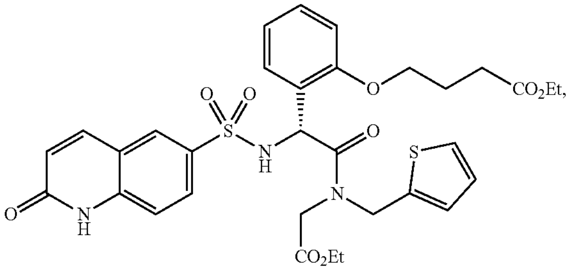

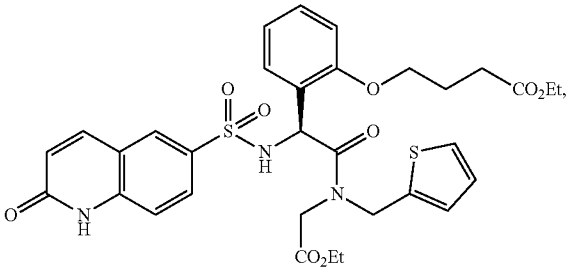

-continued

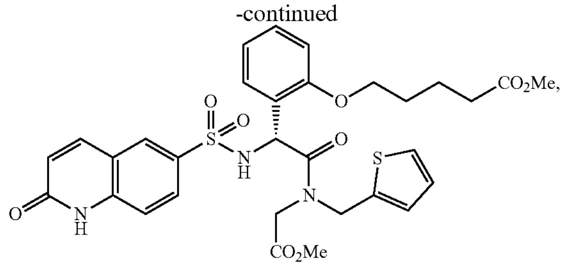

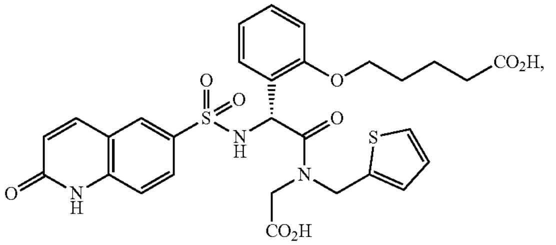

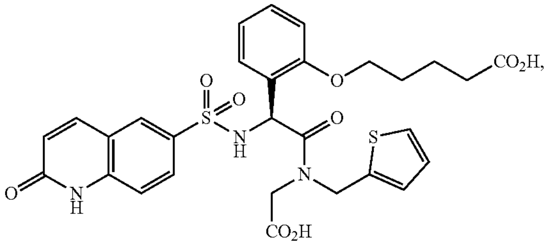

and pharmaceutically acceptable salts, solvates, hydrates, polymorphs, co-crystals, tautomers, stereoisomers, isotopically labeled derivatives, and prodrugs thereof.

Exemplary compounds of Formulae (I'), (I), and (I-A) described herein include, but are not limited to, compounds of Examples 1-3A, and pharmaceutically acceptable salts, solvates, hydrates, polymorphs, co-crystals, tautomers, stereoisomers, isotopically labeled derivatives, and prodrugs thereof. In certain embodiments, exemplary compounds of Formulae (I'), (I), and (I-A) described herein include, but are not limited to, compounds of Examples 1-3A, and pharmaceutically acceptable salts thereof. In certain embodiments, exemplary compounds of Formulae (I'), (I), and (I-A) described herein include, but are not limited to, compounds of FIG. 1A, and pharmaceutically acceptable salts thereof.

In another aspect, the present invention provides methods of treatment comprising administering an inventive compound to a subject. The compounds of the invention or pharmaceutical compositions thereof may be used to treat any disease including diabetes and complications thereof, cardiovascular disease associated with poor insulin regulation (e.g., insulin resistance), insulin resistance, neurodegenerative diseases such as Alzheimer's disease, proliferative diseases (e.g., cancer), autoimmune diseases, and inflammatory diseases. The compounds or pharmaceutical compositions thereof described herein may be used to treat an OGT-associated disease or condition in a subject. The compounds or pharmaceutical compositions thereof described herein may be used to inhibit OGT activity in a subject or biological sample (e.g., cell, tissue). The compounds of the invention may be used to treat disease in humans and other animals, including domesticated and experimental animals. The inventive compounds may also be used as probes of biological pathways.

In yet another aspect, the present invention provides pharmaceutical compositions comprising the inventive compounds. The pharmaceutical composition typically comprises a therapeutically effective amount of an inventive compound to inhibit OGT and/or treat diabetes and complications thereof, cardiovascular disease associated with poor insulin regulation (e.g., insulin resistance), insulin resistance, neurodegenerative diseases such as Alzheimer's disease, proliferative diseases (e.g., cancer), autoimmune diseases, and inflammatory diseases. The pharmaceutical compositions may optionally include a pharmaceutically acceptable excipient. Any mode of administration including oral, parenteral, and topical administration of the inventive compound or pharmaceutical composition thereof may be used.

In yet another aspect, the present disclosure provides compounds of Formula (I'), and pharmaceutically acceptable salts, solvates, hydrates, polymorphs, co-crystals, tautomers, stereoisomers, isotopically labeled derivatives, prodrugs, and compositions thereof, for use in the treatment of a disease (e.g., diabetes and complications thereof, cardiovascular disease associated with poor insulin regulation (e.g., insulin resistance), insulin resistance, neurodegenerative diseases such as Alzheimer's disease, proliferative diseases (e.g., cancer), autoimmune diseases, and inflammatory diseases) in a subject.

Another aspect of the present disclosure relates to kits comprising a container with a compound, or pharmaceutical composition thereof, as described herein. The kits described herein may include a single dose or multiple doses of the compound or pharmaceutical composition. The kits may be useful in a method of the disclosure. In certain embodiments, the kit further includes instructions for using the compound or pharmaceutical composition. A kit described herein may also include information (e.g. prescribing information) as required by a regulatory agency, such as the U.S. Food and Drug Administration (FDA).

The details of one or more embodiments of the invention are set forth herein. Other features, objects, and advantages of the invention will be apparent from the Detailed Description, Examples, Figures, and Claims.

References cited in this application are incorporated herein by reference.

Definitions

Definitions of specific functional groups and chemical terms are described in more detail below. The chemical elements are identified in accordance with the Periodic Table of the Elements, CAS version, *Handbook of Chemistry and Physics*, $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

When a range of values is listed, it is intended to encompass each value and sub-range within the range. For example, "$C_{1-6}$" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

"Hydrocarbon chain" refers to a substituted or unsubstituted divalent alkyl, alkenyl, or alkynyl group. A hydrocarbon chain includes at least one chain, each node ("carbon unit") of which including at least one carbon atom, between the two radicals of the hydrocarbon chain. For example, hydrocarbon chain $—C^AH(C^BH_2C^CH_3)—$ includes only one carbon unit $C^A$. The term "$C_x$ hydrocarbon chain," wherein x is a positive integer, refers to a hydrocarbon chain that includes x number of carbon unit(s) between the two radicals of the hydrocarbon chain. If there is more than one possible value of x, the smallest possible value of x is used for the definition of the hydrocarbon chain. For example, $—CH(C_2H_5)—$ is a $C_1$ hydrocarbon chain, and

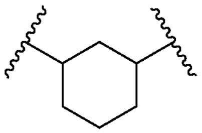 [SMILES: *C1CCCC(*)C1]

is a $C_3$ hydrocarbon chain. When a range of values is used, e.g., a $C_{1-6}$ hydrocarbon chain, the meaning of the range is as described herein. A hydrocarbon chain may be saturated (e.g., $—(CH_2)_4—$). A hydrocarbon chain may also be unsaturated and include one or more C═C and/or C≡C bonds anywhere in the hydrocarbon chain. For instance, $—CH═CH—(CH_2)_2—$, $—CH_2—C≡C—CH_2—$, and —C≡C—CH═CH— are all examples of a unsubstituted and unsaturated hydrocarbon chain. In certain embodiments, the hydrocarbon chain is unsubstituted (e.g., $—(CH_2)_4—$). In certain embodiments, the hydrocarbon chain is substituted (e.g., $—CH(C_2H_5)—$ and $—CF_2—$). Any two substituents on the hydrocarbon chain may be joined to form an optionally substituted carbocyclyl, optionally substituted heterocyclyl, optionally substituted aryl, or optionally substituted heteroaryl ring. For instance,

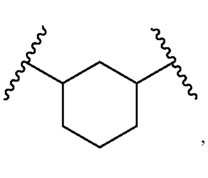 , 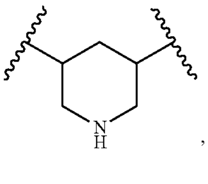 ,

-continued

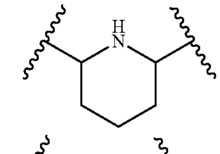 , 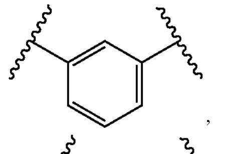 ,

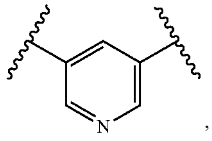 , and 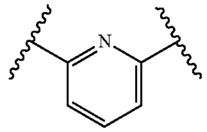

are all examples of a hydrocarbon chain. In contrast, in certain embodiments

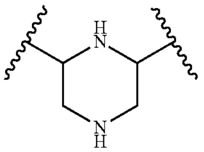 and 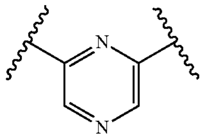

H and N are not within the scope of the hydrocarbon chains described herein.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl").

In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and $_{ww}$ero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_5$_cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from the group consisting of nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from the group consisting of nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from the group consisting of nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from the group consisting of nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, aziridinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from the group consisting of nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from the group consisting of nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from the group consisting of nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from the group consisting of nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation but is not intended to include aromatic groups (e.g., aryl or heteroaryl groups) as defined herein. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups are further referred to using the suffix -ene, e.g., alkylene, alkenylene, alkynylene, carbocyclylene, heterocyclylene, arylene, and heteroarylene.

The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —$NO_2$, —$N_3$, —$SO_2H$, —$SO_3H$, —OH, —OR—, —$ON(R^{bb})_2$, —$N(R^{bb})_2$, —$N(R^{bb})_3^+X^-$, —$N(OR^{cc})R^{bb}$, —SH, —$SR^{aa}$—, —$SSR^{cc}$, —$C(═O)R^{aa}$, —$CO_2H$, —CHO, —$C(OR^{cc})_2$, —$CO_2R^{aa}$, —$OC(═O)R^{aa}$, —$OCO_2R^{aa}$, —$C(═O)N(R^{bb})_2$, —$OC(═O)N(R^{bb})_2$, —$NR^{bb}C(═O)R^{aa}$, —$NR^{bb}CO_2R^{aa}$, —$NR^{bb}C(═O)N(R^{bb})_2$, —$C(═NR^{bb})R^{aa}$, —$C(═NR^{bb})OR^{aa}$, —$OC(═NR^{bb})R^{aa}$, —$OC(═NR^{bb})OR^{aa}$, —$C(═NR^{bb})N(R^{bb})_2$, —$OC(═NR^{bb})N(R^{bb})_2$, —$NR^{bb}C(═NR^{bb})N(R^{bb})_2$, —$C(═O)NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —$S(═O)R^{aa}$, —$OS(═O)R^{aa}$, —$Si(R^{aa})_3$, —$OSi(R^{aa})_3$—$C(═S)N(R^{bb})_2$, —$C(═O)SR^{aa}$, —$C(═S)SR^{aa}$, —$SC(═S)SR^{aa}$, —$SC(═O)SR^{aa}$, —$OC(═O)SR^{aa}$, —$SC(═O)OR^{aa}$, —$SC(═O)R^{aa}$, —$P(═O)(R^{aa})_2$, —$P(═O)(OR^{cc})_2$, —$OP(═O)(R^{aa})_2$, —$OP(═O)(OR^{cc})_2$, —$P(═O)(N(R^{bb})_2)_2$, —$OP(═O)(N(R^{bb})_2)_2$, —$NR^{bb}P(═O)(R^{aa})_2$, —$NR^{bb}P(═O)(OR^{cc})_2$, —$NR^{bb}P(═O)(N(R^{bb})_2)_2$, —$P(R^{cc})_2$, —$P(OR^{cc})_2$, —$P(R^{cc})_3^+X^-$, —$P(OR^{cc})_3^+X^-$, —$P(R^{cc})_4$, —$P(OR^{cc})_4$, —$OP(R^{cc})_2$, —$OP(R^{cc})_3^+X^-$, —$OP(OR^{cc})_2$, —$OP(OR^{cc})_3^+X^-$, —$OP(R^{cc})_4$, —$OP(OR^{cc})_4$, —$B(R^{aa})_2$, —$B(OR^{cc})_2$, —$BR^{aa}(OR^{cc})$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group ═O, ═S, ═$NN(R^{bb})_2$, ═$NNR^{bb}C(═O)R^{aa}$, ═$NNR^{bb}C(═O)OR^{aa}$, ═$NNR^{bb}S(═O)_2R^{aa}$, ═$NR^{bb}$, or ═$NOR^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —$N(R^{cc})_2$, —CN, —$C(═O)R^{aa}$, —$C(═O)N(R^{cc})_2$, —$CO_2R^{aa}$, —$SO_2R^{aa}$, —$C(═NR^{cc})OR^{aa}$, —$C(═NR^{cc})N(R^{cc})_2$, —$SO_2N(R^{cc})_2$, —$SO_2R^{cc}$, —$SO_2OR^{cc}$, —$SOR^{aa}$, —$C(═S)N(R^{cc})_2$, —$C(═O)SR^{cc}$, —$C(═S)SR^{cc}$, —$P(═O)(R^{aa})_2$, —$P(═O)(OR^{cc})_2$, —$P(═O)(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{ee}$, —$ON(R^{ff})_2$, —$N(R^{ff})_2$, —$N(R^{ff})_3^+X^-$, —$N(OR^{ee})R^{ff}$, —SH, —$SR^{ee}$, —$SSR^{ee}$, —$C(═O)R^{ee}$, —$CO_2H$, —$CO_2R^{ee}$, —$OC(═O)R^{ee}$, —$OCO_2R^{ee}$, —$C(═O)N(R^{ff})_2$, —$OC(═O)N(R^{ff})_2$, —$NR^{ff}C(═O)R^{ee}$, —$NR^{ff}CO_2R^{ee}$, —$NR^{ff}C(═O)N(R^{ff})_2$, —$C(═NR^{ff})OR^{ee}$, —$OC(═NR^{ff})R^{ee}$, —$OC(═NR^{ff})OR^{ee}$, —$C(═NR^{ff})N(R^{ff})_2$, —$OC(═NR^{ff})N(R^{ff})_2$, —$NR^{ff}C(═NR^{ff})N(R^{f}f)_2$, —$NR^{ff}SO_2R^{ee}$, —$SO_2N(R^{ff})_2$, —$SO_2R^{ee}$, —$SO_2OR^{ee}$, —$OSO_2R^{ee}$, —$S(═O)R^{ee}$, —$Si(R^{ee})_3$, —$OSi(R^{ee})_3$, —$C(═S)N(R^{ff})_2$, —$C(═O)SR^{ee}$, —$C(═S)SR^{ee}$, —$SC(═S)SR^{ee}$, —$P(═O)(OR^{ee})_2$, —$P(═O)(R^{ee})_2$, —$OP(═O)(R^{ee})_2$, —$OP(═O)(OR^{ee})_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form ═O or ═S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{f}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3^+X^-$, —$NH(C_{1-6}$ alkyl$)_2^+X^-$, —$NH_2(C_{1-6}$ alkyl$)^+X^-$, —$NH_3^+X^-$, —$N(OC_{1-6}$ alkyl$)(C_{1-6}$ alkyl), —$N(OH)(C_{1-6}$ alkyl), —NH(OH), —SH, —$SC_{1-6}$ alkyl, —$SS(C_{1-6}$ alkyl), —C(=O)($C_{1-6}$ alkyl), —$CO_2H$, —$CO_2(C_{1-6}$ alkyl), —OC(=O)($C_{1-6}$ alkyl), —$OCO_2(C_{1-6}$ alkyl), —C(=O)$NH_2$, —C(=O)N($C_{1-6}$ alkyl$)_2$, —OC(=O)NH($C_{1-6}$ alkyl), —NHC(=O)($C_{1-6}$ alkyl), —N($C_{1-6}$ alkyl)C(=O)($C_{1-6}$ alkyl), —$NHCO_2$($C_{1-6}$ alkyl), —NHC(=O)N($C_{1-6}$ alkyl$)_2$, —NHC(=O)NH($C_{1-6}$ alkyl), —NHC(=O)$NH_2$, —C(=NH)O($C_{1-6}$ alkyl), —OC(=NH)($C_{1-6}$ alkyl), —OC(=NH)$OC_{1-6}$ alkyl, —C(=NH)N($C_{1-6}$ alkyl$)_2$, —C(=NH)NH($C_{1-6}$ alkyl), —C(=NH)$NH_2$, —OC(=NH)N($C_{1-6}$ alkyl$)_2$, —OC(NH)NH($C_{1-6}$ alkyl), —OC(NH)$NH_2$, —NHC(NH)N($C_{1-6}$ alkyl$)_2$, —NHC(=NH)$NH_2$, —$NHSO_2(C_{1-6}$ alkyl), —$SO_2N(C_{1-6}$ alkyl$)_2$, —$SO_2NH(C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —Si($C_{1-6}$ alkyl$)_3$, —OSi($C_{1-6}$ alkyl$)_3$-C(=S)N($C_{1-6}$ alkyl$)_2$, C(=S)NH($C_{1-6}$ alkyl), C(=S)$NH_2$, —C(=O)S($C_{1-6}$ alkyl), —C(=S)$SC_{1-6}$ alkyl, —SC(=S)$SC_{1-6}$ alkyl, —P(=O)($OC_{1-6}$ alkyl$)_2$, —P(=O)($C_{1-6}$ alkyl$)_2$, —OP(=O)($C_{1-6}$ alkyl$)_2$, —OP(=O)($OC_{1-6}$ alkyl$)_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4]^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

The term "acyl" refers to a group having the general formula —C(=O)$R^{X1}$, —C(=O)O$R^{X1}$, —C(=O)—O—C(=O)$R^{X1}$, —C(=O)S$R^{X1}$, —C(=O)N($R^{X1}$)$_2$, —C(=S)$R^{X1}$, —C(=S)N($R^{X1}$)$_2$, and —C(=S)S($R^{X1}$), —C(=N$R^{X1}$)$R^{X1}$, —C(=N$R^{X1}$)O$R^{X1}$, —C(=N$R^{X1}$)S$R^{X1}$, and —C(=N$R^{X1}$)N($R^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

"Alkoxy" or "alkoxyl" refers to a radical of the formula: —O-alkyl.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —$CO_2R^{aa}$, —$SO_2$R—, —C(=N$R^{bb}$)$R^{aa}$, —C(=N$R^{cc}$)O$R^{aa}$, —C(=N$R^{cc}$)N($R^{cc}$)$_2$, —$SO_2$N($R^{cc}$)$_2$, —$SO_2R^{cc}$, —$SO_2OR^{cc}$, —SO$R^{aa}$, —C(=S)N($R^{cc}$)$_2$, —C(=O)S$R^{cc}$, —C(=S)S$R^{cc}$, —P(=O)(O$R^{cc}$)$_2$, —P(=O)($R^{aa}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on a nitrogen atom is a nitrogen protecting group (also referred to as an amino protecting group). Nitrogen protecting groups include, but are not limited to, —OH, —$OR^{aa}$, —$N(R^{cc})_2$, —C(=O)$R^{aa}$, —C(=O)$N(R^{cc})_2$, —$CO_2R^{aa}$, —$SO_2R^{aa}$, —C(=$NR^{cc}$)$R^{aa}$, —C(=$NR^{cc}$)$OR^{aa}$, —C(=$NR^{cc}$)N$(R^{cc})_2$, —$SO_2N(R^{cc})_2$, —$SO_2R^{cc}$, —$SO_2OR^{cc}$, —$SOR^{aa}$, —C(=S)$N(R^{cc})_2$, —C(=O)$SR^{cc}$, —C(=S)$SR^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)$OR^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonoethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2R^{aa}$) include, but are not limited to, p-toluenesulfonamide (Ts), benzenesulfonamide, 2,3,6, -trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —C(═O)S$R^{aa}$, —C(═O)$R^{aa}$, —$CO_2R^{aa}$, —C(═O)N$(R^{bb})_2$, —C(═N$R^{bb}$)$R^{aa}$, —C(═N$R^{bb}$)O$R^{aa}$, —C(═N$R^{bb}$)N$(R^{bb})_2$, —S(═O)$R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —P(═O)$(R^{aa})_2$, —P(═O)$(OR^{cc})_2$, and —P(═O)$(N(R^{bb})_2)_2$, wherein $X^-$, $R^{aa}$, $R^{bb}$, and $R^{cc}$ are as defined herein. Oxygen protecting groups are well known in the art and include those described in detail in *Protecting Groups in Organic Synthesis, T. W. Greene and P. G. M. Wuts,* 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —C(═O)S$R^{aa}$, —C(═O)R—, —$CO_2R^{aa}$, —C(═O)N$(R^{bb})_2$, —C(═N$R^{bb}$)$R^{aa}$, —C(═N$R^{bb}$)O$R^{aa}$, —C(═N$R^{bb}$)N$(R^{bb})_2$, —S(═O)Ra, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —P(═O)$(R^{aa})_2$, —P(═O)$(OR^{cc})_2$, and —P(═O)$(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

As used herein, a "leaving group" (LG) is an art-understood term referring to a molecular fragment that departs with a pair of electrons in a heterolytic bond cleavage, wherein the molecular fragment is an anion or neutral molecule. As used herein, a leaving group can be an atom or a group capable of being displaced by a nucleophile. See, for example, Smith, *March Advanced Organic Chemistry* 6th ed. (501-502). Exemplary leaving groups include, but are not limited to, halo (e.g., chloro, bromo, iodo) and activated substituted hydroxyl groups (e.g., —OC(═O)S$R^{aa}$, —OC(═O)$R^{aa}$, —O$CO_2R^{aa}$, —OC(═O)N$(R^{bb})_2$, —OC(═N$R^{bb}$)$R^{aa}$, —OC(═N$R^{bb}$)O$R^{aa}$, —OC(═N$R^{bb}$)N$(R^{bb})_2$, —OS(═O)$R^{aa}$, —O$SO_2R^{aa}$, —O$P(R^{cc})_2$, —O$P(R^{cc})_3$, —OP(═O)$_2R^{aa}$, —OP(═O)$(R^{aa})_2$, —OP(═O)$(OR^{cc})_2$, —OP(═O)$_2$N$(R^{bb})_2$, and —OP(═O)(N$R^{bb}$)$_2$, wherein $R^{aa}$, $R^{bb}$, and $R^{cc}$ are as defined herein). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, amines, ammonia, alcohols, ether moieties, sulfur-containing moieties, thioether moieties, zinc halides, magnesium moieties, diazonium salts, and copper moieties.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formula (I') may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\ H_2O$, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates ($R \cdot 0.5H_2O$)), and polyhydrates (x is a number greater than 1, e.g., dihydrates ($R \cdot 2H_2O$) and hexahydrates ($R \cdot 6H_2O$)).

The term "tautomers" refer to compounds that are interchangeable forms of a particular compound structure, and that vary in the displacement of hydrogen atoms and electrons. Thus, two structures may be in equilibrium through the movement of J electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds of Formula (I'), which have cleavable groups and become by solvolysis or under physiological conditions the compounds of Formula (I') which are pharmaceutically active in vivo. Such examples include, but are not limited to, ester derivatives and the like. Other derivatives of the compounds of this invention have activity in both their acid and acid derivative forms, but in the acid sensitive form often offers advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy) alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of Formula (I') may be preferred.

The terms “administer,” “administering,” or “administration,” refers to implanting, absorbing, ingesting, injecting, inhaling, or otherwise introducing an inventive compound, or a pharmaceutical composition thereof.

The terms “treatment,” “treat,” and “treating” refer to reversing, alleviating, delaying the onset of, or inhibiting the progress of a “pathological condition” (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

The terms “condition,” “disease,” and “disorder” are used interchangeably.

These and other exemplary substituents are described in more detail in the Detailed Description, Examples, and claims. The invention is not intended to be limited in any manner by the above exemplary listing of substituents.

Other Definitions

A “subject” to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

The term “biological sample” refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments, or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a biological sample.

The term “tissue” refers to any biological tissue of a subject (including a group of cells, a body part, or an organ) or a part thereof, including blood and/or lymph vessels, which is the object to which a compound, particle, and/or composition of the invention is delivered.

A tissue may be an abnormal or unhealthy tissue, which may need to be treated. A tissue may also be a normal or healthy tissue that is under a higher than normal risk of becoming abnormal or unhealthy, which may need to be prevented. In certain embodiments, the tissue is the central nervous system. In certain embodiments, the tissue is the brain.

The terms “administer,” “administering,” or “administration,” as used herein refers to implanting, absorbing, ingesting, injecting, or inhaling the inventive compound.

As used herein the term “inhibit” means to reduce the amount of OGT activity and/or O-GlcNAcylation to a level or amount that is statistically significantly less than an initial level, which may be a baseline level of OGT activity and/or O-GlcNAcylation.

As used herein, the terms “treatment,” “treat,” and “treating” refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The terms “effective amount” and “therapeutically effective amount,” as used herein, refer to the amount or concentration of an inventive compound, that, when administered to a subject, is effective to at least partially treat a condition from which the subject is suffering.

As used herein, the terms “O-GlcNAcylation-associated disease or disorder” and “OGT-associated disease or disorder” include, but are not limited to diseases and disorders in which there is abnormal OGT activity and/or abnormal levels of O-GlcNAcylation. “OGT” refers to O-linked N-acetylglucosamine (O-GlcNAc) transferase. As used herein, the term “OGT activity” means OGT-mediated O-GlcNAcylation. An abnormal level of OGT activity and/or O-GlcNAcylation may be a level that is higher than a normal level or may be a level that is lower than a normal level, wherein a “normal” level is the level in a subject who does not have a disease or disorder associated with OGT activity or O-GlcNAcylation. Examples of diseases and disorders associated with OGT activity and/or O-GlcNAcylation levels include, but are not limited to neurodegenerative disorders such as Alzheimer’s disease; proliferative disease (e.g., cancer); diabetes mellitus, cardiovascular disease associated with poor insulin regulation (e.g., insulin resistance), insulin resistance, and complications of diabetes or other OGT-associated diseases.

The term “metabolic disorder” refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., Type I diabetes, Type II diabetes, gestational diabetes), hyperglycemia, hyperinsulinemia, insulin resistance, and obesity.

As used herein, the term "complication of diabetes" is used to mean a disorder that is associated with diabetes. Non-limiting examples of complications of diabetes include microvascular damage, insulin resistance, vascular damage, nephropathy, skin ulcers, circulatory damage, diabetic nephropathy, diabetic retinopathy, macro-vascular disease, micro-vascular disease, cardiac dysfunction, and diabetic neuropathy.

The term "diabetic" as used herein, means a subject who, at the time the sample is taken, has a primary deficiency of insulin. The term diabetic includes, but is not limited to, individuals with juvenile diabetes (Type 1 diabetes), adult-onset diabetes (Type 2 diabetes), gestational diabetes, and any other conditions of insulin deficiency. The terms "diabetic" and "diabetes" are terms of art, known and understood by those practicing in the medical profession, a formal definition of which can be found in *Harrison's Principles of Medicine* (Harrisons, Vol 14, *Principles of Internal Medicine*, Eds. Fauci, A. S., E. Braunwald, K. J. Isselbacher, J. D. Wilson, J. B. Martin, D. L. Kasper, S. L. Hauser, D. L. Longo, McGraw-Hill, New York, 1999).

Subjects with blood glucose levels that are higher than normal but not yet in the range associated with a diagnosis of diabetes may be considered to have "pre-diabetes." Pre-diabetes is also known in the art as "impaired fasting glucose" (IFG) or "impaired glucose tolerance" (IGT). Subjects with pre-diabetes have a higher risk of developing type 2 diabetes, which is also known as adult-onset diabetes or noninsulin-dependent diabetes.

The term "cardiovascular disease" or "heart disease" refers to diseases associated the heart and/or blood vessels. Exemplary cardiovascular diseases include, but are not limited to, coronary heart disease, stroke or cerebrovascular disease, congenital heart defects, peripheral artery disease, heart disease associated with atherosclerosis, ischemic heart disease, hypertensive heart disease, rheumatic heart disease, cardiac arrhythmias, heart failure, congenital heart disease, inflammatory heart disease, cardiomyopathy, pericardial disease, and valvular heart disease. In certain embodiments, the cardiovascular disease is associated with and/or results from poor insulin regulation.

"Insulin resistance," as used herein, is a condition in which the tissues of the body fail to respond normally to insulin. DeFronzo, R. A. *J. Cardiomuscular Pharmacology* 20 (Suppl. 11): S1-S16 (1992). Insulin resistance manifests itself in pathologically elevated endogenous insulin and glucose levels and predisposes one who suffers from said resistance to the development of a cluster of abnormalities, including some degree of impaired glucose tolerance, an increase in plasma triglycerides and low density lipoprotein cholesterol (LDL) levels, a decrease in high-density lipoprotein cholesterol (HDL) levels, high blood pressure, hyperuricemia, a decrease in plasma fibrinolytic activity, an increase in cardiovascular disease and atherosclerosis. Reaven, G. M. *Physiol-Rev.* 75(3): 473-86 (1995).

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, autoinflammatory diseases, and autoimmune diseases.

The terms "neoplasm" and "tumor" are used interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (*Stedman's Medical Dictionary,* 25th ed.; Hensyl ed.; Williams & Wilkins: Philadelphia, 1990). Cancers which migrate from their original location and seed vital organs can eventually lead to the death of the subject through the functional deterioration of the affected organs. Carcinomas are malignant cancers that arise from epithelial cells and include adenocarcinoma and squamous cell carcinoma. Sarcomas are cancer of the connective or supportive tissue and include osteosarcoma, chondrosarcoma and gastrointestinal stromal tumor. Hematopoietic cancers, such as leukemia, are able to outcompete the normal hematopoietic compartments in a subject, thereby leading to hematopoietic failure (in the form of anemia, thrombocytopenia and neutropenia) ultimately causing death. A person of ordinary skill in the art can classify a cancer as a sarcoma, carcinoma or hematopoietic cancer.

Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplamacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrinetumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and the growth of new blood vessels. Normal angiogenesis occurs in the healthy body of a subject for healing wounds and for restoring blood flow to tissues after injury. The healthy body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal or pathological angiogenesis refers to angiogenesis greater than that in a normal body, especially angiogenesis in an adult not related to normal angiogenesis (e.g., menstruation or wound healing). Abnormal angiogenesis can provide new blood vessels that feed diseased tissues and/or destroy normal tissues, and in the case of cancer, the new vessels can allow tumor cells to escape into the circulation and lodge in other organs (tumor metastases). In certain embodiments, the angiogenesis is pathological angiogenesis.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; gliosis; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

BRIEF DESCRIPTION OF THE DRAWINGS

FIG. 1A shows structures of exemplary OGT inhibitors. FIG. 1B shows an overview of the OGT: 1a structure (gray) showing exemplary OGT inhibitor 1a bound in the active site. All crystals were obtained using a TPR-binding peptide derived from HCF-1 to improve resolution.[4c] FIG. 1C shows an overlay of exemplary OGT inhibitor 1a and UDP-GlcNAc (PDB: 4N3C) showing that the Q6S moiety mimics uridine. Dashed lines indicate inferred hydrogen bonds from exemplary OGT inhibitor 1a to OGT. FIG. 1D is a schematic showing that the U-shaped conformation of exemplary OGT inhibitor 1a enables the amide substituents to fill the space above the quinolinone. FIG. 1E shows an overlay of exemplary OGT inhibitors 1a, 2a, and 3a. Dashed lines indicate hydrogen bond contacts to $Thr^{921}$ from exemplary OGT inhibitors 2a and 3a, and to backbone amides from 3a. Indicated sticks show the side chains in the exemplary OGT inhibitor 2a and 3a complexes, respectively. See FIGS. 8, 10, and 11 for additional views. FIG. 1F shows space-filling views of exemplary OGT inhibitors 1a and 4a with the 1a hydrogen and 4a chlorine shown with arrows.

FIG. 2A shows MST binding curves for exemplary OGT inhibitors 2a, 3a, and 4a, with dissociation constants of selected exemplary OGT inhibitors listed (inset). Error bars represent S.E.M. of at least three replicates. See Table 1 for all $K_d$s and FIG. 12 for other MST curves. FIG. 2B shows the O-GlcNAc (RL-2) blot of HEK293T cell lysates after treatment with exemplary OGT inhibitor 4b for 24 hours. FIG. 2C shows the O-GlcNAc blot of HCT116 cells after treatment for 4 hours with exemplary OGT inhibitors 1b and 2b. FIG. 2D shows the O-GlcNAc blot of HEK293T cell lysates after treatment for 24 hr with exemplary OGT inhibitors 1b, 2b, and their enantiomers. FIG. 2E shows treating HEK293T cells with 20 μM of exemplary OGT inhibitors 2b or 4b for 48 hours blocked HCF-1 cleavage. Asterisk (*): uncleaved HCF-1; arrows: cleavage products.

FIG. 3A shows a volcano plot of proteomic data (including reciprocal changes in the abundance of OGT and OGA) after treating HEK293T cells with 20 μM of exemplary OGT inhibitor 1b for 24 hours. FIG. 3B shows a bar graph summarizing quantitative PCR results using primers to OGT's detained intron (intron 4) and spliced exons (exon 4 and 5) after 2-hour treatment of HEK293T cells with 10 μM of exemplary OGT inhibitors 1b, 2b and 4b. Error bars represent s.d. (n=3). FIG. 3C shows a volcano plot of proteomic data (for changes in multiple proteins involved in ER stress and sterol metabolism, including SQSTM1 (sequestosome-1), a protein involved in autophagy that was shown to increase upon conditional deletion of OGT in the liver, as well as additional proteins involved in autophagy) after treating HEK293T cells with 20 μM of exemplary OGT inhibitor 4b for 24 hours. FIG. 3D shows a heatmap of proteins involved in indicated processes after treatment with of exemplary OGT inhibitor 4b.

FIG. 4 shows OGT substrates adopt a stacked geometry. A peptide sugar acceptor (derived from CKII), lies above UDP-GlcNAc, filling the active site of OGT (PDB accession code 4GYY). FIG. 5 shows the active site of OGT is large and hydrophilic as calculated by SiteMap,[1] making it hard to design inhibitors for OGT.

FIG. 7A shows the conformation of 1a when bound to OGT shown next to a representative of the five lowest energy conformers (gray), calculated by MacroModel, shows a different starting conformer before geometry optimization. FIG. 7B shows an overlay of the conformation of 1a in the OGT:1a crystal with the lowest energy conformer as determined by Density-Functional Theory calculations binding shows remarkably close agreement between the bound and calculated conformations.

FIGS. 11A and 11B show overlays of 1a, 2a, and 3a with residues to which inhibitors are expected to make contacts overlaid as labeled. Hydrogen bond contacts to $Ala^{896}$, $Lys^{898}$, and $Arg^{904}$ are shown with dashed lines. $His^{901}$ engages in a pi-stacking interaction with the Q6S group. FIG. 11C shows a superposition of compound 3a with UDP-GlcNAc (PDB: 4N3C) shows close overlap of a carboxylate oxygen of 3a with a phosphate oxygen of UDP that is anchored to the N-terminus of a nearby α-helix.

FIG. 13A shows Western blotting for O-GlcNAc levels ((α-RL2) after treatment of cells with inhibitors at 20 μM (1b, 2b, 3b) or 50 μM (2b, 3b) show that compound 1b and 2b are more effective than 3b. “C” denotes DMSO control. FIG. 13B shows treatment with 20 μM of 1b and 2b for 4 and 24 hours. Both compounds caused similar reductions in O-GlcNAc levels at 4 hours. O-GlcNAc levels recover after 24 hours of treatment with 1b but not 2b. FIG. 13C shows dose dependent decreases in global O-GlcNAc levels were observed in cells upon treatment with 1b and 2b for 4 hours. FIG. 13D shows that O-GlcNAc levels remain low at 16 hours post-treatment with 1b, but begin to recover at 24 hours post-treatment. FIG. 13E shows treatment of cells with 20 μM of 1b and 2b results in decreased protein O-GlcNAcylation in as little as 2 hours, whereas treatment with their respective enantiomers has no effect. Upon treatment with 50 μM of 1b and 2b, robust effects continue at 24 hours. After 96 hours of treatment with 2b O-GlcNAc levels remain very low but recover in cells treated with compound 1b. In all cases, little to no reduction in O-GlcNAc levels is observed in cells treated with the enantiomers of 1b or 2b.

FIGS. 14A and 14B show treatment of HCT116 colon cancer cells with 20-80 μM of 1b, 2b, and 3b at 4 hours (FIG. 14A) or 24 hours (FIG. 14B) resulted in dose dependent decreases in O-GlcNAc levels. FIGS. 14C and 14D show 1b and 2b are effective in prostate cancer cells. Decreases in O-GlcNAc levels are observed after treatment of PC3 (FIG. 14C) and LNCaP (FIG. 14D) cells with 1b and 2b.

FIG. 15A shows Western blotting for global O-GlcNAc after 24 hours of treatment with 20 or 50 μM of 2b and 4b shows that greater reductions in O-GlcNAc levels are observed upon treatment with 4b in HEK293T cells. FIG. 15B shows a comparison of global O-GlcNAc levels in HCT116 cells after 24-hour treatment with 20 μM of 1b, 2b, and 4b shows that 2b and 4b are more effective than 1b at inhibiting OGT in cells. FIGS. 15C and 15D show treatment of HEK293T cells with 4b at 24 hours (FIG. 15C) results in a dose dependent decrease in O-GlcNAc levels with effects seen upon treatment with as little as 5 μM of compound. These effects can be observed in as little as 2 hours (FIG. 15D) or 48 hours (FIG. 15E). FIG. 15F show a plot of concentration of 4b vs. % O-GlcNAc levels relative to untreated control sample as determined by densitometry analysis of the Western blot from FIG. 15C and FIG. 2B, and corrected for actin levels indicates that the $EC_{50}$ of 4b in cells is ~3 μM. Error bars represent s.d. of 2 replicates.

FIG. 16A show Western blotting shows a time dependent increase in uncleaved HCF-1 over 96 hours after treatment of HEK293T cells with both 1b and 2b. More pronounced effects are observed upon treatment with 2b. An asterisk (*) denotes uncleaved HCF-1. FIG. 16B shows a comparison of HCF cleavage between 2b and 4b after treatment of HEK293T cells with 20 μM of compound for 24 hours shows that 4b is more effective at reducing HCF-1 cleavage. FIG. 16C shows a comparison of HCF cleavage between 1b, and 2b after treatment of HCT116 cells with 20-80 μM of compound for 24 hours indicates that 2b is more effective at reducing HCF-1 cleavage.

FIG. 17A shows treatment with OGT inhibitors reduces cellular confluency. Images of HCT116 cells in culture at 1 and 4 days after treatment with DMSO, or 40 μM of 1b, 2b, or 4b. At 24 hours, confluency is similar to DMSO control for all compounds. At 96 hours, confluency is reduced for all compounds relative to DMSO control, with the greatest reductions observed in cells treated with 2b. FIG. 17B shows graphical representations of confluence after treatment with DMSO (negative control), 10 or 40 μM of 1b, 2b, or 4b, or M staurosporine (positive control). Similar confluence was observed in all samples except staurosporine control at 24 hours and reductions in confluence of inhibitor treated samples becoming more pronounced after 40 hours of compound treatment. Error bars represent s.d. of at least three replicates. FIG. 17C shows treating HCT116 cells for 96 hours with either 10 or 40 μM of 1b, 2b, or 4b resulted in reduced cell growth compared with the control. "S" denotes staurosporine. Error bars represent s.d. of at least three replicates. FIG. 17D shows treating HEK293T cells for 24 hours with increasing concentrations of 1b, 2b, or 4b (0-50 μM) did not result in cytotoxic cell death. "S" denotes staurosporine. Error bars represent s.d. of three replicates.

FIG. 19A shows volcano plots of quantitative proteomic analysis showing $\log_2$ fold change versus $-\log_{10}$ P value of 1b at 20 μM for 8, 16, and 24 hours. Boxed circles represent proteins that exhibited greater than 1.3-fold change in abundance and a p-value <0.05 relative to DMSO. FIG. 19B shows OGT and OGA showed a time-dependent change in their protein abundance with 20 μM 1b. Error bars represent standard deviation (s.d.) of five replicates. FIG. 19C shows Western blotting shows an increase in OGT at 4 and 24 hours after treatment of HEK293T cells with 20 μM 1b, confirming the proteomic studies.

DETAILED DESCRIPTION OF CERTAIN EMBODIMENTS OF THE INVENTION

Figure 1A:
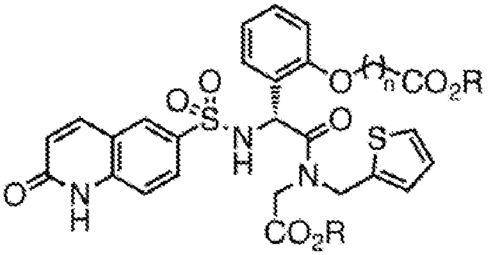
FIGS. 1A to 1F show structures of OGT:inhibitor complexes and structure-based improvements.
Figure 1A:
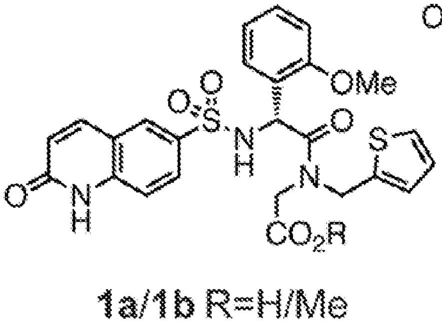
Figure 1A:
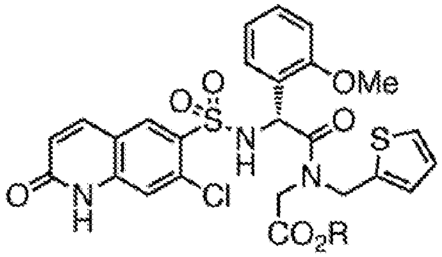

Provided herein are inhibitors of O-GlcNAc transferase (OGT). The compounds of the present invention are useful in the treatment of OGT-related diseases or disorders. Specifically, the compounds are useful in the treatment of diabetes and complications thereof, neurological diseases, proliferative diseases such as cancers, and autoimmune diseases, and inflammatory diseases. Also provided herein are pharmaceutical compositions and methods of using the inventive compounds for the treatment of various diseases. OGT inhibitors have been reported in U.S. Ser. No. 13/375,036, filed Jan. 9, 2012, and in U.S. Ser. No. 15/323,206, filed Dec. 30, 2016, each of which is incorporated herein by reference.

Compounds

Compounds of the present invention include inhibitors of OGT. In certain embodiments, the compounds have an $IC_{50}$ of less than approximately 100 μM, e.g., less than approximately 10 μM, e.g., less than approximately 1 μM, e.g., less than approximately 0.1 μM, less than approximately 0.01 μM, less than approximately 0.01 μM, less than approximately 0.001 μM, or e.g., less than approximately 0.01 μM, or less than approximately 0.0001 μM. The inventive compounds may be useful in the treatment of a variety of diseases. In certain embodiments, the compounds are useful in the treatment of diabetes and complications thereof, and insulin resistance. Certain compounds are also useful in treating neurological diseases, such as neurodegenerative diseases. In certain embodiments, the compounds are useful in the treatment of certain types of cancers. In other embodiments, the compounds are useful in treating autoimmune diseases or inflammatory diseases.

In certain embodiments, the invention provides a compound of Formula (I'), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (I'), or a pharmaceutically acceptable salt thereof.

In one aspect, disclosed are compounds of Formula (I'):

(I')

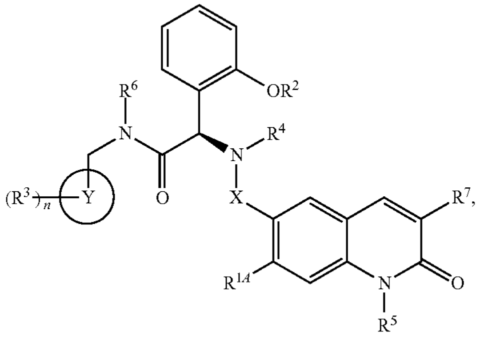

or a pharmaceutically acceptable salt, solvate, hydrate, polymorph, co-crystal, tautomer, stereoisomer, isotopically labeled derivative, or prodrug thereof, wherein X is —$SO_2$—, —SO—, or —C(═O)—;

Ring Y is 5-membered heterocyclyl or 5-membered heteroaryl with 1-2 heteroatoms selected from the group consisting of N and S;

$R^{1A}$ is hydrogen, halogen, optionally substituted alkyl, or —CN;

$R^2$ is hydrogen, optionally substituted acyl, optionally substituted alkyl, or an oxygen protecting group;

$R^3$ is halogen, —CN, —SCN, —$NO_2$, —$N_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —$OR^a$, —$N(R^b)_2$, or —$SR^a$;

each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl;

$R^4$ is hydrogen, optionally substituted alkyl, or a nitrogen protecting group;

$R^5$ is hydrogen, optionally substituted alkyl, or a nitrogen protecting group;

$R^6$ is hydrogen, optionally substituted alkyl, or a nitrogen protecting group;

$R^7$ is hydrogen, halogen, optionally substituted alkyl, or —CN; and n is 0, 1, 2, 3, 4, or 5.

In certain embodiments, a compound of Formula (I') is a compound of Formula (I-A) or (I). In certain embodiments, a compound of Formula (I') is a compound of Formula (I-A).

In certain embodiments, a compound of Formula (I') described herein is of Formula (I-A):

(I-A)

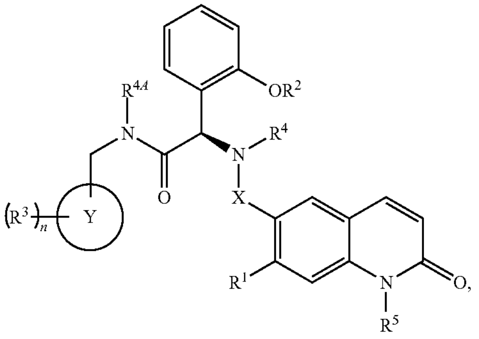

or a pharmaceutically acceptable salt, solvate, hydrate, polymorph, co-crystal, tautomer, stereoisomer, isotopically labeled derivative, or prodrug thereof, wherein X is $—SO_2—$, —SO—, or —C(═O)—;

Ring Y is 5-membered heterocyclyl or 5-membered heteroaryl with 1-2 heteroatoms selected from the group consisting of N and S;

$R^1$ is halogen, optionally substituted alkyl, or —CN;

$R^2$ is hydrogen, optionally substituted acyl, optionally substituted alkyl, or an oxygen protecting group;

$R^3$ is halogen, —CN, —SCN, $—NO_2$, $—N_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, $—OR^a$, $—N(R^b)_2$, or $—SR^a$;

each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl;

$R^4$ is hydrogen, optionally substituted alkyl, or a nitrogen protecting group;

$R^5$ is hydrogen, optionally substituted alkyl, or a nitrogen protecting group;

$R^6$ is hydrogen, optionally substituted alkyl, or a nitrogen protecting group; and n is 0, 1, 2, 3, 4, or 5.

In certain embodiments, a compound described herein is of Formula (I):

(I)

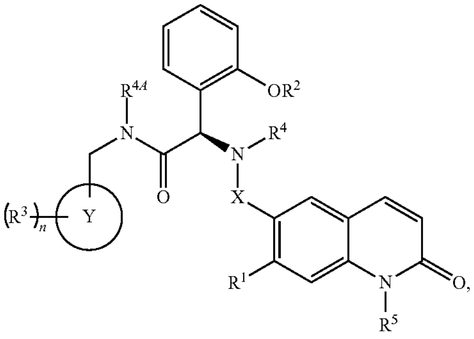

or a pharmaceutically acceptable salt, solvate, hydrate, polymorph, co-crystal, tautomer, stereoisomer, isotopically labeled derivative, or prodrug thereof, wherein X is $—SO_2—$, —SO—, or —C(═O)—;

Ring Y is a 5-membered heterocyclyl or 5-membered heteroaryl with 1-2 heteroatoms selected from the group consisting of N and S;

$R^1$ is halogen, optionally substituted alkyl, or —CN;

$R^2$ is hydrogen, optionally substituted acyl, optionally substituted alkyl, or an oxygen protecting group;

$R^3$ is halogen, —CN, —SCN, $—NO_2$, $—N_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, $—OR^a$, $—N(R^b)_2$, or $—SR^a$;

each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl;

$R^4$ is hydrogen, optionally substituted alkyl, or a nitrogen protecting group;

$R^6$ is hydrogen, optionally substituted alkyl, or a nitrogen protecting group;

$R^5$ is hydrogen, optionally substituted alkyl, or a nitrogen protecting group; and n is 0, 1, 2, 3, 4, or 5.

Formula (I') includes substituent $R^{1A}$. In certain embodiments, $R^{1A}$ is hydrogen, halogen, optionally substituted alkyl, or —CN. In certain embodiments, $R^{1A}$ is hydrogen. In certain embodiments, $R^{1A}$ is halogen (e.g., F, Cl, Br, or I). In certain embodiments, $R^{1A}$ is Cl or F. In certain embodiments, $R^{1A}$ is Cl. In certain embodiments, $R^{1A}$ is F. In certain embodiments, $R^{1A}$ is optionally substituted alkyl (e.g., substituted or unsubstituted $C_{1-6}$ alkyl). In certain embodiments, $R^{1A}$ is optionally substituted $C_{1-6}$ alkyl. In certain embodiments, $R^{1A}$ is substituted or unsubstituted methyl. In certain embodiments, $R^{1A}$ is unsubstituted methyl. In certain embodiments, $R^{1A}$ is substituted methyl. In certain embodiments, $R^{1A}$ is $—CF_3$. In certain embodiments, $R^{1A}$ is substituted or unsubstituted ethyl. In certain embodiments, $R^{1A}$ is unsubstituted ethyl. In certain embodiments, $R^{1A}$ is substituted ethyl. In certain embodiments, $R^{1A}$ is substituted or unsubstituted propyl. In certain embodiments, $R^{1A}$ is unsubstituted propyl. In certain embodiments, $R^{1A}$ is substituted propyl. In certain embodiments, $R^{1A}$ is substituted or unsubstituted butyl. In certain embodiments, $R^{1A}$ is unsubstituted butyl. In certain embodiments, $R^{1A}$ is substituted butyl. In certain embodiments, $R^{1A}$ is —CN. In certain embodiments, in Formula (I'), $R^{1A}$ is halogen, optionally substituted alkyl, or —CN. In certain embodiments, in Formula (I'), $R^{1A}$ is hydrogen, halogen, unsubstituted $C_{1-6}$ alkyl, $C_{1-6}$ alkyl substituted with halogen, or —CN. In certain embodiments, in Formula (I'), $R^{1A}$ is halogen, unsubstituted $C_{1-6}$ alkyl, $C_{1-6}$ alkyl substituted with halogen, or —CN. In certain embodiments, in Formula (I'), $R^{1A}$ is not hydrogen. In certain embodiments, in Formula (I'), $R^{1A}$ is halogen, or optionally substituted $C_{1-6}$ alkyl. In certain embodiments, $R^{1A}$ is $R^1$.

Formulae (I) and (I-A) include substituent $R^1$. In certain embodiments, $R^1$ is halogen, optionally substituted alkyl, or —CN. In certain embodiments, $R^1$ is halogen (e.g., F, Cl, Br, or I). In certain embodiments, $R^1$ is Cl or F. In certain embodiments, $R^1$ is Cl. In certain embodiments, $R^1$ is F. In certain embodiments, $R^1$ is optionally substituted alkyl (e.g., substituted or unsubstituted $C_{1-6}$ alkyl). In certain embodiments, $R^1$ is optionally substituted $C_{1-6}$ alkyl. In certain embodiments, $R^1$ is substituted or unsubstituted methyl. In certain embodiments, $R^1$ is methyl optionally substituted with halogen (e.g., F, Cl, Br, or I). In certain embodiments, $R^1$ is unsubstituted methyl. In certain embodiments, $R^1$ is substituted methyl. In certain embodiments, $R^1$ is methyl substituted with halogen, wherein the halogen is F, Cl, Br, or I. In certain embodiments, $R^1$ is $—CF_3$. In certain embodiments, $R^1$ is substituted or unsubstituted ethyl. In certain embodiments, $R^1$ is unsubstituted ethyl. In certain embodiments, $R^1$ is substituted ethyl. In certain embodiments, $R^1$ is substituted or unsubstituted propyl. In certain embodiments, $R^1$ is unsubstituted propyl. In certain embodiments, $R^1$ is substituted propyl. In certain embodiments, $R^1$ is substituted or unsubstituted butyl. In certain embodiments, $R^1$ is unsubstituted butyl. In certain embodiments, $R^1$ is substituted butyl. In certain embodiments, $R^1$ is —CN.

Formula (I') includes substituent $R^2$. In certain embodiments, $R^2$ is hydrogen, optionally substituted acyl, optionally substituted alkyl, or an oxygen protecting group. In certain embodiments, $R^2$ is hydrogen. In certain embodiments, $R^2$ is substituted or unsubstituted acyl (e.g., —C(═O)Me). In certain embodiments, $R^2$ is optionally substituted alkyl (e.g., substituted or unsubstituted $C_{1-6}$ alkyl). In certain embodiments, $R^2$ is optionally substituted $C_{1-6}$ alkyl. In certain embodiments, $R^2$ is hydrogen. In certain embodiments, $R^2$ is unsubstituted methyl. In certain embodiments, $R^2$ is of the formula:

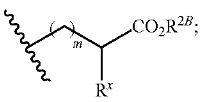

wherein: m is 1, 2, 3, or 4; $R^X$ is hydrogen, optionally substituted $C_{1-6}$ alkyl, or optionally substituted $C_{3-10}$ carbocyclyl; and $R^{2B}$ is hydrogen or optionally substituted $C_{1-6}$ alkyl. In certain embodiments, $R^2$ is of the formula:

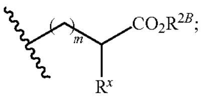

wherein: m is 1, 2, 3, or 4; $R^X$ is optionally substituted $C_{1-6}$ alkyl or optionally substituted $C_{3-10}$ carbocyclyl; and $R^{2B}$ is hydrogen or optionally substituted $C_{1-6}$ alkyl. In certain embodiments, $R^X$ is hydrogen. In certain embodiments, $R^X$ is optionally substituted $C_{1-6}$ alkyl, or optionally substituted $C_{3-10}$ carbocyclyl In certain embodiments, $R^X$ is optionally substituted $C_{1-6}$ alkyl (e.g., optionally substituted methyl, optionally substituted ethyl, optionally substituted n-propyl). In certain embodiments, $R^X$ is optionally substituted $C_{3-10}$ carbocyclyl (e.g., optionally substituted cyclopropyl, optionally substituted cyclopentyl). In certain embodiments, $R^2$ is of the formula:

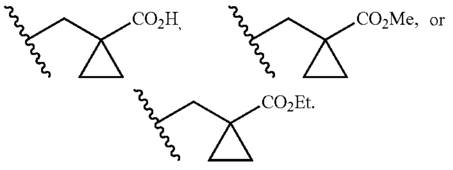

In certain embodiments, $R^2$ is of the formula: $—(CH_2)_mC(═O)OR^{2A}$, wherein: m is 1, 2, 3, 4, 5, or 6; and $R^{2A}$ is hydrogen or optionally substituted $C_{1-6}$ alkyl. In certain embodiments, $R^2$ is of the formula: $—(CH_2)_mC(═O)OR^{2A}$, wherein: m is 1, 2, 3, or 4; and $R^{2A}$ is hydrogen or optionally substituted $C_{1-6}$ alkyl. In certain embodiments, $R^2$ is optionally substituted $C_{1-6}$ alkyl or of the formula: $—(CH_2)_mC(═O)OR^{2A}$, wherein: m is 1, 2, 3, 4, 5, or 6; and $R^{2A}$ is hydrogen or optionally substituted $C_{1-6}$ alkyl. In certain embodiments, m is 1. In certain embodiments, m is 2. In certain embodiments, m is 3. In certain embodiments, m is 4. In certain embodiments, m is 5. In certain embodiments, m is 6. In certain embodiments, $R^{2A}$ is hydrogen. In certain embodiments, $R^{2A}$ is optionally substituted $C_{1-6}$ alkyl (e.g., optionally substituted methyl, optionally substituted ethyl, optionally substituted n-propyl, optionally substituted i-propyl, optionally substituted n-butyl). In certain embodiments, $R^{2B}$ is hydrogen. In certain embodiments, $R^{2B}$ is optionally substituted $C_{1-6}$ alkyl (e.g., optionally substituted methyl, optionally substituted ethyl, optionally substituted n-propyl, optionally substituted i-propyl, optionally substituted n-butyl). In certain embodiments, $R^{2B}$ is hydrogen, unsubstituted methyl, substituted ethyl, or optionally substituted $C_{3-6}$ alkyl, In certain embodiments, $R^2$ is of the formula: $—(CH_2)_mC(=O)OR^{2A}$, wherein: m is 1, 2, 3, or 4; and $R^{2A}$ is hydrogen or optionally substituted ethyl. In certain embodiments, $R^2$ is of the formula: $—(CH_2)_3C(=O)OH$, $—(CH_2)_3C(=O)OMe$, or $—(CH_2)_3C(=O)OEt$. In certain embodiments, $R^2$ is of the formula: $—(CH_2)_3C(=O)OH$, $—(CH_2)_3C(=O)OMe$, $—(CH_2)_3C(=O)OEt$, $—(CH_2)_4C(=O)OH$, or $—(CH_2)_4C(=O)OMe$. In certain embodiments, $R^2$ is of the formula: -Me, $—(CH_2)_3C(=O)OH$, $—(CH_2)_3C(=O)OEt$, $—(CH_2)_4C(=O)OH$, or $—(CH_2)_4C(=O)OMe$. In certain embodiments, $R^2$ is of the formula: $—(CH_2)C(=O)OH$, $—(CH_2)C(=O)OEt$, $—(CH_2)_2C(=O)OH$, $—(CH_2)_2C(=O)OEt$, $—(CH_2)_3C(=O)OH$, $—(CH_2)_3C(=O)OMe$, $—(CH_2)_3C(=O)OEt$, $—(CH_2)_4C(=O)OH$, $—(CH_2)_4C(=O)OMe$,

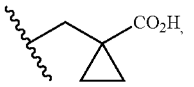
or
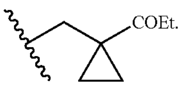

In certain embodiments, $R^2$ is of the formula: $—(CH_2)_3C(=O)OEt$. In certain embodiments, $R^2$ is an oxygen protecting group. In certain embodiments, $R^2$ is of the formula:

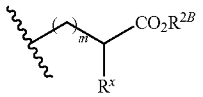

or of the formula: $—(CH_2)_mC(=O)OR^{2B}$; wherein: m is 1, 2, 3, or 4; $R^X$ is hydrogen, optionally substituted $C_{1-6}$ alkyl, or optionally substituted $C_{3-10}$ carbocyclyl; and $R^{2B}$ is hydrogen or optionally substituted $C_{1-6}$ alkyl. In certain embodiments, $R^2$ is of the formula:

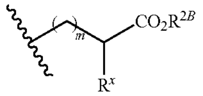

or of the formula: $—(CH_2)_mC(=O)OR^{2A}$; wherein: m is 1, 2, 3, or 4; $R^X$ is hydrogen, optionally substituted $C_{1-6}$ alkyl, or optionally substituted $C_{3-10}$ carbocyclyl; and $R^{2A}$ is hydrogen, unsubstituted methyl, substituted ethyl, or optionally substituted $C_{3-6}$ alkyl, and $R^{2B}$ is hydrogen or optionally substituted $C_{1-6}$ alkyl.

Formula (I') includes Ring Y. In certain embodiments, Ring Y is 5- to 6-membered heterocyclyl or 5- to 6-membered heteroaryl with 1-2 heteroatoms selected from the group consisting of N, O, and S. In certain embodiments, Ring Y is 5-membered heterocyclyl or 5-membered heteroaryl with 1-2 heteroatoms selected from the group consisting of N and S. In certain embodiments, Ring Y is 5-membered heterocyclyl with 1-2 heteroatoms selected from the group consisting of N and S. In certain embodiments, Ring Y is 5-membered heteroaryl with 1-2 heteroatoms selected from the group consisting of N and S. In certain embodiments, Ring Y is 5-membered heteroaryl with 1-2 heteroatoms selected from the group consisting of N, O, and S. In certain embodiments, Ring Y is furanyl. In certain embodiments, Ring Y is thiophenyl. In certain embodiments, Ring Y is isothiazolyl. In certain embodiments, Ring Y is thiazolyl.

Formula (I') includes zero or more instances of substituent $R^3$ on Ring Y. In certain embodiments, n is 0. In certain embodiments, n is 1. In certain embodiments, n is 2. In certain embodiments, n is 3. In certain embodiments, n is 4. In certain embodiments, at least one instance of $R^3$ is halogen, —CN, —SCN, $—NO_2$, $—N_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, $—OR^a$, $—N(R^b)_2$, or $—SR^a$, where $R^a$ and $R^b$ are as described herein. In certain embodiments, at least one instance of $R^3$ is halogen (e.g., F, Cl, Br, or I). In certain embodiments, at least one instance of $R^3$ is —CN. In certain embodiments, at least one instance of $R^3$ is —SCN. In certain embodiments, at least one instance of $R^3$ is $—NO_2$. In certain embodiments, at least one instance of $R^3$ is $—N_3$. In certain embodiments, at least one instance of $R^3$ is substituted or unsubstituted alkyl (e.g., substituted or unsubstituted $C_{1-6}$ alkyl). In certain embodiments, at least one instance of $R^3$ is substituted or unsubstituted methyl. In certain embodiments, at least one instance of $R^3$ is substituted or unsubstituted ethyl. In certain embodiments, at least one instance of $R^3$ is substituted or unsubstituted propyl. In certain embodiments, at least one instance of $R^3$ is optionally substituted acyl (e.g., —C(=O)Me). In certain embodiments, at least one instance of $R^3$ is optionally substituted alkenyl (e.g., substituted or unsubstituted $C_{2-6}$ alkenyl). In certain embodiments, at least one instance of $R^3$ is optionally substituted alkynyl (e.g., substituted or unsubstituted $C_{2-6}$ alkynyl). In certain embodiments, at least one instance of $R^3$ is optionally substituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^3$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^3$ is optionally substituted aryl (e.g., substituted or unsubstituted, 6- to 10-membered aryl). In certain embodiments, at least one instance of $R^3$ is optionally substituted benzyl. In certain embodiments, at least one instance of $R^3$ is optionally substituted phenyl. In certain embodiments, at least one instance of $R^3$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^3$ is $—OR^a$ (e.g., —OH or —OMe). In certain embodiments, at least one instance of $R^3$ is —OH. In certain embodiments, at least one instance of $R^3$ is —OMe. In certain embodiments, at least one instance of $R^3$ is $—N(R^b)_2$ (e.g., $—NMe_2$). In certain embodiments, at least one instance of $R^3$ is $—NMe_2$. In certain embodiments, at least one instance of $R^3$ is $—SR^a$ (e.g., —SH, —SMe). In certain embodiments, each instance of Ra is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom. In certain embodiments, each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl. In certain embodiments, at least one instance of $R^a$ is optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom. In certain embodiments, at least one instance of $R^b$ is hydrogen. In certain embodiments, at least one instance of $R^b$ is optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl.

In certain embodiments, the moiety

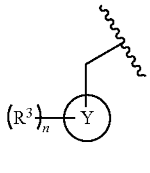

is of the formula:

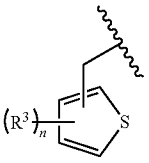

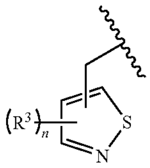

, or

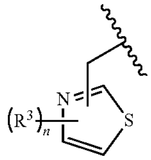

.

In certain embodiments, the moiety

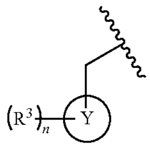

is of the formula:

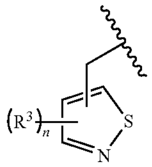

.

In certain embodiments, the moiety

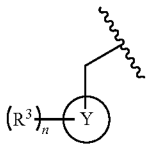

is of the formula:

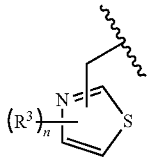

.

In certain embodiments, the moiety

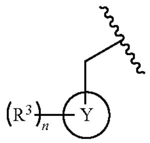

is of the formula:

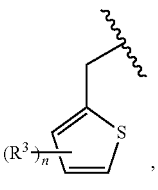

,

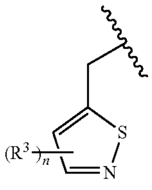

,

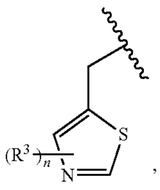

, or

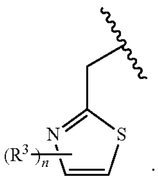

.

In certain embodiments, the moiety

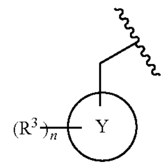

is of the formula:

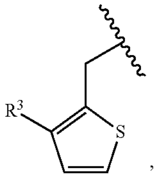 , 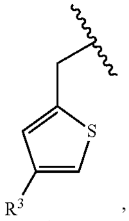 , 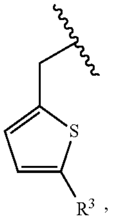 ,

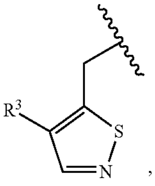 , 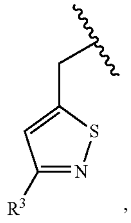 , 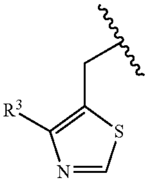 ,

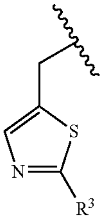 , 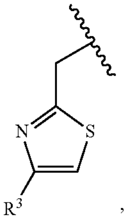 , or 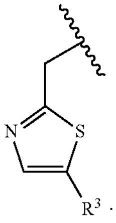 .

In certain embodiments, $R^{4A}$ is $R^6$.

Formula (I') includes substituent $R^6$. In certain embodiments, $R^6$ is hydrogen, optionally substituted alkyl, or a nitrogen protecting group. In certain embodiments, $R^6$ is hydrogen. In certain embodiments, $R^6$ is optionally substituted alkyl (e.g., substituted or unsubstituted $C_{1-6}$ alkyl). In certain embodiments, $R^6$ is optionally substituted $C_{1-6}$ alkyl. In certain embodiments, $R^6$ is optionally substituted ethyl. In certain embodiments, $R^6$ is unsubstituted ethyl. In certain embodiments, $R^6$ is optionally substituted methyl. In certain embodiments, $R^6$ is unsubstituted methyl. In certain embodiments, $R^6$ is unsubstituted methyl, unsubstituted ethyl, unsubstituted propyl, or unsubstituted butyl. In certain embodiments, $R^6$ is methyl optionally substituted with an optionally substituted heterocyclyl or optionally substituted heteroaryl. In certain embodiments, $R^6$ is methyl optionally substituted with an optionally substituted 3- to 10-membered heterocyclyl having ring carbon atoms and 1 to 4 ring heteroatoms, wherein each heteroatom is independently selected from the group consisting of nitrogen, oxygen, sulfur; or $R^6$ is methyl optionally substituted with optionally substituted 5-10 membered heteroaryl with ring carbon atoms and 1-4 ring heteroatoms selected from the group consisting of nitrogen, oxygen and sulfur. In certain embodiments, $R^6$ is methyl substituted with optionally substituted 5-10 membered heteroaryl with ring carbon atoms and 1-4 ring heteroatoms selected from the group consisting of nitrogen, oxygen and sulfur. In certain embodiments, $R^6$ is methyl substituted with optionally substituted furanyl, optionally substituted thiophenyl, optionally substituted pyrrolyl, optionally substituted thioazole, or optionally substituted imidazole. In certain embodiments, $R^6$ is methyl substituted with unsubstituted furanyl, unsubstituted thiophenyl, or unsubstituted pyrrolyl. In certain embodiments, $R^6$ is methyl substituted with unsubstituted furanyl or unsubstituted thiophenyl. In certain embodiments, $R^6$ is unsubstituted methyl. In certain embodiments, $R^6$ is of the formula: $-(CH_2)_xC(=O)OR^{4b}$, wherein: x is 1, 2, 3, 4, 5, or 6; and $R^{4b}$ is hydrogen or optionally substituted $C_{1-6}$ alkyl. In certain embodiments, x is 1. In certain embodiments, x is 2. In certain embodiments, x is 3. In certain embodiments, x is 4. In certain embodiments, x is 5. In certain embodiments, x is 6. In certain embodiments, $R^{4b}$ is hydrogen. In certain embodiments, $R^{4b}$ is optionally substituted $C_{1-6}$ alkyl. In certain embodiments, $R^{4b}$ is optionally substituted $C_{2-4}$ alkyl. In certain embodiments, $R^{4b}$ is optionally substituted methyl. In certain embodiments, $R^{4b}$ is optionally substituted ethyl. In certain embodiments, $R^{4b}$ is not hydrogen or unsubstituted ethyl. In certain embodiments, $R^6$ is of the formula: $-(CH_2)_xC(=O)OR^{4b}$, wherein: x is 1, 2, 3, 4, 5, or 6; and $R^{4b}$ is hydrogen. In certain embodiments, $R^6$ is of the formula: $-(CH_2)_xC(=O)OR^{4b}$, wherein: x is 1, 2, 3, 4, 5, or 6; and $R^{4b}$ is optionally substituted $C_{2-4}$ alkyl. In certain embodiments, $R^6$ is of the formula: $-(CH_2)_xC(=O)OR^{4b}$, wherein: x is 1, 2, 3, 4, 5, or 6; and $R^{4b}$ is optionally substituted $C_{2-6}$ alkyl. In certain embodiments, $R^6$ is optionally substituted $C_{1-6}$ alkyl or of the formula: $-(CH_2)_xC(=O)OR^{4b}$, wherein: x is 1, 2, 3, 4, 5, or 6; and $R^{4b}$ is optionally substituted $C_{2-6}$ alkyl. In certain embodiments, $R^6$ is optionally substituted $C_{1-6}$ alkyl or of the formula: $-(CH_2)_xC(=O)OR^{4b}$, wherein: x is 1, 2, 3, 4, 5, or 6; and $R^{4b}$ is methyl, substituted ethyl, or optionally substituted $C_{3-6}$ alkyl. In certain embodiments, $R^6$ is optionally substituted $C_{1-6}$ alkyl or of the formula: $-(CH_2)C(=O)OH$ or $-(CH_2)C(=O)OMe$. In certain embodiments, $R^6$ is of the formula: $-(CH_2)C(=O)OH$, $-(CH_2)C(=O)OMe$, or $-(CH_2)C(=O)OEt$. In certain embodiments, $R^6$ is of the formula: $-(CH_2)C(=O)OH$. In certain embodiments, $R^6$ is of the formula: $-(CH_2)C(=O)OEt$. In certain embodiments, $R^6$ is of the formula: $-(CH_2)C(=O)OH$ or $-(CH_2)C(=O)OEt$. In certain embodiments, $R^6$ is of the formula: $-(CH_2)_xC(=O)N(R^4)_2$, wherein: x is 1, 2, 3, 4, 5, or 6; and each instance of $R^{4c}$ is independently hydrogen or optionally substituted $C_{1-6}$ alkyl. In certain embodiments, at least one instance of $R^{4c}$ is hydrogen. In certain embodiments, at least one instance of $R^{4c}$ is optionally substituted $C_{1-6}$ alkyl. In certain embodiments, at least one instance of $R^{4c}$ is hydrogen and the other instance of $R^{4c}$ is optionally substituted $C_{1-6}$ alkyl. In certain embodiments, at least one instance of $R^{4c}$ is optionally substituted $C_{2-4}$ alkyl. In certain embodiments, at least one instance of $R^{4c}$ is optionally substituted methyl. In certain embodiments, at least one instance of $R^{4c}$ is unsubstituted methyl. In certain embodiments, at least one instance of $R^{4c}$ is substituted methyl. In certain embodiments, at least one instance of $R^{4c}$ is $-CH_2OMe$. In certain embodiments, at least one instance of $R^{4c}$ is methyl optionally substituted with $-OR^{4'}$, wherein $R^{4'}$ is hydrogen or unsubstituted $C_{1-6}$ alkyl. In certain embodiments, at least one instance of $R^{4c}$ is optionally substituted ethyl. In certain embodiments, at least one instance of $R^{4c}$ is optionally substituted n-propyl. In certain embodiments, at least one instance of $R^{4c}$ is unsubstituted n-propyl. In certain embodiments, at least one instance of $R^{4c}$ is optionally substituted n-butyl. In certain embodiments, at least one instance of $R^{4c}$ is optionally substituted n-pentyl. In certain embodiments, $R^6$ is of the formula: $-(CH_2)C(=O)NH(\text{n-propyl})$. In certain embodiments, $R^6$ is of the formula: —$(CH_2)C(=O)NH(CH_2OMe)$. In certain embodiments, $R^6$ is of the formula: —$(CH_2)C(=O)NH(Me)$, —$(CH_2)C(=O)NH(Et)$, —$(CH_2)C(=O)NH$(n-propyl), or —$(CH_2)C(=O)NH(CH_2)_2OMe$. In certain embodiments, $R^6$ is of the formula: —$(CH_2)C(=O)NH$(n-propyl) or —$(CH_2)C(=O)NH(CH_2)_2OMe$. In certain embodiments, $R^6$ is of the formula: —$(CH_2)C(=O)NH$(n-propyl). In certain embodiments, $R^6$ is of the formula: —$(CH_2)C(=O)NH(CH_2)_2OMe$. In certain embodiments, $R^6$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, $R^6$ is unsubstituted $C_{1-3}$ alkyl, of the formula: —$(CH_2)_xC(=O)OR^{4b}$, wherein: x is 1, 2, 3, 4, 5, or 6; and $R^{4b}$ is hydrogen or optionally substituted $C_{1-6}$ alkyl; or of the formula: —$(CH_2)_xC(=O)N(R^{4c})_2$, wherein: x is 1, 2, 3, 4, 5, or 6; and each instance of $R^{4C}$ is independently hydrogen or optionally substituted $C_{1-6}$ alkyl.

Formula (I') includes substituent $R^7$. In certain embodiments, $R^7$ is hydrogen, halogen, optionally substituted alkyl, or —CN. In certain embodiments, $R^7$ is hydrogen. In certain embodiments, $R^7$ is halogen (e.g., F, Cl, Br, or I). In certain embodiments, $R^7$ is Cl or F. In certain embodiments, $R^7$ is Cl. In certain embodiments, $R^7$ is F. In certain embodiments, $R^{1A}$ is optionally substituted alkyl (e.g., substituted or unsubstituted $C_{1-6}$ alkyl). In certain embodiments, $R^7$ is optionally substituted $C_{1-6}$ alkyl. In certain embodiments, $R^7$ is substituted or unsubstituted methyl. In certain embodiments, $R^7$ is unsubstituted methyl. In certain embodiments, $R^7$ is substituted methyl. In certain embodiments, $R^7$ is —$CF_3$. In certain embodiments, $R^7$ is substituted or unsubstituted ethyl. In certain embodiments, $R^7$ is substituted or unsubstituted propyl. In certain embodiments, $R^7$ is —CN.

Formula (I') includes substituent $R^4$. In certain embodiments, $R^4$ is hydrogen, optionally substituted alkyl, or a nitrogen protecting group. In certain embodiments, $R^4$ is hydrogen. In certain embodiments, $R^4$ is optionally substituted alkyl (e.g., substituted or unsubstituted $C_{1-6}$ alkyl). In certain embodiments, $R^4$ is optionally substituted $C_{1-6}$ alkyl. In certain embodiments, $R^4$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

Formula (I') includes substituent X. In certain embodiments, X is —$SO_2$—, —SO—, or —C═O. In certain embodiments, X is —$SO_2$—. In certain embodiments, X is —SO—. In certain embodiments, X is —C(═O)—.

Formula (I') includes substituent $R^5$. In certain embodiments, $R^5$ is hydrogen, optionally substituted alkyl, or a nitrogen protecting group. In certain embodiments, $R^5$ is hydrogen. In certain embodiments, $R^5$ is optionally substituted alkyl (e.g., substituted or unsubstituted $C_{1-6}$ alkyl). In certain embodiments, $R^5$ is optionally substituted $C_{1-6}$ alkyl. In certain embodiments, $R^5$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In certain embodiments, the compound of Formula (I') is of the formula:

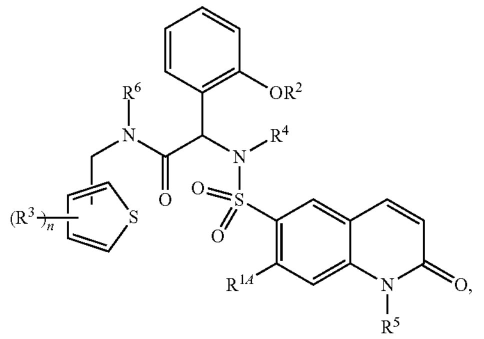

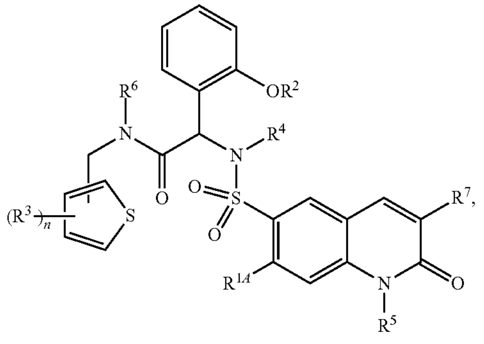

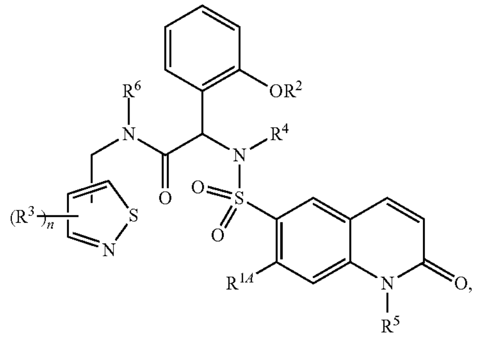

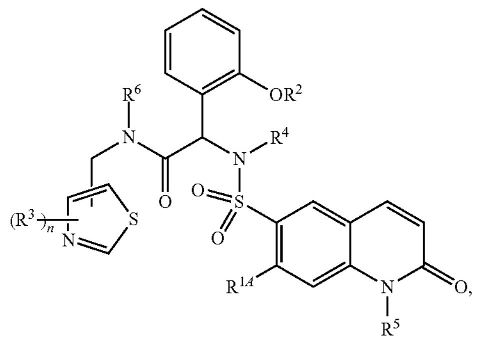

or a pharmaceutically acceptable salt, solvate, hydrate, polymorph, co-crystal, tautomer, stereoisomer, isotopically labeled derivative, or prodrug thereof.

In certain embodiments, the compound of Formula (I') is of the formula:
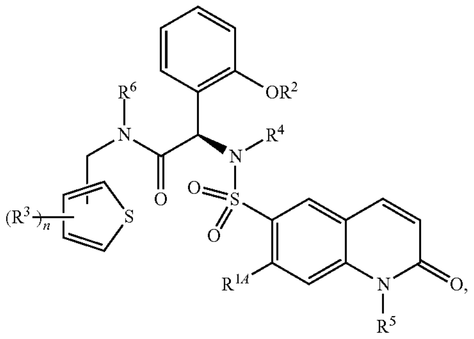
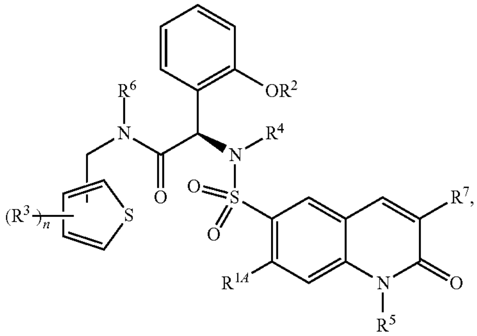
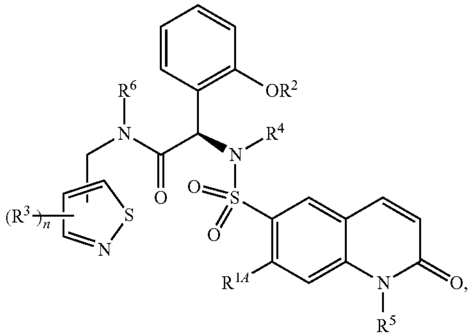
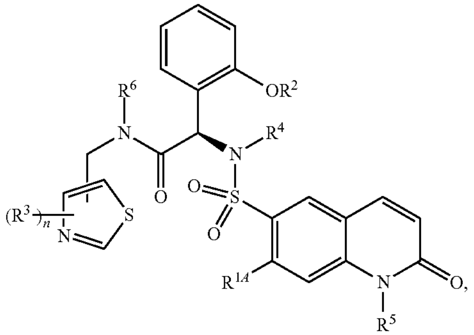
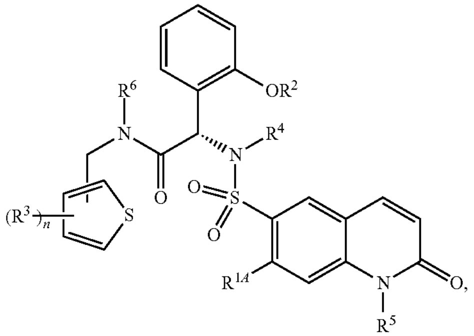
-continued
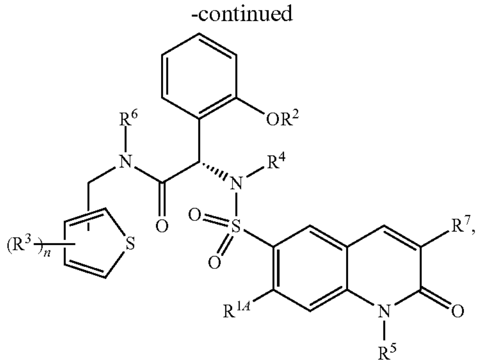
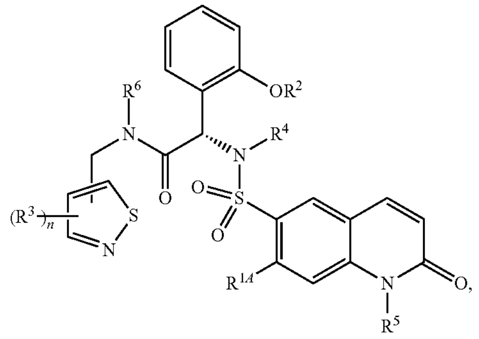
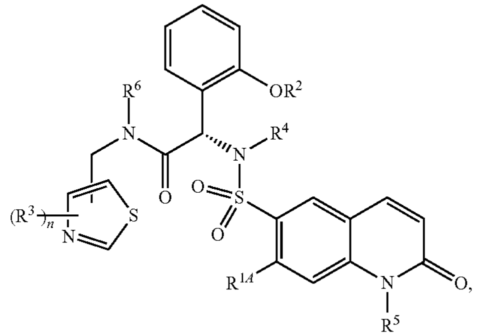
or a pharmaceutically acceptable salt, solvate, hydrate, polymorph, co-crystal, tautomer, stereoisomer, isotopically labeled derivative, or prodrug thereof.
In certain embodiments, the compound of Formula (I') is of the formula:
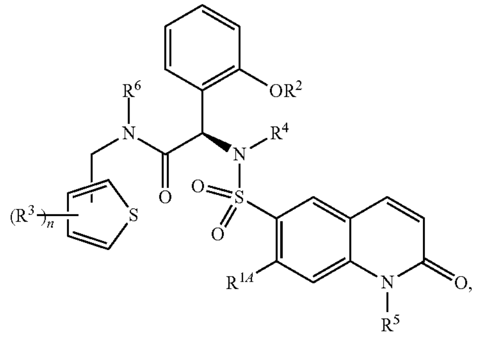

-continued

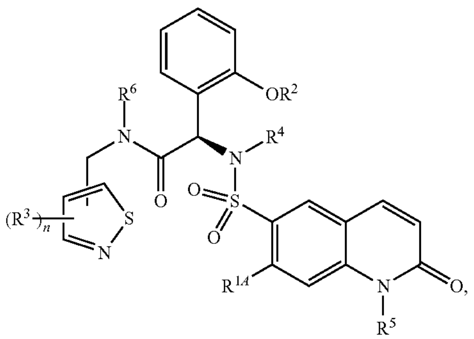

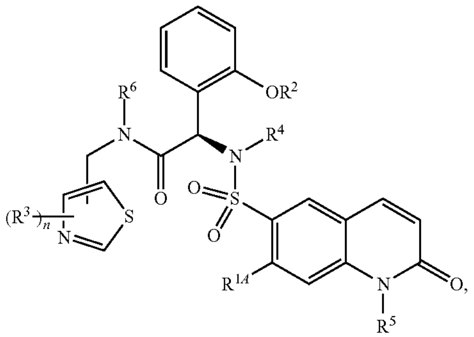

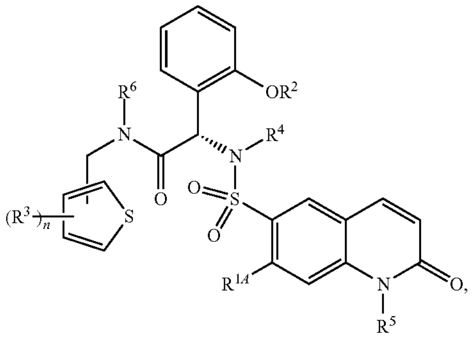

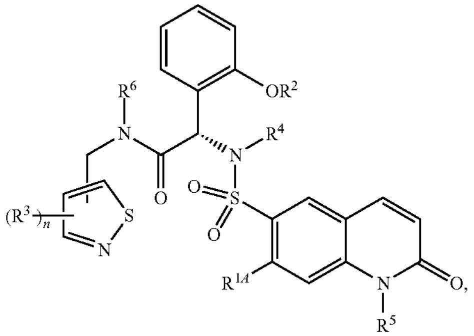

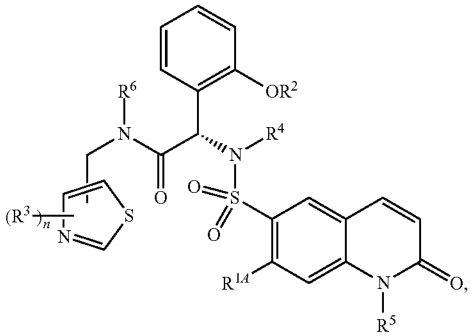

or a pharmaceutically acceptable salt, solvate, hydrate, polymorph, co-crystal, tautomer, stereoisomer, isotopically labeled derivative, or prodrug thereof.

In certain embodiments, the compound of Formula (I') is of the formula:

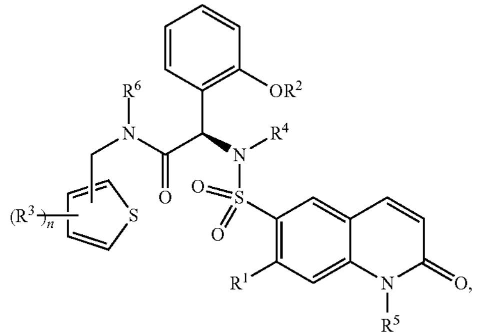

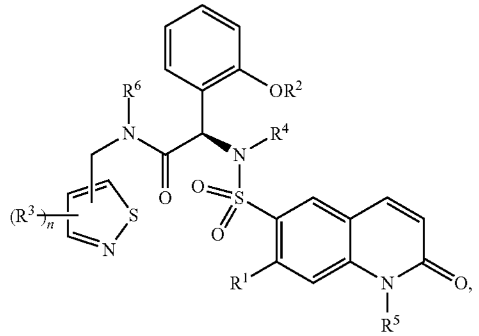

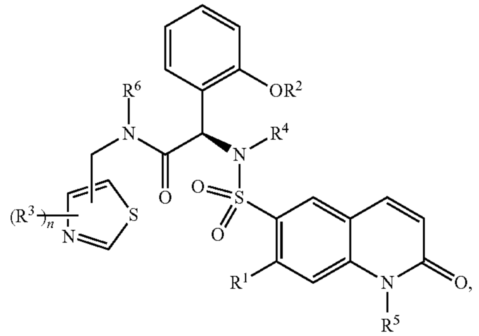

or a pharmaceutically acceptable salt, solvate, hydrate, polymorph, co-crystal, tautomer, stereoisomer, isotopically labeled derivative, or prodrug thereof.

In certain embodiments, the compound of Formula (I') is of the formula:

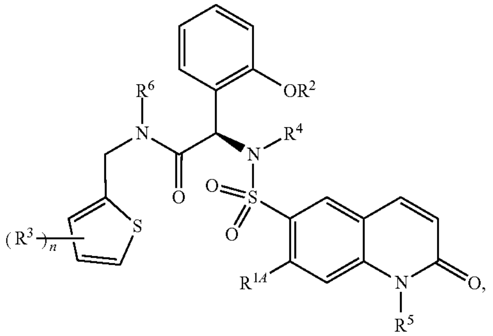

-continued
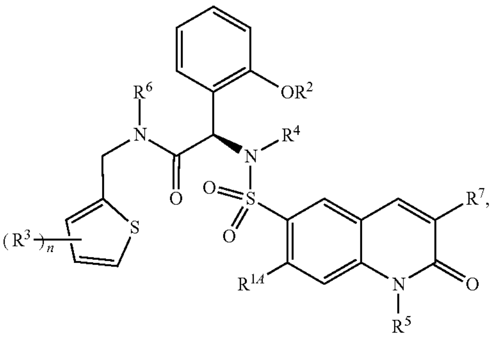
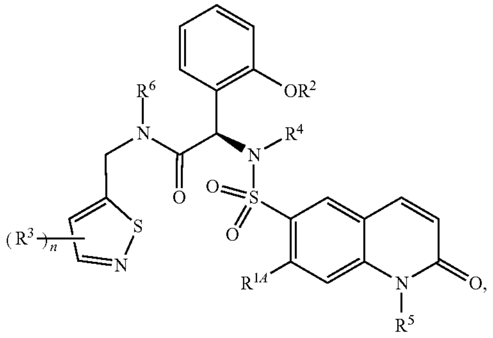
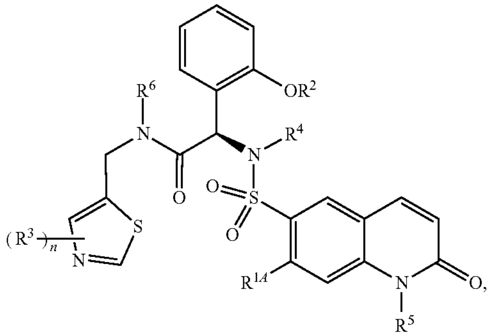
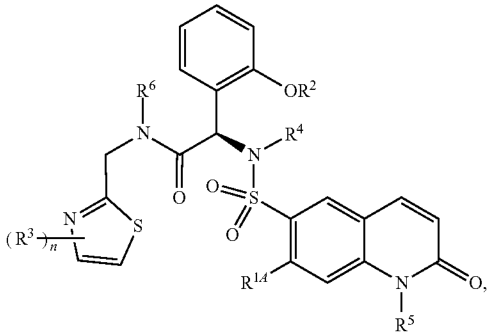
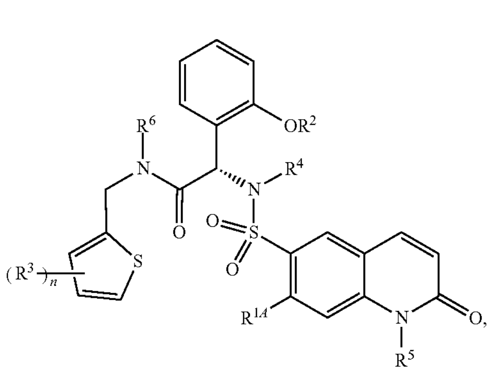
-continued
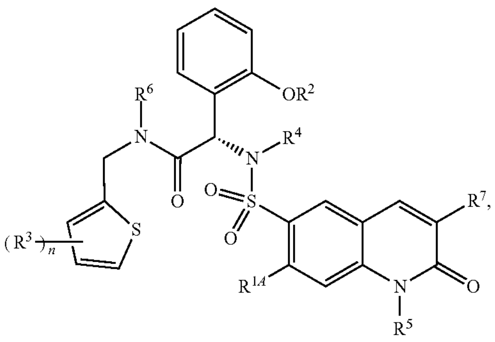
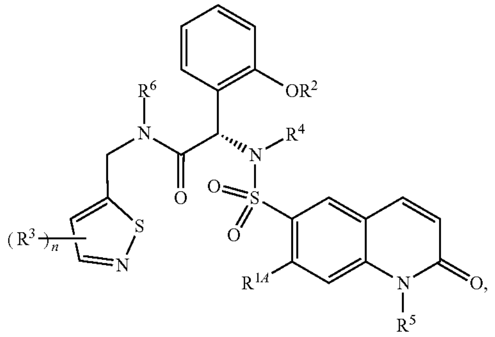
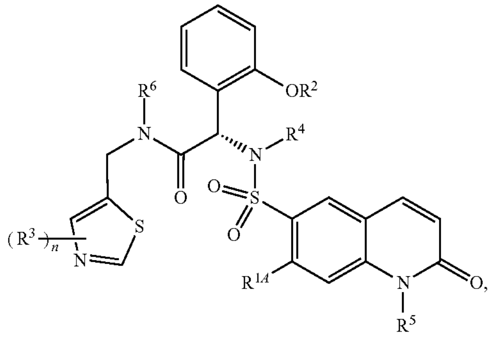
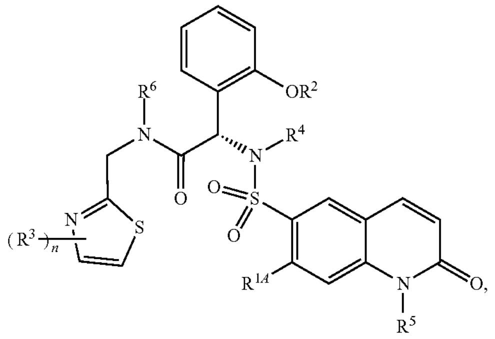
or a pharmaceutically acceptable salt, solvate, hydrate, polymorph, co-crystal, tautomer, stereoisomer, isotopically labeled derivative, or prodrug thereof.
In certain embodiments, the compound of Formula (I') is of the formula:

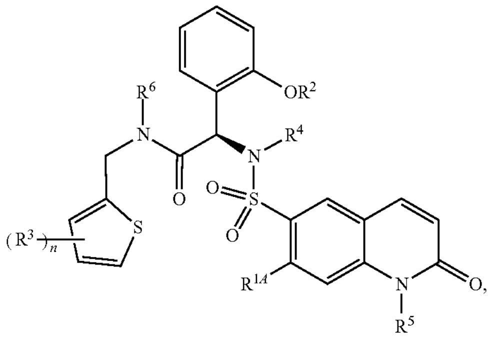
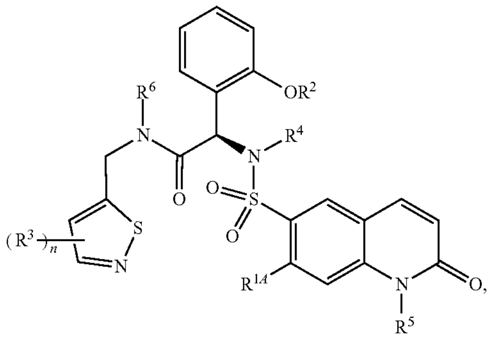
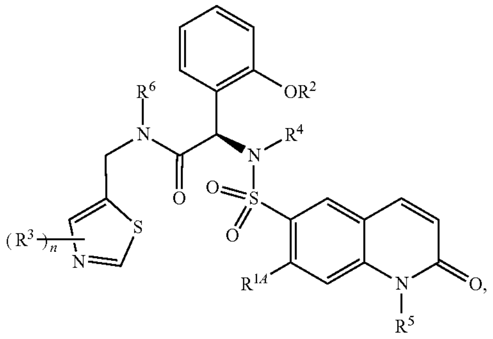
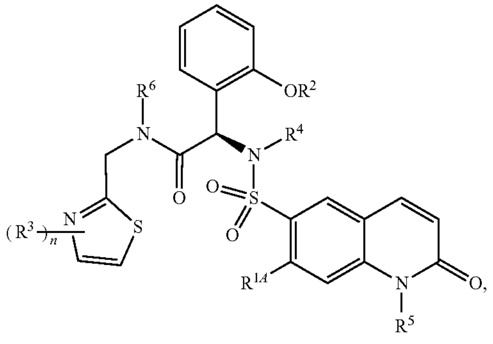
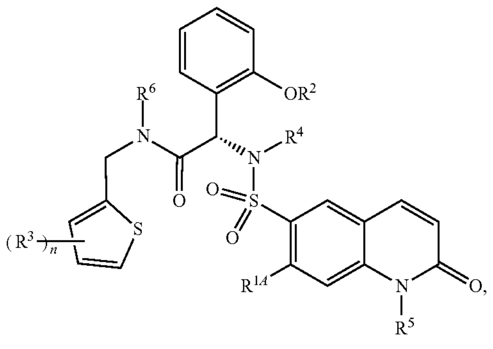
-continued
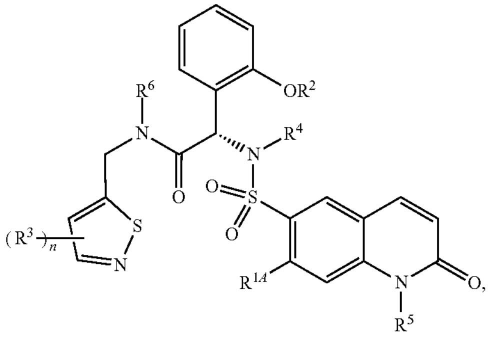
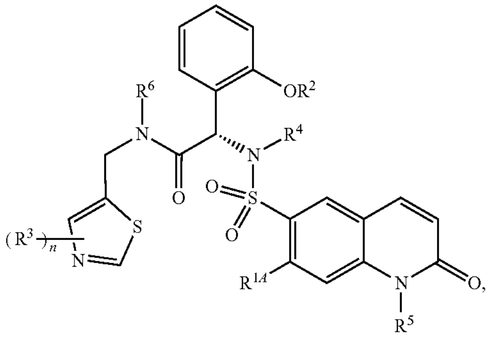
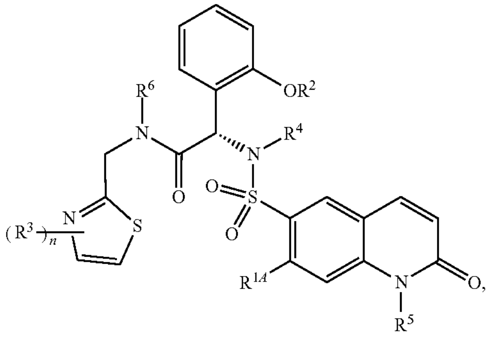
or a pharmaceutically acceptable salt, solvate, hydrate, polymorph, co-crystal, tautomer, stereoisomer, isotopically labeled derivative, or prodrug thereof.
In certain embodiments, the compound of Formula (I') is of the formula:
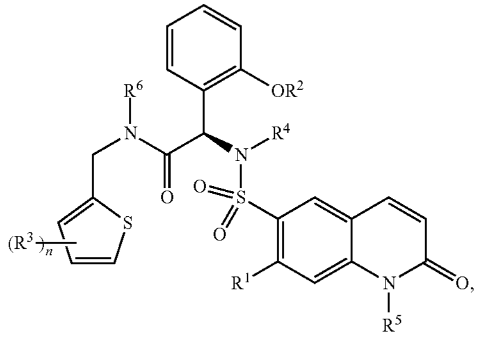

-continued
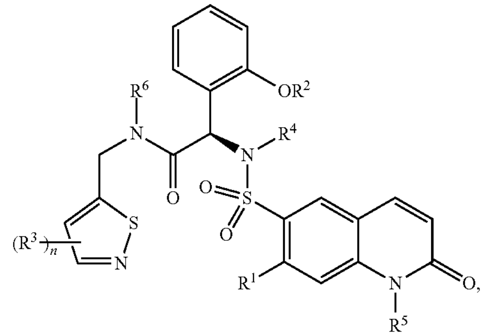
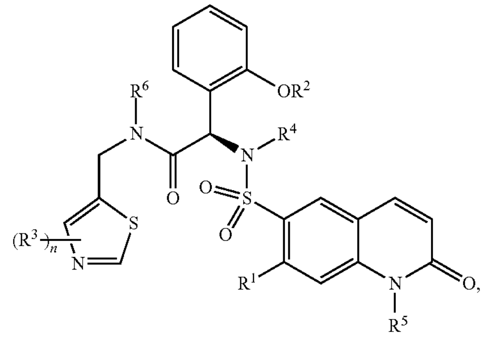
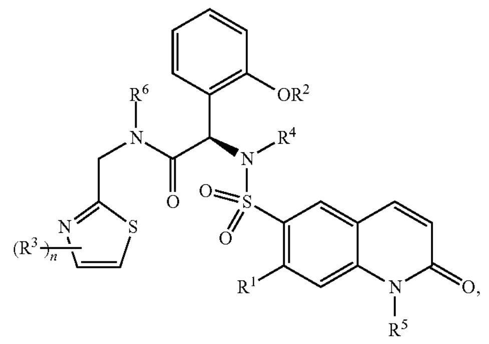
or a pharmaceutically acceptable salt, solvate, hydrate, polymorph, co-crystal, tautomer, stereoisomer, isotopically labeled derivative, or prodrug thereof.
In certain embodiments, the compound of Formula (I') is of the formula:
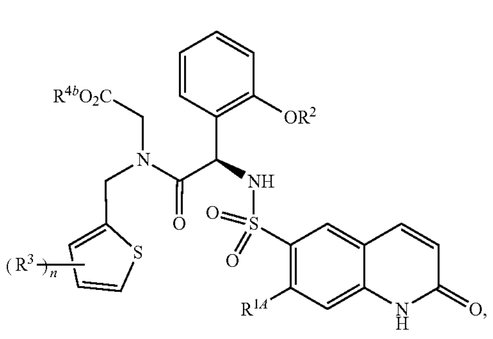
-continued
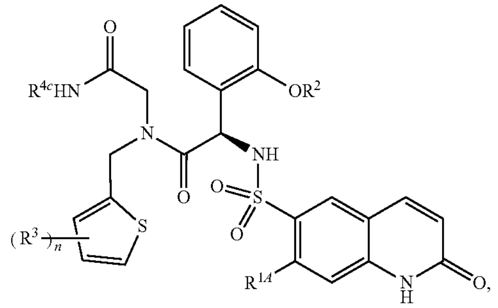
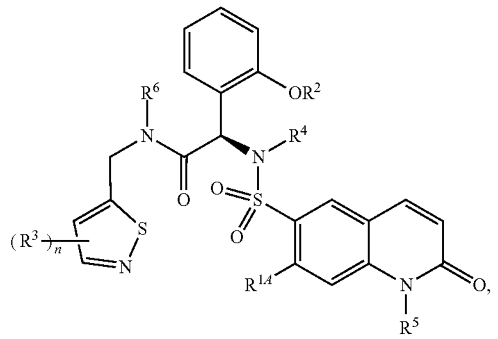
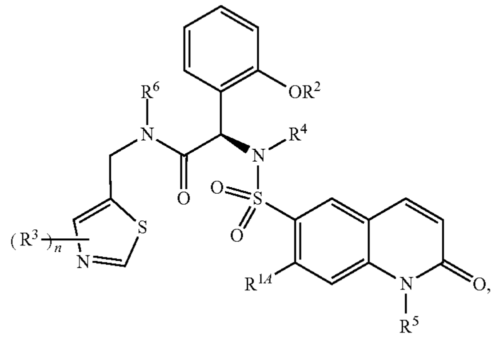
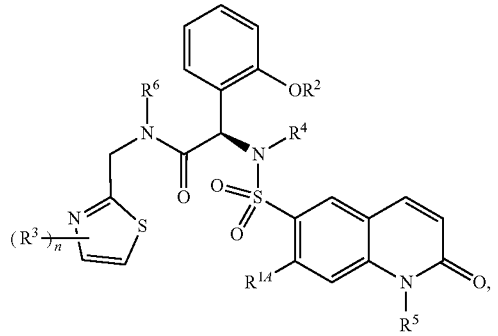
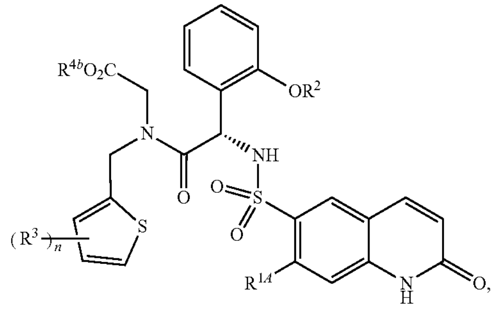

-continued
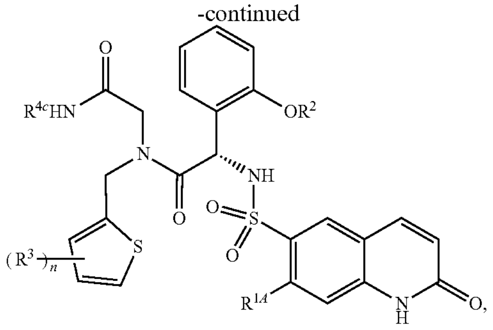
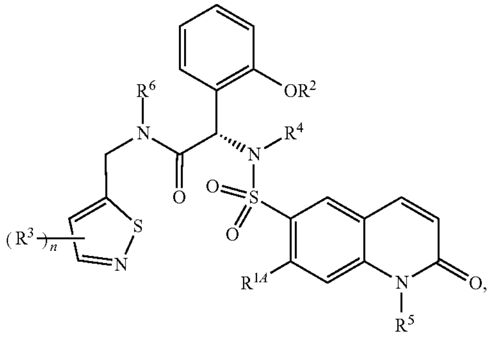
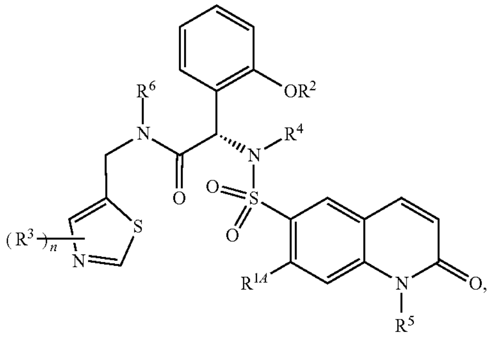
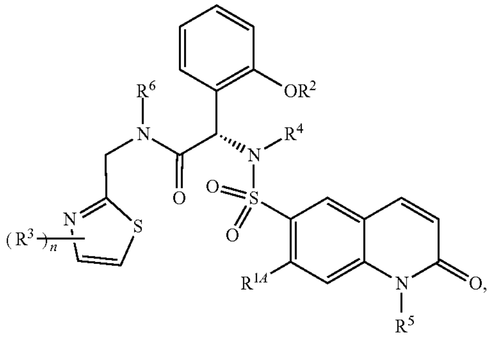
or a pharmaceutically acceptable salt, solvate, hydrate, polymorph, co-crystal, tautomer, stereoisomer, isotopically labeled derivative, or prodrug thereof.
In certain embodiments, the compound of Formula (I') is of the formula:
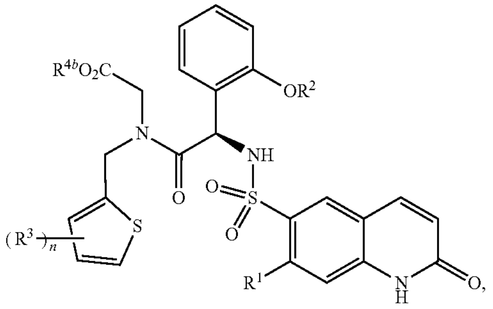
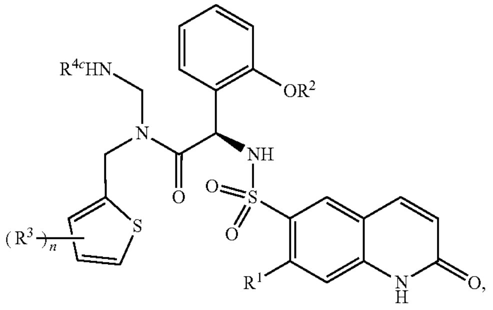
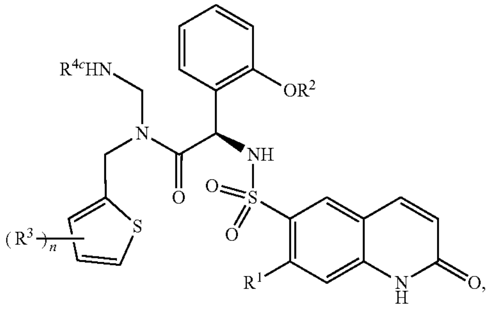
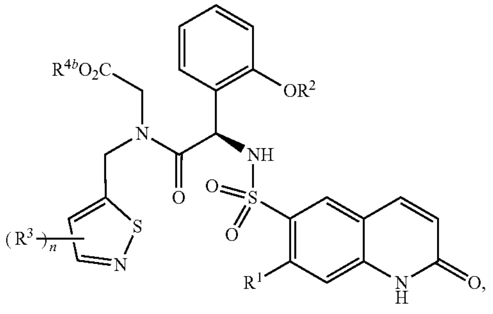
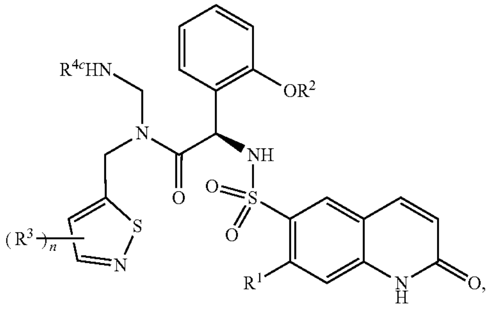

-continued
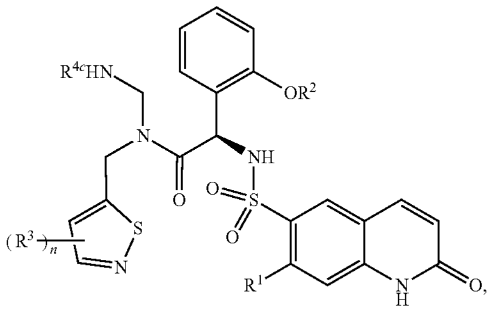
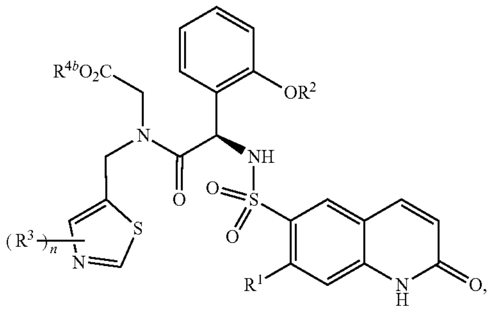
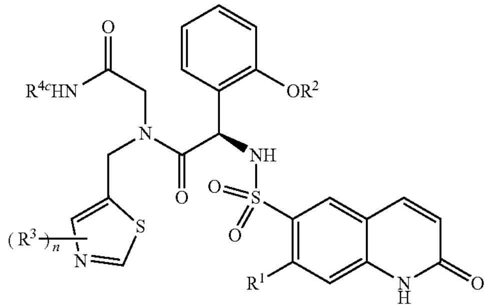
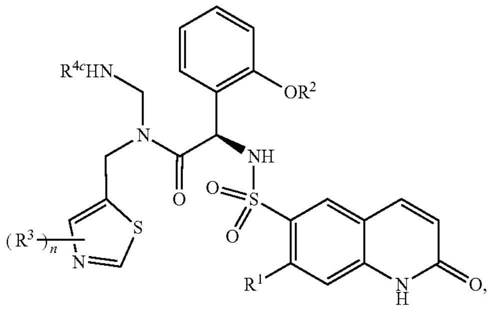
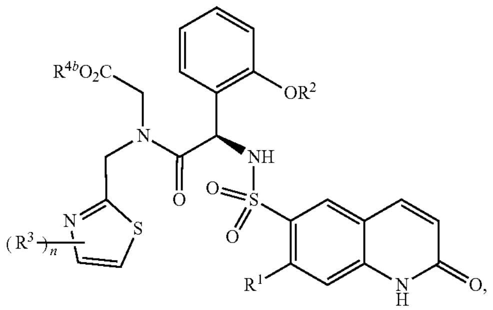
-continued
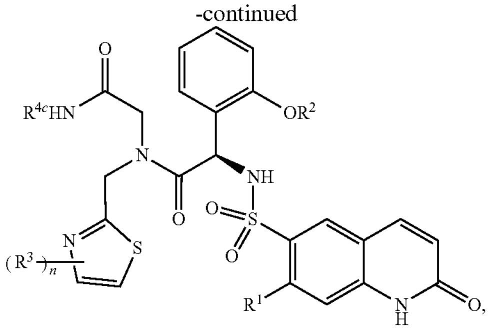
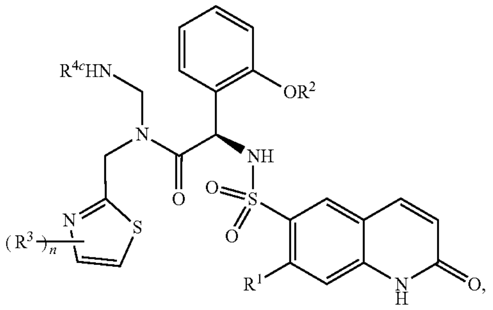
or a pharmaceutically acceptable salt, solvate, hydrate, polymorph, co-crystal, tautomer, stereoisomer, isotopically labeled derivative, or prodrug thereof.
In certain embodiments, the compound of Formula (I') is of the formula:
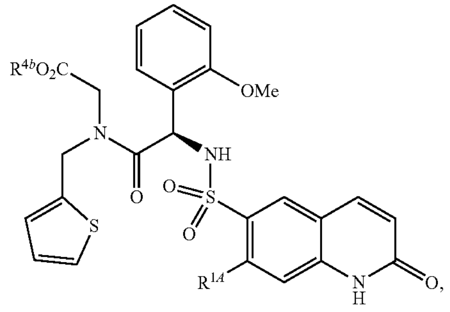
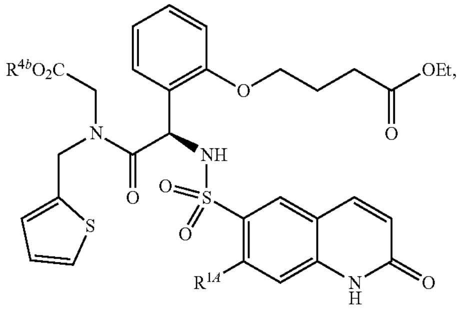

-continued
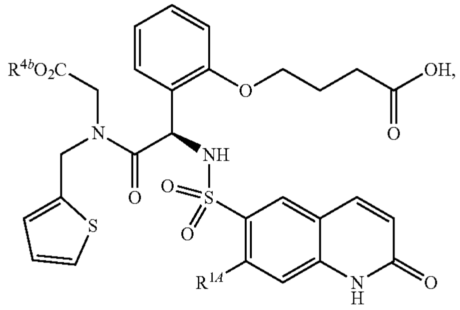
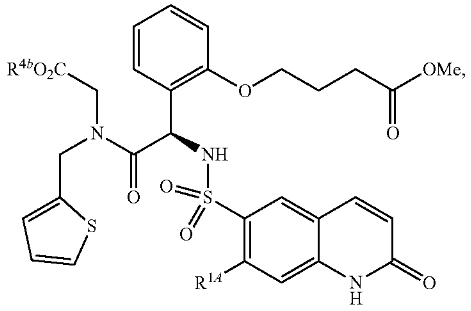
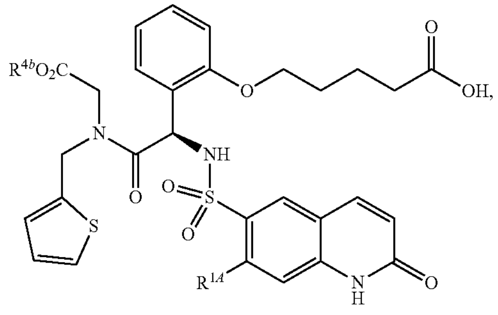
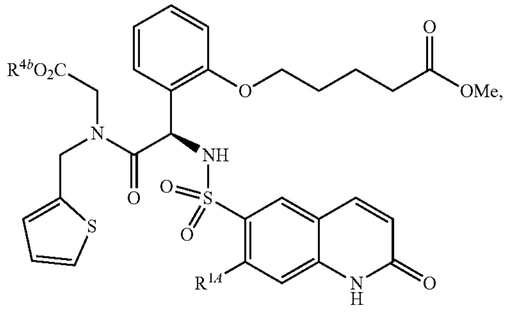
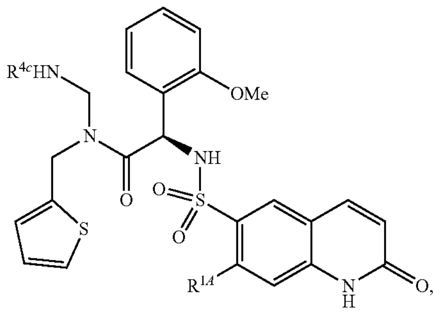
-continued
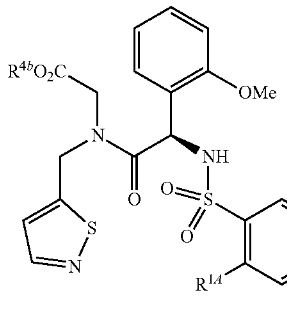
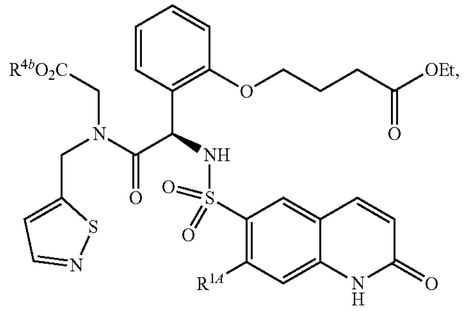
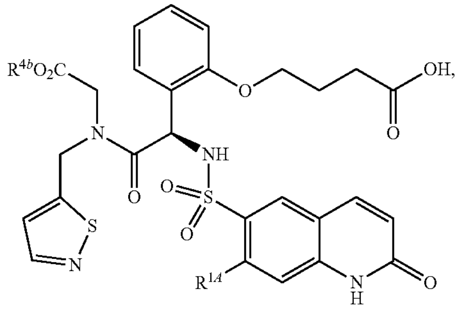
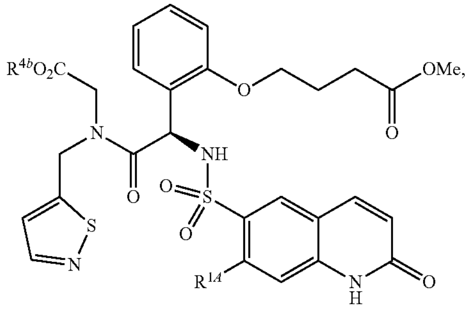
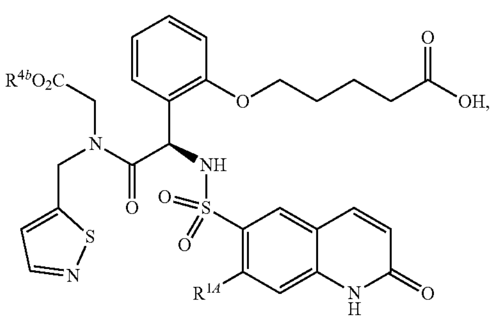

-continued
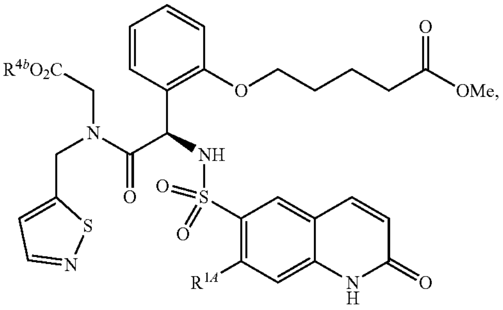
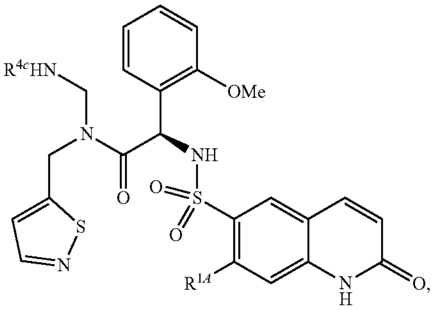
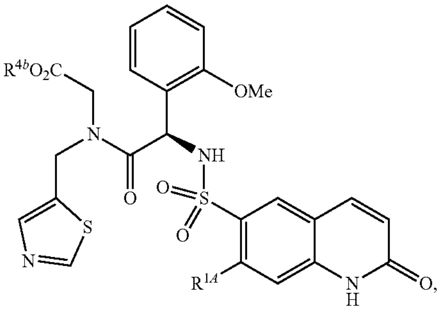
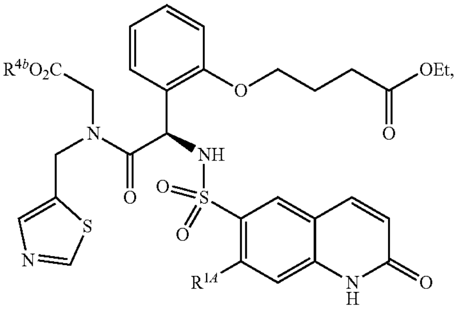
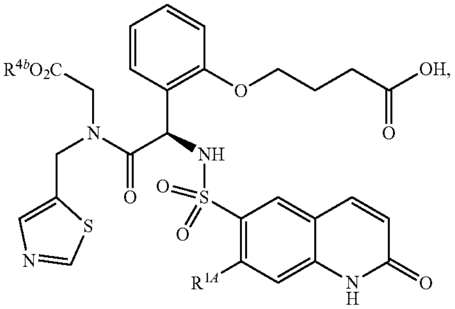
-continued
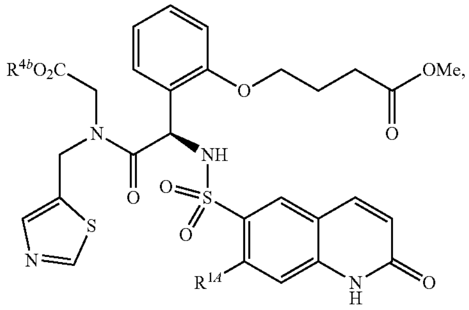
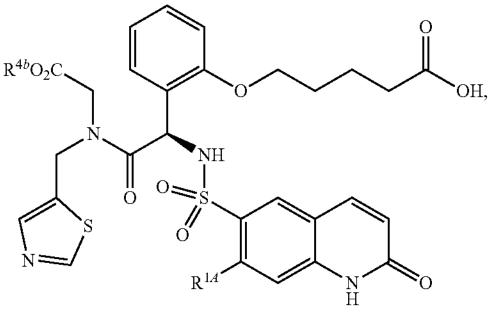
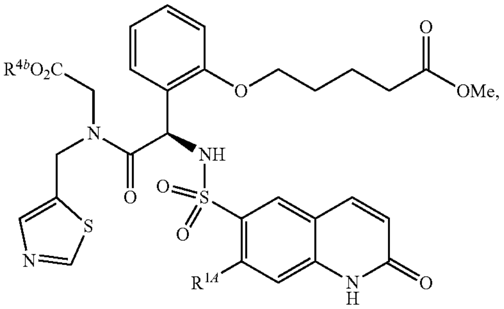
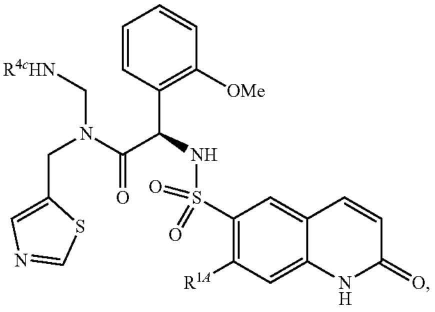
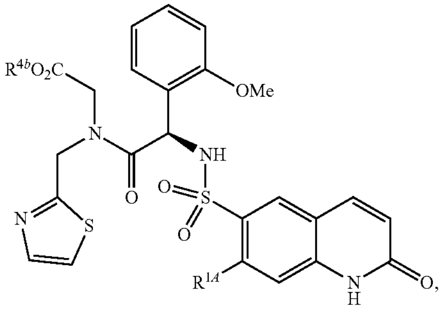

-continued
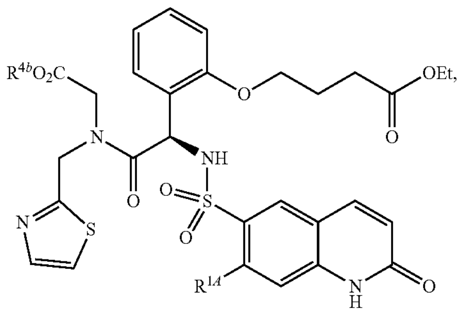
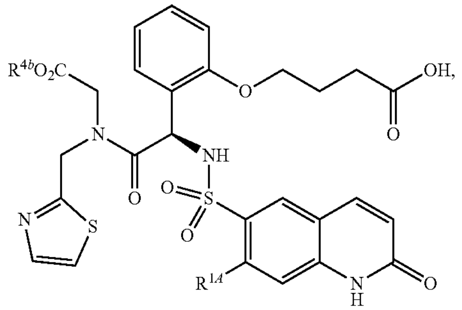
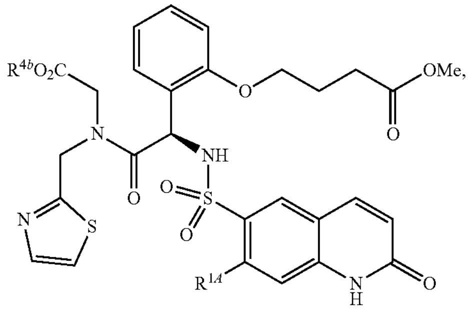
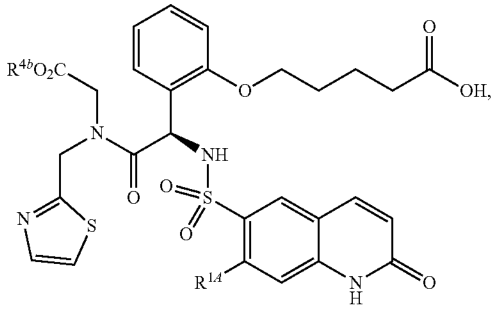
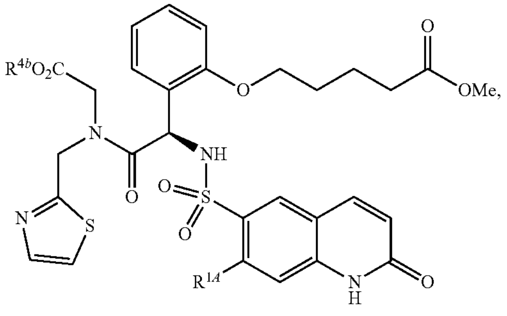
-continued
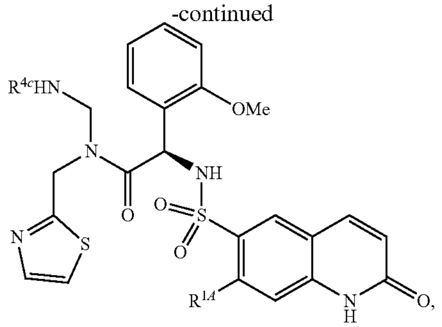
or a pharmaceutically acceptable salt, solvate, hydrate, polymorph, co-crystal, tautomer, stereoisomer, isotopically labeled derivative, or prodrug thereof.
In certain embodiments, the compound of Formula (I') is of the formula:
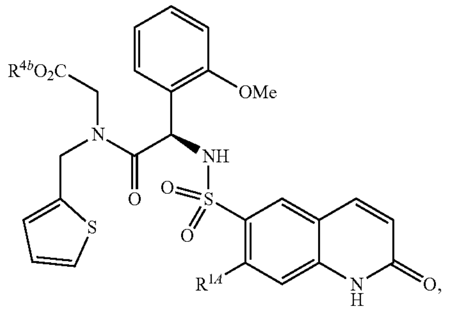
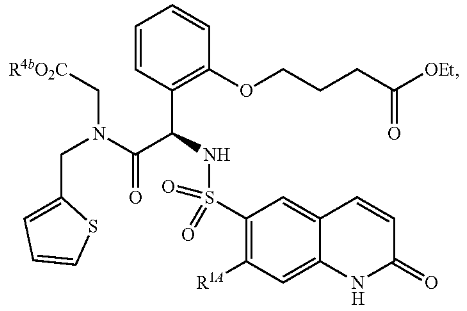
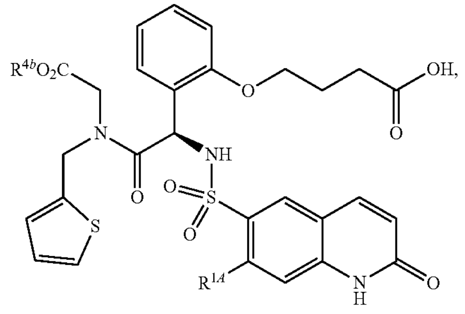

-continued
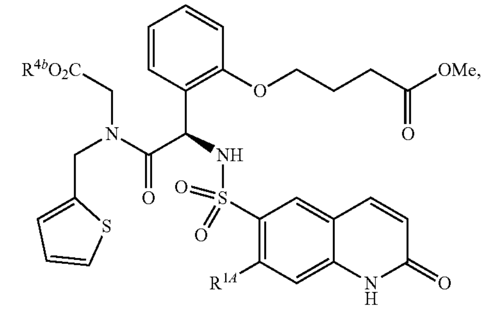
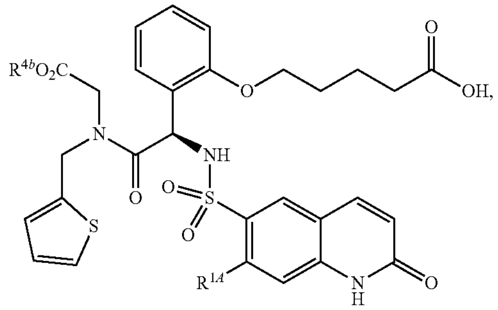
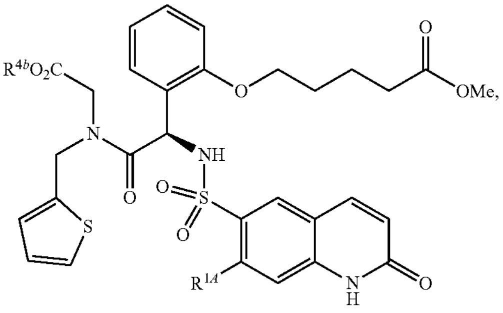
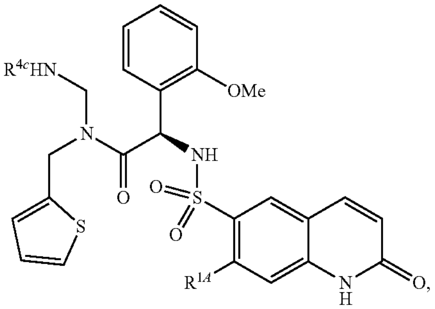
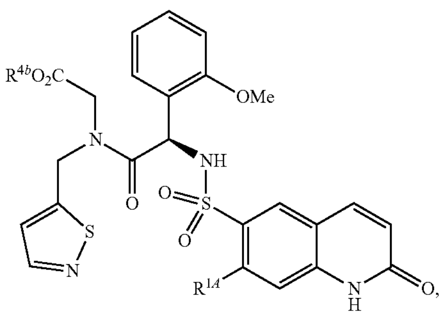
-continued
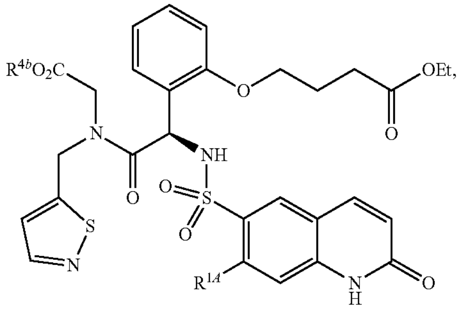
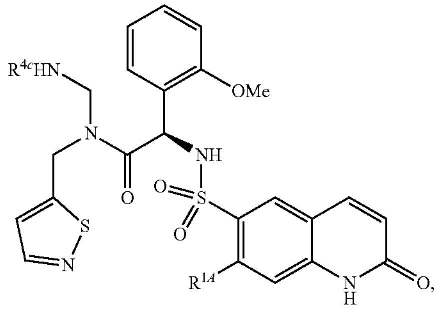
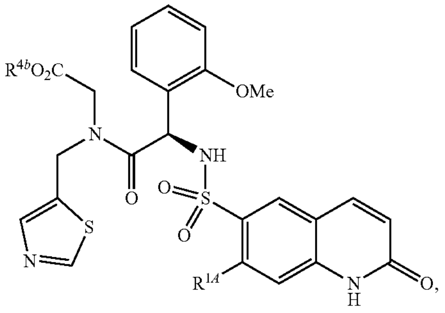
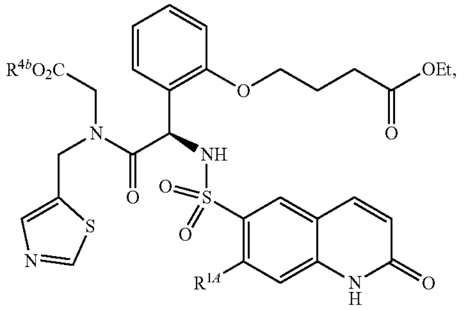
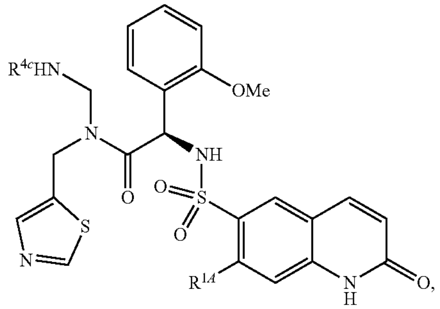

-continued
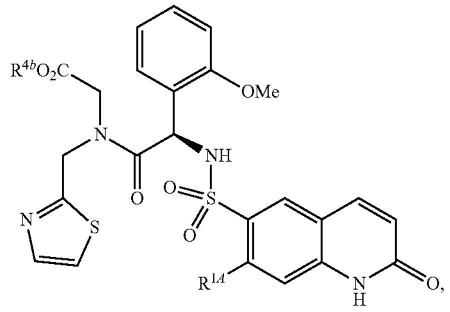
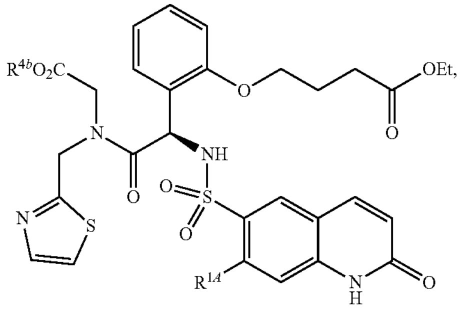
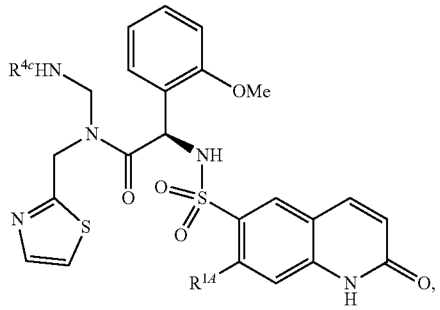
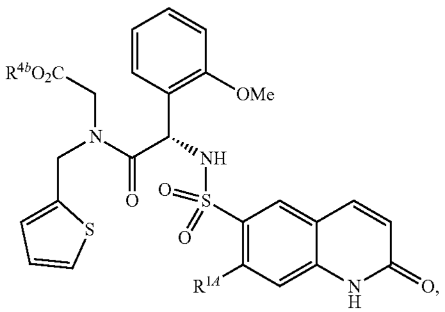
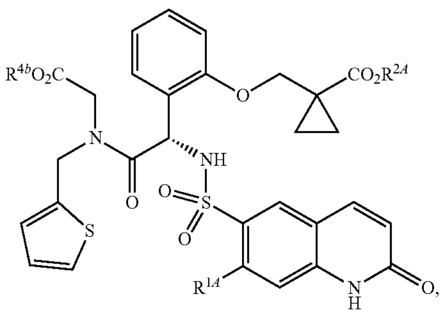
-continued
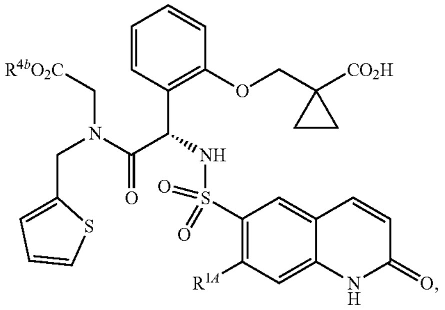
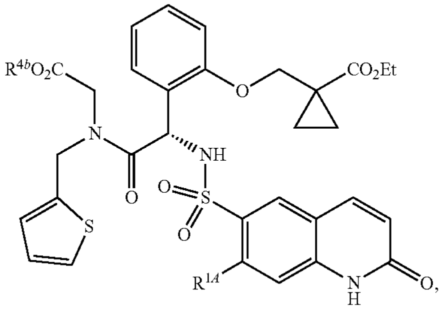
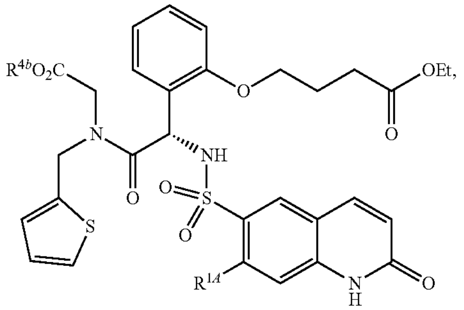
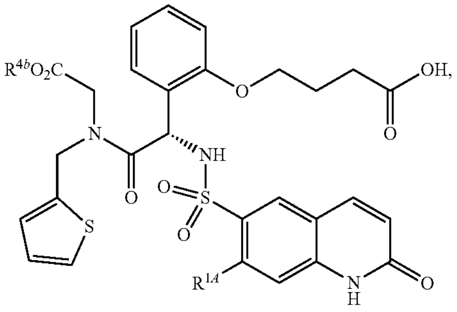
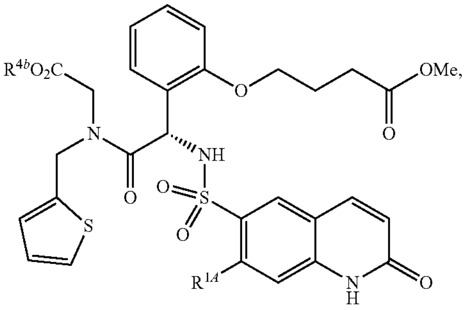

-continued
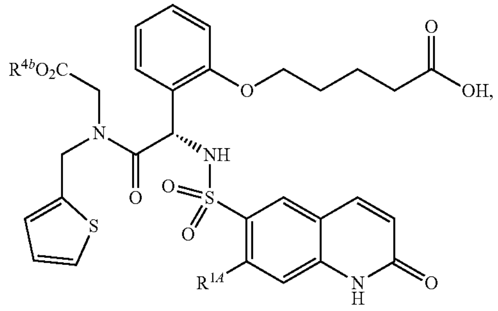
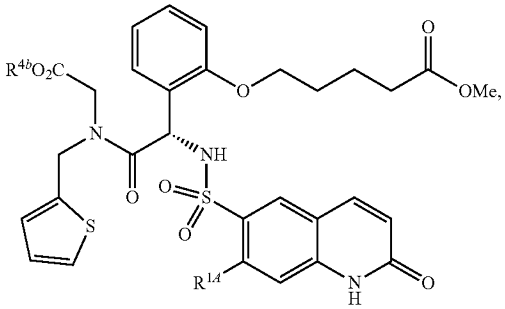
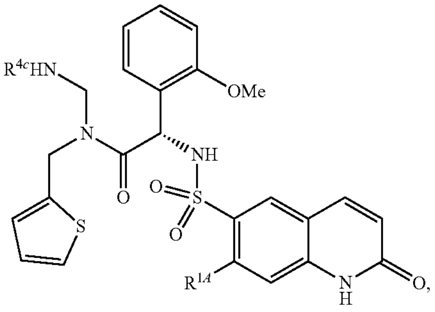
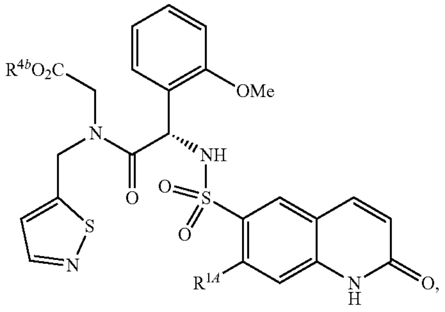
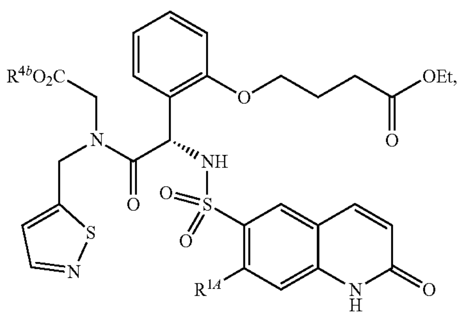
-continued
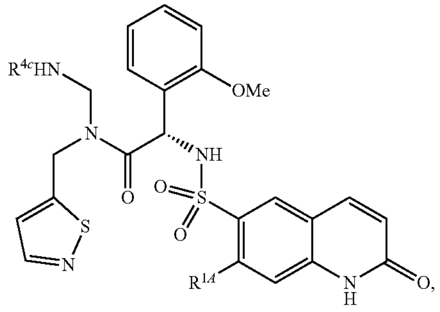
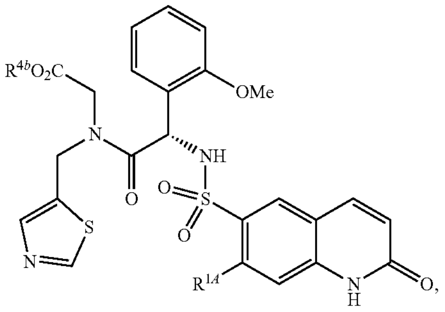
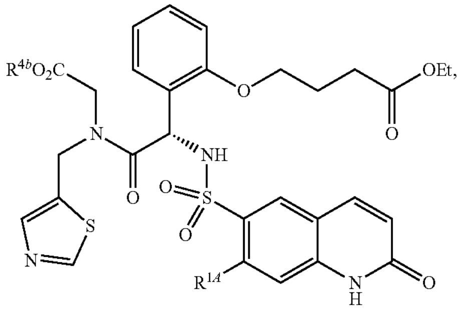
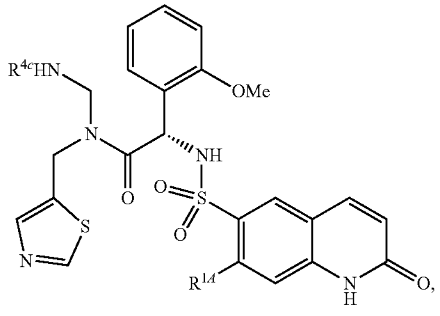
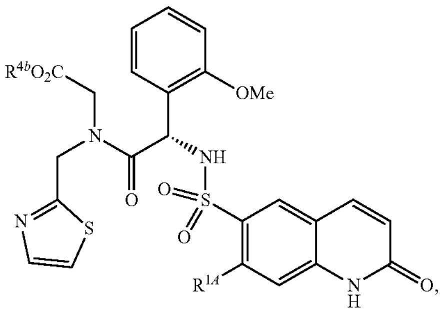

-continued
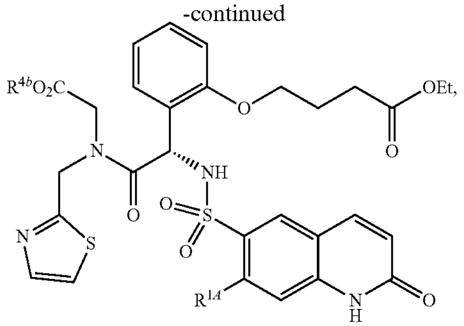
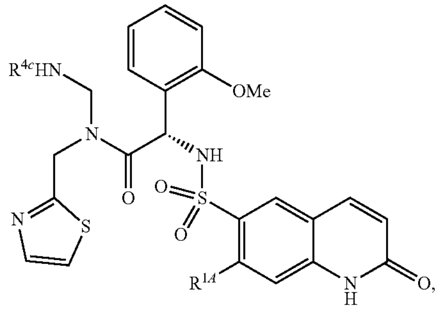
or a pharmaceutically acceptable salt, solvate, hydrate, polymorph, co-crystal, tautomer, stereoisomer, isotopically labeled derivative, or prodrug thereof.
In certain embodiments, the compound of Formula (I') is of the formula:
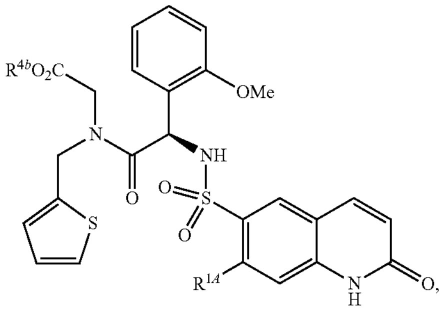
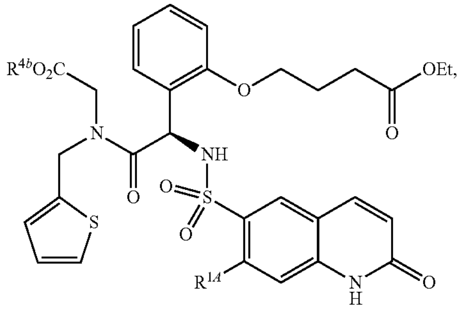
-continued
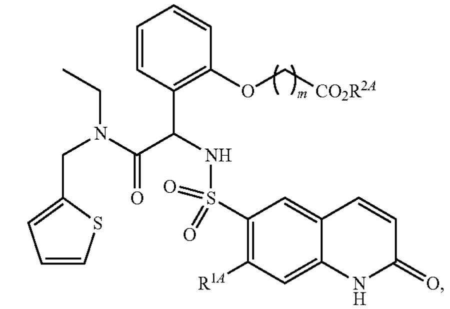
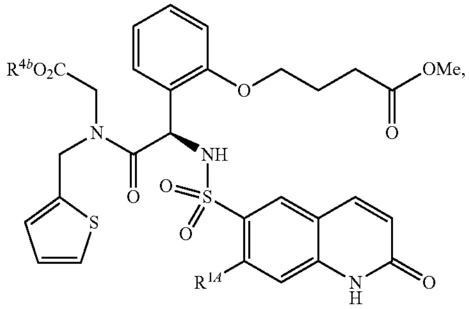
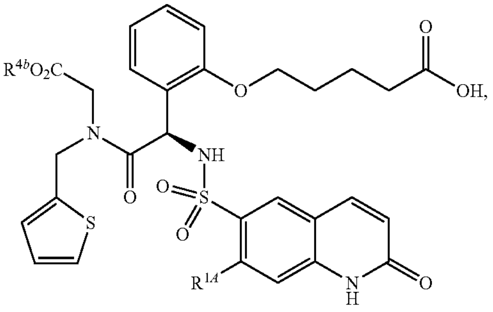
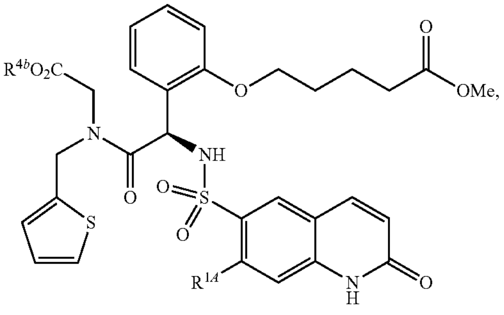
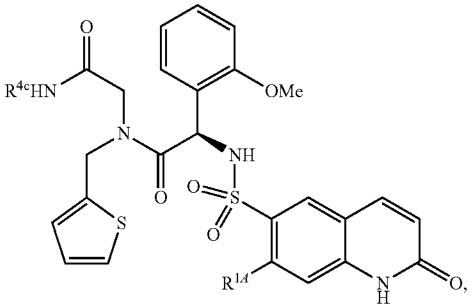

-continued
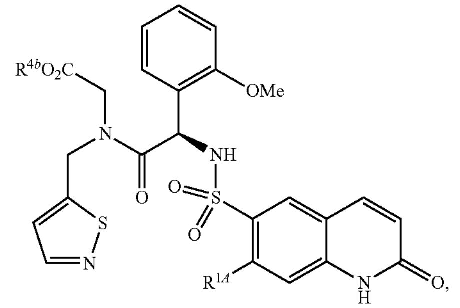
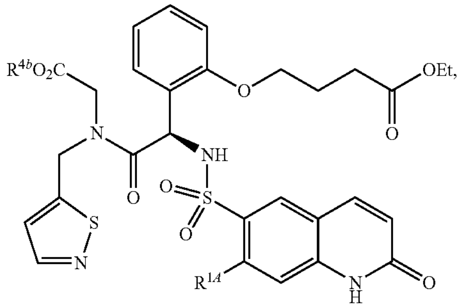
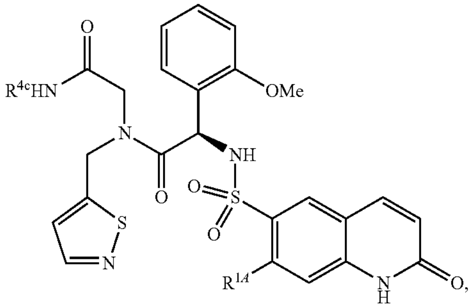
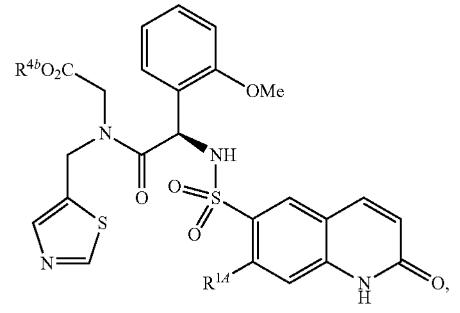
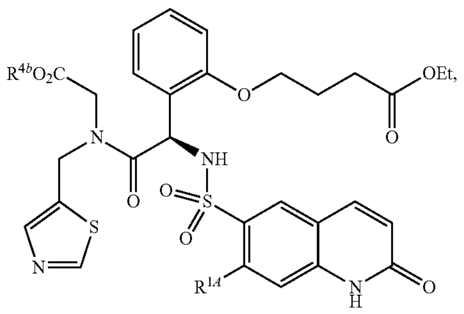
-continued
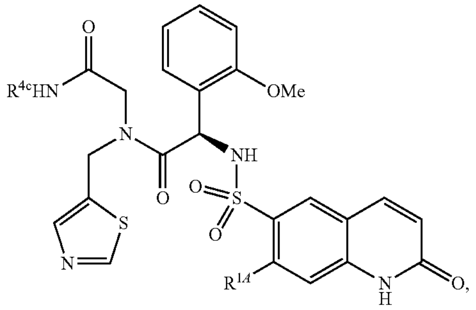
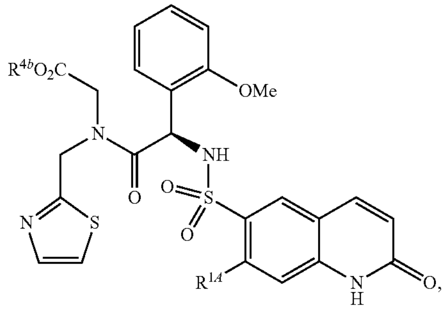
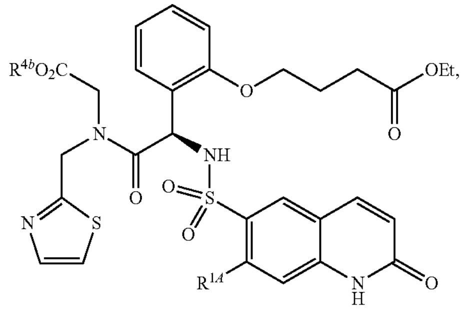
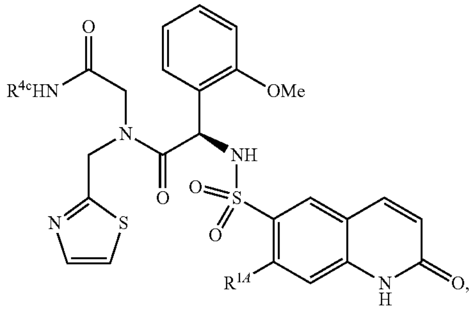
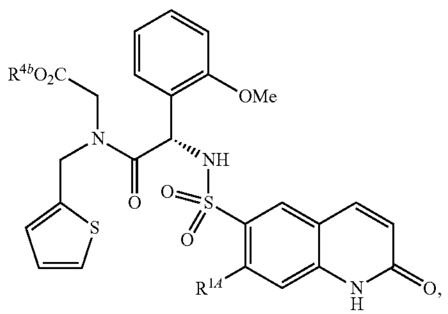

-continued
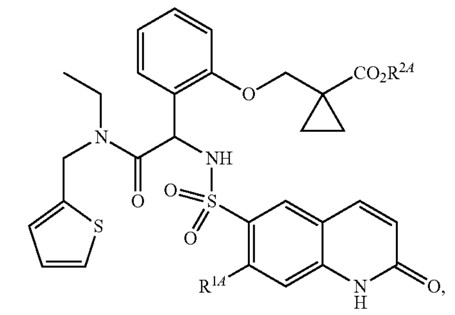
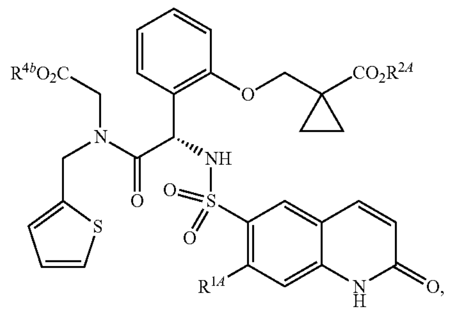
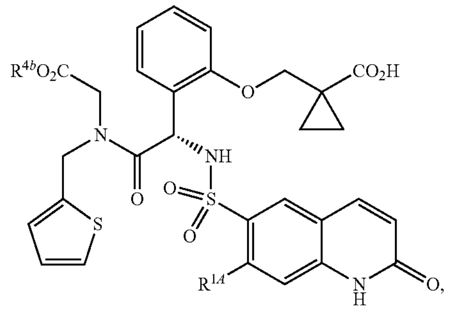
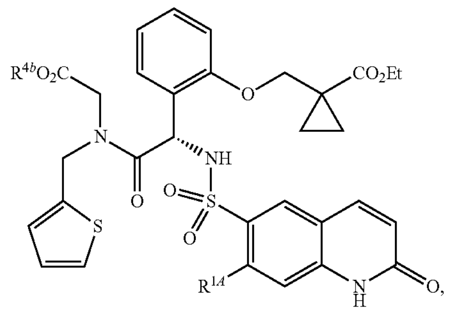
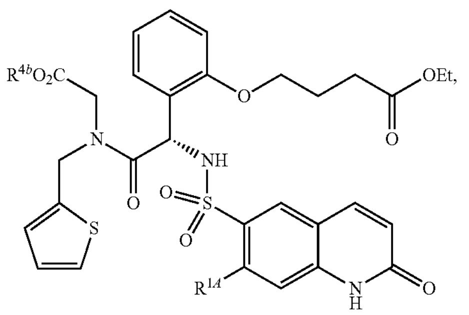
-continued
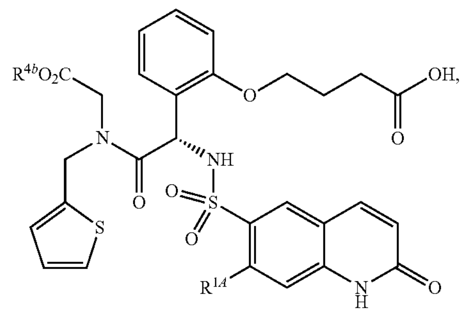
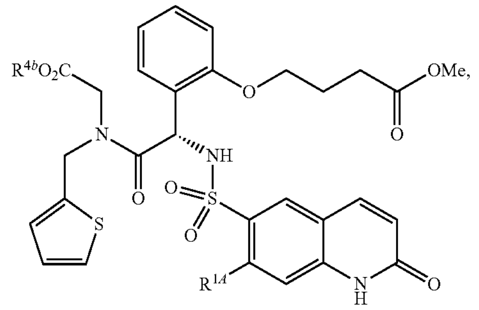
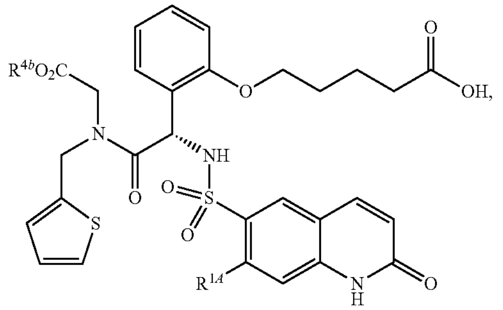
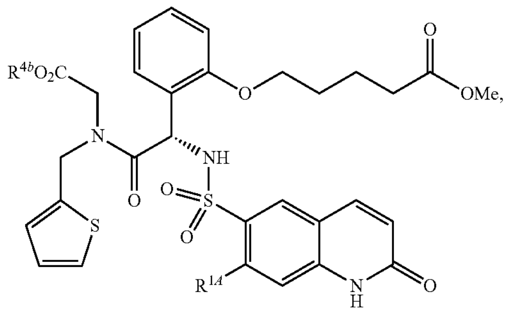
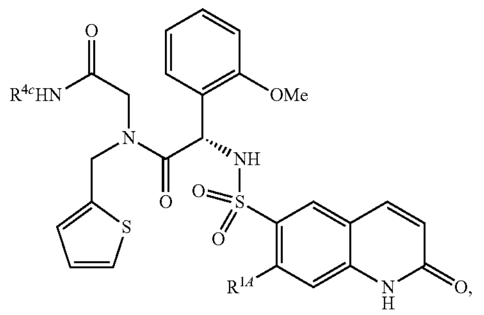

-continued
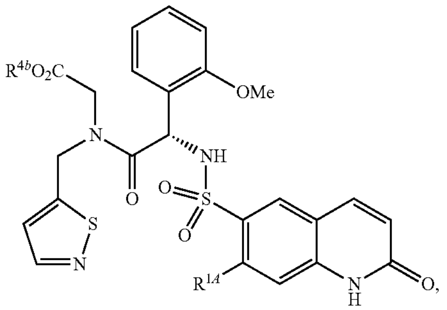
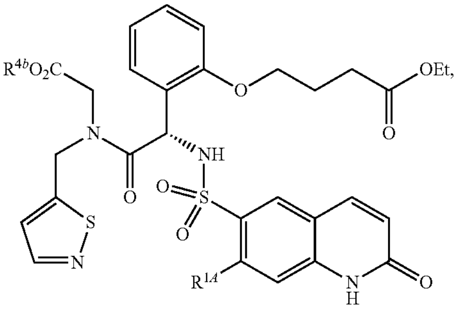
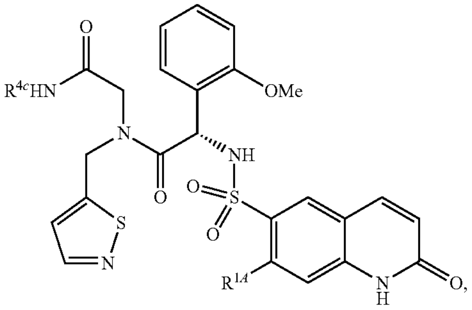
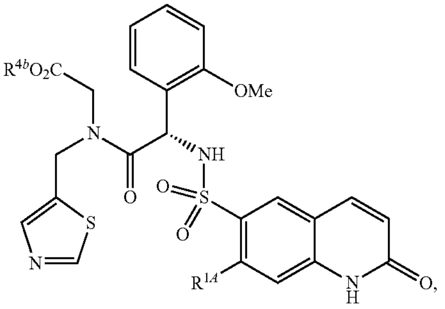
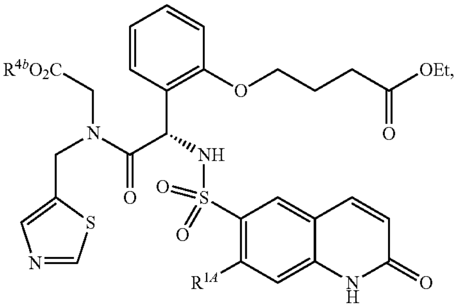
-continued
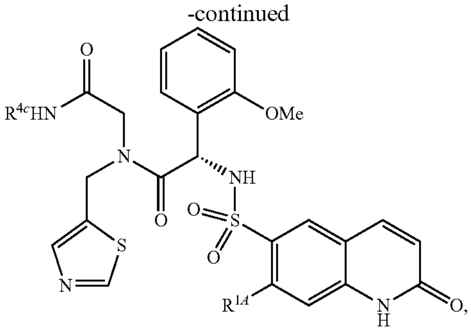
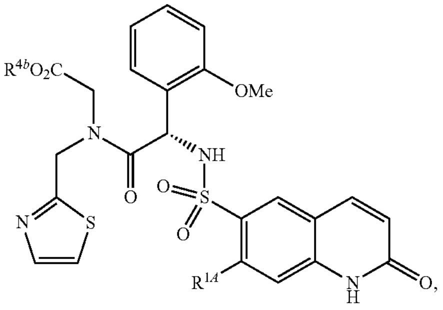
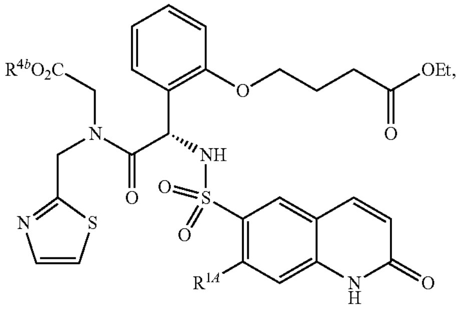
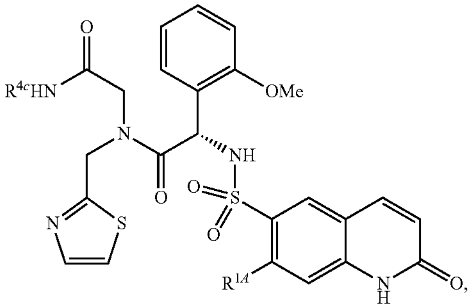
or a pharmaceutically acceptable salt, solvate, hydrate, polymorph, co-crystal, tautomer, stereoisomer, isotopically labeled derivative, or prodrug thereof;
wherein $R^{4b}$ is optionally substituted $C_{1-6}$ alkyl.
In certain embodiments, the compound of Formula (I') is of the formula:

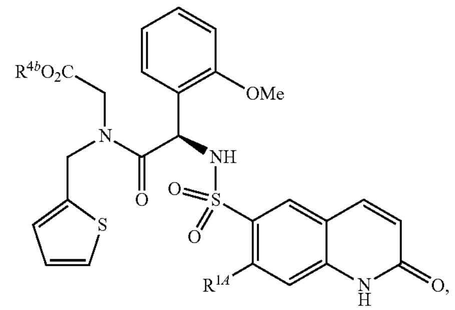
,
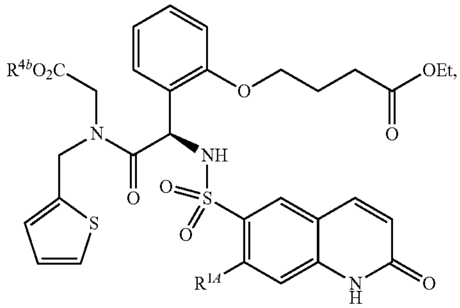
,
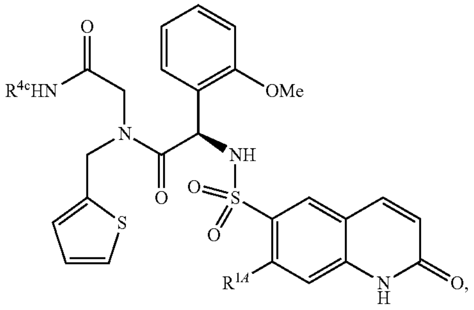
,
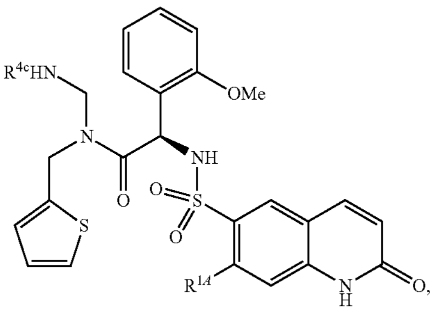
,
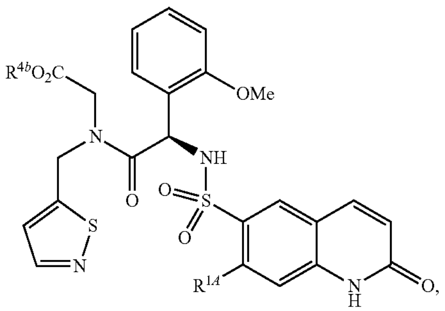
,
-continued
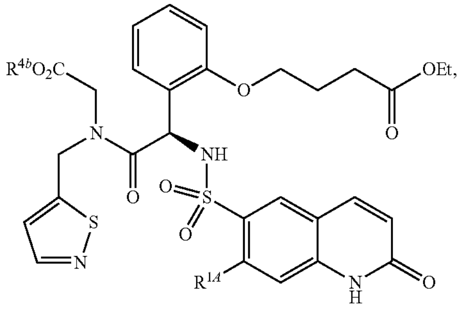
,
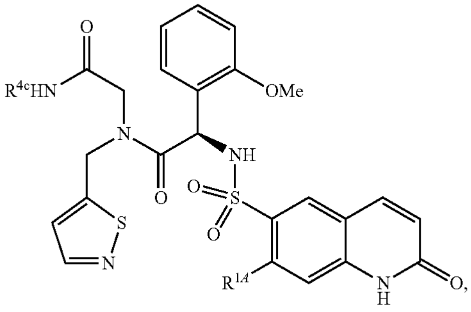
,
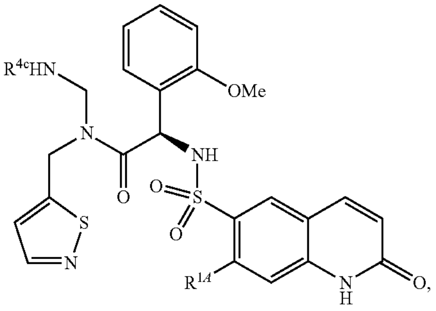
,
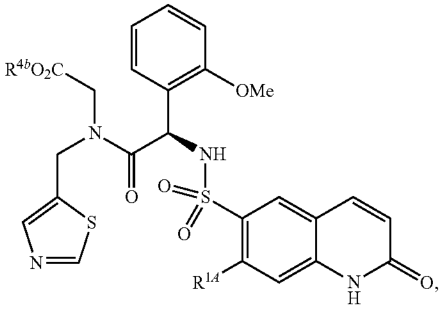
,
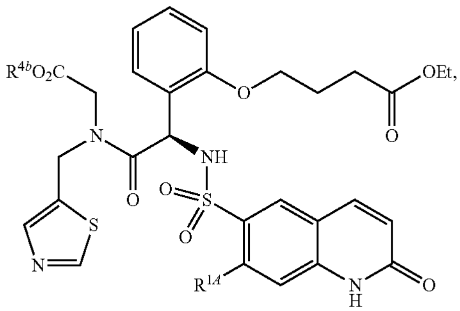
, -continued
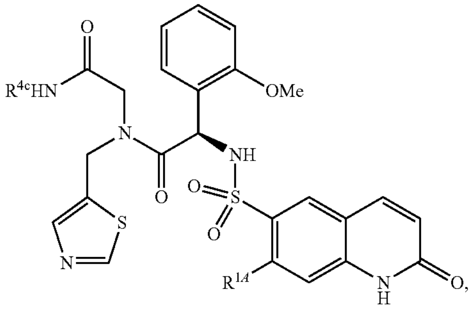
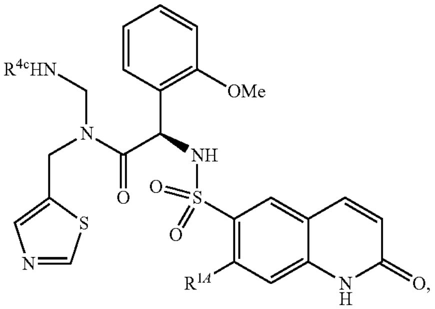
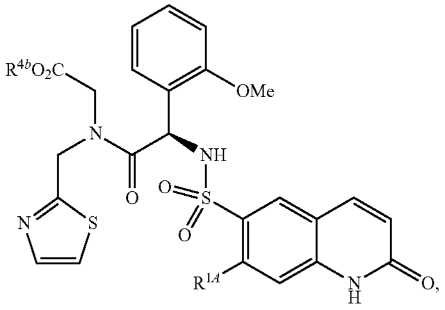
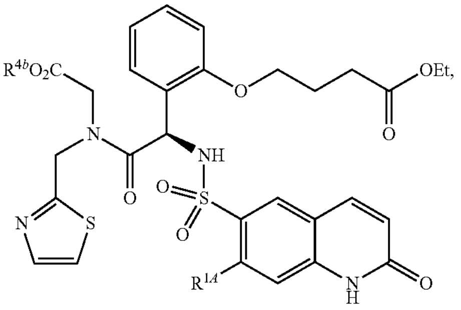
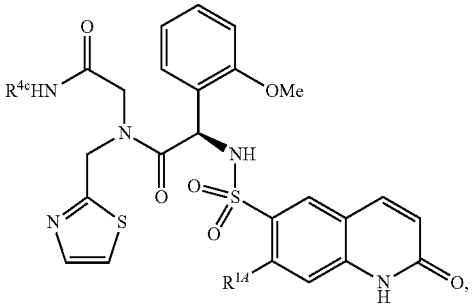
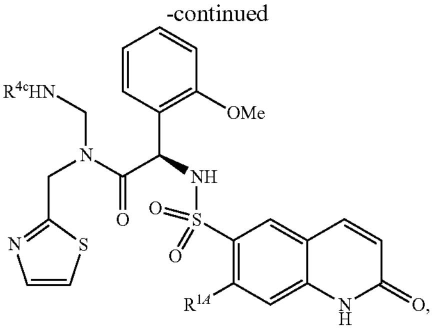
or a pharmaceutically acceptable salt, solvate, hydrate, polymorph, co-crystal, tautomer, stereoisomer, isotopically labeled derivative, or prodrug thereof.
In certain embodiments, the compound of Formula (I') is of the formula:
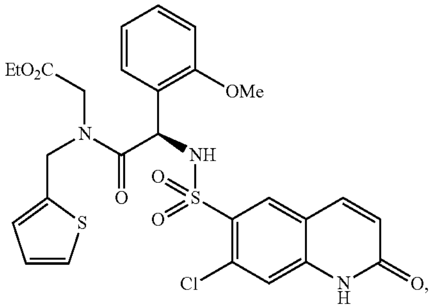
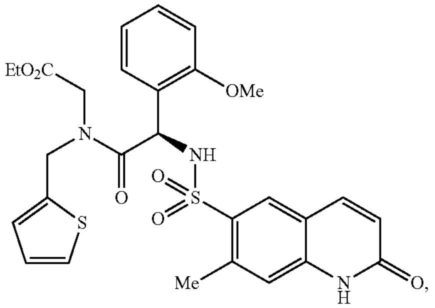
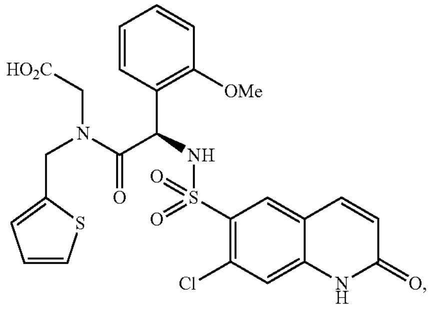

-continued
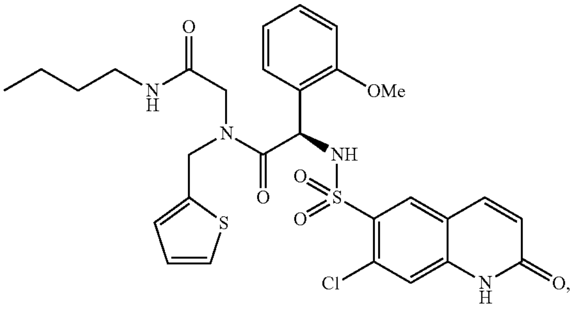
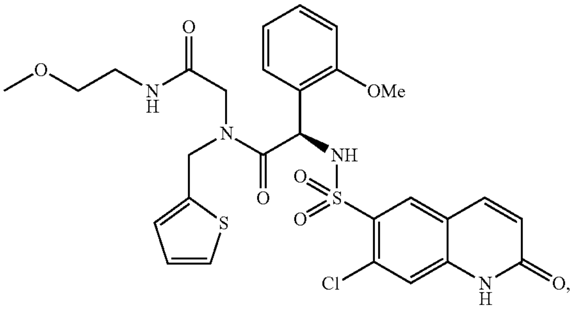
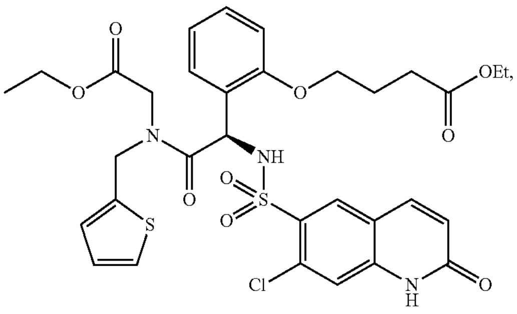
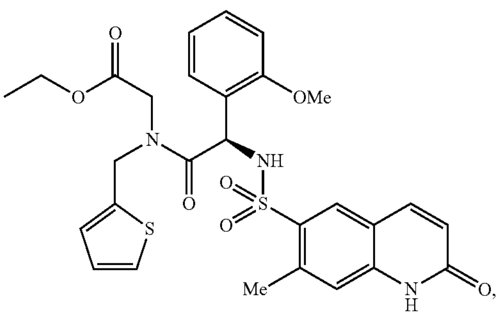
or a pharmaceutically acceptable salt, solvate, hydrate, polymorph, co-crystal, tautomer, stereoisomer, isotopically labeled derivative, or prodrug thereof.
In certain embodiments, a compound of Formula (I') is of the formula:
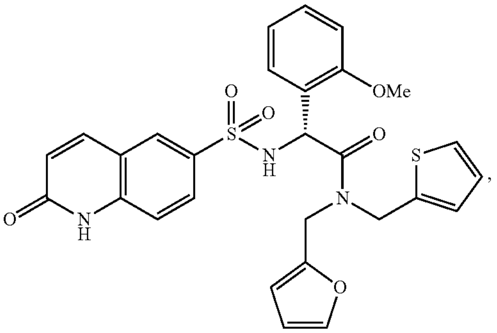
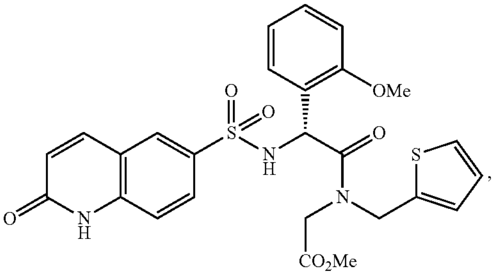
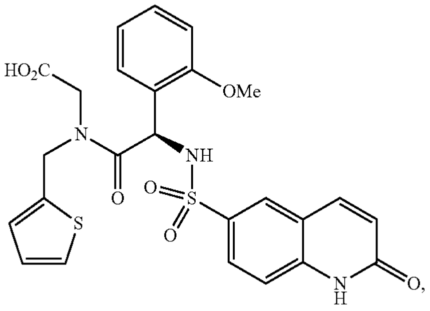
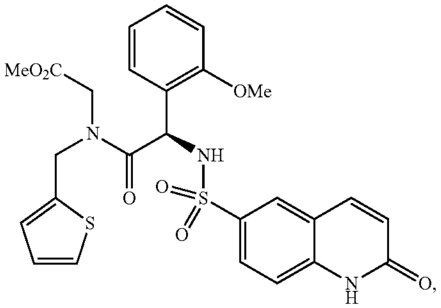
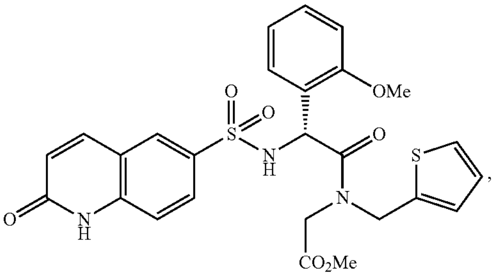

-continued
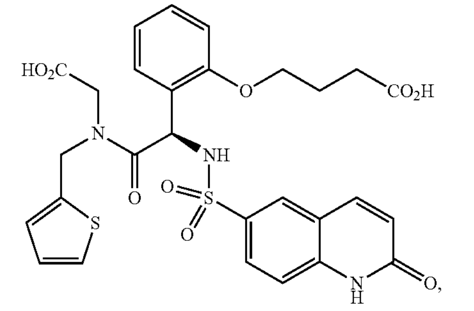
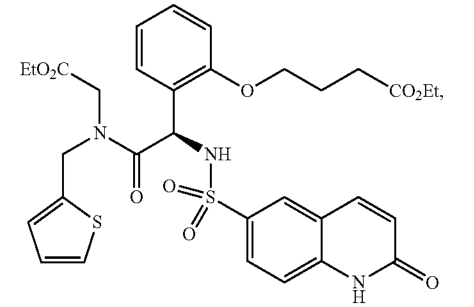
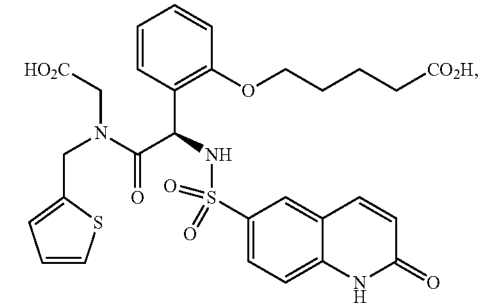
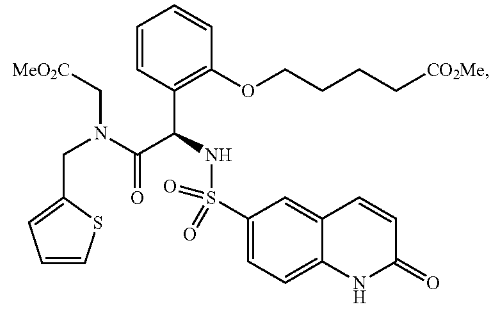
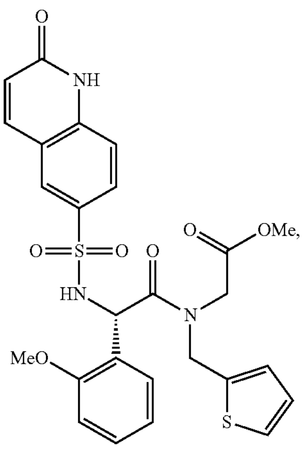
-continued
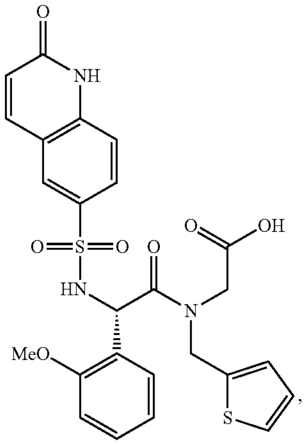
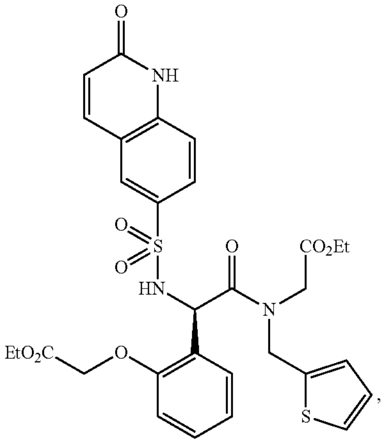
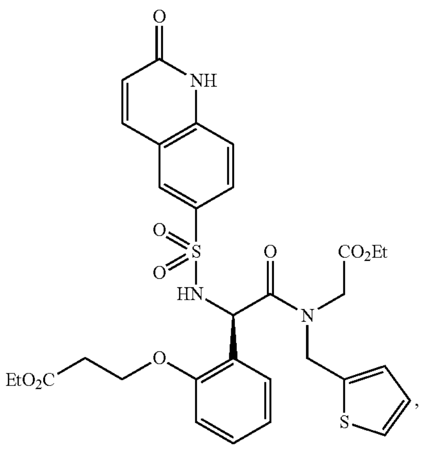

-continued
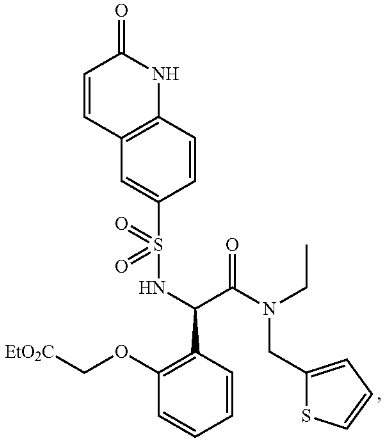
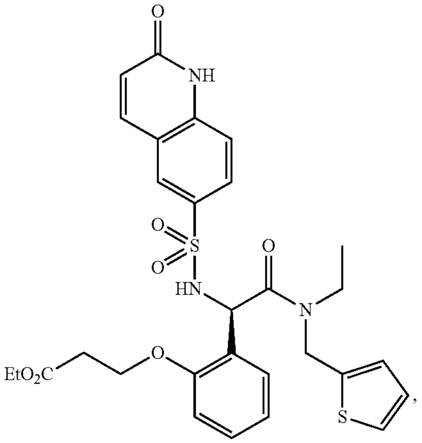
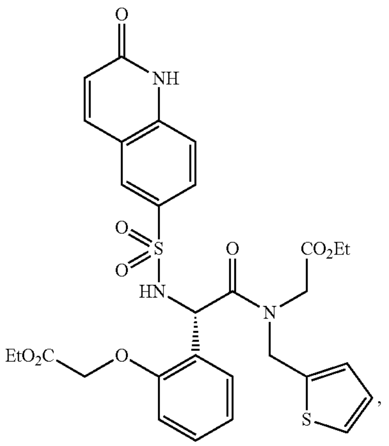
-continued
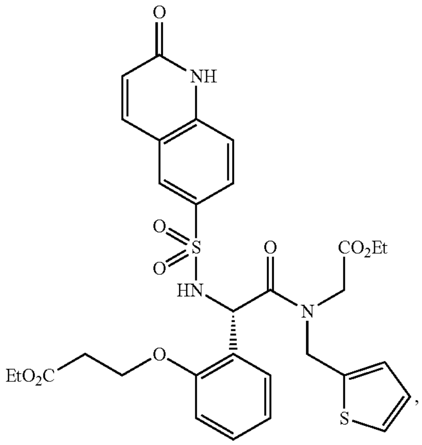
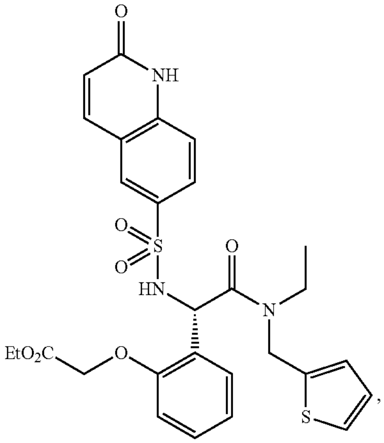
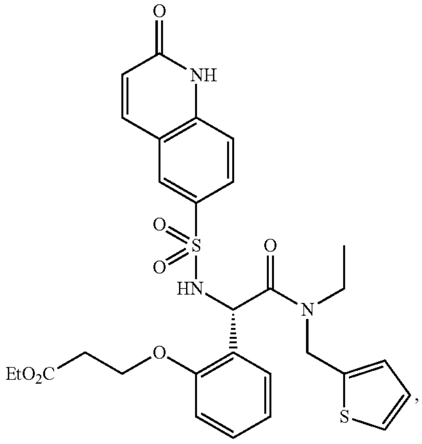

-continued
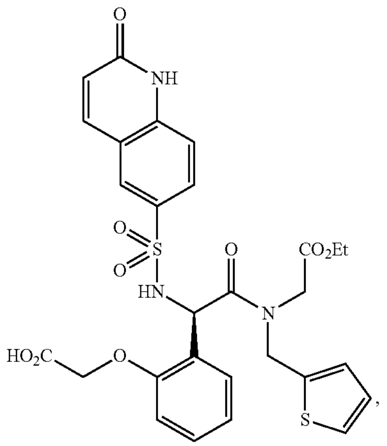
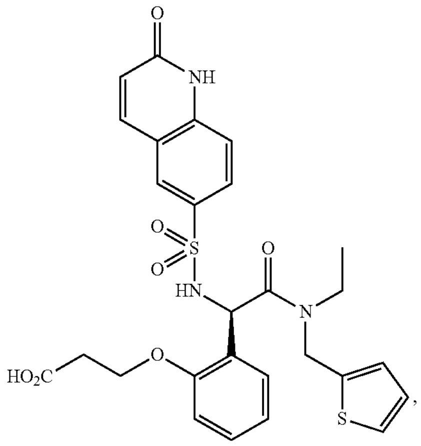
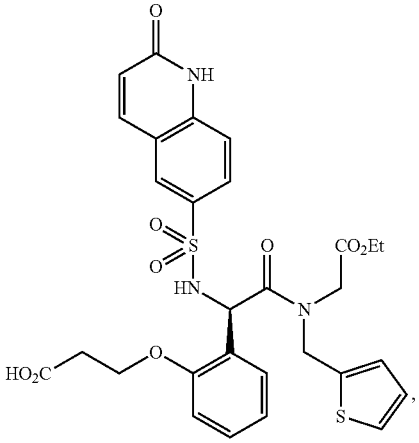
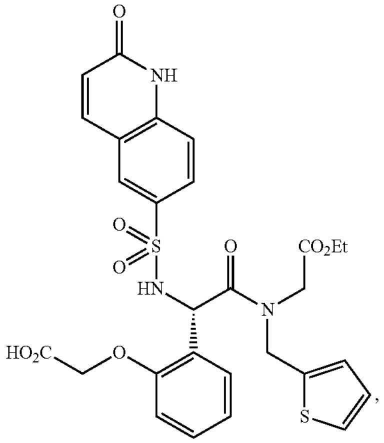
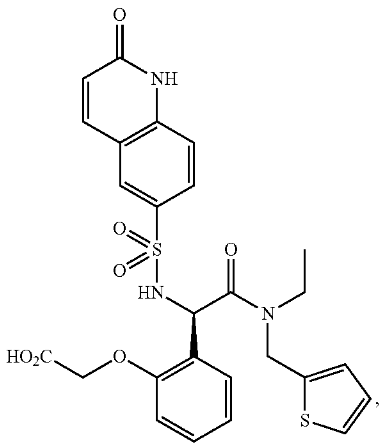
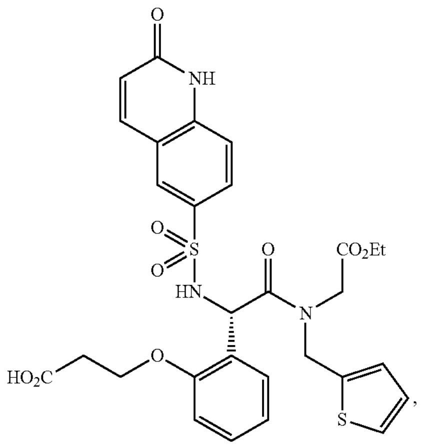

-continued
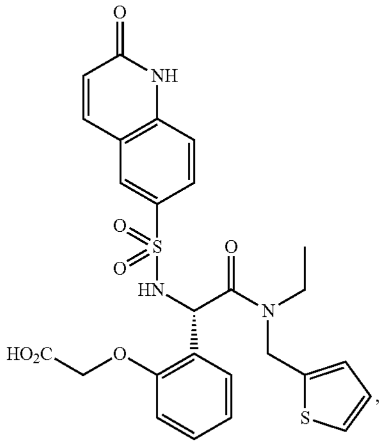
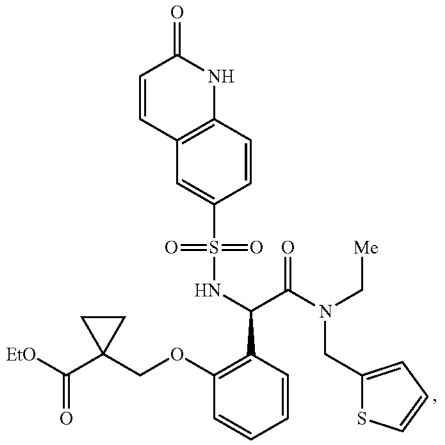
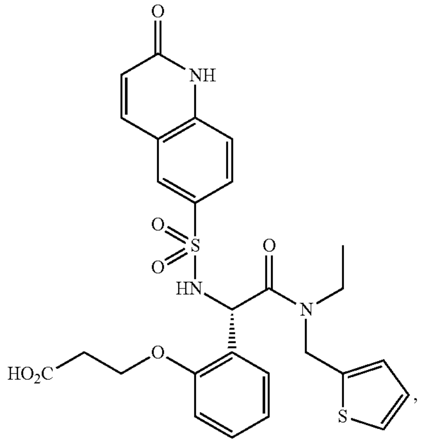
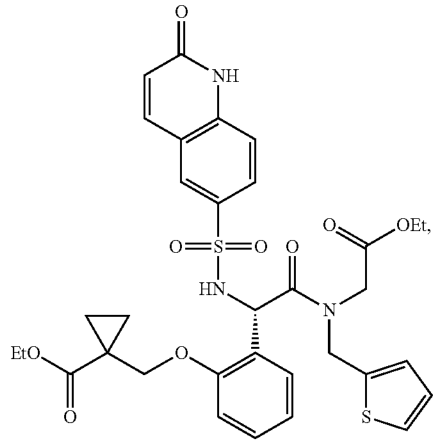
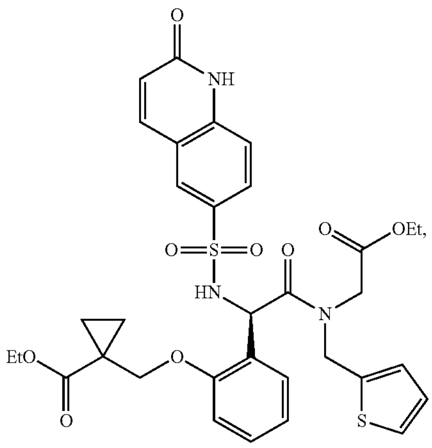
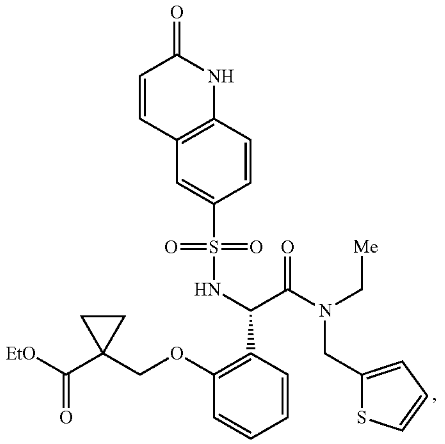
-continued -continued
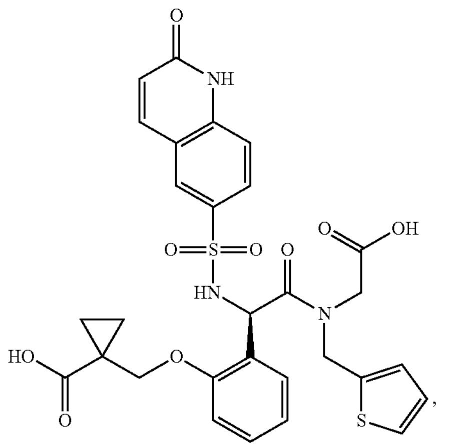
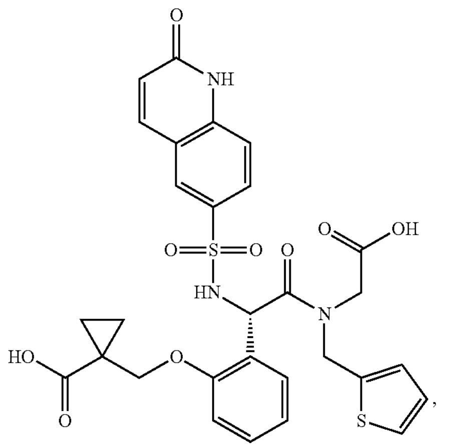
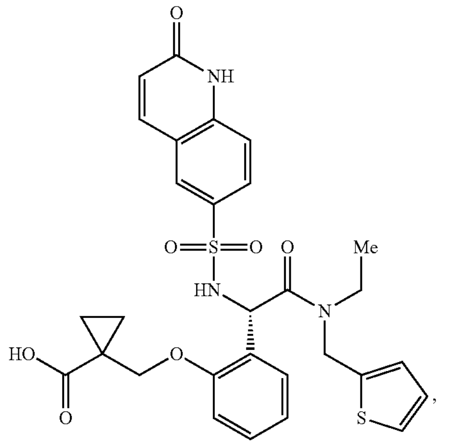
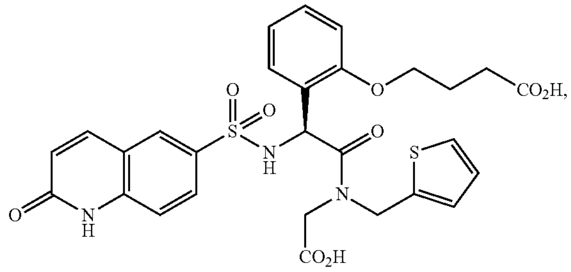
-continued
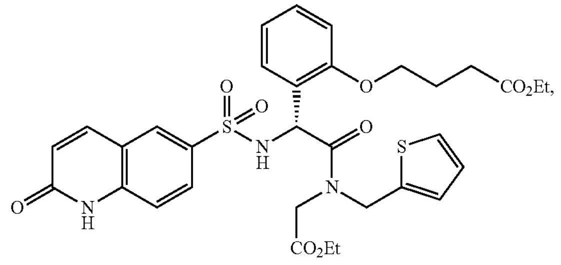
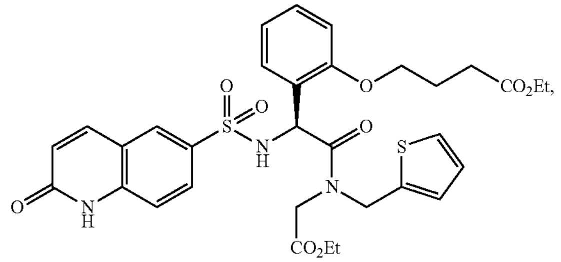
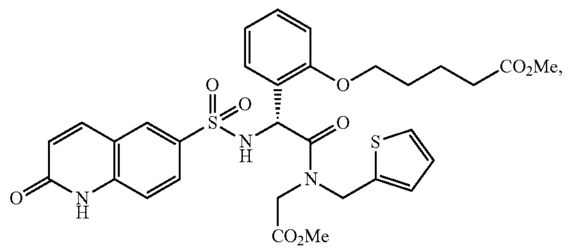
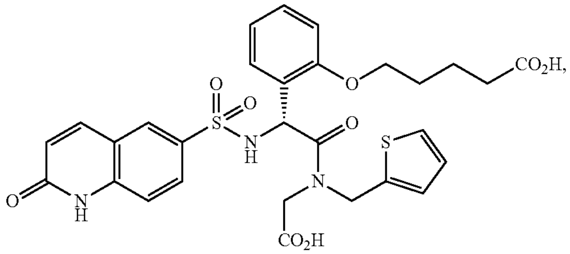
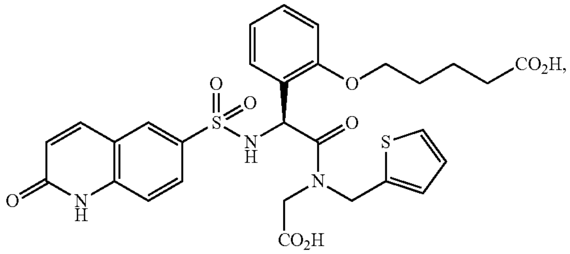
or a pharmaceutically acceptable salt, solvate, hydrate, polymorph, co-crystal, tautomer, stereoisomer, isotopically labeled derivative, or prodrug thereof.
In certain embodiments, a compound of Formula (I') is not of the formula:

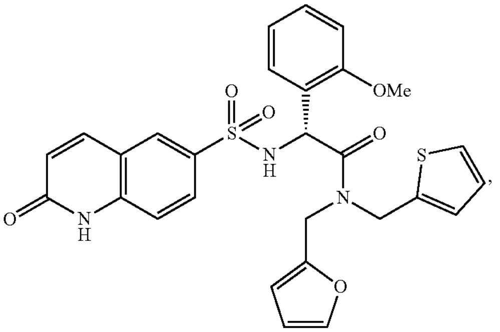

,

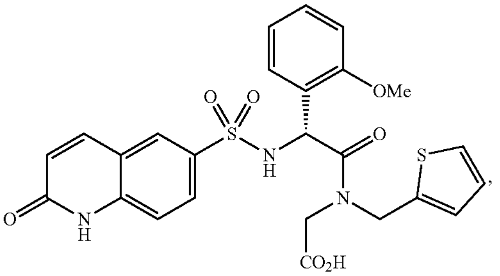

,

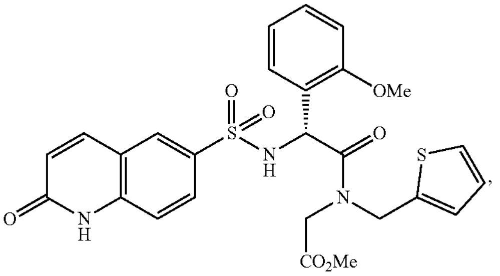

,

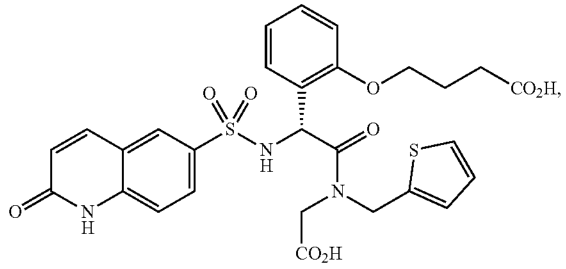

,

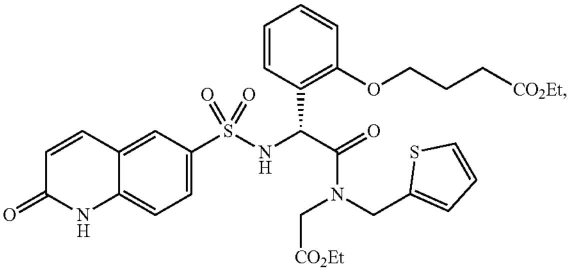

, or a pharmaceutically acceptable salt, solvate, hydrate, polymorph, co-crystal, tautomer, stereoisomer, isotopically labeled derivative, or prodrug thereof.

Pharmaceutical Compositions, Kits, and Administration

The invention further provides methods of treating a disease using a compound of the invention. Methods provided herein involve the administration of a therapeutically effective amount of an inventive compound to a subject (including, but not limited to, a human or other animal) in need of it.

Compounds and compositions described herein are generally useful for the inhibition of the activity of O-GlcNAc transferase (OGT) or a mutant thereof. OGT has been implicated in diabetes and complications thereof, proliferative diseases (e.g., cancers), neurodegenerative diseases, autoimmune diseases, and inflammatory diseases (Golks, et al., *EMBO Reports* (2008) 9: 748-753; Liu, et al., *Proc. Natl. Acad. Sci. USA* (2004) 101: 10804-10809; Jones, *Circulation Research* (2005) 96: 925-926; Golks, et al., *EMBO J.* (2007) 26: 4369-4379; Ohn, et al., *Nature Cell Biol.* (2008) 10: 1224-1231).

The compounds or pharmaceutical compositions thereof described herein may be used to inhibit OGT activity in a subject or biological sample (e.g., cell, tissue). The compounds and pharmaceutical compositions of the invention may be used in treating or preventing any disease or condition including, but not limited to, diabetes and complications thereof, proliferative diseases (e.g., cancer, benign neoplasms, diabetic retinopathy), neurodegenerative diseases, autoimmune diseases (e.g., rheumatoid arthritis, lupus, multiple sclerosis) and inflammatory diseases and disorders. The inventive compounds and pharmaceutical compositions may be administered to animals, preferably mammals (e.g., domesticated animals, cats, dogs, mice, rats), and more preferably humans. Any method of administration may be used to deliver the inventive compound or pharmaceutical composition to the animal. In certain embodiments, the compound or pharmaceutical composition is administered orally. In other embodiments, the compound or pharmaceutical composition is administered parenterally.

In certain embodiments, the invention provides methods for treating or lessening the severity of diabetes and complications thereof including, but not limited to, diabetes mellitus Type 1, diabetes mellitus Type 2, cardiovascular disease associated with poor insulin regulation (e.g., insulin resistance), insulin resistance, vascular disease, skin ulcers, circulatory damage, cardiac dysfunction, diabetic nephropathy, diabetic retinopathy, microvascular disease, macrovascular disease, and diabetic neuropathy.

In some embodiments, the invention provides methods for treating tumorogenesis.

In certain embodiments, the inventive compounds are useful in treating a proliferative disease. In some embodiments, the invention provides methods for treating cancer. Examples of cancers treated with compounds according to the invention include, but are not limited to, tumors of the breast; biliary tract; bladder; bone; brain, including glioblastomas and medulloblastomas; central and peripheral nervous system; cervix; colon; connective tissue; endocrine glands (e.g., thyroid and adrenal cortex); esophagus; endometrium; germ cells; gastrointestinal tract; head and neck; kidney; liver; lung; larynx and hypopharynx; mesothelioma; muscle; ovary, including those arising from epithelial cells, stromal cells, germ cells and mesenchymal cells; pancreas; prostate; rectum; renal, including adenocarcinoma and Wilms tumor; small intestine; soft tissue; testis, including germinal tumors such as seminoma, non-seminoma (teratomas, choriocarcinomas), stromal tumors, and germ cell tumors; thyroid, including thyroid adenocarcinoma and medullar carcinoma; stomach; skin, including melanoma, Kaposi's sarcoma, basocellular cancer, and squamous cell cancer; ureter; vagina; and vulva; retinoblastoma; leukemia and lymphoma, namely non-Hodgkins disease, lymphocytic lymphomas, chronic and acute myeloid leukemia (CML/AML), acute lymphoblastic leukemia (ALL), chronic lymphocytic leukemia (CLL), Hodgkins disease, multiple myeloma, and T-cell lymphoma; myelodysplastic syndrome; plasma cell neoplasia; paraneoplastic syndromes; intraepithelial neoplasms including Bowen's disease and Paget's disease; neuroblastomas; oral cancer including squamous cell carcinoma; sarcomas including leiomyosarcoma, rhabdomyosarcoma, liposarcoma, fibrosarcoma, and osteosarcoma; cancers of unknown primary site; and AIDS-related malignancies. Other cancers will be known to one of ordinary skill in the art.

In certain embodiments, the invention provides methods for treating or lessening the severity of autoimmune diseases including, but not limited to, inflammatory bowel disease, arthritis, systemic lupus erythematosus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjogren's syndrome, multiple sclerosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, or vulvodynia.

In some embodiments, the invention provides a method for treating or lessening the severity of one or more diseases and conditions, wherein the disease or condition is selected from immune-related conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In some embodiments, the present invention provides a method for treating or lessening the severity of an inflammatory disease including, but not limited to, asthma, appendicitis, Blau syndrome, blepharitis, bronchiolitis, bronchitis, bursitis, cervicitis, cholangitis, cholecystitis, chronic obstructive pulmonary disease (COPD), chronic recurrent multifocal osteomyelitis (CRMO), colitis, conjunctivitis, cryopyrin associated periodic syndrome (CAPS), cystitis, dacryoadenitis, dermatitis, dermatomyositis, dry eye syndrome, encephalitis, endocarditis, endometritis, enteritis, enterocolitis, epicondylitis, epididymitis, familial cold-induced autoinflammatory syndrome, familial Mediterranean fever (FMF), fasciitis, fibrositis, gastritis, gastroenteritis, hepatitis, hidradenitis suppurativa, laryngitis, mastitis, meningitis, mevalonate kinase deficiency (MKD), Muckle-Well syndrome, myelitis myocarditis, myositis, nephritis, oophoritis, orchitis, osteitis, inflammatory osteolysis, otitis, pancreatitis, parotitis, pericarditis, peritonitis, pharyngitis, pleuritis, phlebitis, pneumonitis, pneumonia, proctitis, prostatitis, pulmonary fibrosis, pyelonephritis, pyoderma gangrenosum and acne syndrome (PAPA), pyogenic sterile arthritis, rhinitis, salpingitis, sinusitis, stomatitis, synovitis, systemic juvenile rheumatoid arthritis, tendonitis, TNF receptor associated periodic syndrome (TRAPS), tonsillitis, undifferentiated spondyloarthropathy, undifferentiated arthropathy, uveitis, vaginitis, vasculitis, vulvitis, chronic inflammation resulting from chronic viral or bacteria infections, or psoriasis (e.g., plaque psoriasis, pustular psoriasis, erythrodermic psoriasis, guttate psoriasis or inverse psoriasis).

In certain embodiments, the present invention provides methods for treating or lessening the severity of arthropathies and osteopathological diseases including, but not limited to, rheumatoid arthritis, osteoarthritis, gout, polyarthritis, and psoriatic arthritis.

In certain embodiments, the present invention provides methods for treating or lessening the severity of acute and chronic inflammatory diseases including, but not limited to, ulcerative colitis, inflammatory bowel disease, Crohn's disease, dry eye syndrome, allergic rhinitis, allergic dermatitis, cystic fibrosis, chronic obstructive bronchitis, and asthma.

In certain embodiments, the invention provides methods for treating or lessening the severity of hyperproliferative diseases including, but not limited to, psoriasis or smooth muscle cell proliferation including vascular proliferative disorders, atherosclerosis, and restenosis. In certain embodiments, the invention provides methods for treating or lessening the severity of endometriosis, uterine fibroids, endometrial hyperplasia, and benign prostate hyperplasia.

In certain embodiments, the invention provides methods for treating or lessening the severity of neurodegenerative disorders and/or tauopathies including, but not limited to, Alzheimer's disease, progressive supranuclear palsy, corticobasal degeneration, frontotemporal lobar degeneration, Pick's disease, Parkinson's disease, Lewy body disease, or amyotropic lateral sclerosis (ALS).

The invention further includes a method for the treatment of mammals, including humans, which are suffering from one of the above-mentioned conditions, illnesses, disorders, or diseases. The method comprises that a therapeutically effective amount of one or more of the compounds according to this invention or a composition thereof is administered to the subject in need of such treatment.

The invention further includes a method for inhibiting OGT in a biological sample (e.g., a cell or tissue) using a compound of the invention. The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, metabolic disorder, autoimmune disease, or neurological disease). In certain embodiments, the additional pharmaceutical agent is a pharmaceutical agent useful for treating and/or preventing a disease (e.g., diabetes and complications thereof, proliferative diseases (e.g., cancer, benign neoplasms, diabetic retinopathy), neurodegenerative diseases, autoimmune diseases (e.g., rheumatoid arthritis, lupus, multiple sclerosis) and inflammatory diseases and disorders)). In certain embodiments, the additional pharmaceutical agent is an anti-proliferative agent.

The invention further relates to the use of the inventive compounds for the production of pharmaceutical compositions which are employed for the treatment and/or prophylaxis and/or amelioration of the diseases, disorders, illnesses, and/or conditions as mentioned herein.

The invention further relates to the use of the inventive compounds for the production of pharmaceutical compositions that inhibit OGT.

The invention further relates to the use of the inventive compounds for the production of pharmaceutical compositions which can be used for treating, preventing, or ameliorating diseases responsive to inhibiting OGT, such as diabetes and complications thereof, neurodegenerative diseases, proliferative diseases such as cancers, autoimmune diseases, and inflammatory diseases, such as any of those diseases mentioned herein.

The exact amount required will vary from subject to subject, depending on the species, age, and general condition of the subject, the particular compound, its mode of administration, its mode of activity, and the like. The compounds of the invention are preferably formulated in dosage unit form for ease of administration and uniformity of dosage. It will be understood, however, that the total daily usage of the proteins and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific protein employed; the specific composition employed; the age, body weight, general health, sex, and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like. In certain embodiments, the compounds of the invention may be administered orally or parenterally at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, and from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

Liquid dosage forms for oral and parenteral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. In certain embodiments for parenteral administration, the compounds of the invention are mixed with solubilizing agents such polyethoxylated castor oil, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as poly(lactide-co-glycolide). Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active protein may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for topical administration include liquid or semi-liquid preparations such as liniments, lotions, gels, applicants, oil-in-water or water-in-oil emulsions such as creams, ointments, or pastes; or solutions or suspensions such as drops. Formulations for topical administration to the skin surface can be prepared by dispersing the drug with a dermatologically acceptable carrier such as a lotion, cream, ointment, or soap. Useful carriers are capable of forming a film or layer over the skin to localize application and inhibit removal. For topical administration to internal tissue surfaces, the agent can be dispersed in a liquid tissue adhesive or other substance known to enhance adsorption to a tissue surface.

For example, hydroxypropylcellulose or fibrinogen/thrombin solutions can be used to advantage. Alternatively, tissue-coating solutions such as pectin-containing formulations can be used. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Additionally, the carrier for a topical formulation can be in the form of a hydroalcoholic system (e.g., liquids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems.

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

In yet another aspect, the present disclosure provides compounds of Formula (I'), and pharmaceutically acceptable salts, solvates, hydrates, polymorphs, co-crystals, tautomers, stereoisomers, isotopically labeled derivatives, prodrugs, and compositions thereof, for use in the treatment of a disease (e.g., diabetes and complications thereof, cardiovascular disease associated with poor insulin regulation (e.g., insulin resistance), insulin resistance, neurodegenerative diseases such as Alzheimer's disease, proliferative diseases (e.g., cancer), autoimmune diseases, and inflammatory diseases) in a subject. In still another aspect, the present invention also provides a pharmaceutical pack or kit comprising one or more containers filled with one or more of the ingredients of the pharmaceutical compositions of the invention, and in certain embodiments, includes an additional approved therapeutic agent for use as a combination therapy. In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a proliferative disease in a subject in need thereof, preventing a disease, such as diabetes and complications thereof, proliferative diseases (e.g., cancer, benign neoplasms, diabetic retinopathy), neurodegenerative diseases, autoimmune diseases (e.g., rheumatoid arthritis, lupus, multiple sclerosis) and inflammatory diseases and disorders) in a subject in need thereof, inhibiting OGT activity in a subject, biological sample, tissue, or cell. A kit described herein may include one or more additional pharmaceutical agents described herein as a separate composition.

These and other aspects of the present invention will be further appreciated upon consideration of the following Examples, which are intended to illustrate certain particular embodiments of the invention but are not intended to limit its scope, as defined by the claims.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Figure 1B:
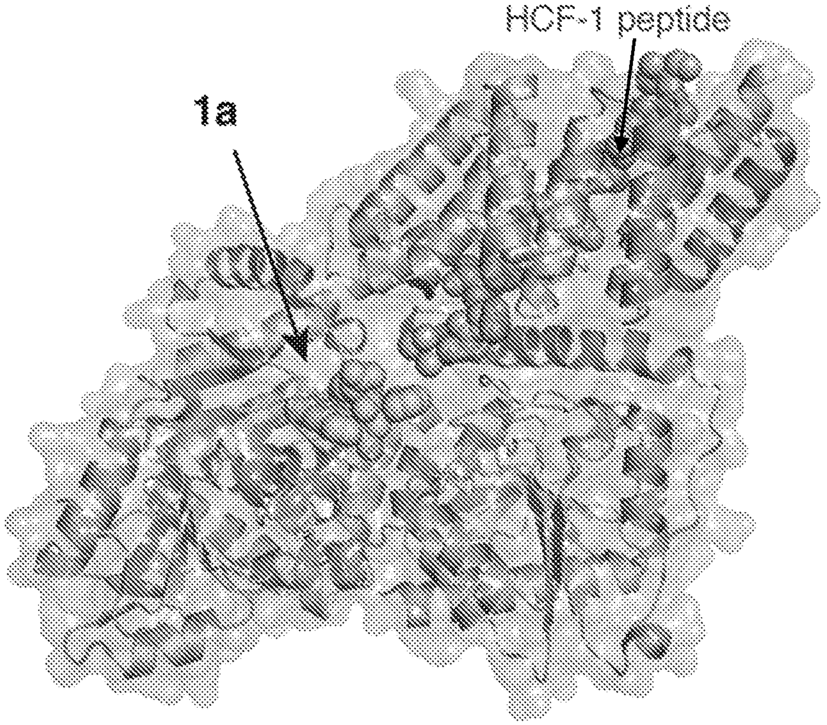
Figure 1C:
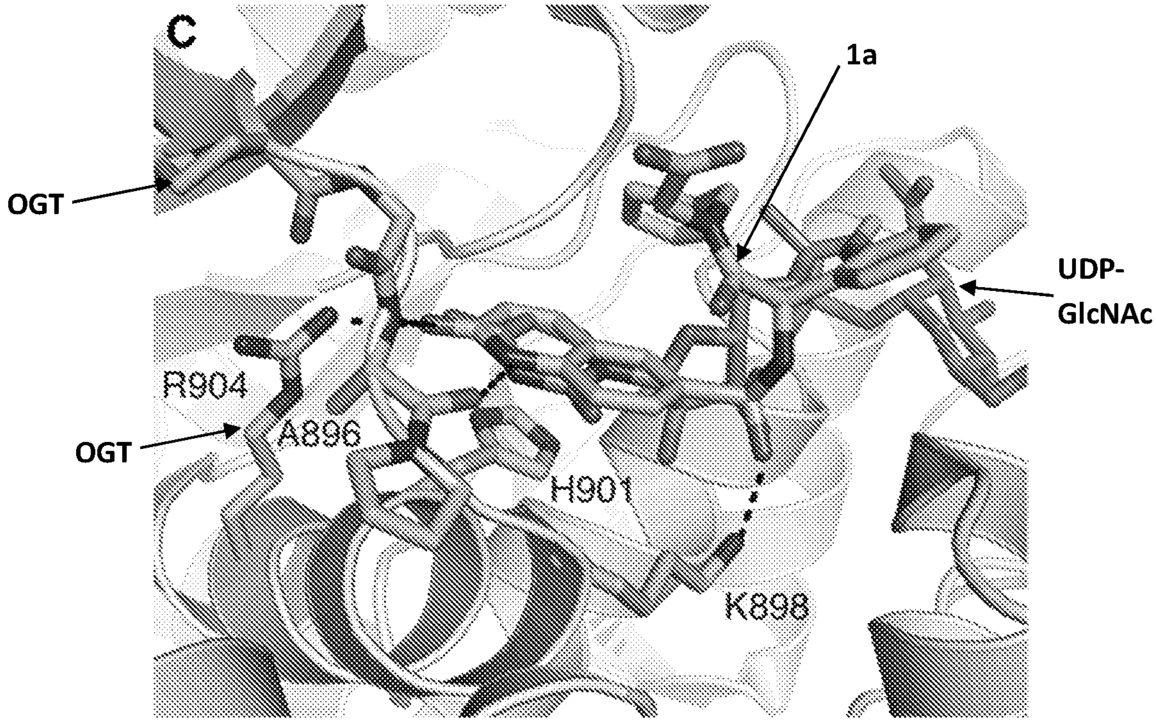
Figure 6A:
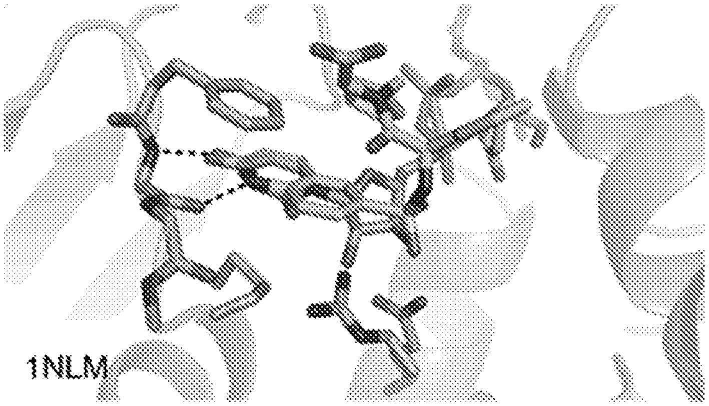
FIGS. 6A to 6C show that Q6S may be a privileged fragment. The Q6S group may serve as a useful starting point for design of inhibitors for other UDP-sugar dependent glycosyltransferases. Shown here are superpositions of the Q6S in 2a with (FIG. 6A) a MurG:UDP-GlcNAc complex (PDB: 1NLM), (FIG. 6B) a complex between sucrose synthase-1 and a breakdown product of UDP-glucose (PDB: 3S28), and (FIG. 6C) UDP-glucosyltransferase UGT74F2 in complex with UDP, β-D-glucose, and salicylic acid (PDB: 5U6M). Dashed lines indicate expected hydrogen bond contacts between a Q6S group and the protein.
Figure 6B:
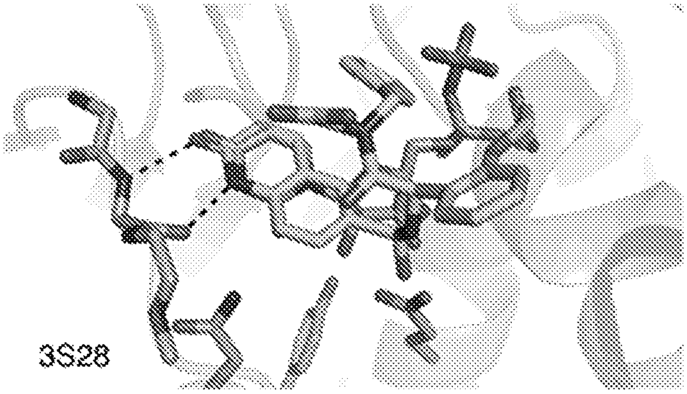
Figure 6C:
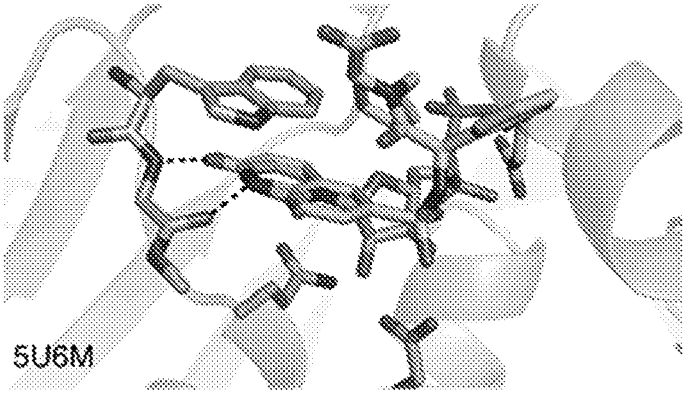

Example 1. Structure-Based Evolution of Low Nanomolar O-GlcNAc Transferase Inhibitor A series of compounds containing the Q6S scaffold were made and a crystal structure of OGT bound to compound 1a was obtained (FIGS. 1A and 1B). This structure inspired three related agents, 2a, 3a, and 4a, that were also crystallized with OGT (FIG. 1A). The structures of these complexes revealed that the Q6S moiety is a faithful uridine mimic (FIG. 1C). Like uracil, the quinolinone ring stacks directly over the imidazole of $His^{901}$; the nitrogen and adjacent carbonyl of the heterocycle make the same contacts to $Arg^{904}$ and $Ala^{896}$ as N3 and O4 of uracil. In addition, a sulfonamide oxygen hydrogen bonds with $Lys^{898}$, mimicking contacts made by the ribose hydroxyls. The remarkable overlap between the quinolinone and uridine suggests this motif may serve as a privileged fragment for designing inhibitors against other glycosyltransferases (FIG. 6).

Figure 1D:
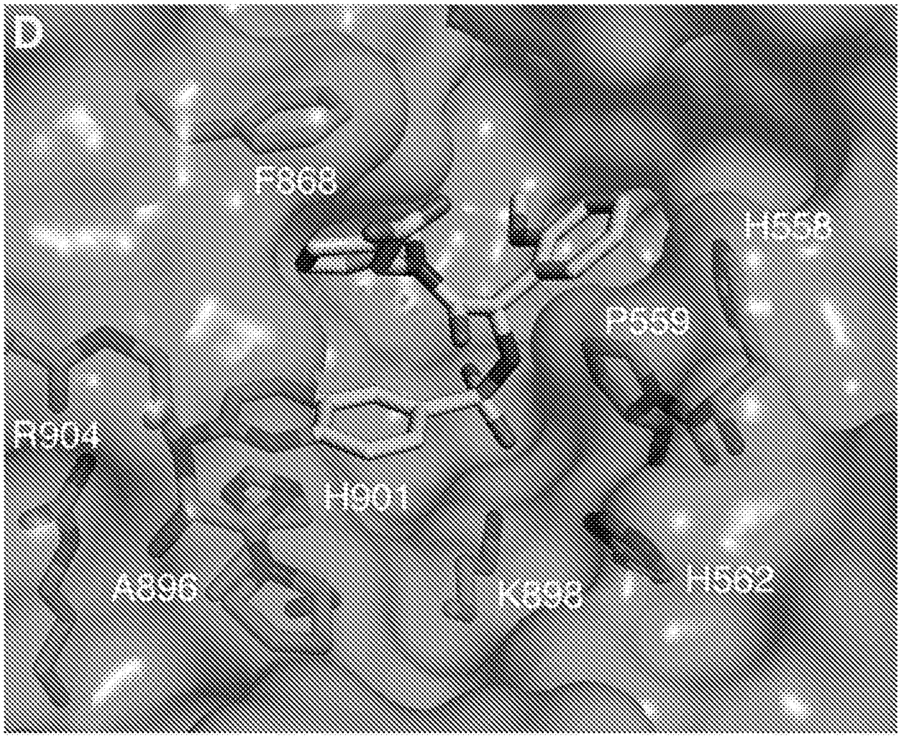
Figure 7A:
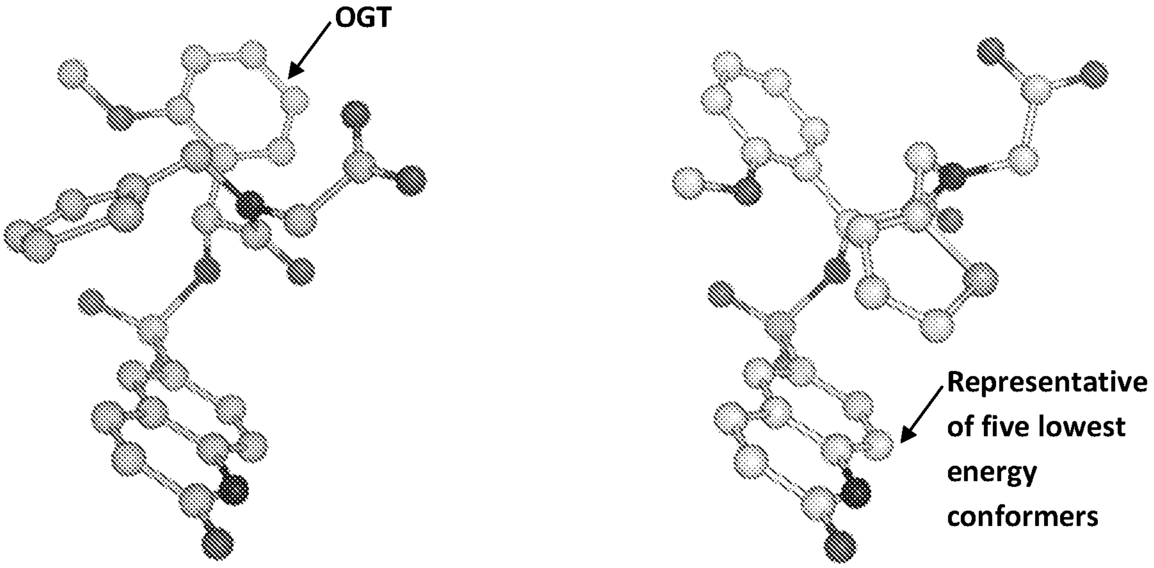
FIGS. 7A and 7B show that the most stable conformer of 1a matches that observed in the OGT:1a structure.
Figure 7B:
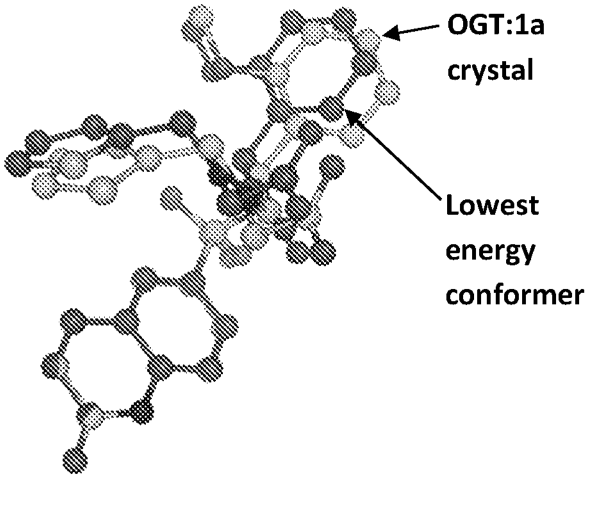
Figure 8:
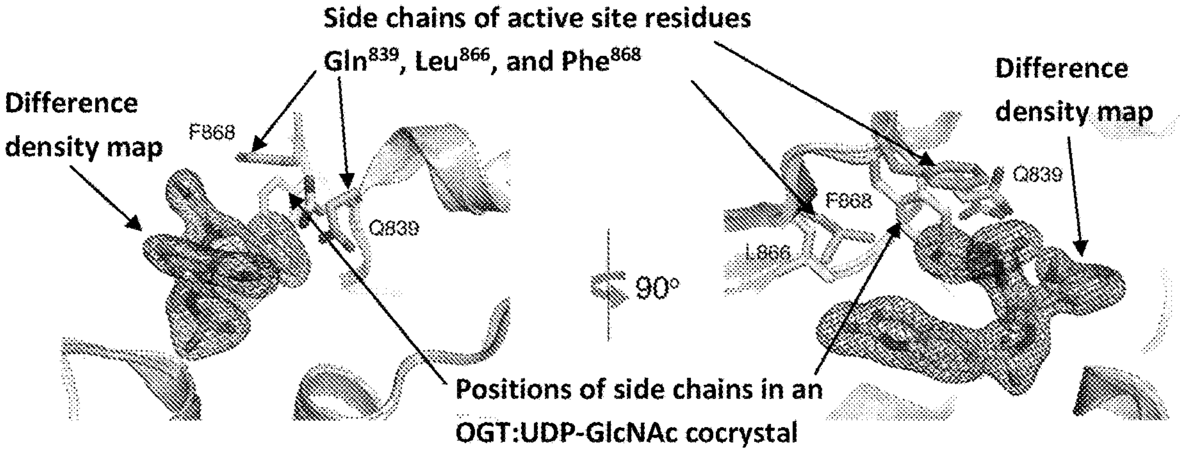
FIG. 8 shows the thiophene in 1a forces shifts in active site side chains that are not observed upon UDP-GlcNAc binding. Side chains of active site residues $Gln^{839}$, $Leu^{866}$, and $Phes^{68}$ shift upon binding of 1a. Positions of those side chains in an OGT:UDP-GlcNAc cocrystal are labeled (PDB: 4N3C). The difference density map, $F_0$-$F_c$, of 1a is shown in mesh as labeled, contoured to 3a. A 900 rotation shows an alternate view of the crystal.

The structures showed that the Q6S compounds have a U-shaped architecture that helps explain their ability to inhibit OGT. The S—N bond veers up from the plane of the quinolinone ring and the backbone of the molecule folds back over it, positioning the substituents on the disubstituted amide directly over the quinolinone (FIG. 1D). Density functional theory calculations show that the conformer observed in the crystal structures is also the most stable conformer (FIG. 7). The inhibitor's U-shape allows it to fully occupy a space that accommodates the uridine and the segment of peptide that lies over it. Indeed, the thiophene substituent on the disubstituted amide penetrates so deeply into the active site that $Gln^{839}$, $Leu^{866}$, and $Phes^{68}$ must rotate to make room (FIG. 8).

Figure 9:
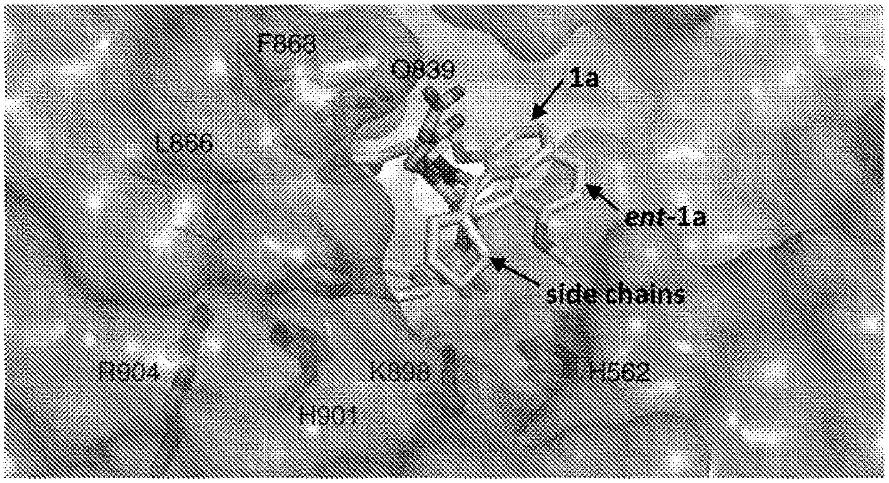
FIG. 9 shows that the crystal structure of the S-enantiomer of 1a confirms the importance of the Q6S group. An overlay of 1a with the enantiomer of 1a (ent-1a) confirms that the Q6S group binds identically to OGT regardless of inhibitor stereochemistry. However, fewer contacts are made by ent-1a to the active site as indicated by the lack of shifts in the side chains of $Gln^{839}$, $Leu^{866}$, and $Phe^{868}$ in the ent-1a:OGT structure.

A structure of OGT bound to the S-enantiomer of exemplary OGT inhibitor 1a (ent-1a), which binds more weakly to OGT than the R-enantiomer, was also obtained (Table 1). The Q6S element in ent-1a binds exactly as in 1a, confirming the importance of this fragment in binding (FIG. 9). The switch in chirality of the substituted phenylglycine means that the substituents on the disubstituted amide project away from, rather than into, the deeper recesses of the active site. The weaker interactions of the amide substituents with active site residues undoubtedly drive the lower affinity of the S-configured compounds.

TABLE 1

| Binding of compounds to OGT[a]. | |
|---|---|
| UDP | 1.0 ± 0.2 (0.54 ± 0.01)[b] |
| UDP-GlcNAc | 16 ± 4 (16.1 ± 0.1)[b] |
| 1a | 0.14 ± 0.06 |
| ent-1a[c] | 4.1 ± 3.0 |
| 2a | 0.005 ± 0.001 |
| ent-2a | 0.14 ± 0.05 |
| 3a | 0.045 ± 0.02 |
| 4a | 0.008 ± 0.001 |

Figure 1E:
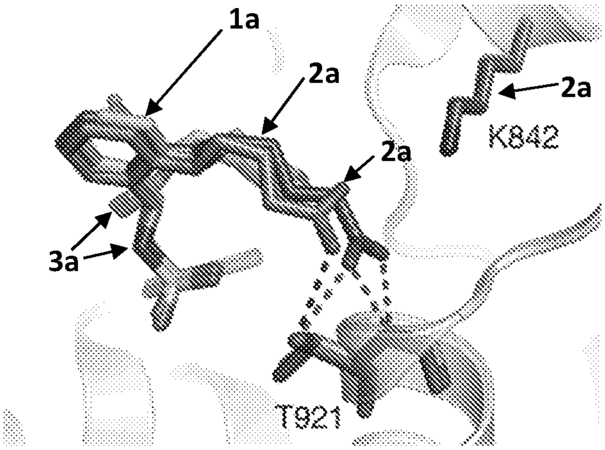
Figure 10:
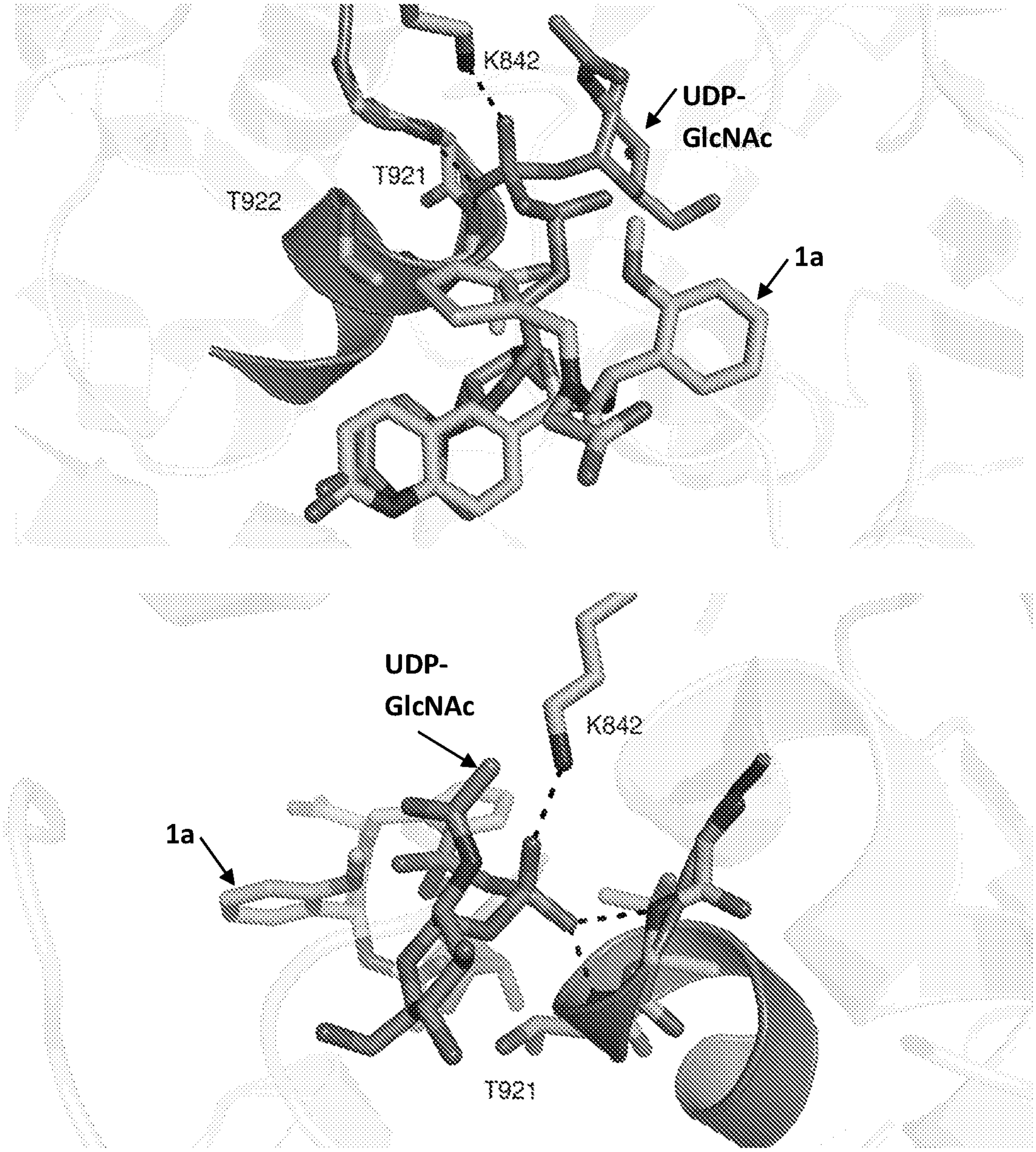
FIG. 10 shows the methoxy group of 1a points toward an unoccupied region of the active site. An overlay of 1a with UDP-GlcNAc (PDB: 4N3C) shows that a large portion of the OGT active site remains unsampled by 1a. Phosphate oxygens make contacts to residues $Lys^{842}$ and $Thr^{921}$.
Figure 11A:
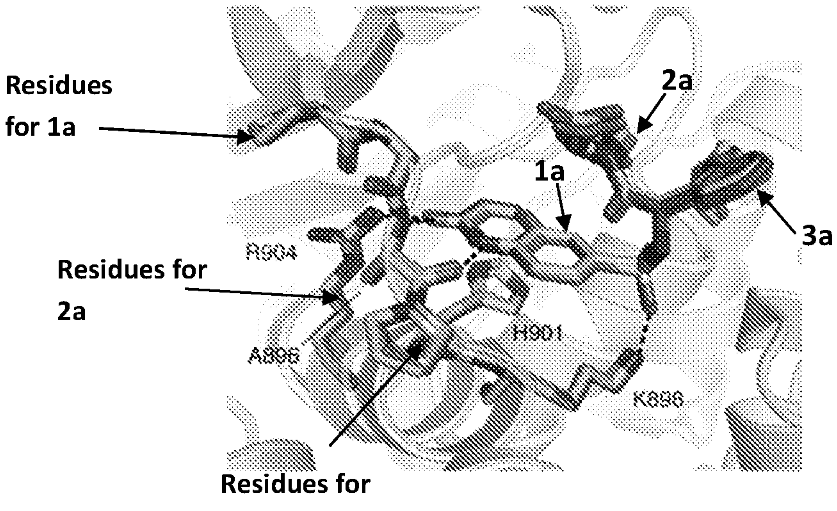
FIGS. 11A to 11C show a comparison of inhibitor structures.
Figure 11B:
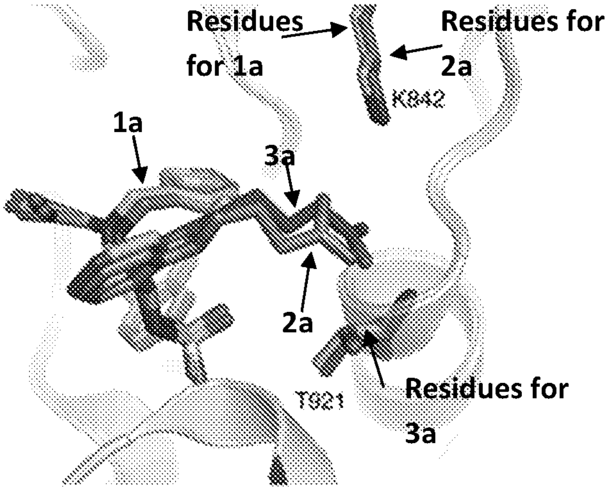
Figure 11C:
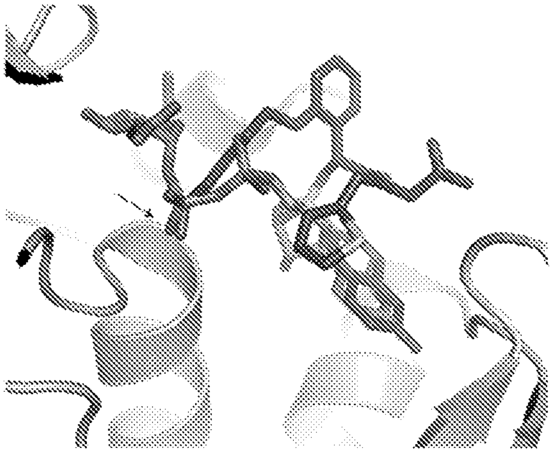

[a]Binding affinity ($K_d$ ± s.d.) in μM,
[b]determined by SPR[16],
[c]ent = enantiomer Analysis of the OGT complex with exemplary OGT inhibitor 1a suggested two strategies to modify these inhibitors to make additional contacts. One strategy exploited the observation that the ortho-methoxy group points toward an unoccupied region of the active site where the diphosphate of UDP-GlcNAc would bind (FIG. 10). Previous structural studies of the OGT:UDP-GlcNAc complex showed that one of the anomeric phosphate oxygens forms hydrogen bonds to the backbone amides at the N-terminus of a proximal helix[4b], while another contacts the side chain amine of catalytically essential $Lys^{842}$.[4a-d] The binding pose of 1a suggested that it would be possible to mimic these interactions by attaching a carboxylate to the phenyl ring via a sufficiently long linker to bridge the distance to the phosphate binding site. Compounds 2a and 3a were prepared with linkers containing three and four methylenes and structures of OGT bound to both inhibitors were solved. Both compounds make additional contacts to OGT in the expected region of the active site (FIGS. 1E, 11A, 11B). Strikingly, the pendant carboxylate of compound 3a overlaps almost perfectly with the UDP-GlcNAc phosphate and makes the same interactions with the proximal helix (FIG. 11C). While the carboxylate on 2a is not within H-bonding distance of the N-terminal amides, one of its oxygens interacts with the side chain of $Thr^{921}$ while the other is oriented towards $Lys^{842}$, which is 3.7 Å away (FIG. 1E).

Figure 1F:
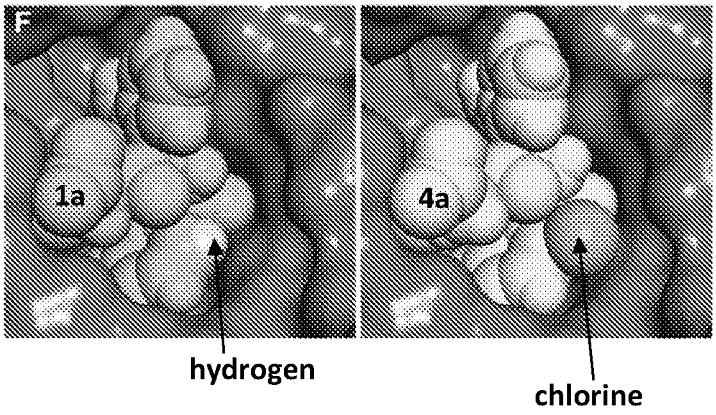

The second strategy focused on including a small substituent on the quinolinone ortho to the sulfonamide because analysis of the crystal structures suggested it would be possible to achieve a tighter fit in the uridine pocket. Chlorine derivative 4a was prepared and the crystal structure of the complex with OGT confirmed the expected binding pose (FIG. 1F).

Figure 2A:
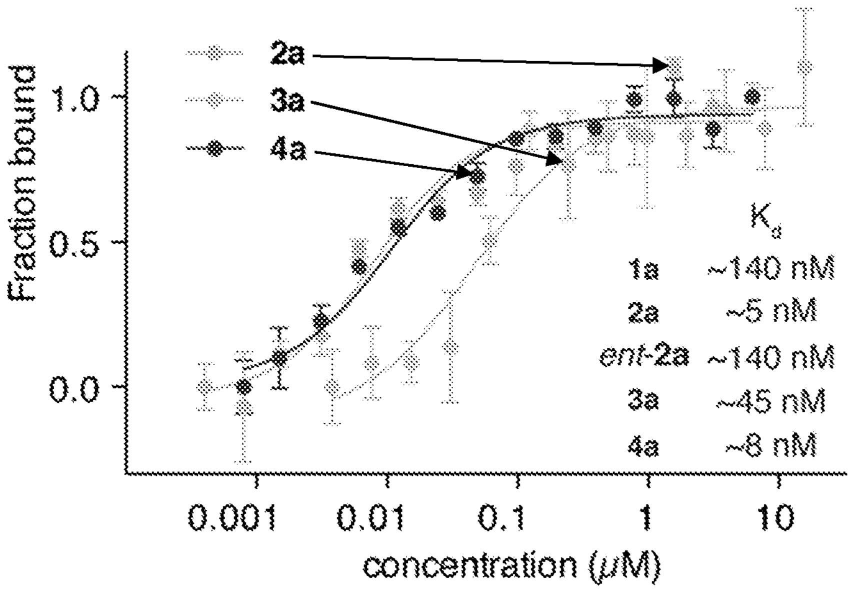
FIGS. 2A to 2E show exemplary OGT inhibitors bind OGT with nanomolar affinity and block OGT activity in cells.
Figure 12:
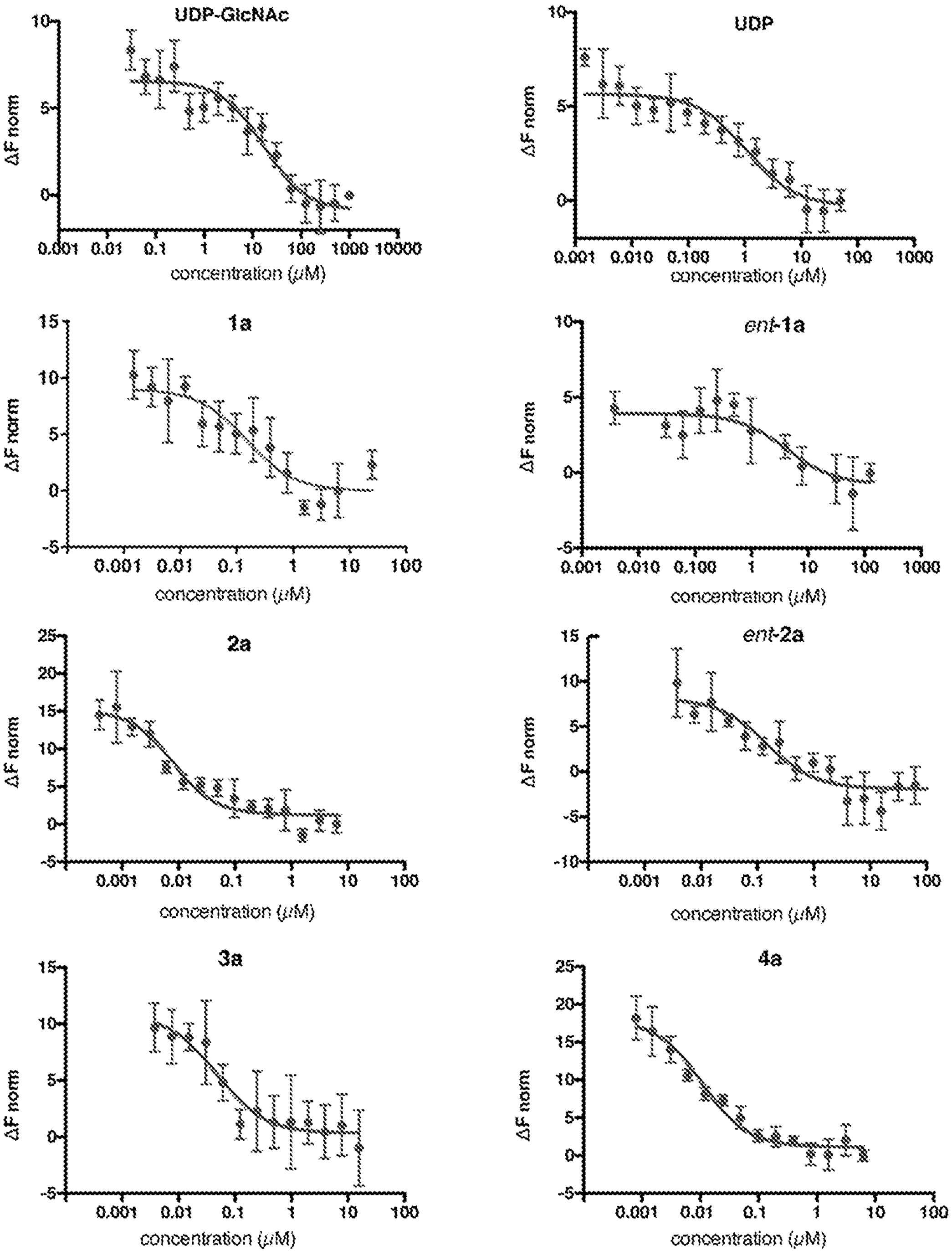
FIG. 12 shows binding curves of inhibitors with wild-type OGT as determined by MST. Data shown as normalized change in fluorescence ($\Delta F_{norm}$) relative to highest concentration used vs. inhibitor concentration (μM). Error bars represent standard deviation (s.d.) at least three replicates.
Figure 13A:
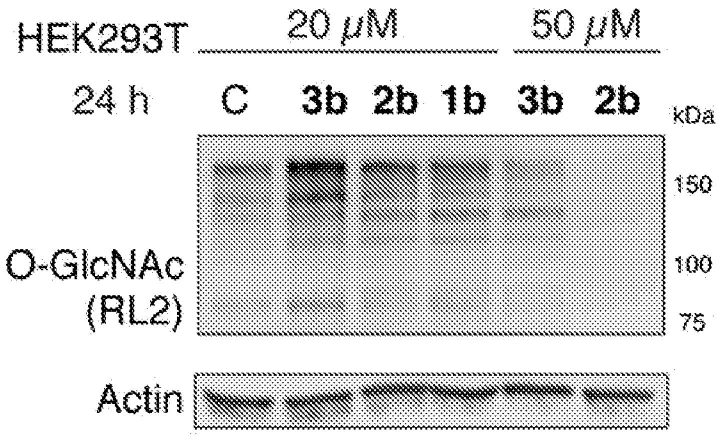
FIGS. 13A to 13E show effects of O-GlcNAcylation levels after treating HEK293T cells with 1b, 2b, ent-1b, and ent-2b.
Figure 13B:
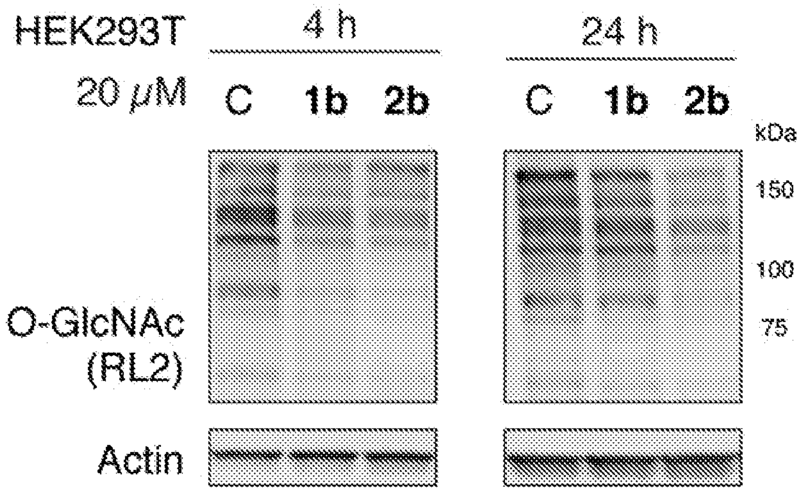
Figure 13C:
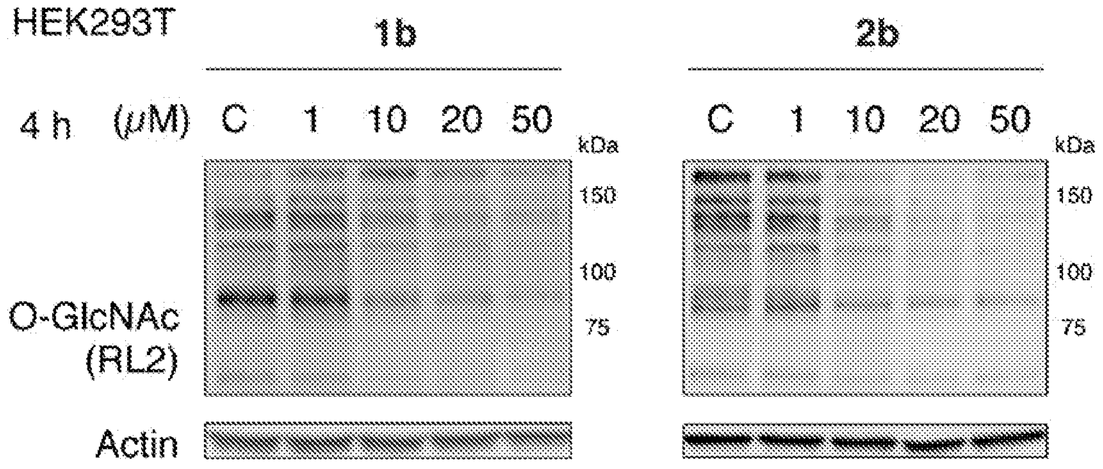
Figure 13D:
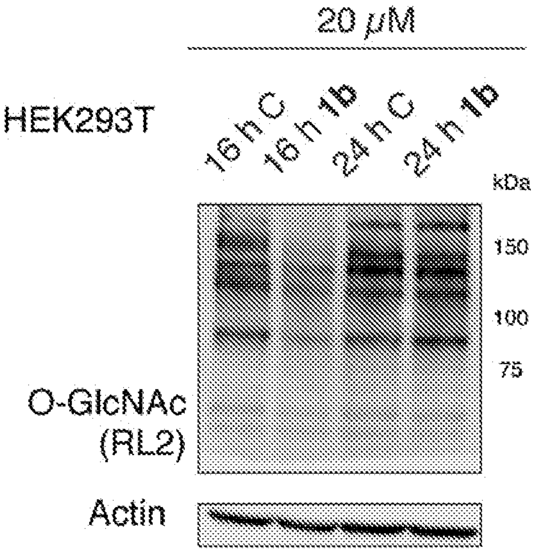
Figure 13E:
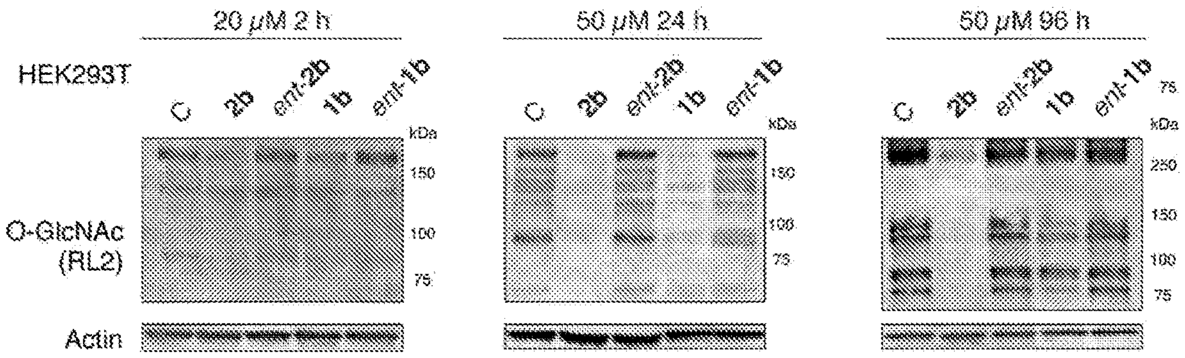
Figure 14A:
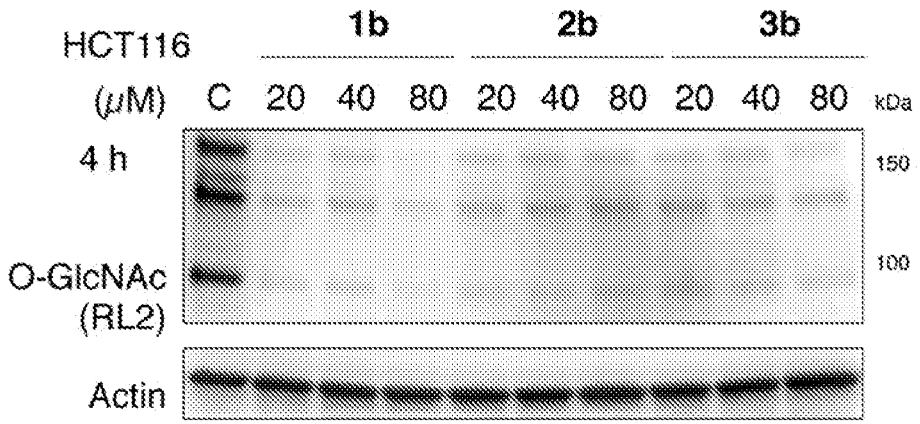
FIGS. 14A to 14D show the inhibitors are effective at reducing O-GlcNAc levels in cell lines that model colon and prostate cancers.
Figure 14B:
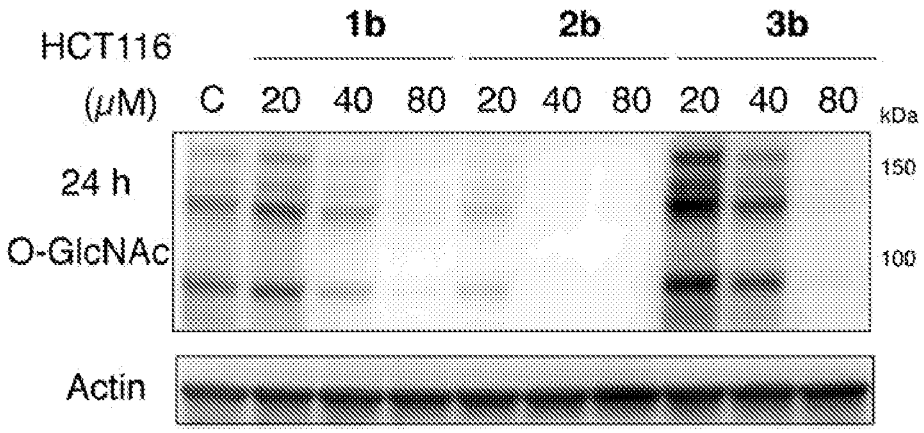
Figure 14C:
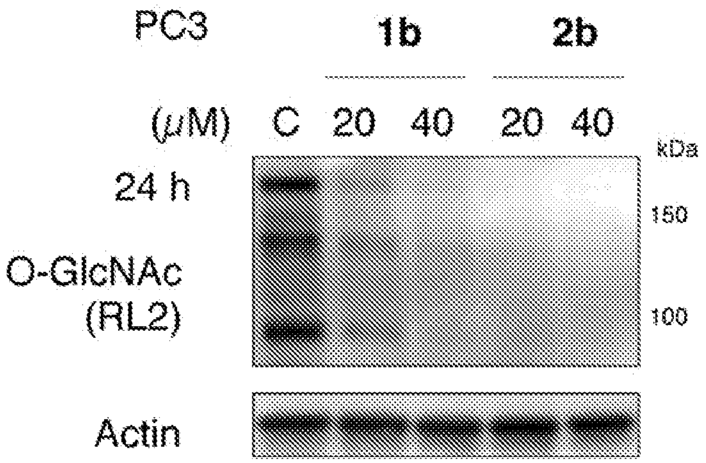
Figure 14D:
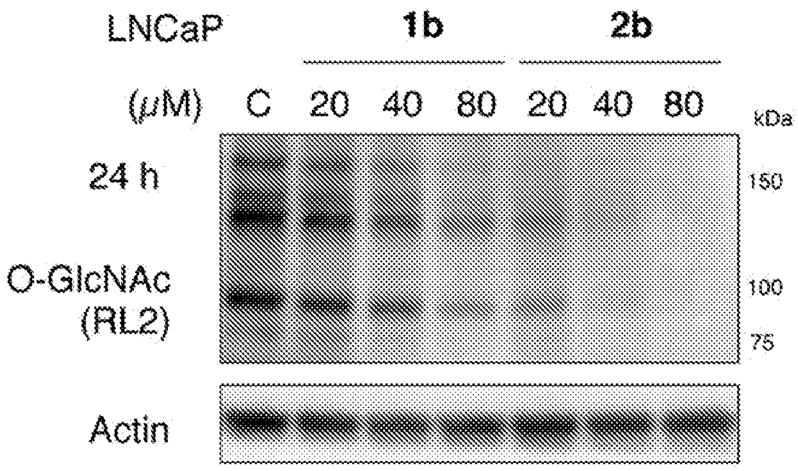
Figure 15A:
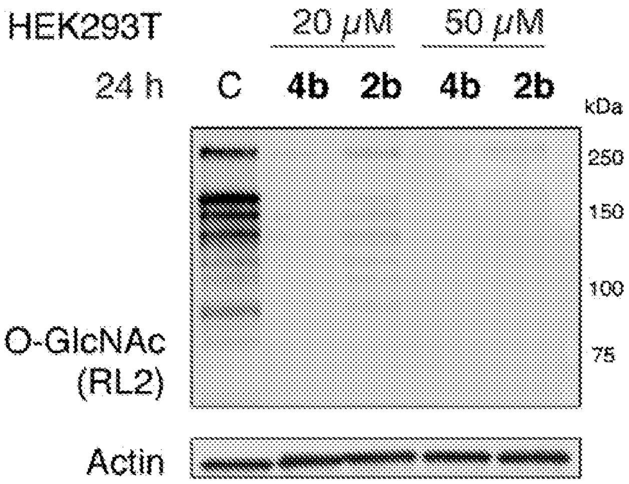
FIGS. 15A to 15F show exemplary compound 4b is more effective than other compounds at inhibiting OGT in cells.
Figure 15B:
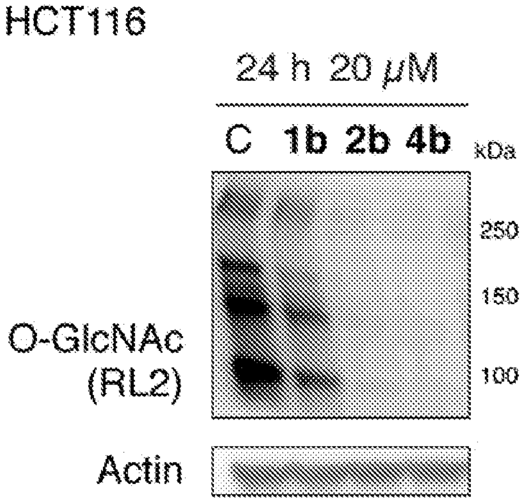
Figure 15C:
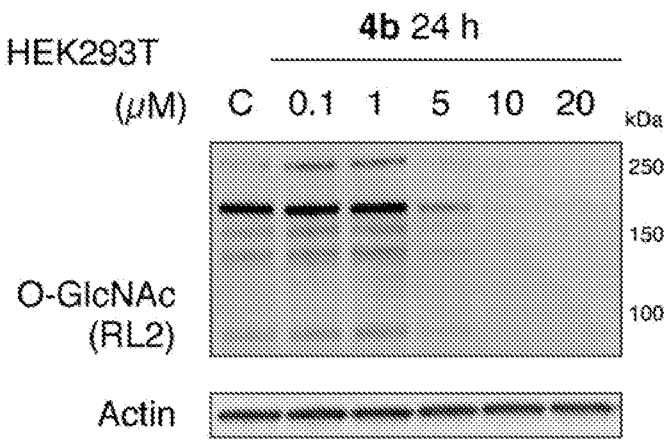
Figure 15D:
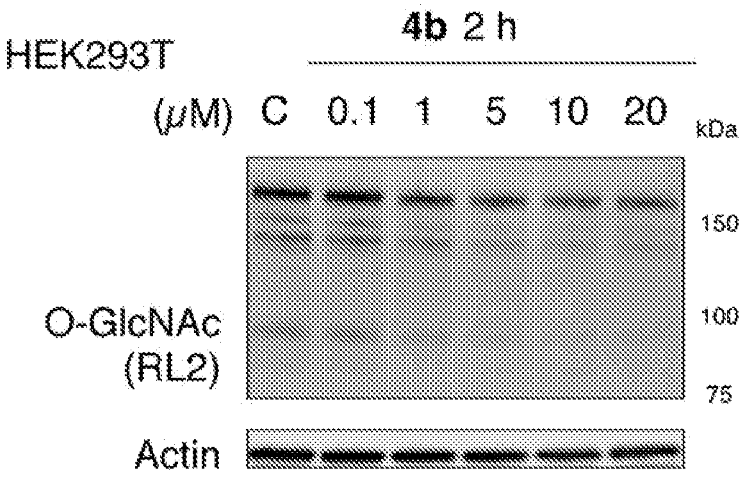
Figure 15E:
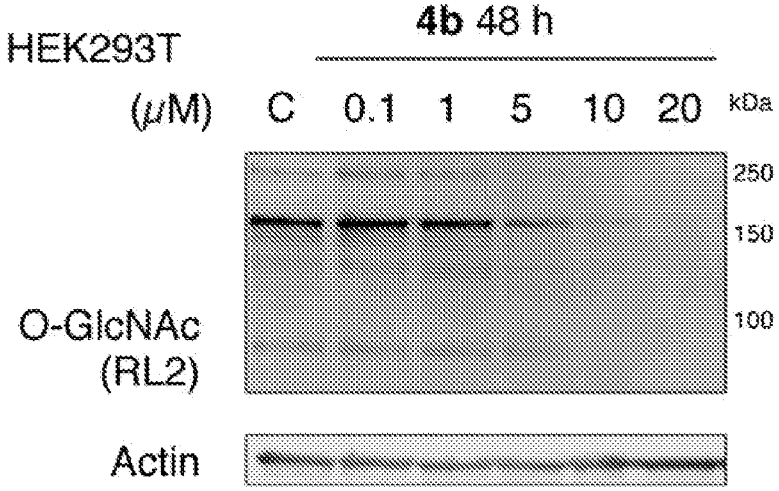
Figure 15F:
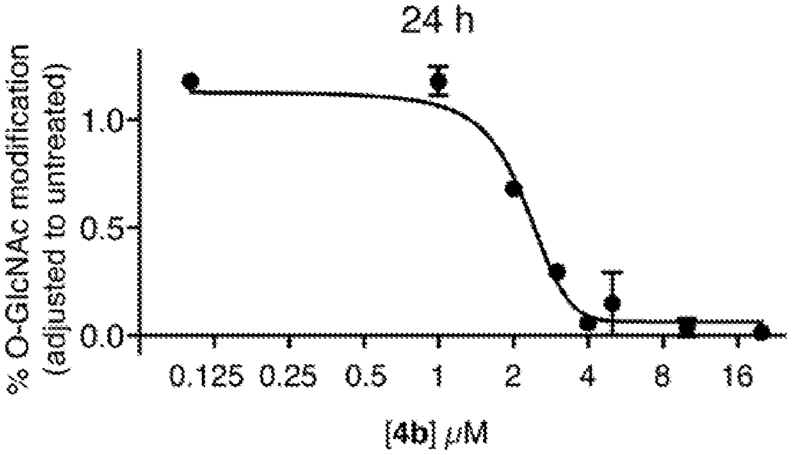

To measure the dissociation constants for each of the inhibitors and their enantiomers, microscale thermophoresis (MST) was used after it was confirmed that the method produced $K_d$s for UDP and UDP-GlcNAc similar to those obtained by surface plasmon resonance (Table 1, FIG. 12).[4d] Compounds 2a and 4a bound OGT with $K_d$s of ~5 and ~8 nM, respectively, while the $K_d$s of 1a and 3a were an order of magnitude or more higher (FIG. 2A). The S-enantiomers tested bound at least ten-fold more weakly to OGT than the corresponding R-enantiomers. The tighter binding of 2a compared with 3a is likely explained by a stronger interaction of the negatively-charged carboxylate of 2a with the positively charged $Lys^{842}$ amine combined with a smaller loss in conformational entropy due to immobilization of the shorter linker. The tighter binding of 4a compared with 1a is attributed to its snugger fit in the binding pocket.

Figure 2B:
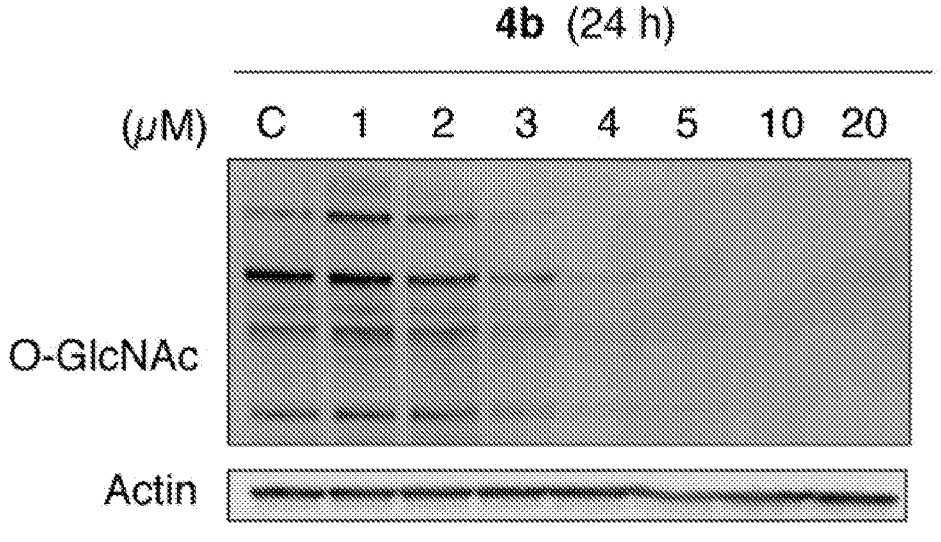
Figure 2C:
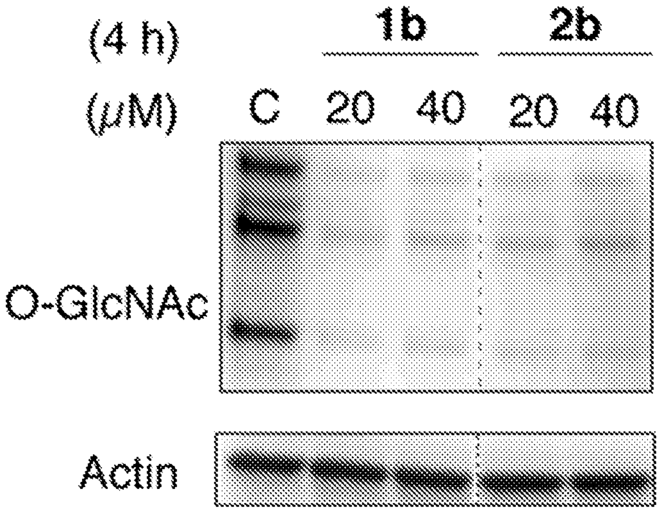
Figure 2D:
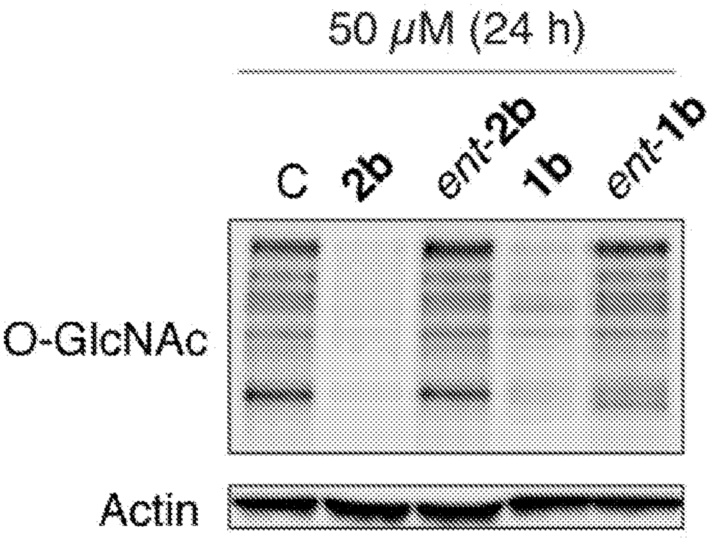

To assess the cellular activity of these inhibitors, the corresponding ester derivatives were prepared (compounds 1b-4b) to enhance cell penetration and their ability to inhibit global O-GlcNAcylation in HCT116, HEK293T, PC3, and LNCaP cells was examined (FIGS. 2B-E, 13-15). Intracellular esterases cleave esters rapidly, and the corresponding carboxylic acid forms of these compounds are likely the active species in cells. Compounds 2b and 4b had the best activity, with 4b reducing O-GlcNAc levels almost completely by 5 μM (FIGS. 2B, 15). At short treatment times (<8 hr), 1b was also a decent inhibitor (FIGS. 2C, 13A); however, O-GlcNAc levels began to recover at longer treatment times with this compound (FIGS. 13B-13D, 14A, 14B). The more sustained cellular effects of 2b and 4b compared with 1b are attributed to the greater affinity of their de-esterification products (2a and 4a) for OGT. The enantiomers tested did not substantially affect protein O-GlcNAc levels (FIG. 2D, 13D).

Figure 2E:
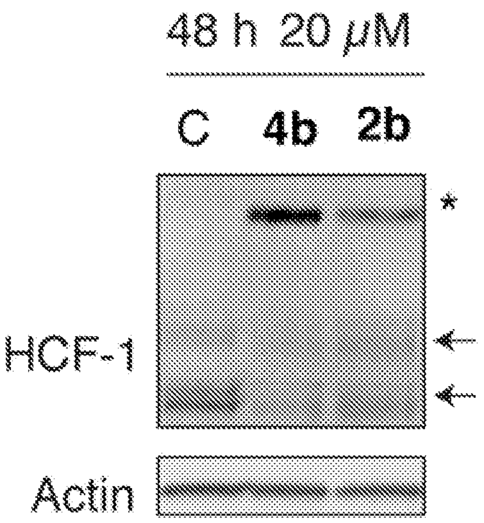
Figure 16A:
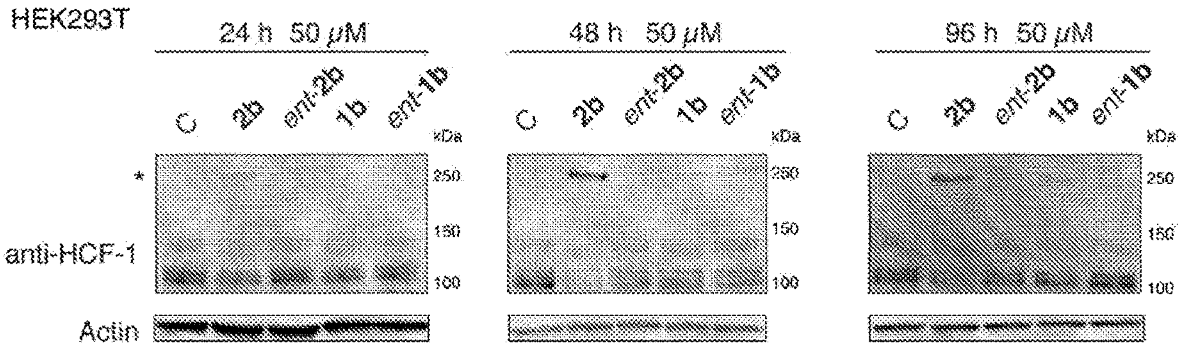
FIGS. 16A to 16C show treatment with OGT inhibitors results in reduced cleavage of HCF-1.
Figure 16B:
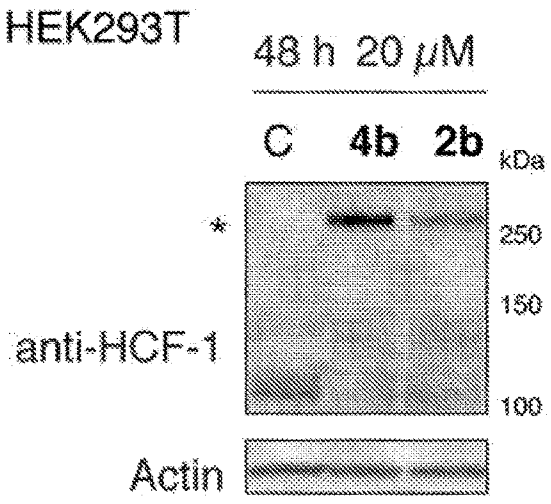
Figure 16C:
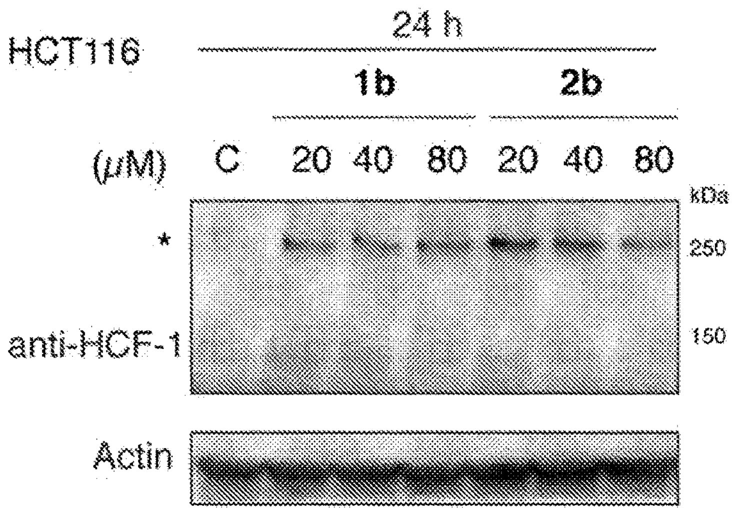
Figure 17A:
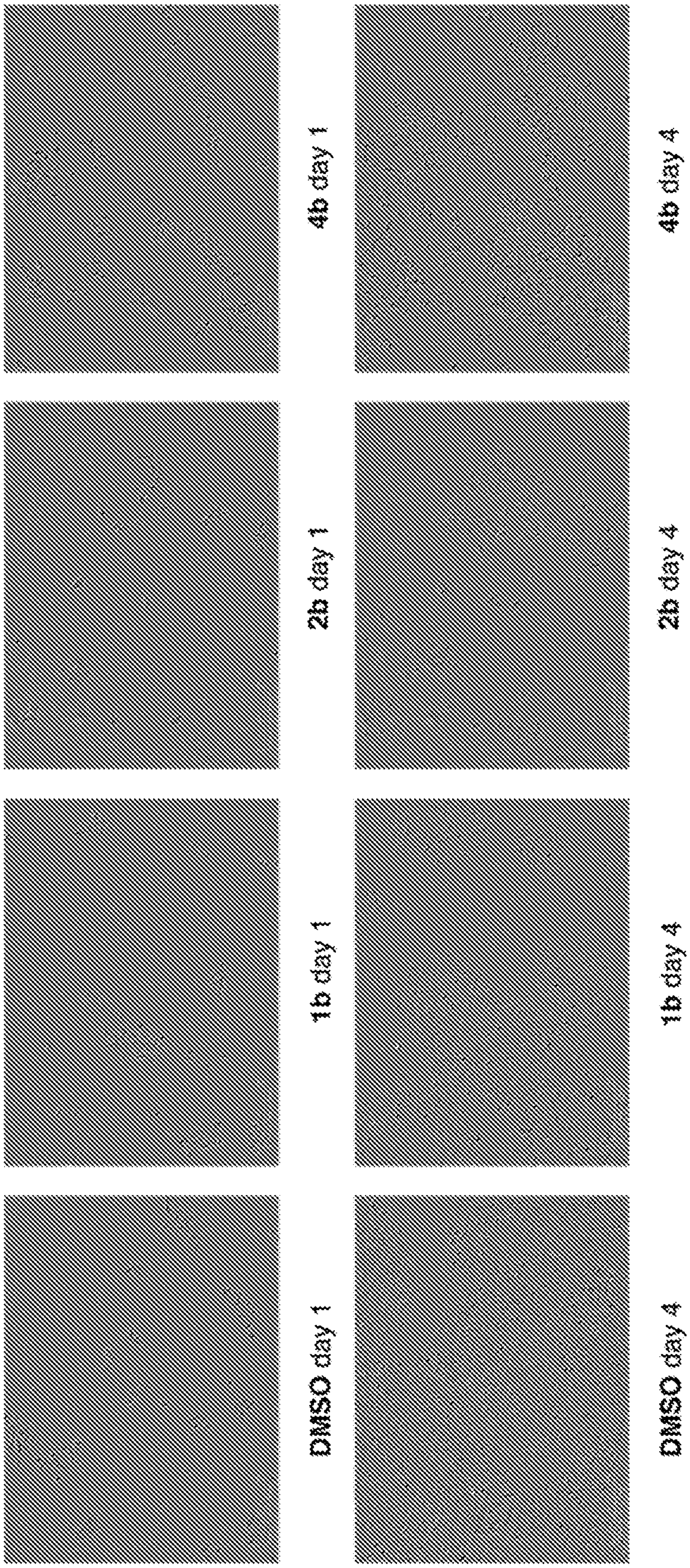
FIGS. 17A to 17D show treating cells with inhibitors causes a reduction in cells growth.
Figure 17B:
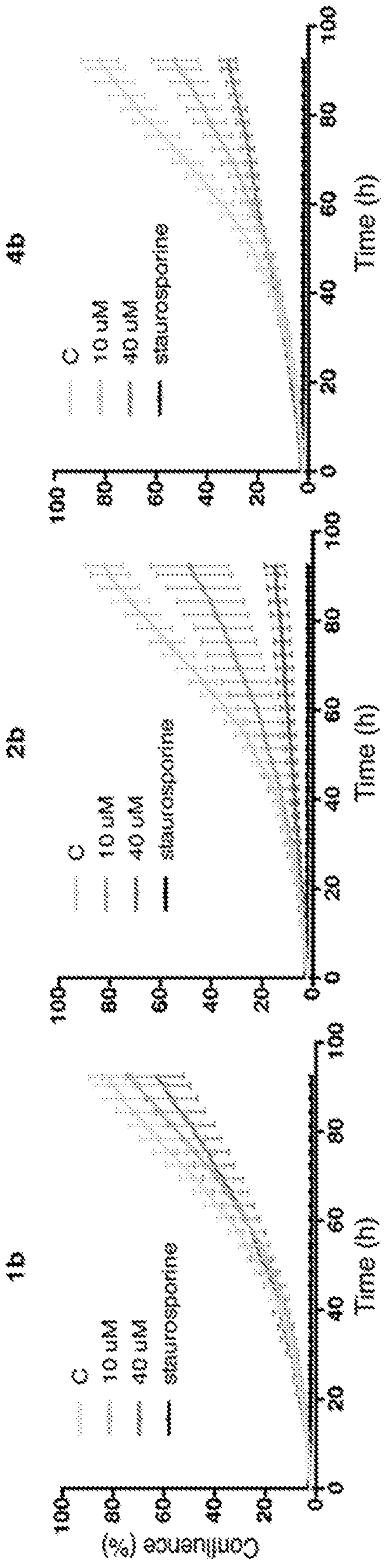
Figure 17C:
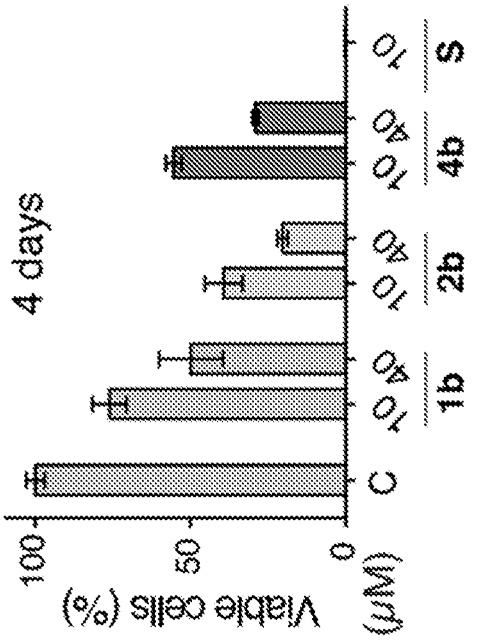
Figure 17D:
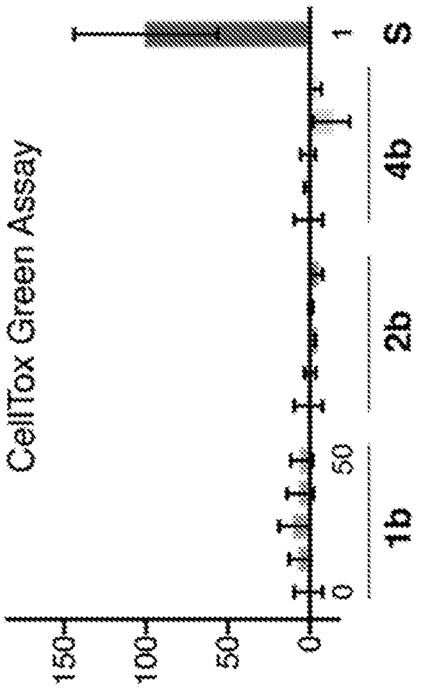

In addition to glycosylating Ser/Thr residues of proteins, OGT catalyzes cleavage of the cell-cycle regulator HCF-1 by glycosylating a glutamate in the HCF-1 cleavage sequence.[4c,7] An OGT inhibitor would be expected to block cleavage. Indeed, a decrease in HCF-1 cleavage products and the appearance of uncleaved HCF-1 in cells treated with 1b, 2b or 4b was observed (FIGS. 2E, 16). Because OGT knockdown is known to decrease cell proliferation,[8] the effects of 1b, 2b, and 4b on cell growth in culture over 96 hours were also monitored. Although there was no evidence of apoptosis, reduced growth of cells was observed over time (FIG. 17), consistent with the knockdown results.

Figure 3A:
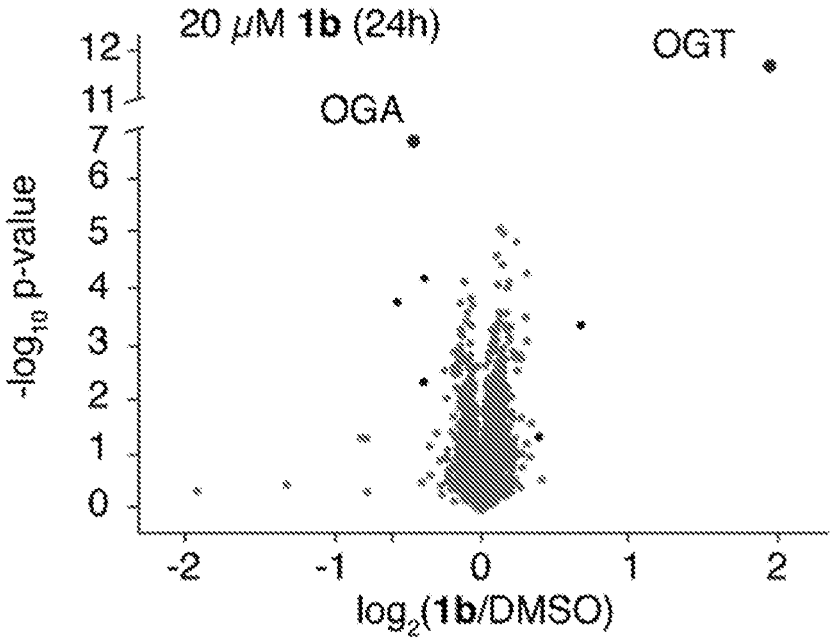
FIGS. 3A to 3D show that OGT inhibition results in increased abundance of OGT and changes in multiple proteins involved in ER stress and sterol metabolism.
Figure 3B:
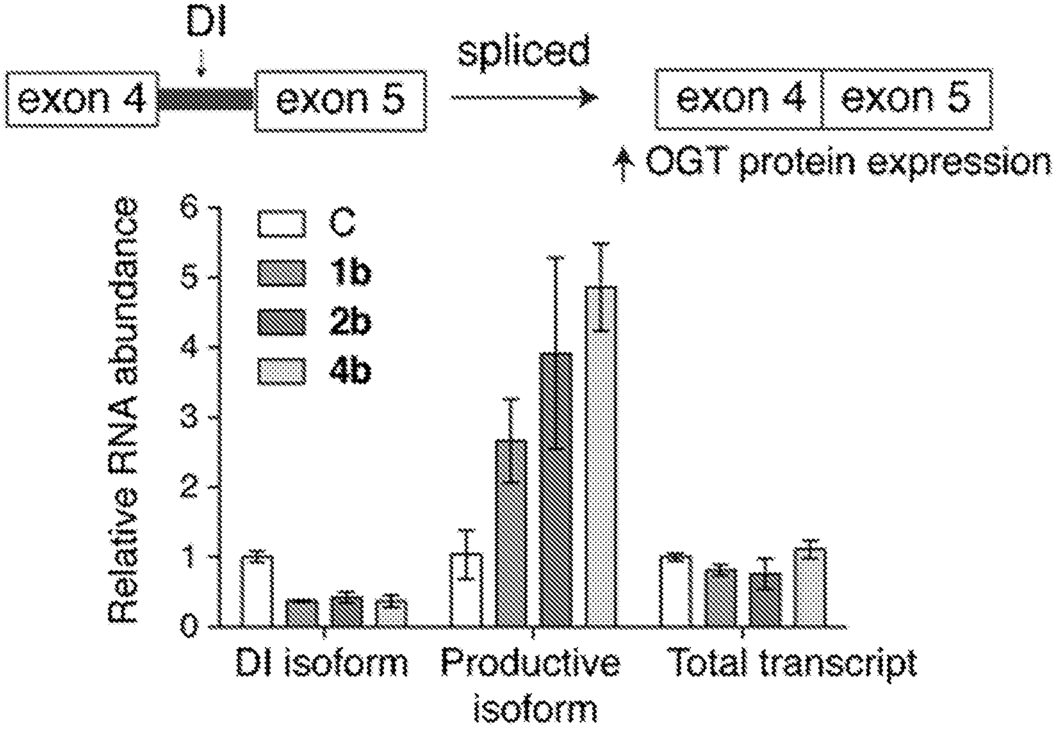
Figure 18:
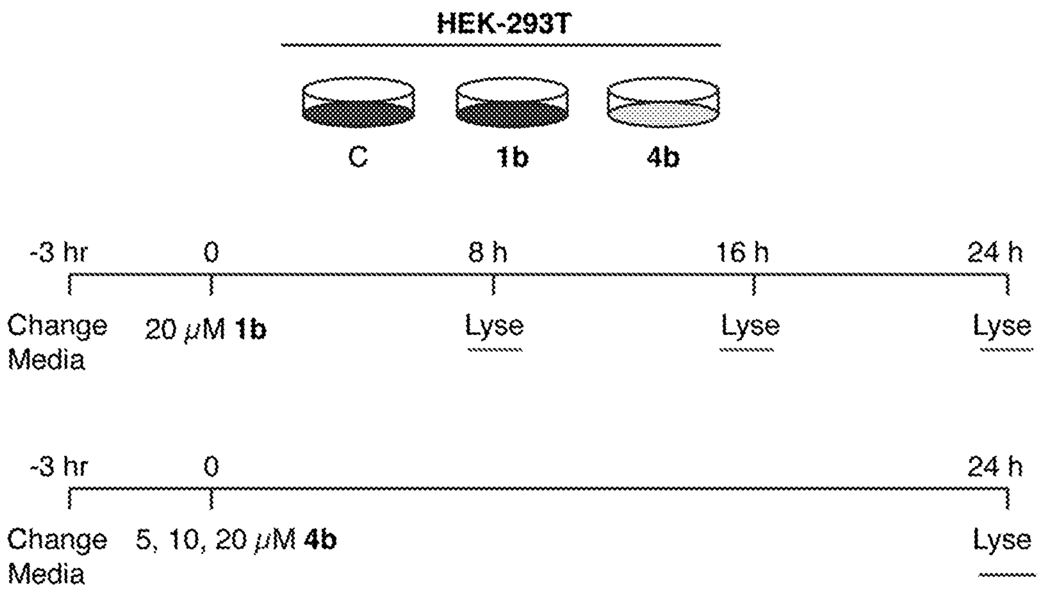
FIG. 18 shows schematics for proteomic experiments summarizing treatment conditions for 1b (top timeline) or 4b (bottom timeline). Media was changed 3 hours before treatment.
Figure 19A:
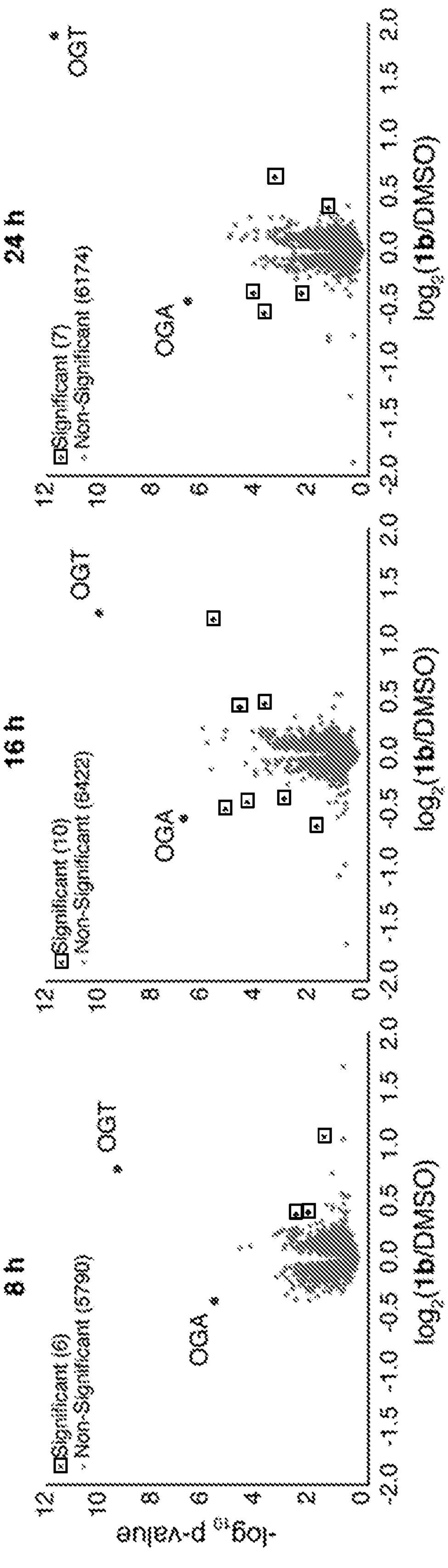
FIGS. 19A to 19C show proteomic analysis of exemplary inhibitor 1b in HEK293T cells.
Figure 19B:
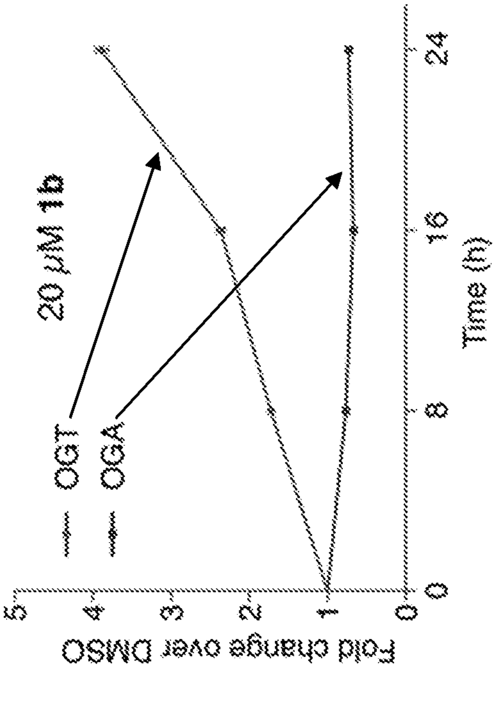
Figure 19C:
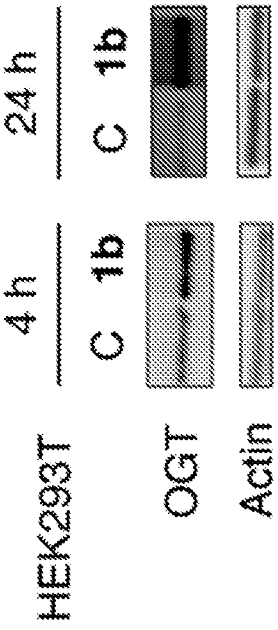

Quantitative proteomics were performed to assess how HEK293T cells responded to inhibitor treatment (FIG. 18). A time course performed with 20 μM 1b showed reciprocal changes in the abundance of OGT and OGA (FIGS. 3A, 19), which may explain the recovery in O-GlcNAc levels with this compound. Few significant changes were observed in abundance of other proteins at 24 hr with 1b, suggesting minimal off-target activity. Compensatory changes in OGT and OGA abundance have been observed previously when levels or activity of these proteins are perturbed.[3a,3b,8-9] Cells contain a large nuclear pool of partially spliced OGT transcript, and one mechanism for the rapid increase in OGT levels is increased cotranscriptional splicing of a detained intron to form productive mRNA.[9-10] Indeed, it was found that 2-hour treatment with 10 μM 1b, 2b or 4b increased detained intron splicing (FIG. 3B). That OGT transcript splicing is responsive to OGT inhibition indicates a feedback mechanism linking splicing with enzymatic activity, and highlights the importance of maintaining adequate cellular O-GlcNAc.

Figure 3C:
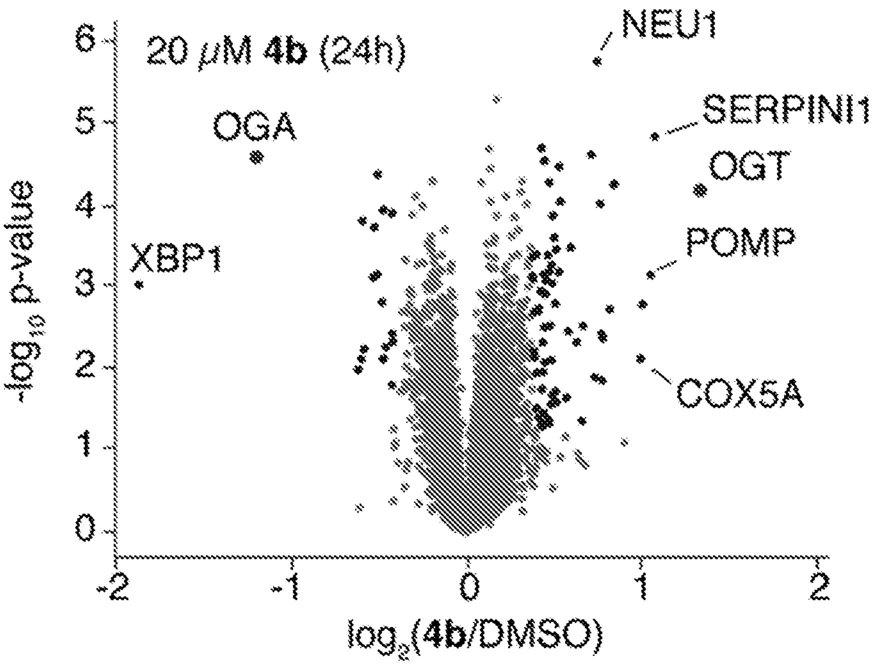
Figure 3D:
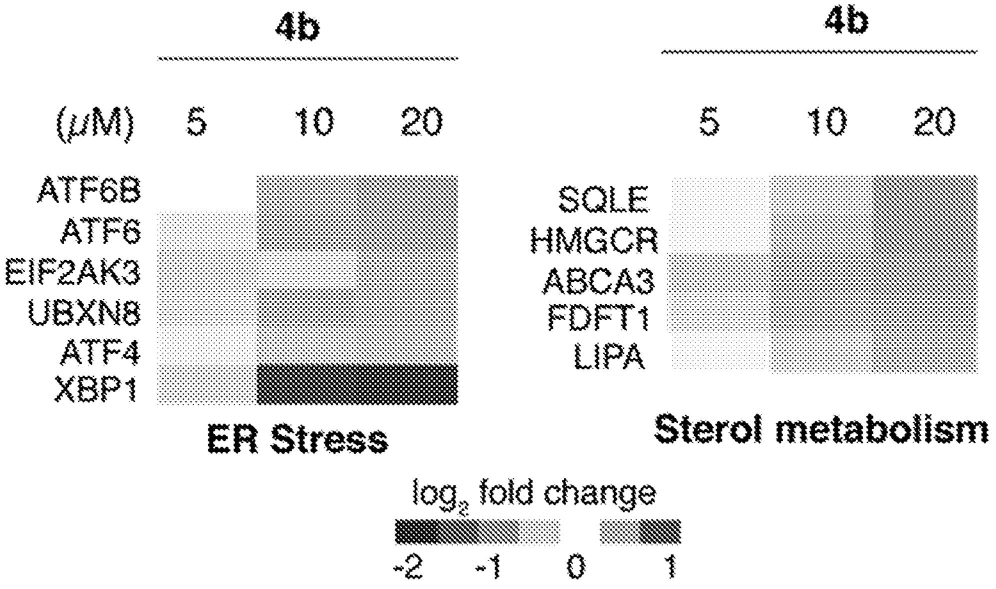
Figure 4:
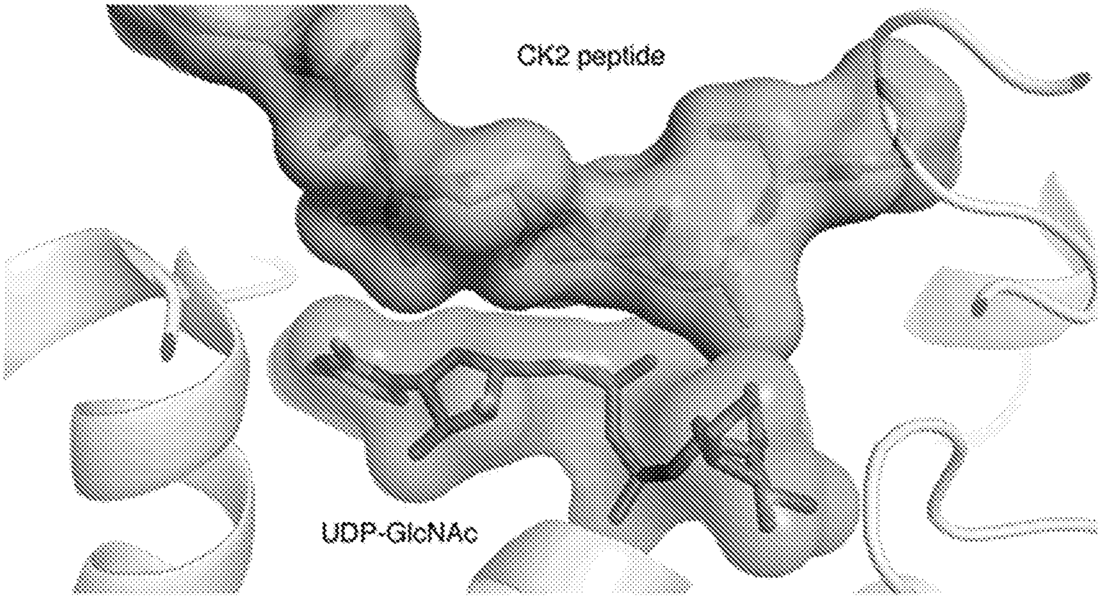
FIGS. 4 and 5 show that the OGT active site is large and hydrophilic.
Figure 5:
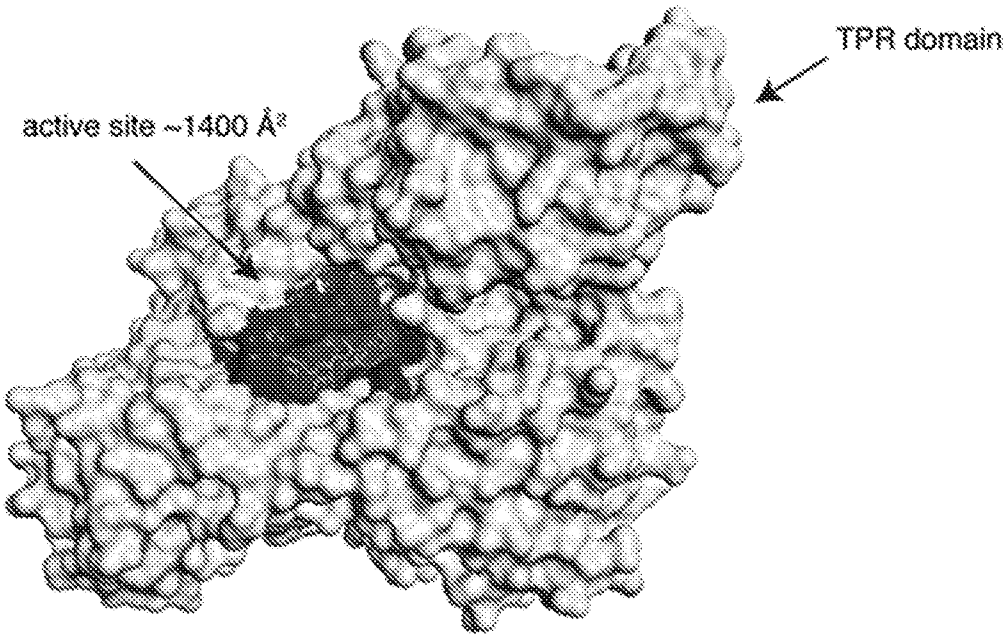
Figure 20A:
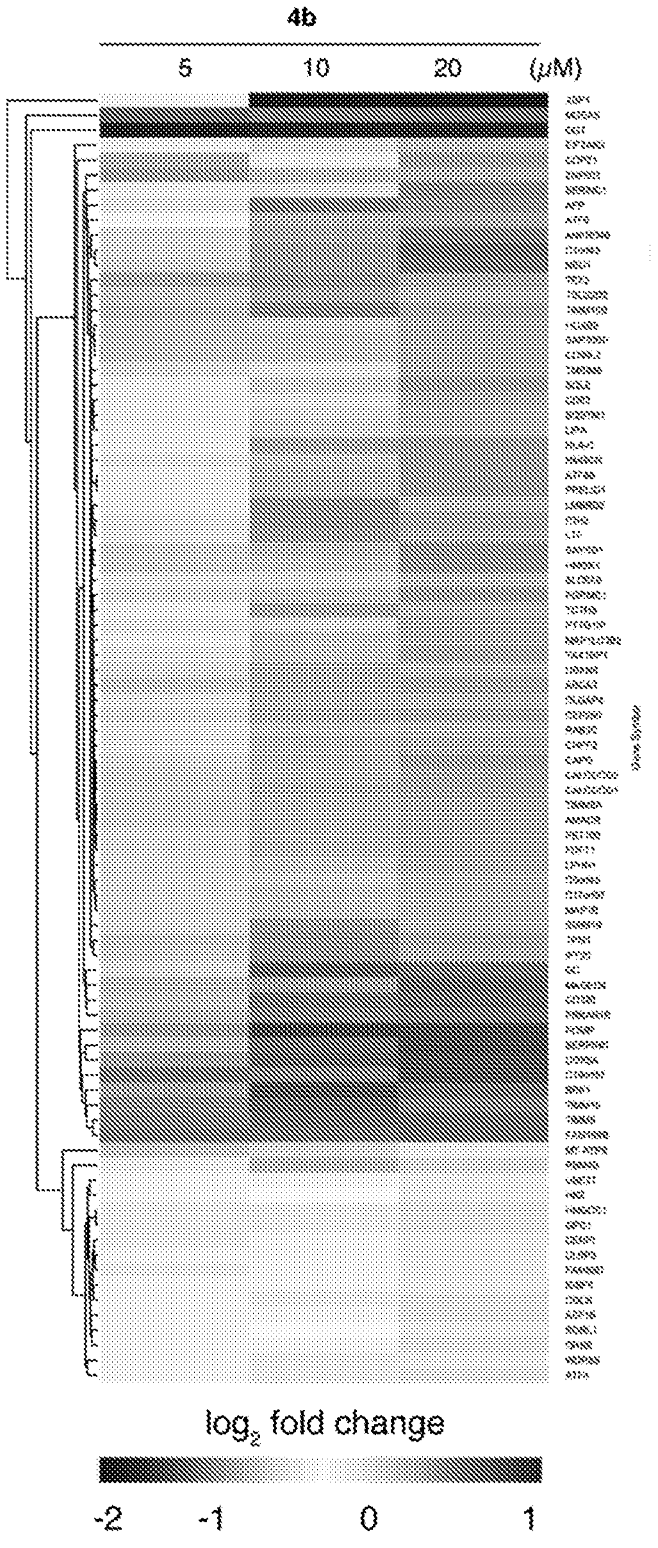
FIG. 20A shows an extended heatmap of proteins that exhibited significant changes in abundance after treatment of HEK293T cells with 20 μM 4b.
Figure 20B:
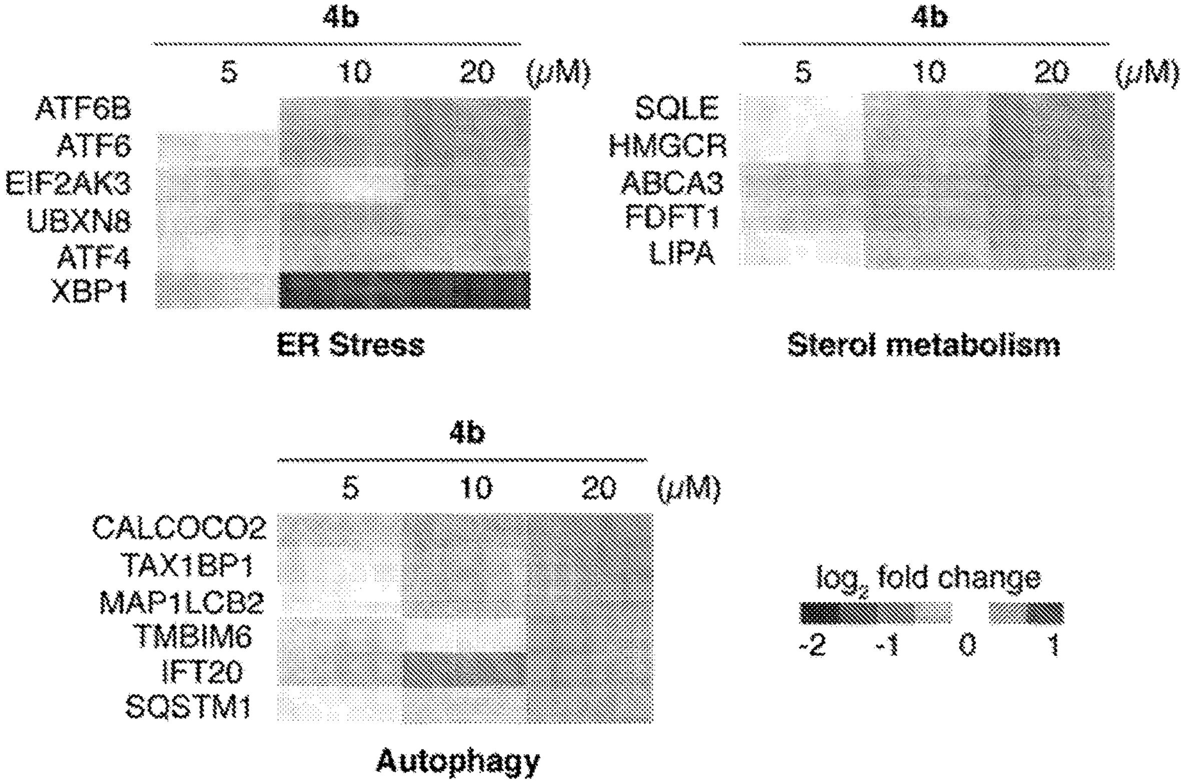
FIG. 20B shows the clusters of hits that were found centering around ER stress, sterol metabolism, and autophagy.

Quantitative proteomics were also performed with 4b, which causes prolonged inhibition of O-GlcNAc over 24 hr. 86 proteins, most showing increased abundance, changed significantly (FIGS. 3C, 20). These proteins included SQSTM1 (sequestosome-1), a protein involved in autophagy that was shown to increase upon conditional deletion of OGT in the liver,[11] as well as additional proteins involved in autophagy. Proteins involved in other processes previously linked to OGT,[12] including transcription and ER stress (FIG. 3D), also changed. Increased abundance of key enzymes involved in the biosynthesis of cholesterol were also observed, including 3-Hydroxy-3-methylglutaryl-CoA reductase (HMGCR), which catalyzes the rate-limiting step in cholesterol synthesis, squalene synthase (FDFT1), which catalyzes the first committed step of cholesterol synthesis, and squalene epoxidase (SQLE). This finding suggests a connection between OGT activity and sterol homeostasis.

In conclusion, the structure-based evolution of small molecule OGT inhibitors has been described and three useful cell-permeable compounds, henceforth known as OSMI-2 (1b), OSMI-3 (2b), and OSMI-4 (4b), have been reported. The active forms of OSMI-3 and OSMI-4 (2a and 4a) have low nanomolar binding affinities, a milestone in glycosyltransferase inhibitor development. Indeed, OSMI-4 is the best OGT inhibitor reported to date, with a ~3 μM $EC_{50}$ in cells (FIG. 15F), making it especially attractive for probing OGT's complex biology. Addressing a longstanding need in the field, the inhibitor:OGT complexes described herein may also provide a framework to guide inhibitor development for other glycosyltransferases.

Example 2. Assay Data on Inhibition Constant, Inhibitory Activity, Solubility, Permeability, and Stability

TABLE 1A

Substitution on the Q6S ring.

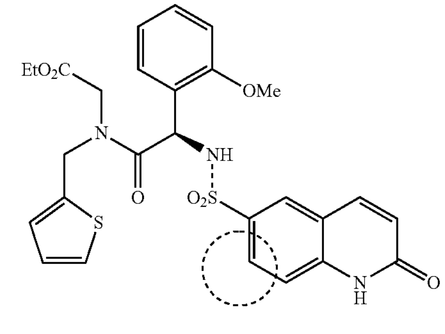

| R-group variation | Ki (uM)[a] | Ki SD | $IC_{50}$ (uM)[b] | $IC_{50}$ SD | Solubility (μg/mL)[c] | Permeability ($10^{-6}$ cm/s)[d] | RLM Stability ($t_{1/2}$ – min)[e] |
|---|---|---|---|---|---|---|---|
| 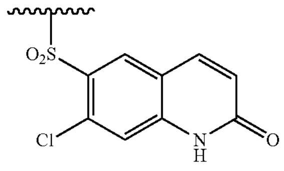 [SMILES: *S(=O)(=O)c1cc2ccc(=O)[nH]c2cc1Cl] | 0.021 | 0.004 | 0.4 | 0.1 | 19.0 | 540 | 1.9 |

TABLE 1A-continued

| | | | | | | | |
|---|---|---|---|---|---|---|---|
| 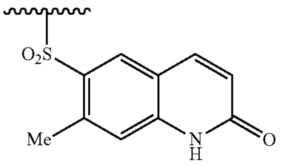 [SMILES: *S(=O)(=O)c1cc2ccc(=O)[nH]c2cc1C] | 0.103 | 0.041 | 1.8 | 0.7 | 21.1 | 511 | 1.3 |

[a]The equation used to calculate $IC_{50}$ has been rearranged to calculate Ki from $IC_{50}$s as determined by UDP-Glo Assay. Ki = ($IC_{50}$ − ([OGT]/2))/(1 + ([UDP-GlcNAc]/Km UDP-GlcNAc)). [b]UDP-Glo assay − $IC_{50}$ = (Ki)(1 + ([UDP-GlcNAc]/Km UDP-GlcNAc)) + [OGT]/2. [c]Kinetic solubility (μg/mL). [d]PAMPA assay ($10^{-6}$ cm/s). [e]RLM: rat liver microsome stability assay $t_{1/2}$ (min).

Table 1A above provides data for exemplary OGT inhibitors, including inhibition constant $K_i$, $IC_{50}$, solubility, permeability, and rat liver microsome stability assay $t_{1/2}$ (min). Protocol for measuring $IC_{50}/K_i$ depicted in Table 1A above: Measuring $IC_{50}/K_i$ Values Using the UDP-Glo™ Glycosyltransferase Assay Materials for this assay were obtained from Promega (catalog #V6961). The experiment was performed largely as outlined by the manufacturer and as previously disclosed, unless otherwise noted.[12] $IC_{50}$ values were determined in the range of 0 to 50 μM (eleven concentration points). Assays were performed in white, 384-well or H volume 96-well plates. Quantities in parenthesis apply to reactions run in H volume 96-well plates. Reaction volumes were 12 (24) μL. Reactions contained the following components: 300 nM ncOGT, 125 μM CKII3K peptide acceptor and 40 μM UDP-GlcNAc in 1×PBS pH 7.4 supplemented with 1 mM THP. Reactions were incubated for 5 minutes at 37° C. and quenched by the addition of an equal volume of UDP-Glo nucleotide detection reagent, prepared and used according to manufacturer guidelines. The quenched reactions were then mixed briefly by shaking at 600 rpm in a Thermomixer C, spun down at 400×g for 1 minute, and incubated for one hour at room temperature prior to reading luminescence, as per the manufacturer's guidelines. Data were analyzed by Microsoft Excel and Prism 7 (Graphpad). $IC_{50}$ values for the most potent compounds converted to $K_i$ using the Cheng-Prusoff equation. Each sample was run in duplicate, unless otherwise specified.

Materials and Methods

Molecular Modelling

Structures of OGT complexes with bound UDP-GlcNAc (PDB IDS: 4N3C) were prepared using Protein Prep Wizard Schrödinger.[14] The SiteMap package within the Schrödinger suite was used to calculate the Dscore, size, hydrophilicity and hydrophobicity in the UDP-GlcNAc binding pocket, using the default parameters.[13]

For the superposition of 2a into the other Gtfs, the uridine ring from OGT (PDB IDS:4N3C) was first superimposed onto the uridine ring from the respective complexes with the Superposition panel in Maestro within the Schrödinger suite. Then 2a:OGT complexes were aligned onto OGT (PDB IDS:4N3C) in PyMOL to generate the overlay.

Density Functional Theory Calculations

To find the lowest energy conformers, a solution phase conformational search using MacroModel was performed,[15] with OPLS3[16] as the force field with the default settings, on 1a extracted from the crystal structure. A representative of the five lowest energy conformers were geometry optimized using density functional theory (DFT) calculations with B3LYP as the functional and the 6-31+G(d) basis set.[17] The vibrational frequencies were computed at the same level to verify that the optimized structure is an energy minima and to evaluate zero-point vibrational energies (ZPVE) and thermal corrections at 298 K. The calculations were performed using SMD solvent continuum as the solvent method.[18] All calculations were performed using Gaussian09 software.[19]

Protein Expression and Purification

Full length human OGT (ncOGT) and human $OGT_{4.5}$ ($hOGT_{4.5}$) were prepared as previously described with minor variations.[20] Cultures were grown at 37° C. after diluting an overnight culture 1 to 100 in fresh LB media. Cells were grown to an $A_{600}$ of 1, at which point they were cooled to a temperature of 16° C. After letting the cells grow at 16° C. for 1 hour, they were induced with 0.2 mM IPTG and grown at 16° C. for 16 h. Cells were pelleted, resuspended in TBS (20 mM Tris, pH 7.4, 250 mM NaCl) supplemented with 1 mM PMSF and 0.1 mg/mL lysozyme, lysed, and the lysate was centrifuged at 5,000×g for 20 min to remove unbroken cells. Imidazole was then added to the supernatant to a final concentration of 40 mM before the lysate was incubated with Ni-NTA agarose superflow resin (Qiagen) which was prewashed with TBS+40 mM imidazole for batch nickel affinity purification. After incubating the lysate and the resin with gentle rocking at 4° C., the flowthrough was removed, and the resin was washed with 10 column volumes of TBS+50 mM imidazole. The protein was then eluted with 4 column volumes of TBS+250 mM imidazole. The eluate was supplemented with 1 mM THP (Novagen) to prevent aggregation and then concentrated with centrifugal concentrators (Millipore). After protein concentration determination, for $hOGT_{4.5}$ the N-terminal tags were cleaved by adding HRV3C protease (EMD, M02905) to the concentrated purified protein at a ratio of 1 unit/150 mg of protein (determined by NanoDrop, MW=80876 Da, ε=77240 $M^{-1}$ $cm^{-1}$) and incubating at 4° C. for 16 h. Following cleavage, the protein was further purified by gel filtration on a Superdex 200 column (GE Healthcare) in TBS (20 mM Tris, pH 8.0, 150 mM NaCl) and fractions were supplemented with 1 mM THP after gel filtration. The fractions were collected and again concentrated using centrifugal concentrators. The protein was monomeric in solution as determined by gel filtration. The $hOGT_{4.5}$ was then diluted 1:1 in water before setting up crystals.

Protein Crystallization with Inhibitors

The HCF-1 peptide (THETGTTNTATTATSN) (SEQ ID NO: 1) was purchased from Biomatik or Neo Bio Lab (≥95% purity, HPLC). All complexes were prepared by incubating $hOGT_{4.5}$ at 7 mg/ml with small molecule inhibitor (0.2 mM) and peptide (3 mM). All crystals were grown with the hanging drop method by combining 3 μL protein complex with 1 μL reservoir solution. Crystals were grown with reservoir consisting of 1.05 M sodium citrate and 0.1 M Tris pH 8.5. Crystals were grown at room temperature and cryoprotected in solutions consisting of the reservoir solution plus 28% xylitol and flash frozen in liquid nitrogen.

Data Collection, Structure Determination, and Refinement

All data were collected at APS beamlines 24-ID-C and 24-ID-E at Argonne National Laboratory. Data was processed and integrated using iMosflm[21] and scaled with Aimless[22] in the CCP4 software suite.[23] The previously determined OGT-UDP-HCF peptide ternary complex structure (PDB code 4N3A)[24] was used as a search model for molecular replacement in this work. The structures were solved by rigid body refinement in Phenix.[25] The models were subsequently refined using Phenix, with multiple rounds of coordinate, atomic displacement parameter (ADP or B-factor), occupancy, and TLS refinement, determined using the TLSMD server,[26] with interspersed manual adjustments using Coot.[27] Geometric restraints for the inhibitors were generated using Phenix Elbow,[28] and these restraints were used throughout refinement. All structural figures were made with Pymol.[29] Crystallization software installation support was provided by SBGrid.[30]

Measuring Dissociation Constants Using Microscale Thermophoresis

The binding of 1a-4a, ent-1a, ent-2a, UDP-GlcNAc and UDP to OGT was measured using microscale thermophoresis with a NanoTemper monolith NT.115Pico instrument.[31] Purified full length OGT was fluorescently labeled with Alexa Fluor™ 647 NHS Ester (ThermoFisher) (NHS-ester:OGT=1.5:1 mole ratio) in labeling buffer (PBS pH 8.5, 1 mM DTT) for 1 hour at room temperature with end to end rotation in the dark. Excess NHS-ester was removed with a Zeba™ Spin desalting column (ThermoFisher). A range of concentrations of the ligand were prepared in which the concentration of labeled OGT was kept constant at 5 nM, and all experiments were performed in MST running buffer (PBS, pH 7.4, 0.05% Tween-20, 1 mM DTT, 2% glycerol, 0.5% DMSO). Mixtures were incubated for at least 10 minutes to facilitate binding before MST experiments. MST experiments were carried out using 60% LED power and 20% MST power in standard capillaries (from NanoTemper Technologies). Experiments were performed with at least three biological replicates except for ent-1 (two replicates). $K_d$ values were calculated using a user-defined mass action equation in the GraphPad Prism 6 software (GraphPad Software, Inc.).

Cells and Reagents

HEK293T, LNCaP, PC3 and HCT116 were purchased from American Type Culture Collection (ATCC). HEK293T cells were grown in DMEM media supplemented with 10% FBS and 1× Penicillin-Streptomycin solution (Corning). LNCaP and PC3 were maintained in RPMI media supplemented with 10% FBS, and HCT116 cells were cultured in McCoy's 5A media supplemented with 10% FBS. Antibodies against OGT were obtained from Cell Signaling Technology (24083S), against O-GlcNAc (R12) and Actin from Abcam (ab2739, ab49900, respectively) and against HCF-1 from Bethyl Laboratories (A301-400A).

Cell Culture

Cells were plated and grown in their respective media until they reached a confluency of 60-80%. For HEK293T cells, media was changed 3 hours before compounds were added; compounds were added directly to each well at the indicated concentrations. For all other cell lines, compounds were dissolved in 0.2 mL of fresh media and then added directly to the cells.

Preparation of Cell Lysates and Western Blotting

Cell lysates for from HEK293T, LNCaP, HCT116 and PC3 cells were prepared for western blotting in the following manner, and all the steps were conducted at 4° C. Cells were washed once with PBS, collected in PBS, centrifuged and 100 μL of cell lysis buffer was added (10 mM Tris-HCl, pH 8.0, 1 mM EDTA, 1% Triton X-100, 0.1% SDS (2% for HEK293T cells), 150 mM NaCl supplemented with Complete protease inhibitor mixture (Sigma), complete phosphatase inhibitor mixture (Sigma), and 50 μM PUGNAc (Sigma). After this, samples were lysed using a Bioruptor sonicator, centrifuged at 14,000×g for 5-10 minutes, and supernatants were collected. Protein concentration was determined using the BCA assay and 10-25 μg of sample was loaded on 4-15% or 4-20% SDS-PAGE (Bio-Rad). Samples were transferred to a nitrocellulose membrane (Bio-Rad). Membranes were blocked with 5% bovine serum albumin in TBST and probed with primary antibodies overnight at 4° C. and for 1 h at RT with peroxidase conjugated secondary antibodies, as indicated in each figure. Blots were developed using enhanced chemiluminescence (Pierce) and visualized with an Amersham Imager 600.

Measurement of Cell Viability and Live-Cell Imaging

HCT116 cells were plated into 384-well plate one day prior to treatment with compounds (300 cells per well). Compounds were dispensed using a D300e Digital Dispenser (Tecan). Cells were imaged every 3 hours using an IncuCyte ZOOM instrument (Sartorius) to generate growth curves. After four days of treatment, cell viability was assessed using the CellTiter-Glo® Luminescent Cell Viability Assay (Promega). Luminescence signal was recorded using the GloMax® Explorer System (Promega). For Cytotoxicity, HEK293T cells were plated into a 96-well plate two days prior to treatment with compounds at 80% confluency. The number of dead cells were assessed by CellTox™ Green Cytotoxicity Assay (Promega).

RT-PCR

Total RNA was harvested directly from tissue culture plates using Trizol (Life Technologies) according to the manufacturer's directions. In all experiments, total RNA was treated with Turbo DNase (Life Technologies) to remove any residual DNA contamination, extracted in acid-buffered phenol/chloroform, and ethanol-precipitated. Reverse transcription was performed using 2 μg of DNase-treated total RNA in a 20 μL reaction following the manufacturer's protocol (SuperScript III, Life Technologies) for 1 h at 50° C. cDNA reactions were digested with diluted 1:10, and 1 μL was used in each PCR reaction. Real-time qRT-PCR was performed using PowerUp SYBR Green (Life Technologies) on a StepOne-Plus Real-Time PCR System (Applied Biosystems). Normalization to the highly stable mRNA of actin was used to compare samples using a ΔΔCt calculation.

Quantitative Proteomics

For quantitative analysis of the proteome, HEK293T cells in fresh media (changed 3 hours before treatment) were treated with 20 μM 1b/OSMI-2 or DMSO in five biological replicates (5 treatment and 5 DMSO at each time point) for 8 hours, 16 hours or 24 hours; DMSO, 5 and 20 μM 4b/OSMI-3 in triplicates, and 10 μM in duplicates (11-plex). At the indicated time point, cells were lysed in lysis buffer (2% SDS 50 mM Tris-HCl and 150 mM NaCl), sonicated (BioDisruptor) and protein concentration determined with the BCA assay. Samples were reduced with 5 mM DTT for 45 mins at 60° C., then alkylated with 14 mM iodoacetamide for 45 mins at room temperature in the dark. Then 100 μg of protein was precipitated using chloroform/methanol.[32] Protein pellets were resuspended in 200 mM HEPES pH 8.5 to 1 mg/mL. Proteins were digested with LysC (Wako) (substrate:enzyme=100) overnight at 37° C. and then with sequencing grade Trypsin (Promega) (substrate:enzyme=100) for 6 hours at 37° C. The resulting peptide solutions were then labelled with TMT 10/11-plex reagents (Thermo Scientific) for 1.5 hours at room temperature. Reactions were stopped by addition of 5% hydroxylamine for 30 minutes. Equal amounts of peptide samples were combined, dried by vacuum centrifugation and desalted on a Waters C18 solid phase extraction Sep-Pak. TMT-labeled peptide samples were fractionated via basic-pH reverse-phase (BPRP) HPLC to 96 fractions and then consolidated to 12 fractions. These fractions were subsequently acidified with 1% formic acid, vacuum centrifuged to near dryness and desalted with C18 stagetips.[32] Dried peptides were resuspended in 5% acetonitrile/5% formic acid for LC-MS/MS processing.

Mass-Spectrometry Analysis

The mass spectrometry data were collected using an Orbitrap Fusion Lumos mass spectrometer (ThermoFisher Scientific, San Jose, CA) coupled to a Proxeon EASY-nLC 1200 liquid chromatography (LC) pump (ThermoFisher Scientific). Peptides were separated on a 100 μm inner diameter microcapillary column packed with 35 cm of Accucore C18 resin (2.6 μm, 150 Å, ThermoFisher). For each analysis, ~2 μg was loaded onto the column.

Separation was in-line with the mass spectrometer and was performed using a 3 hr gradient of 6 to 26% acetonitrile in 0.125% formic acid at a flow rate of ~450 nL/min. Each analysis used an TMT-based TMT method[33] which has been shown to reduce ion interference compared to MS2 quantification.[34] The scan sequence began with an MS1 spectrum (Orbitrap analysis; resolution 120,000; mass range 400-1400 m/z; automatic gain control (AGC) target $5\times10^5$; maximum injection time 100 ms). Precursors for MS2/MS3 analysis were selected using a Top10 method. MS2 analysis consisted of collision-induced dissociation (CID); AGC $2.0\times10^4$; normalized collision energy (NCE) 35; maximum injection time 120 ms; and isolation window of 0.4 Da. Following acquisition of each MS2 spectrum, an MS3 spectrum was collected using the recently described method in which multiple MS2 fragment ions were captured in the MS3 precursor population using isolation waveforms with multiple frequency notches.[33b] MS3 precursors were fragmented by high energy collision-induced dissociation (HCD) and analyzed using the Orbitrap (NCE 65; AGC $1.5\times10^5$; maximum injection time 150 ms, resolution was 50,000 at 400 Th, isolation window 0.7 Da).

Mass spectra were processed using a SEQUEST-based pipeline[23] Spectra were converted to mzXML using a modified version of ReAdW.exe. Database searching included all entries from the human UniProt database. This database was concatenated with one composed of all protein sequences in the reversed order. Searches were performed using a 50 ppm precursor ion tolerance for total protein level analysis. The product ion tolerance was set to 0.9 Da. These wide mass tolerance windows were chosen to maximize sensitivity in conjunction with Sequest searches and linear discriminant analysis.[35-36] TMT tags on lysine residues and peptide N termini (+229.163 Da) and carbamidomethylation of cysteine residues (+57.021 Da) were set as static modifications, while oxidation of methionine residues (+15.995 Da) was set as a variable modification.

Peptide-spectrum matches (PSMs) were adjusted to a 1% false discovery rate (FDR)[37] PSM filtering was performed using a linear discriminant analysis, as described previously,[35] while considering the following parameters: XCorr, ΔCn, missed cleavages, peptide length, charge state, and precursor mass accuracy. For TMT-based reporter ion quantitation, the signal-to-noise (S:N) ratio was extracted for each TMT channel and found the closest matching centroid to the expected mass of the TMT reporter ion. PSMs were identified, quantified, and collapsed to a 1% peptide false discovery rate (FDR) and then collapsed further to a final protein-level FDR of 1%. Moreover, protein assembly was guided by principles of parsimony to produce the smallest set necessary to account for all observed peptides.

Peptide intensities were quantified by summing reporter ion counts across all matching PSMs, as described previously.[33b,38] Briefly, a 0.003 Th window around the theoretical m/z of each reporter ion was scanned for ions, and the maximum intensity nearest the theoretical m/z was used. PSMs with poor quality, MS3 spectra with TMT reporter summed signal-to-noise ratio less than 100, or no MS3 spectra were excluded from quantitation, and isolation specificity ≥0.7 was required.[38]

Organic Synthesis

All reactions were carried out under an atmosphere of dry nitrogen. Indicated reaction temperatures refer to those of the reaction bath, while room temperature is noted as 23° C. All solvents, diisopropylethylamine, and triethylamine were of anhydrous quality purchased from MilliporeSigma or EMD and used as received or dried on alumina according to published procedures.[39] Commercially available starting materials and reagents were purchased from Sigma-Aldrich, AAPPtec, Enamine, or Peptech and were used as received. 2-((tert-butoxycarbonyl)amino)-2-(2-hydroxyphenyl)acetic acid (Netchem), was taken up in methanol, filtered, and concentrated under reduced pressure to remove impurities prior to use. All other chemicals were purchased from commercial sources as noted below and used as received. 2-oxo-1,2-dihydroquinoline-6-sulfonyl chloride (S1) was synthesized according to a published procedure.[40] Reaction mixtures were dried with magnesium sulfate unless otherwise noted. Brine refers to a saturated solution of NaCl. Solvents used for flash silica chromatography were ACS grade or above. O/N refers to overnight.

Chromatography on silica gel was performed using forced flow (liquid) of the indicated solvent system on pre-packed silica columns (Teledyne Isco) on a Combi Flash automated chromatography system. Analytical thin-layer chromatography (TLC) was performed on precoated glass plates (EMD, 5 cm×20 cm, F60, 254 μm) and visualized by UV or by staining with $KMnO_4$. Samples were analyzed for purity on an Agilent 1100 series LC/MS instrument equipped with a diode array detector and a Phenomenex Luna C18 reverse phase (5 μm, 4.6 mm×250 mm) column at a flow rate of 0.5 mL/min. The mobile phase was a mixture of acetonitrile (0.1% FA) and $H_2O$ (0.1% FA) beginning at 20% acetonitrile (5 min) with a gradient to 80% $H_2O$ over 25 minutes, remaining at 80% $H_2O$ for 3 minutes, and returning to 20% acetonitrile over 2 minutes. Purity of final compounds was determined using a 10 μL injection with quantitation by area under curve at 254 and 280 nm (unless otherwise noted) (Method A). If needed, products were purified via an Agilent 1200 series preparative HPLC instrument equipped with a Phenomenex Luna C18 reverse phase (5 μm, 10 mm×250 mm) column at room temperature with a flow rate of 3 mL/min or a Luna C18 reverse phase (5 μm, 21.2 mm×250 mm) column with a flow rate of 12 mL/min. The mobile phase was a mixture of acetonitrile (0.1% FA) and $H_2O$ (0.1% FA) beginning at 20% acetonitrile (3 min) with a gradient to 80% $H_2O$ over 32 minutes, remaining at 80% $H_2O$ for 3 minutes, returning to 20% acetonitrile over 2 minutes, and remaining at 20% acetonitrile for 1 minute (Method B). Resolution of enantiomers by preparative chiral HPLC were carried out as detailed below. After chiral resolution, chemical purity was determined by using a single quadrupole mass spectrometer equipped with a diode array detector and a Phenomenex Luna C18 reverse phase (3 μm, 3 mm×75 mm) column. The mobile phase was a mixture of acetonitrile (0.05% TFA) and $H_2O$ (0.05% TFA) beginning at 4% acetonitrile with a gradient to 100% $H_2O$ over 7 minutes (Method C). All solvents were HPLC grade. OSMI-3 and 3b were synthesized as racemic compounds, and the enantiomers were resolved using HPLC as indicated below.

NMR spectra were recorded on a Varian Mercury 400 or Varian Inova 500 (400 and 500 MHz for $^1H$, respectively) instrument in deuterated solvent and were recorded at ambient temperatures. Chemical shifts are reported in parts per million (ppm). $^1H$ NMR spectra were calibrated using the residual protio-solvent as a standard ($CDCl_3$ 7.26 ppm, $CD_3OD$-$d_4$ 3.31 ppm, $CH_2Cl_2$-$d_2$ 5.32 ppm, DMSO-$d_6$2.50 ppm). Data are reported as follows: chemical shift, multiplicity (s=singlet, d=doublet, t=triplet, q=quartet, quin=quintet, br=broad, m=multiplet), coupling constants, and number of protons. Low-resolution mass spectra (LRMS) were obtained on an Agilent Technologies 1100 series LC/MS instrument using electrospray ionization (ESI). High-resolution mass spectra (HRMS) were obtained on a Bruker micrOTOFQ-II mass spectrometer. Optical rotations ($[\alpha]_D^{23}$) were measured on a Jasco DIP 370 digital polarimeter at 589 nm (sodium D line) at ambient temperature using a 1 mL cell with a 0.5 dm path length.

Example 3A. Synthesis of Exemplary OGT Inhibitor Compounds

In some embodiments, compounds of the invention may be synthesized according to the exemplary synthetic procedures provided below in Examples 3A and 3B.

Unless otherwise stated, all reactions were carried out under an atmosphere of dry argon or nitrogen in dried glassware. Indicated reaction temperatures refer to those of the reaction bath, while room temperature is noted as 23° C. All solvents were of anhydrous quality purchased from Sigma Chemical Co. and used as received. Commercially available starting materials and reagents were used as received.

Analytical thin layer chromatography (TLC) was performed with Sigma Aldrich TLC plates (5 cm×20 cm, 60 Å, 250 μm). Visualization was accomplished by irradiation under a 254 nm UV lamp.

Chromatography on silica gel was performed using forced flow (liquid) of the indicated solvent system on Teledyne Isco RediSep® Normal-phase Silica Flash Columns cartridges and using the Teledyne Isco CombiFlash® Systems chromatography system.

$^1H$ and $^{13}C$ NMR spectra were recorded on a Varian Inova 400 MHz spectrometer or on a Varian Inova 500 MHz spectrometer. Chemical shifts are reported in ppm with the solvent resonance as the internal standard (Acetonitrile_$d_3$ 1.94 ppm, 1.39 ppm; Chloroform_d 7.26 ppm, 77.00 ppm; DMSO-$d_6$ 2.50 ppm, 39.50 ppm; Methanol-$d_4$ 3.30 ppm, 49.15 ppm, for $^1H$, $^{13}C$, respectively). Data are reported as follows: chemical shift, multiplicity (s=singlet, d=doublet, t=triplet, q=quartet, quin=quintet, br=broad, m=multiplet), coupling constants, and number of protons.

Optical rotations ($[\alpha]_D^{23}$) were measured on a Jasco DIP 370 digital polarimeter at 589 nm (sodium D line) at ambient temperature using a 1 mL cell with a 0.5 dm path length.

Low resolution mass spectra (electrospray ionization) were acquired on an Agilent Technologies 6130 quadrupole spectrometer coupled to the HPLC system.

High resolution mass spectral data were collected in-house using an Agilent 6210 time-of-flight mass spectrometer, also coupled to an Agilent Technologies 1200 series HPLC system.

If needed, products were purified via a Waters semi-preparative HPLC instrument equipped with a Phenomenex Luna C18 reverse phase (5 μm, 30 mm×75 mm) column having a flow rate of 45 mL/min. The mobile phase was a mixture of acetonitrile (0.025% TFA) and $H_2O$ (0.05% TFA), and the temperature was maintained at 50° C.

Purity of final compounds was determined to be >95% following one of two methods: 1) Using an Agilent 1200 series LC/MS instrument equipped with a Luna C18 reverse phase (3 μm, 3 mm×75 mm) column having a flow rate of 0.8-1.0 mL/min over a 7 min gradient and an 8.5 min run time. Purity of final compounds was determined using a 3 L injection with quantitation by area under the curve at 220 and 254 nm (Agilent diode array detector) (Method A). 2) Using an Agilent 1100 series LC/MS instrument equipped with a diode array detector and a Phenomenex Luna C18 reverse phase (5 μm, 4.6 mm×250 mm) column at a flow rate of 0.5 mL/min. The mobile phase was a mixture of acetonitrile (0.1% FA) and $H_2O$ (0.1% FA) beginning at 20% acetonitrile (5 min) with a gradient to 80% $H_2O$ over 25 minutes, remaining at 80% $H_2O$ for 3 minutes, and returning to 20% acetonitrile over 2 minutes. Purity of final compounds was determined using a 10 μL injection with quantitation by area under curve at 254 and 280 nm (unless otherwise noted) (Method B).

Preparation of 1a and 1b/OSMI-2

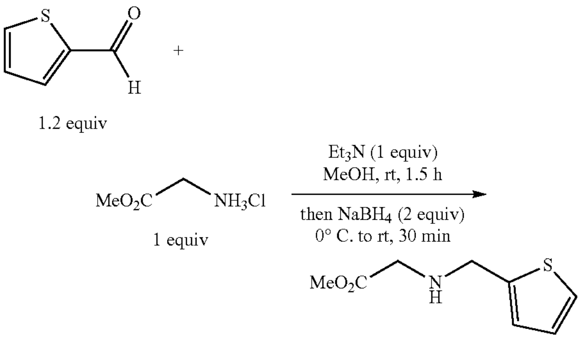

S2

Methyl (thiophen-2-ylmethyl)glycinate (S2) A 100 mL round bottom flask was charged with glycine methyl ester hydrochloride (750 mg, 6 mmol) and a stir bar. MeOH (24 mL, 0.25 M) and $E_{t3}N$ (840 μL, 6 mmol) were added via syringe, followed by thiophene 2-carboxaldehyde (620 μL, 7.2 mmol). Reaction was stirred 1.5 h at rt, and the presence of imine was confirmed using ESI/MS. The solution was chilled to 0-5° C. using an ice bath, and sodium borohydride (450 mg, 12 mmol) was slowly added to the reaction mixture in portions. The ice bath was removed, and the reaction was allowed to warm to rt over 30 minutes. MeOH was then removed under reduced pressure, and the reaction mixture was partitioned between EtOAc (10 mL) and $H_2O$ (10 mL). The $H_2O$ layer was removed, and EtOAc washed with $H_2O$ (2×10 mL) and brine (10 mL). The reaction was dried, filtered, and concentrated under reduced pressure. The residue was purified using flash silica chromatography, eluting with 5-50% EtOAc/Hexanes to yield 308 mg (28%) of S2 as a clear oil. $^1H$ NMR (500 MHz, $CDCl_3$) δ 7.24 (dt, J=4.9, 1.2

Hz, 1H), 7.05-6.88 (m, 2H), 4.04 (q, J=1.3 Hz, 2H), 3.86-3.65 (m, 3H), 3.56-3.41 (m, 2H), 2.25-1.96 (m, 1H). $^{13}C$ NMR (126 MHz, $CDCl_3$) δ 172.71, 143.08, 126.65, 125.34, 124.77, 51.82, 49.47, 47.75. MS (ESI) 186.1 $[M+H]^+$.

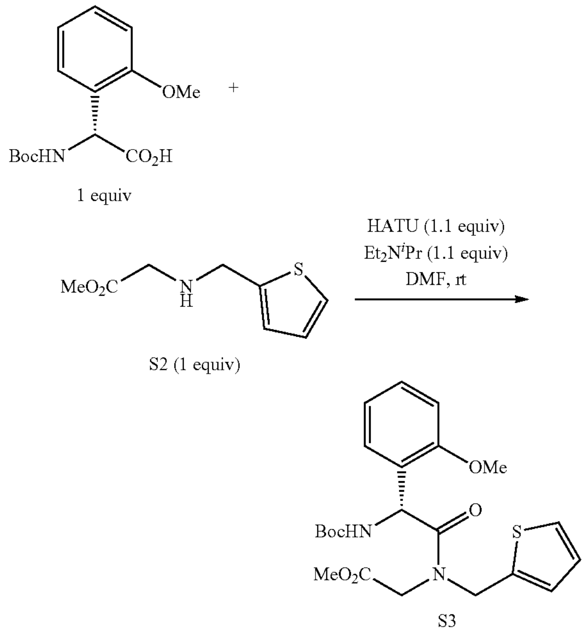

1 equiv

S2 (1 equiv)

S3

Methyl (R)—N-(2-((tert-butoxycarbonyl)amino)-2-(2-methoxyphenyl)acetyl)-N-(thiophen-2-ylmethyl)glycinate (S3) A 25 mL round bottom flask was charged with (R)-2-((tert-butoxycarbonyl)amino)-2-(2-methoxyphenyl)acetic acid (420 mg, 1.5 mmol), S2 (280 mg, 1.5 mmol) and a stir bar. The flask was capped with a septum and purged with nitrogen for 5 minutes. Dimethylformamide (DMF) was added via syringe (6 mL, 0.25 M), followed by HATU (630 mg, 1.65 mmol) by briefly removing the septum cap. Diisopropylethylamine (290 μL, 1.65 mmol) was added via syringe, and the reaction was stirred at rt for 5 h. The reaction mixture was partitioned between EtOAc (5 mL) and $H_2O$ (5 mL). The organic layer was removed, and the $H_2O$ was extracted with EtOAc (2×5 mL). The combined organic layers were washed with brine (5 mL), dried, filtered, and concentrated under reduced pressure. The resulting oil was purified using flash silica chromatography, eluting with 10-50% EtOAc/Hexanes to yield 580 mg (86%) of S3 as a clear oil. (mixture of rotamers) $^1H$ NMR (500 MHz, $CDCl_3$) δ 7.43-7.28 (m, 4H), 7.23-7.12 (m, 2H), 6.99 (tq, J=21.1, 7.5 Hz, 2H), 6.92-6.75 (m, 3H), 6.67 (s, 1H), 6.35-5.64 (m, 4H), 4.96 (d, J=15.4 Hz, 1H), 4.86-4.63 (m, 2H), 4.60 (d, J=15.4 Hz, 1H), 4.04-3.90 (m, 4H), 3.90-3.71 (m, 6H), 3.67 (d, J=1.6 Hz, 4H), 3.47 (d, J=1.6 Hz, 4H), 1.43 (dd, J=21.4, 3.0 Hz, 18H). $^{13}C$ NMR (126 MHz, $CDCl_3$) δ 169.42, 168.88, 154.99, 151.80, 129.90, 129.68, 128.94, 128.79, 127.39, 126.99, 126.71, 126.17, 126.07, 121.44, 111.54, 111.09, 110.13, 77.16, 60.54, 55.98, 55.83, 52.28, 52.19, 49.46, 46.95, 46.34, 46.20, 45.13, 28.52, 14.35. MS (ESI) 471.1 $[M+Na]^+$.

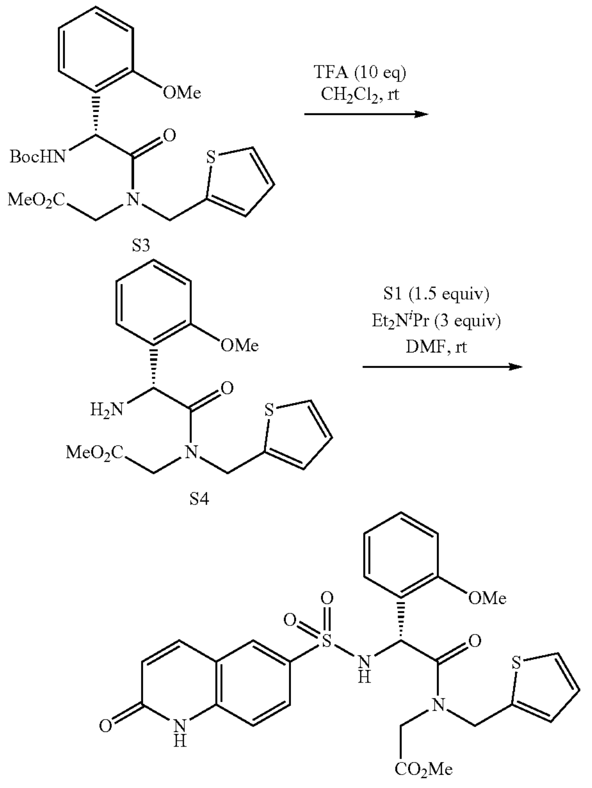

S3

S4

1b/OSMI-2

Methyl (R)—N-(2-(2-methoxyphenyl)-2-((2-oxo-1,2-dihydroquinoline)-6-sulfonamido)acetyl)-N-(thiophen-2-ylmethyl)glycinate (1b/OSMI-2) A solution of S3 (450 mg, 1 mmol) in dichloromethane (DCM, 10 mL. 0.1 M) was treated with trifluoroacetic acid (770 μL, 10 mmol) at rt for 1.5 h in a 25 mL round bottom flask. The reaction mixture was concentrated under reduced pressure, then the residue was taken up in toluene (approx. 2 mL), and the resulting mixture was concentrated again under reduced pressure. This process was repeated twice, and the remaining volatiles were removed. A stir bar was added to the vial containing the resulting crude amine (S4), and the vial was sealed with a septum cap and purged for 5 minutes with nitrogen. DMF (5 mL, 0.2 M) was added via syringe. Then the top was opened briefly, and Si (365 mg, 1.5 mmol) was added by briefly opening the vial. Diisopropylethylamine (490 μL, 3 mmol) was added via syringe, and the reaction was stirred at rt for 60 minutes. The reaction mixture was partitioned between EtOAc (5 mL) and $H_2O$ (5 mL). The organic layer was removed, and the $H_2O$ was extracted with EtOAc (2×5 mL). The combined organic layers were washed with brine (5 mL), dried, filtered, and concentrated under reduced pressure. The resulting oil was purified using flash silica chromatography, eluting with 1-10% DCM/MeOH to yield 251 mg (45%) of OSMI-2 as a white solid. (~1:1 mixture of rotamers) $^1H$ NMR (500 MHz, $cdcl_3$) δ 12.10 (d, J=19.1 Hz, 2H), 7.93 (dd, J=19.7, 2.0 Hz, 2H), 7.81 (dd, J=8.7, 2.0 Hz, 1H), 7.76-7.69 (m, 1H), 7.64 (dd, J=9.5, 4.0 Hz, 2H), 7.31-7.11 (m, 9H), 7.00-6.84 (m, 5H), 6.83-6.74 (m, 2H), 6.74-6.59 (m, 3H), 6.25 (d, J=8.3 Hz, 1H), 5.95 (d, J=8.3 Hz, 1H), 4.95 (d, J=15.3 Hz, 1H), 4.65 (dd, J=15.5, 12.4 Hz, 3H), 4.16-3.92 (m, 5H), 3.82 (s, 3H), 3.77 (s, 3H), 3.69 (s, 3H), 3.53 (s, 3H). $^{13}C$ NMR (126 MHz, $CDCl_3$) δ 171.23, 171.16, 168.91, 168.48, 164.14, 164.08, 155.97, 155.74, 140.83, 140.80, 140.60, 137.98, 137.39, 135.07, 135.03, 130.65, 130.49, 129.09, 128.93, 128.87, 127.90, 127.85, 127.71, 127.31, 127.15, 126.80, 126.61, 126.44, 124.03, 123.52, 122.55, 122.52, 121.63, 118.62, 118.54, 116.47, 116.43, 111.48, 111.14, 55.96, 55.87, 52.54, 52.34, 52.27, 51.86, 46.97, 46.88, 46.45, 45.65. LC/MS (Method A), 27.4 min (>95% pure), 556.1 $[M+H]^+$. HRMS (ESI) m/z calcd for $[C_{26}H_{25}N_3O_7S_2]$: 578.1026 $[M+Na]^+$. found 578.1037. $[\alpha]_D^{23}$=−138.9±0.2 (c=1.05, $CHCl_3$).

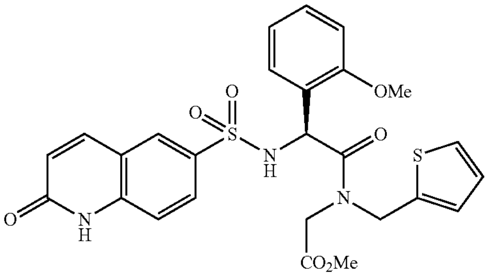

ent-1b/ent-OSMI-2

Methyl (S)—N-(2-(2-methoxyphenyl)-2-((2-oxo-1,2-dihydroquinoline)-6-sulfonamido)acetyl)-N-(thiophen-2-ylmethyl)glycinate (ent-1b/ent-OSMI-2) Compound was prepared using the same procedure as for 1b/OSMI-2, beginning from (S)-2-((tert-butoxycarbonyl)amino)-2-(2-methoxyphenyl)acetic acid. (~1:1 mixture of rotamers) $^1H$ NMR (500 MHz, $CDCl_3$) δ 11.90 (s, 2H), 7.92 (dd, J=20.7, 2.0 Hz, 2H), 7.81 (dd, J=8.7, 2.0 Hz, 1H), 7.73 (dd, J=8.7, 2.0 Hz, 1H), 7.64 (dd, J=9.5, 2.4 Hz, 2H), 7.38-7.03 (m, 8H), 6.96-6.83 (m, 5H), 6.83-6.75 (m, 2H), 6.73-6.62 (m, 3H), 6.24 (d, J=8.3 Hz, 1H), 5.94 (d, J=8.3 Hz, 1H), 4.95 (d, J=15.3 Hz, 1H), 4.73-4.53 (m, 3H), 4.03-3.90 (m, 4H), 3.83 (d, J=1.0 Hz, 4H), 3.78 (d, J=0.9 Hz, 4H), 3.69 (d, J=0.9 Hz, 4H), 3.53 (d, J=0.9 Hz, 4H). $^{13}C$ NMR (126 MHz, $CDCl_3$) δ 171.22, 168.91, 168.49, 164.06, 164.00, 155.97, 155.73, 140.82, 140.78, 140.59, 137.97, 137.38, 135.06, 135.03, 130.66, 130.49, 129.09, 128.93, 128.88, 128.85, 127.90, 127.86, 127.72, 127.32, 127.15, 126.80, 126.62, 126.45, 124.03, 123.51, 122.57, 121.64, 118.62, 118.54, 116.42, 116.37, 111.48, 111.13, 77.16, 55.97, 55.88, 52.56, 52.35, 52.28, 51.87, 46.96, 46.86, 46.45, 45.64. LC/MS (Method A), 27.2 min (>95% pure), 556.0 $[M+H]^+$. HRMS (ESI) m/z calcd for $[C_{26}H_{25}N_3O_7S_2]$: 578.1026 $[M+Na]^+$. found 578.1054. $[\alpha]_D^{23}$=115.6±0.5 (c=1.01, $CHCl_3$).

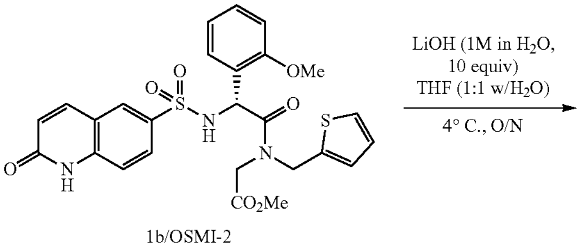

1b/OSMI-2

-continued

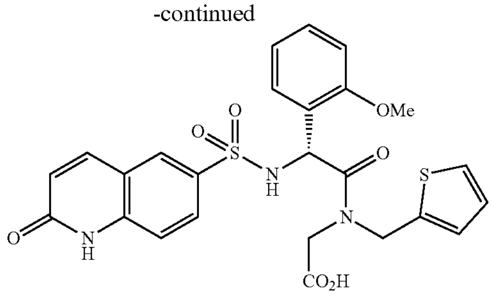

1a (R)—N-(2-(2-methoxyphenyl)-2-((2-oxo-1,2-dihydroquinoline)-6-sulfonamido)acetyl)-N-(thiophen-2-ylmethyl)glycine (1a) A vial was charged with 4/OSMI-2 (50 mg, 0.09 mmol) and stir bar under air. LiOH (900 μL, 0.9 mmol) and THF (900 μL, 0.1 M) were added. The reaction was stirred at 4° C. overnight. The reaction mixture was partitioned between EtOAc (1 mL) and $H_2O$ (1 mL). The organic layer was removed, and the $H_2O$ was extracted with EtOAc (2×1 mL). The aqueous layer was acidified with 3M HCl and concentrated under reduced pressure. The resulting white solid was purified using flash silica chromatography, eluting with 5-15% DCM/MeOH to yield 27 mg (55%) of 1a as a white solid. LC/MS (Method A), 24.7 min (>95% pure), 542.1 $[M+H]^+$. HRMS (ESI) m/z calcd for $[C_{25}H_{23}N_3O_7S_2]$: 564.0875 $[M+Na]^+$. found 564.0847. $[\alpha]_D^{23}$=−118.9±13.4 (c=0.24, MeCN).

ent-1a

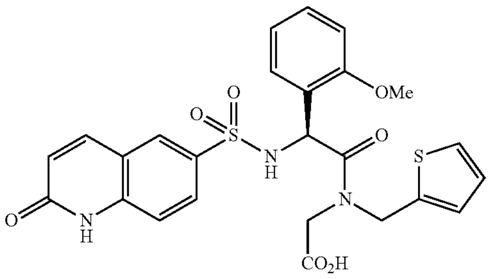

(S)—N-(2-(2-methoxyphenyl)-2-((2-oxo-1,2-dihydroquinoline)-6-sulfonamido)acetyl)-N-(thiophen-2-ylmethyl)glycine (ent-1a) Compound was prepared using the same procedure as 1, beginning from ent-1b/ent-OSMI-2 (20 mg, 0.036 mmol), LiOH (360 μL, 0.36 mmol) and THF (360 μL) to yield 16 mg (82%) of ent-1a as a white solid. LC/MS (Method fA), 24.6 min (>95% pure), 541.9 $[M+H]^+$. HRMS (ESI) m/z calcd for $[C_{25}H_{23}N_3O_7S_2]$: 564.0875 $[M+Na]^+$. found 564.0876. $[\alpha]_D^{23}$=37.0±1.5 (c=0.21, 15% MeOH in MeCN).

Preparation of 2a and 2b/OSMI-3

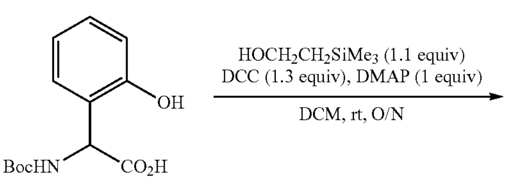

-continued

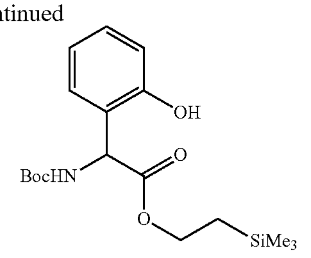

S5

2-(trimethylsilyl)ethyl 2-((tert-butoxycarbonyl)amino)-2-(2-hydroxyphenyl)acetate (S5) A vial was charged with 2-((tert-butoxycarbonyl)amino)-2-(2-hydroxyphenyl)acetic acid (100 mg, 0.37 mmol), N,N'-dimethylaminopyridine (DMAP, 45 mg, 0.37 mmol), N,N'-dicyclohexylcarbodiimide (DCC, 100 mg, 0.48 mmol), and a stir bar and was capped with a septum cap. The vial was purged with nitrogen for five minutes. DCM (2 mL, 0.2 M) and 2-(trimethylsilyl)ethanol (59 μL, 0.41 mmol) were added sequentially via syringe. The reaction was stirred at room temperature overnight. Upon completion, the reaction was cooled to −78° C. (dry ice, acetone). The reaction mixture was filtered through Celite and concentrated under reduced pressure. The residue was purified using flash silica chromatography, eluting with 5-10% EtOAC/Hexanes to yield 81.4 mg (60%) of S5 as a clear oil. $^1$H NMR (399 MHz, $CDCl_3$) δ 8.52 (s, 1H), 7.25-7.20 (m, 1H), 7.05-6.94 (m, 2H), 6.88 (dd, J=8.1, 7.0 Hz, 1H), 5.88 (s, 1H), 5.46 (d, J=7.2 Hz, 1H), 4.34-4.15 (m, 2H), 1.43 (s, 9H), 1.08-0.81 (m, 2H), −0.02 (s, 9H). MS (ESI) 366.2 $[M-H]^-$.

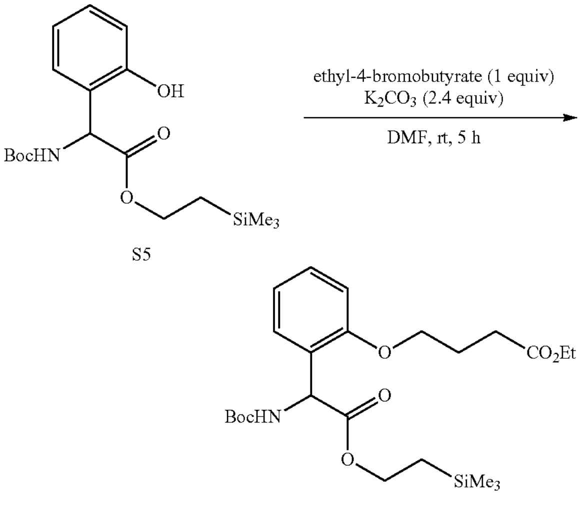

S5

S6

Ethyl 4-(2-(2,2,11,11-tetramethyl-6,9-dioxo-5,10-dioxa-8-aza-2-siladodecan-7-yl)phenoxy)butanoate (S6) A vial was charged with S5 (75 mg, 0.24 mmol) and a stir bar, capped with a septum cap, and purged with nitrogen for five minutes. Then DMF (1.5 mL, 0.16 M) was added via syringe. The top was opened briefly to add $K_2CO_3$ (80 mg, 0.6 mmol). Then ethyl-4-bromobutyrate (34 μL, 0.24 mmol) was added via syringe, and the reaction was stirred at rt for 5 h or until complete. DMF was removed under reduced pressure, and partitioned between 2 mL each of 1M HCl and EtOAc. EtOAc was removed, and the aqueous later extracted with EtOAc (2×2 mL). The combined organic layers were washed with brine, dried, and concentrated under reduced pressure. The reaction mixture was carried forward without further purification. $^1$H NMR (399 MHz, $CDCl_3$) δ 7.42-7.17 (m, 2H), 7.06-6.67 (m, 2H), 5.64 (d, J=9.0 Hz, 1H), 5.44 (d, J=8.8 Hz, 1H), 4.34-3.94 (m, 6H), 2.53 (td, J=7.3, 5.9 Hz, 1H), 2.28-1.99 (m, 2H), 1.54 (d, J=10.3 Hz, 1H), 1.43 (s, 9H), 1.25 (td, J=7.1, 2.9 Hz, 3H), 0.90 (ddd, J=10.0, 6.7, 3.2 Hz, 2H), −0.06 (s, 9H). MS (ESI) 504.1 $[M+Na]^+$.

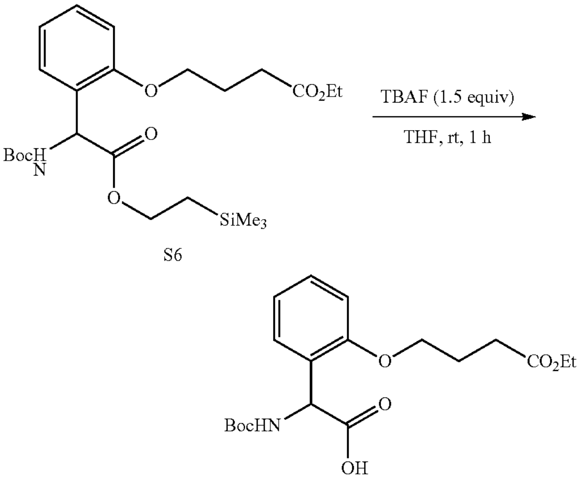

S6

S7

2-((tert-butoxycarbonyl)amino)-2-(2-(4-ethoxy-4-oxobutoxy)phenyl)acetic acid (S7) A vial was charged with S6 (96 mg, 0.20 mmol) and a stir bar and was capped with a septum cap and purged with nitrogen for five minutes. Then tetrahydrofuran (THF, 600 μL, 0.33 M) and tetrabutylammonium fluoride (TBAF, 1M in THF, 300 μL, 0.3 mmol) were added sequentially via syringe. The reactions were stirred 1 h at rt or until complete as determined by TLC or ESI/MS. The reaction mixture was partitioned between 1.5 mL each of EtOAc and $H_2O$, and the EtOAc removed. The $H_2O$ later was extracted with EtOAc (2×2 mL), was dried, filtered, and concentrated under reduced pressure and used without further purification, mixture of rotamers. $^1$H NMR (500 MHz, $cdcl_3$) δ 7.37-7.27 (m, 4H), 6.94 (q, J=7.3 Hz, 2H), 6.86 (dd, J=11.3, 8.3 Hz, 2H), 5.67 (dd, J=22.2, 8.7 Hz, 1H), 5.49 (dd, J=23.2, 8.7 Hz, 1H), 4.06-3.93 (m, 2H), 2.66-2.40 (m, 4H), 2.11 (q, J=6.7 Hz, 4H), 1.88-1.81 (m, 1H), 1.51 (dd, J=9.6, 5.8 Hz, 2H), 1.46-1.37 (m, 18H), 1.33 (h, J=7.1, 6.3 Hz, 4H), 1.25 (dt, J=8.5, 7.1 Hz, 6H), 0.94 (t, J=7.3 Hz, 3H). MS (ESI) 380.2 $[M-H]^-$.

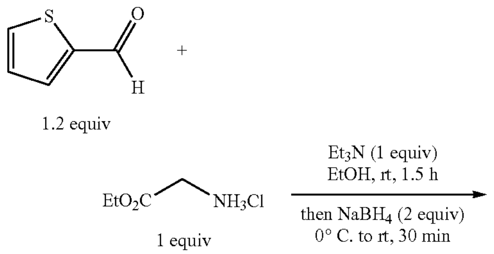

-continued

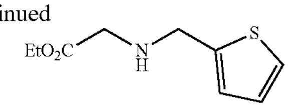

S8

Ethyl (thiophen-2-ylmethyl)glycinate (S8) S8 was synthesized according to the procedure for S2, beginning with glycine ethyl ester hydrochloride (830 mg, 6 mmol), thiophene 2-carboxyaldehyde (620 μL, 7.2 mmol), $Et_3N$ (840 μL, 6 mmol), and MeOH (24 mL, 0.25 M), followed by sodium borohydride (450 mg, 12 mmol) to afford 586 mg (49%) of a light yellow oil. $^1H$ NMR (500 MHz, $CDCl_3$) δ 7.23 (dd, J=4.5, 1.7 Hz, 1H), 6.95 (d, J=4.5 Hz, 2H), 4.20 (q, J=7.1 Hz, 2H), 4.03 (d, J=1.3 Hz, 2H), 3.44 (d, J=0.9 Hz, 2H), 2.08 (s, 1H), 1.28 (t, J=7.1 Hz, 3H). MS (ESI) 200.1 $[M+H]^+$.

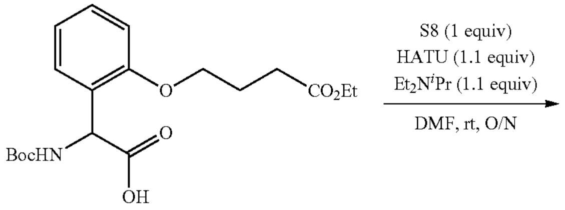

S7

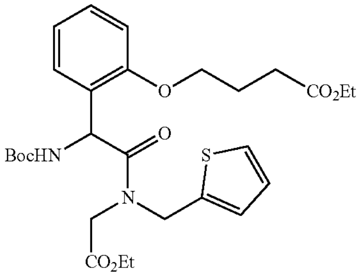

S9

Ethyl 4-(2-(2,2-dimethyl-4,7,10-trioxo-8-(thiophen-2-ylmethyl)-3,11-dioxa-5,8-diazatridecan-6-yl)phenoxy)butanoate (S9) S9 was synthesized according to the procedure for S3, beginning with S7 (38 mg, 0.1 mmol), S8 (20 mg, 0.1 mmol), HATU (42 mg, 0.11 mmol), diisopropylethylamine (20 μL, 0.11 mmol), and DMF (400 μL, 0.25 M) to yield 33.6 mg (60%) of S9 as a clear oil (mixture of rotamers). $^1H$ NMR (400 MHz, $CDCl_3$) δ 7.40-7.27 (m, 4H), 7.24-7.11 (m, 2H), 7.03-6.79 (m, 7H), 6.70 (s, 1H), 6.17 (d, J=8.2 Hz, 1H), 5.77 (dd, J=53.1, 8.9 Hz, 2H), 5.03 (d, J=15.3 Hz, 1H), 4.74-4.51 (m, 3H), 4.20-4.09 (m, 8H), 4.09-3.98 (m, 6H), 3.98-3.80 (m, 4H), 2.64-2.46 (m, 4H), 2.20-2.06 (m, 4H), 1.41 (d, J=4.3 Hz, 20H), 1.30-1.17 (m, 6H), 1.11 (t, J=7.1 Hz, 3H). MS (ESI) 563.1 $[M+H]^+$.

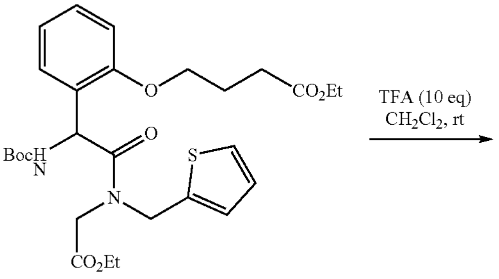

S9

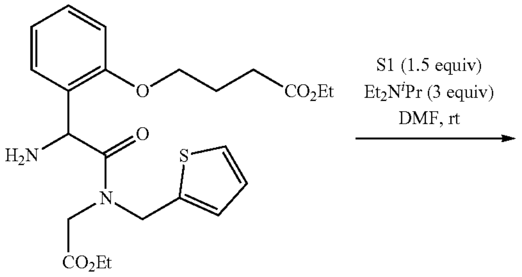

S10

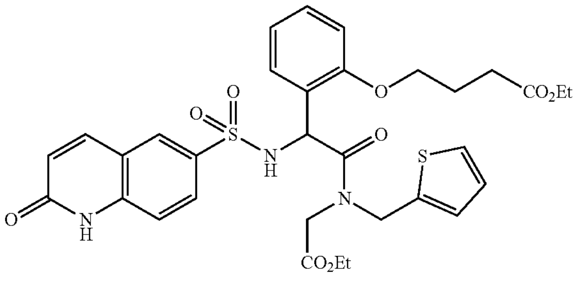

S11

Ethyl 4-(2-(2-((2-ethoxy-2-oxoethyl)(thiophen-2-ylmethyl)amino)-2-oxo-1-((2-oxo-1,2-dihydroquinoline)-6-sulfonamido)ethyl)phenoxy)butanoate (S11) S10 was synthesized according to the procedure for S4 beginning from S9 (34 mg, 0.06 mmol), DCM (500 μL, 0.12 M), and trifluoroacetic acid (39 μL, 0.5 mmol). S11 was synthesized from S10, with S1 (20 mg, 0.08 mmol), diisopropylethylamine (30 μL, 0.17 mmol), and DMF (400 μL, 0.15 M) to yield 19.8 mg (49%) of S11 as a white solid, mixture of rotamers. $^1H$ NMR (400 MHz, $cdcl_3$) δ 11.71 (s, 2H), 7.92 (d, J=2.0 Hz, 1H), 7.85-7.77 (m, 2H), 7.71 (ddd, J=18.9, 8.6, 2.0 Hz, 2H), 7.25-7.08 (m, 6H), 7.08-6.61 (m, 12H), 6.30 (s, 1H), 5.95 (s, 1H), 4.96-4.53 (m, 4H), 4.21-4.07 (m, 6H), 4.07-3.96 (m, 8H), 3.85 (dd, J=28.1, 17.9 Hz, 2H), 2.74-2.33 (m, 4H), 2.30-2.07 (m, 3H), 1.95 (s, 2H), 1.42-0.98 (m, 14H). LC/MS (Method A), 31.0 min (84% pure), 670.1 $[M+H]^+$.

2b/OSMI-3

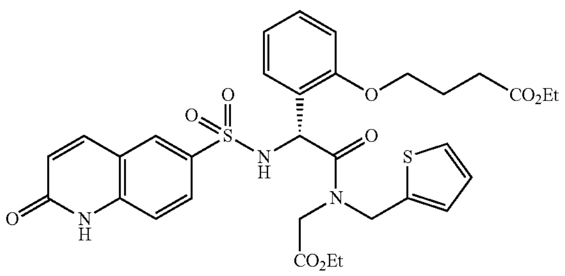

Ethyl (R)-4-(2-(2-((2-ethoxy-2-oxoethyl)(thiophen-2-ylmethyl)amino)-2-oxo-1-((2-oxo-1,2-dihydroquinoline)-6-sulfonamido)ethyl)phenoxy)butanoate (2b/OSMI-3)

S11 was purified using chiral preparatory HPLC under the following conditions: Chiralpak IA column (5×50 cm), eluting with ethanol/methanol/diethylamine (50:50:0.5) at a flow rate of 35 mL/min, with detection at 220 and 254 nm, to afford 2b/OSMI-3 as a white solid. (~1:1 mixture of rotamers) $^{1}$H NMR (500 MHz, $CDCl_3$) δ 11.89 (s, 1H), 7.91 (d, J=2.0 Hz, 1H), 7.87 (d, J=2.0 Hz, 1H), 7.80 (dd, J=8.7, 2.1 Hz, 1H), 7.70 (dd, J=8.7, 2.1 Hz, 1H), 7.63 (dd, J=9.6, 6.3 Hz, 1H), 7.24-7.14 (m, 2H), 6.91-6.83 (m, 2H), 6.77 (dd, J=8.4, 2.9 Hz, 1H), 6.70 (d, J=3.6 Hz, 1H), 6.65 (dd, J=9.5, 5.1 Hz, 1H), 6.22 (d, J=7.5 Hz, 1H), 5.93 (d, J=7.9 Hz, 1H), 4.92 (d, J=15.3 Hz, 1H), 4.68 (d, J=16.3 Hz, 1H), 4.63 (d, J=15.3 Hz, 1H), 4.55 (d, J=16.4 Hz, 1H), 4.20-4.07 (m, 2H), 4.02 (dd, J=15.7, 6.1 Hz, 2H), 3.98-3.89 (m, 2H), 2.81-2.48 (m, 2H), 2.20-2.06 (m, 2H), 1.23 (t, J=7.1 Hz, 3H), 1.17 (dt, J=13.3, 7.1 Hz, 3H). $^{13}$C NMR (126 MHz, $CDCl_3$) δ 173.40, 173.38, 171.07, 170.95, 168.33, 168.03, 164.00, 163.96, 155.30, 155.14, 140.84, 140.82, 140.54, 140.52, 138.01, 137.32, 135.22, 135.12, 130.61, 130.48, 129.13, 129.02, 128.86, 128.74, 127.85, 127.78, 127.72, 127.31, 127.17, 126.79, 126.62, 126.42, 124.09, 123.70, 122.56, 122.51, 121.69, 121.68, 118.67, 118.57, 116.50, 116.45, 112.19, 111.97, 67.62, 67.54, 61.93, 61.50, 60.61, 60.59, 52.49, 52.15, 47.23, 46.98, 46.38, 45.65, 30.67, 30.60, 24.69, 14.39, 14.37, 14.28, 14.14. LC/MS (Method C), 5.18 min (>99% pure, 91.7% ee), 670.2 $[M+H]^+$. HRMS (ESI) m/z calcd for $[C_{32}H_{35}N_3O_9S_2]$: 670.1887 $[M+H]^+$. found 670.1883. $[\alpha]_D^{23}$=−112.4±0.5 (c=0.74, $CHCl_3$).

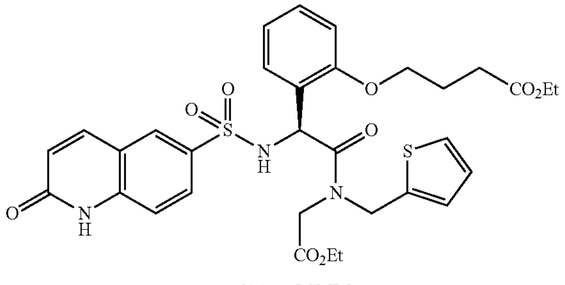

ent-2b/ent-OSMI-3

Ethyl (S)-4-(2-(2-((2-ethoxy-2-oxoethyl)(thiophen-2-ylmethyl)amino)-2-oxo-1-((2-oxo-1,2-dihydroquinoline)-6-sulfonamido)ethyl)phenoxy)butanoate (ent-2b/ent-OSMI-3)

ent-2b/ent-OSMI-3 was isolated from chiral preparatory HPLC as per the procedure for 2b/OSMI-3. White solid (99.6% ee). (mixture of rotamers) $^{1}$H NMR (500 MHz, cdcl$_3$) δ 11.54 (s, 1H), 7.92 (d, J=2.0 Hz, 1H), 7.88 (d, J=2.0 Hz, 1H), 7.82 (dd, J=8.7, 2.0 Hz, 1H), 7.72 (dd, J=8.7, 2.1 Hz, 1H), 7.70-7.61 (m, 1H), 7.24-7.15 (m, 2H), 6.99-6.80 (m, 3H), 6.76 (dd, J=8.1, 2.8 Hz, 1H), 6.71-6.61 (m, 1H), 6.17 (s, 1H), 5.89 (s, 1H), 4.90 (d, J=15.3 Hz, 1H), 4.70-4.34 (m, 3H), 4.12 (qdd, J=8.9, 6.3, 2.8 Hz, 2H), 4.05-3.77 (m, 4H), 2.76-2.48 (m, 2H), 2.21-2.04 (m, 2H), 1.24 (t, J=7.1 Hz, 3H), 1.17 (dt, J=14.9, 7.1 Hz, 3H). LC/MS (Method C), 5.21 min (>99% pure), 670.2 $[M+H]^+$. HRMS (ESI) m/z calcd for $[C_{32}H_{35}N_3O_9S_2]$: 670.1893 $[M+H]^+$. found 670.1863. $[\alpha]_D^{23}$=135.7±0.0 (c=0.51, $CHCl_3$).

2a

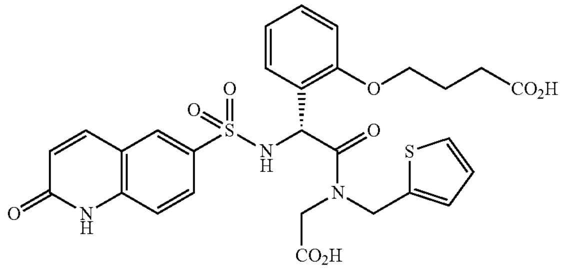

(R)-4-(2-(2-((carboxymethyl)(thiophen-2-ylmethyl)amino)-2-oxo-1-((2-oxo-1,2-dihydroquinoline)-6-sulfonamido)ethyl)phenoxy)butanoic acid (2a) 2 was synthesized according to the procedure for 1, beginning with 5 (2 mg, 0.003 mmol), LiOH (30 μL, 0.03 mmol), and THF (30 μL) to yield 1.5 mg (>99%) of 2a as a white solid. LC/MS (Method A), 23.4 min (>95% pure), 613.8 $[M+H]^+$. HRMS (ESI) m/z calcd for $[C_{28}H_{27}N_3O_9S_2]$: 636.1086 $[M+Na]^+$. found 636.1064. $[\alpha]_D^{23}$=−45±5.0 (c=0.04, 1:1 DCM:MeOH).

ent-2a

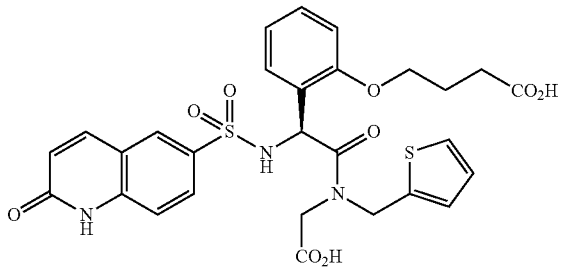

(S)-4-(2-(2-((carboxymethyl)(thiophen-2-ylmethyl)amino)-2-oxo-1-((2-oxo-1,2-dihydroquinoline)-6-sulfonamido)ethyl)phenoxy)butanoic acid (ent-2a)

ent-2a was synthesized according to the procedure for 1a, beginning with ent-2b (2 mg, 0.003 mmol), LiOH (30 μL, 0.03 mmol), and THF (30 μL) to yield 1.5 mg (>99%) as a white solid. LC/MS (Method A), 23.8 min (>95% pure), 613.9 $[M+H]^+$. HRMS (ESI) m/z calcd for $[C_{28}H_{27}N_3O_9S_2]$ 636.1086 $[M+Na]^+$. found 636.1075. $[\alpha]_D^{23}$=60.0±2.3 (c=0.15, 1:1 DCM:MeOH).

Preparation of 3a and 3b

S12

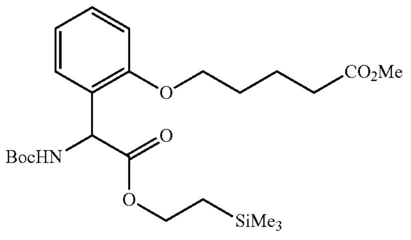

Methyl 5-(2-(2,2,11,11-tetramethyl-6,9-dioxo-5,10-dioxa-8-aza-2-siladodecan-7-yl)phenoxy)pentanoate (S12) S12 was synthesized according to the procedure for S6, beginning from S5 (200 mg, 0.54 mmol), methyl-5-bromovalerate (77 μL, 0.54 mmol), $K_2CO_3$ (180 mg, 1.3 mmol), and DMF (3.4 mL, 0.16 M) to yield 211 mg (81%) of a clear oil that was used without further purification. MS (ESI) 504.0 $[M+Na]^+$.

S13

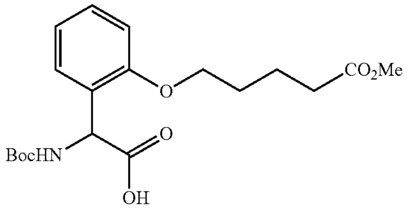

2-((tert-butoxycarbonyl)amino)-2-(2-((5-methoxy-5-oxopentyl)oxy)phenyl)acetic acid (S13) S13 was synthesized according to the procedure for S7, beginning with S12 (189 mg, 0.39 mmol), TBAF (1 M in THF, 590 μL, 0.59 mmol), and THF (1.2 mL, 0.33 M) to yield 169 mg of a crude oil that was used without further purification. MS (ESI) 390.2 $[M-H]^-$.

S14

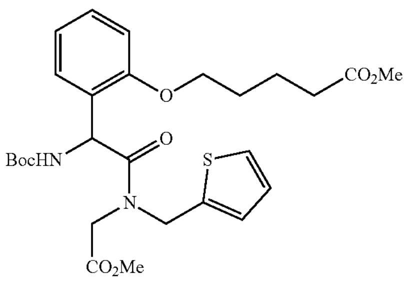

Methyl 5-(2-(11,11-dimethyl-3,6,9-trioxo-5-(thiophen-2-ylmethyl)-2,10-dioxa-5,8-diazadodecan-7-yl)phenoxy)pentanoate (S14) S14 was synthesized according to the procedure for S9, beginning from S13 (140 mg, 0.37 mmol), S2 (68 mg, 0.37 mmol), HATU (154 mg, 0.41 mmol), diisopropylethylamine (71 μL, 0.41 mmol), and DMF (1.34 mL, 0.28 M) to yield 130 mg (64%) of S14 as a solid with minor impurities. MS (ESI) 548.9 $[M+H]^+$.

Methyl 5-(2-(2-((2-methoxy-2-oxoethyl)(thiophen-2-ylmethyl)amino)-2-oxo-1-((2-oxo-1,2-dihydroquinoline)-6-sulfonamido)ethyl)phenoxy)pentanoate

S16

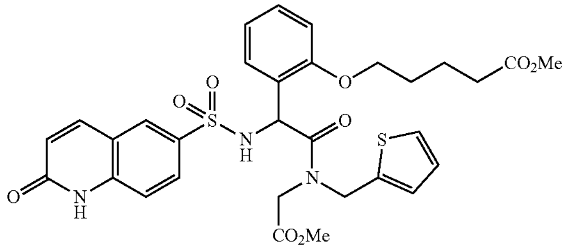

(S16) S16 was synthesized according to the procedures for S10 and S11. S14 (98 mg, 0.18 mmol), trifluoroacetic acid (140 μL, 1.8 mmol), and DCM (1.8 mL, 0.1 M), were reacted to form S15 as a crude oil. S16 was synthesized from S15, with S1 (66 mg, 0.27 mmol), diisopropylethylamine (100 μL, 0.57 mmol), and DMF (1.5 mL, 0.12 M) to yield 62 mg (53%) of S16 as a white solid with 25% of an unknown impurity. S16 was further purified using preparative HPLC (Method B) to yield 52.5 mg (44%) of a white solid. (~1:1 mixture of rotamers) $^1H$ NMR (500 MHz, $CDCl_3$) δ 11.67 (s, 2H), 8.01 (d, J=2.0 Hz, 1H), 7.92 (d, J=2.1 Hz, 1H), 7.76 (dd, J=15.2, 9.5 Hz, 2H), 7.69 (ddd, J=24.0, 8.7, 2.0 Hz, 2H), 7.25-7.17 (m, 5H), 6.95-6.82 (m, 7H), 6.82-6.77 (m, 3H), 6.69 (t, J=10.6 Hz, 4H), 6.39 (d, J=7.6 Hz, 1H), 5.99 (d, J=8.1 Hz, 1H), 4.82 (d, J=15.4 Hz, 1H), 4.76-4.60 (m, 3H), 4.10-3.85 (m, 8H), 3.80 (d, J=17.2 Hz, 2H), 3.70 (s, 4H), 3.66 (d, J=1.4 Hz, 6H), 3.58 (s, 3H), 2.39 (dt, J=33.1, 6.5 Hz, 4H), 1.90 (s, 4H), 1.83 (d, J=6.4 Hz, 2H). $^{13}C$ NMR (126 MHz, $CDCl_3$) δ 174.02, 174.00, 171.55, 171.34, 168.91, 168.70, 163.83, 155.34, 155.22, 141.06, 140.75, 140.52, 137.92, 137.25, 135.32, 130.67, 130.52, 129.12, 128.94, 128.51, 127.84, 127.80, 127.61, 127.48, 127.15, 126.86, 126.58, 126.56, 124.27, 123.64, 122.81, 122.58, 121.72, 121.70, 118.98, 118.96, 115.89, 115.78, 112.35, 112.07, 77.16, 68.26, 52.67, 52.44, 52.42, 52.25, 51.70, 47.10, 46.71, 46.55, 45.69, 33.71, 33.69, 28.75, 21.61, 21.54. LC/MS (Method A), 29.2 min (>95% pure), 655.9 $[M+H]^+$.

3b

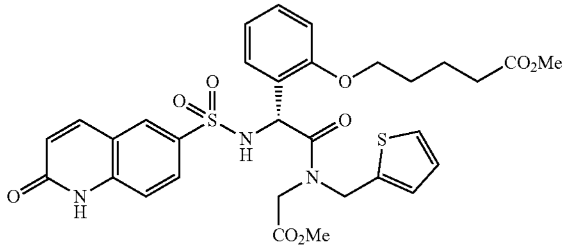

Methyl (R)-5-(2-(2-((2-methoxy-2-oxoethyl)(thiophen-2-ylmethyl)amino)-2-oxo-1-((2-oxo-1,2-dihydroquinoline)-6-sulfonamido)ethyl)phenoxy)pentanoate (3b) S16 was purified using chiral preparatory HPLC under the following conditions: ChiralPak IG column (5×50 mm), eluting with acetonitrile/isopropanol/diethylamine (85:15:0.08), at a flow rate of 30 mL/min, with detection at 220, or 254 nm, to afford a mixture of 3b isomers as a white solid (>98% ee). $^1$H NMR (500 MHz, $CDCl_3$) δ 12.16 (s, 2H), 7.90 (d, J=1.9 Hz, 1H), 7.86 (d, J=2.0 Hz, 1H), 7.78 (dd, J=8.7, 1.8 Hz, 1H), 7.74-7.60 (m, 3H), 7.45 (dd, J=11.1, 8.7 Hz, 2H), 7.21-7.08 (m, 6H), 7.02 (s, 1H), 6.92-6.77 (m, 6H), 6.74-6.55 (m, 5H), 6.13 (d, J=5.2 Hz, 1H), 5.81 (d, J=6.1 Hz, 1H), 4.87 (d, J=15.3 Hz, 1H), 4.63 (d, J=16.3 Hz, 1H), 4.53 (dd, J=15.8, 7.6 Hz, 2H), 4.10-3.86 (m, 8H), 3.76-3.53 (m, 9H), 3.46 (s, 3H), 2.41 (s, 2H), 2.32 (s, 2H), 1.85 (d, J=5.7 Hz, 4H), 1.78 (d, J=6.6 Hz, 4H). LC/MS (Method C), 4.84 min (>95% pure), 656.3 $[M+H]^+$. HRMS (ESI) m/z calcd for $[C_{31}H_{33}N_3O_9S_2]$: 678.1550 $[M+Na]^+$. found 678.1582. $[\alpha]_D^{23}$=−69.8±0.6 (c=2.39, $CHCl_3$).

ent-3b

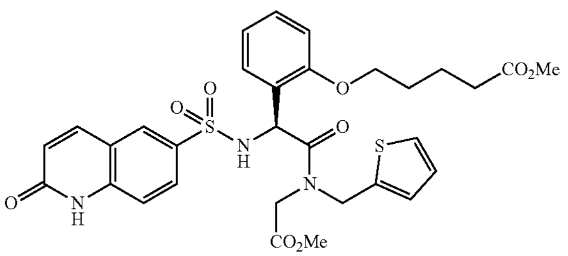

Methyl (S)-5-(2-(2-((2-methoxy-2-oxoethyl)(thiophen-2-ylmethyl)amino)-2-oxo-1-((2-oxo-1,2-dihydroquinoline)-6-sulfonamido)ethyl)phenoxy)pentanoate (ent-3b) ent-3b was isolated as a mixture of isomers from chiral preparatory HPLC as per the procedure for 3b. White solid (99% yield, 91.8% ee). $^1$H NMR (500 MHz, $CDCl_3$) δ 12.16 (s, 2H), 7.91 (d, J=2.0 Hz, 1H), 7.86 (d, J=2.0 Hz, 1H), 7.78 (dd, J=8.7, 2.0 Hz, 1H), 7.73-7.59 (m, 3H), 7.43 (dd, J=12.4, 8.7 Hz, 2H), 7.19-7.14 (m, 6H), 7.05 (s, 1H), 6.93-6.78 (m, 6H), 6.74-6.58 (m, 5H), 6.14 (d, J=5.1 Hz, 1H), 5.81 (d, J=6.1 Hz, 1H), 4.86 (d, J=15.3 Hz, 1H), 4.63 (d, J=16.3 Hz, 1H), 4.53 (dd, J=15.8, 8.3 Hz, 2H), 4.26-3.75 (m, 8H), 3.72-3.56 (m, 9H), 3.47 (s, 3H), 2.41 (s, 2H), 2.32 (s, 2H), 1.85 (d, J=4.8 Hz, 4H), 1.78 (d, J=6.0 Hz, 4H). LC/MS (Method C), 4.83 min (>95% pure), 656.3 $[M+H]^+$. HRMS (ESI) m/z calcd for $[C_{31}H_{33}N_3O_9S_2]$: 678.1550 $[M+Na]^+$. found 678.1520. $[\alpha]_D^{23}$=64.6±0.2 (c=2.38, $CHCl_3$).

3a

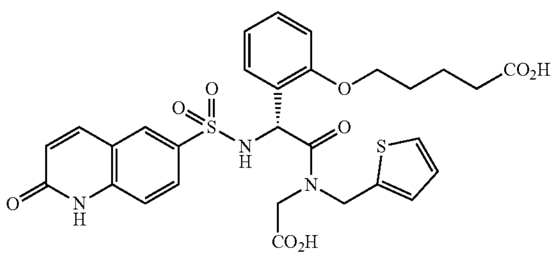

(R)-5-(2-(2-((carboxymethyl)(thiophen-2-ylmethyl)amino)-2-oxo-1-((2-oxo-1,2-dihydroquinoline)-6-sulfonamido)ethyl)phenoxy)pentanoic acid (3a) 3a was synthesized according to the procedure for 2a, beginning with 3b (3 mg, 0.0046 mmol), LiOH (46 μL, 0.046 mmol), and THF (46 μL) to yield 2.0 mg (>99%) as a white solid. LC/MS (Method A), 23.8 min (90% pure), 626.0 $[M-H]^-$. HRMS (ESI) m/z calcd for $[C_{29}H_{29}N_3O_9S_2]$: 626.1272 $[M-H]^-$. found 626.1246. $[\alpha]_D^{23}$=−11.5±0.4 (c=0.29, MeOH)

ent-3a

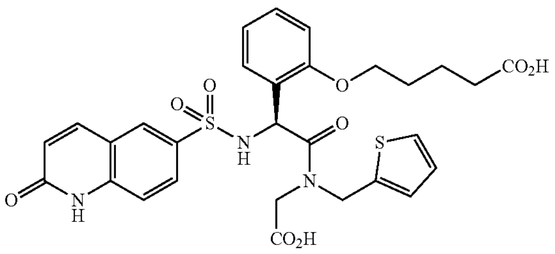

(S)-5-(2-(2-((carboxymethyl)(thiophen-2-ylmethyl)amino)-2-oxo-1-((2-oxo-1,2-dihydroquinoline)-6-sulfonamido)ethyl)phenoxy)pentanoic acid (ent-3a)) ent-3a was synthesized according to the procedure for 2a, beginning with ent-3b (3 mg, 0.0046 mmol), LiOH (46 μL, 0.046 mmol), and THF (46 μL) to yield 2.9 mg (>99%) as a white solid. LC/MS (Method A), 23.8 min (86% pure), 626.0 $[M-H]^-$. HRMS (ESI) m/z calcd for $[C_{29}H_{29}N_3O_9S_2]$: 626.1272 $[M-H]^-$. found 626.1280. $[\alpha]_D^{23}$=9.7±0.7 (c=0.29, MeOH)

Preparation of 4a and 4b/OSMI-4

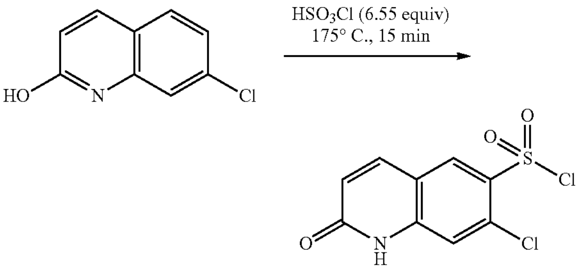

S17

7-chloro-2-oxo-1,2-dihydroquinoline-6-sulfonyl chloride (S17) A 50 mL round bottom flask was charged with 7-chloroquinolin-2(1H)-one (2 g, 11.2 mmol), chlorosulfonic acid (4.8 mL, 22.8 mmol), and a stir bar, and was capped with a septum cap. A vent needle was added. The suspension was heated at 148° C. for 3 h. The reaction mixture was allowed to cool down to room temperature, and was then poured into crushed ice. The precipitate was collected by filtration, and was then dried under reduced pressure to afford crude 7-chloro-2-oxo-1,2-dihydroquinoline-6-sulfonyl chloride (1.61 g, 52% yield) as a light brown solid. $^1$H NMR (400 MHz, DMSO) δ 8.15 (s, 1H), 7.97 (d, J=9.6 Hz, 1H), 7.27 (d, J=10.8 Hz, 1H), 6.49 (d, J=9.6 Hz, 1H).

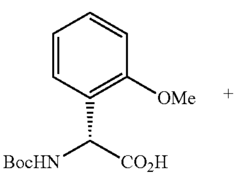

1 equiv

-continued

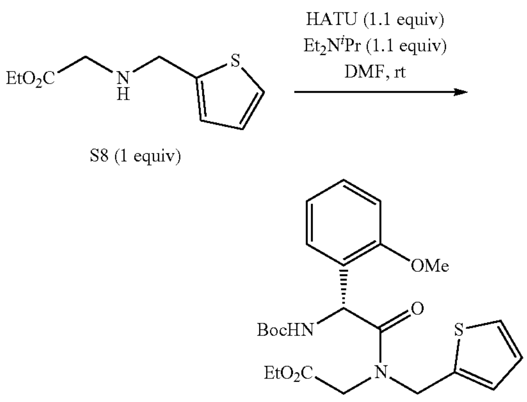

S8 (1 equiv)

S18

Ethyl (R)—N-(2-((tert-butoxycarbonyl)amino)-2-(2-methoxyphenyl)acetyl)-N-(thiophen-2-ylmethyl)glycinate (S18) A 50 mL round bottom flask was charged with (R)-2-((tert-butoxycarbonyl)amino)-2-(2-methoxyphenyl) acetic acid (1 g, 3.56 mmol), S8 (710 mg, 3.56 mmol) and a stir bar. The flask was capped with a septum and purged with nitrogen for 5 minutes. Dimethylformamide (DMF) was added via syringe (14 mL, 0.25 M), followed by HATU (1.5 g, 3.9 mmol) by briefly removing the septum cap. Diisopropylethylamine (700 μL, 3.9 mmol) was added via syringe, and the reaction was stirred at rt for 5 h. The reaction mixture was partitioned between EtOAc (10 mL) and $H_2O$ (10 mL). The organic layer was removed, and the $H_2O$ was extracted with EtOAc (2×10 mL). The combined organic layers were washed with brine (10 mL), dried, filtered, and concentrated under reduced pressure. The resulting oil was purified using flash silica chromatography, eluting with 10-50% EtOAc/Hexanes to yield 1.24 g (76%) of S18 as a light yellow oil. $^1H$ NMR (400 MHz, $CDCl_3$) was analogous to S3. MS (ESI) 463.0 $[M+H]^+$.

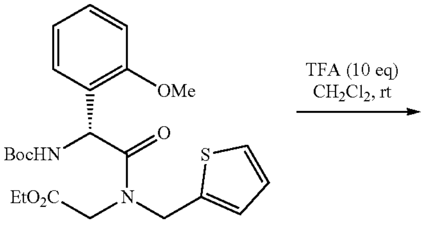

S18

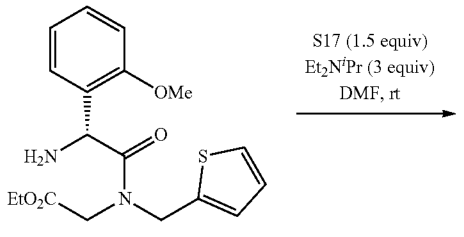

S19

-continued

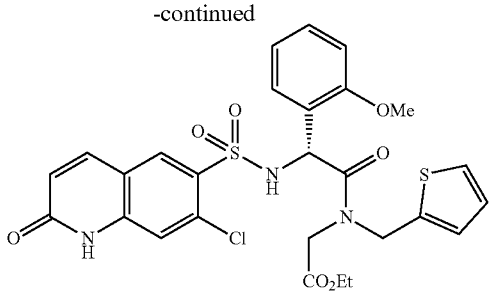

4b/OSMI-4

Ethyl (R)—N-(2-((7-chloro-2-oxo-1,2-dihydroquinoline)-6-sulfonamido)-2-(2-methoxyphenyl)acetyl)-N-(thiophen-2-ylmethyl)glycinate (4b/OSMI-4) A solution of S18 (1.24 g, 2.68 mmol) in dichloromethane (DCM, 26 mL. 0.1 M) was treated with trifluoroacetic acid (2 mL, 26.8 mmol) at rt for 1.5 h in a 50 mL round bottom flask. The reaction mixture was concentrated under reduced pressure, then the residue was taken up in toluene (approx. 10 mL), and the resulting mixture was concentrated again under reduced pressure. This process was repeated twice, and the remaining volatiles were removed. A stir bar was added to the vial containing the resulting crude amine (S19), and the vial was sealed with a septum cap and purged for 5 minutes with nitrogen. To the vial of crude S19 (870 mg, 2.43 mmol) was added a stir bar and a septum cap. The vial was purged with nitrogen for 5 minutes. Then DMF (13 mL, 0.2 M) was added via syringe. Then the top was opened briefly, and S17 (1 g, 3.65 mmol) was added by briefly opening the vial. Diisopropylethylamine (1.3 mL, 7.3 mmol) was added via syringe, and the reaction was stirred at rt for 60 minutes. The reaction mixture was partitioned between EtOAc (20 mL) and $H_2O$ (20 mL). The organic layer was removed, and the $H_2O$ was extracted with EtOAc (2×20 mL). The combined organic layers were washed with $H_2O$ and brine (20 mL each), dried, filtered, and concentrated under reduced pressure. The resulting oil was purified using flash silica chromatography, eluting with 1-10% DCM/MeOH to yield 145 mg (9.9%) of OSMI-4 as a white solid (~1:1 mixture of rotamers). $^1H$ NMR (400 MHz, $CDCl_3$) δ 12.52 (s, 2H), 7.98 (d, J=1.8 Hz, 2H), 7.68-7.53 (m, 2H), 7.34-7.08 (m, 8H), 6.94-6.76 (m, 5H), 6.67 (d, J=9.4 Hz, 6H), 6.26 (s, 1H), 5.90 (s, 1H), 4.94 (d, J=15.3 Hz, 1H), 4.60 (dd, J=22.9, 15.9 Hz, 3H), 4.12 (q, J=7.1 Hz, 2H), 3.97 (d, J=8.8 Hz, 2H), 3.89 (dd, J=6.8, 3.4 Hz, 4H), 3.78 (d, J=8.6 Hz, 6H), 2.03 (s, 1H), 1.29-1.08 (m, 6H). $^{13}C$ NMR (126 MHz, $CDCl_3$) δ 168.34, 167.87, 164.11, 155.92, 155.72, 140.73, 140.29, 137.95, 137.31, 133.53, 132.96, 130.81, 130.78, 130.58, 130.42, 129.06, 128.89, 127.62, 127.34, 127.06, 126.71, 126.43, 126.37, 123.82, 122.59, 121.58, 121.44, 118.21, 117.18, 117.16, 111.19, 110.82, 61.69, 61.45, 55.89, 55.73, 53.10, 52.62, 47.07, 46.84, 46.26, 45.55, 29.82, 14.26, 14.11. LC/MS (Method A), 29.5 min (>95% pure), 603.8 $[M+H]^+$. HRMS (ESI) m/z calcd for $[C_{27}H_{26}ClN_3O_7S_2]$: 626.0798 $[M+Na]^+$. found 626.0776. $[\alpha]_D^{23}$=−84.0±0.4 (c=1.05, $CHCl_3$).

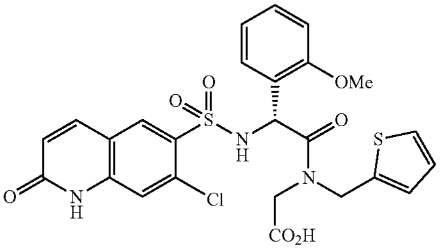

4a (R)—N-(2-((7-chloro-2-oxo-1,2-dihydroquinoline)-6-sulfonamido)-2-(2-methoxyphenyl)acetyl)-N-(thiophen-2-ylmethyl)glycine (4a) 4a was synthesized according to the procedure for 1, beginning with 4b (2 mg, 0.0033 mmol), LiOH (34 μL, 0.033 mmol), and THF (33 μL) to yield 2.0 mg (>99%) as a white solid. LC/MS (Method A), 24.8 min (90% pure), 575.8 $[M+H]^-$. HRMS (ESI) m/z calcd for $[C_{25}H_{22}ClN_3O_7S_2]$: 598.0485 $[M+Na]^+$. found 598.0454. $[\alpha]D_{23}$=−12.6±0.6 (c=0.18, MeOH)

Example 3B. Synthesis of Exemplary OGT Inhibitor Compounds

In some embodiments, compounds of the invention may be synthesized according to the exemplary synthetic procedures provided below in Example 3B. In some embodiments, compounds of the invention may be synthesized according to Scheme 1.

General Scheme 1

Scheme 1

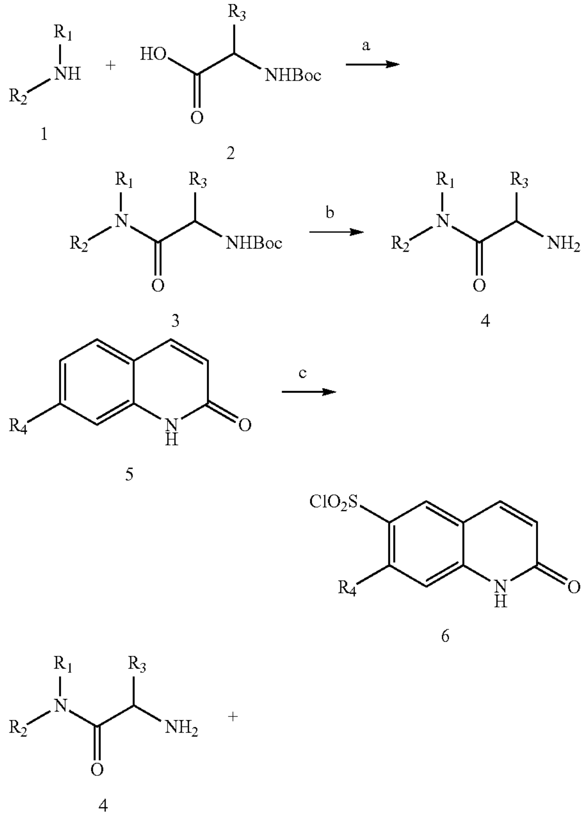

-continued

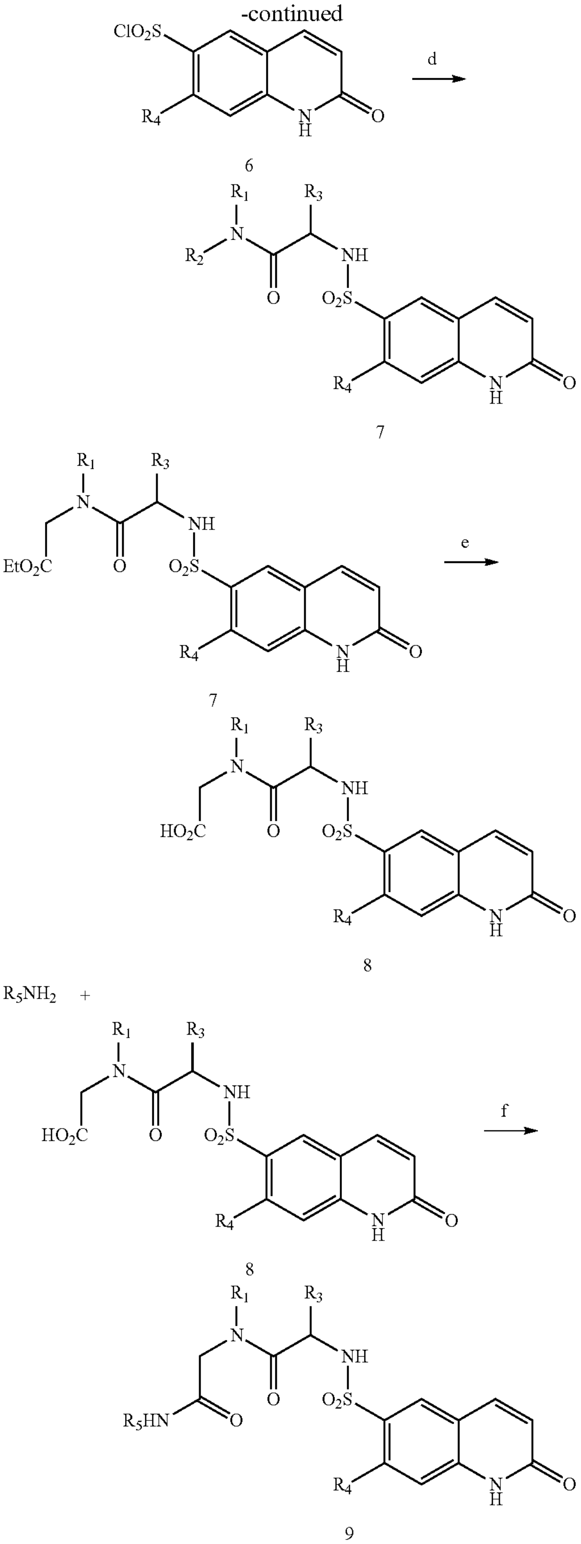

Reagents and conditions: (a) (1) HATU, DIPEA, DMF, 23° C.; (b) TFA, DCM, 23° C., or HCl, Dioxane, 23° C.; (c) $HSO_3Cl$, 90° C.; (d) DIPEA, DMF, 23° C.; (1) NaOH, $H_2O$—EtOH—THF, (2) aq. HCl; (f) EDCI, TEA, DCM, 23° C.

General Synthetic Procedures A to Prepare Amine 1

Procedure A1

A mixture containing the appropriate amine (1.00 equiv.) and the appropriate aldehyde (1.00 equiv.) in EtOH (0.50 M)

was heated in the microwave reactor at 120° C. for 0.5 h. The reaction solution was allowed to cool down to room temperature, was then transferred into a round-bottomed flask, and was then treated with sodium borohydride (2.00 equiv.) at 23° C. for 16 h. The reaction mixture was concentrated under diminished pressure, and the residue was partitioned between DCM and water. The product was extracted with two portions of DCM. The combined organic layer was washed with brine, was then dried ($Na_2SO_4$), and was then concentrated under diminished pressure. The crude residue was applied to a silica gel column; eluting with 90:10-50:50 Hex-EtOAc afforded secondary amine 1.

Procedure A2

A solution containing the amine (1.00 equiv.), ethyl 2-oxoacetate (50% w/w solution in toluene, 1.50 equiv.) and acetic acid (0.05 equiv.) in ethanol (0.15 M) was stirred at 23° C. for 2.0 h. Then, sodium cyanoborohydride (3.00 equiv.) was added, and the resulting solution was stirred at 60° C. for 1.5 h. The reaction mixture was allowed to cool down to room temperature and was then concentrated under diminished pressure. The residue was partitioned between water and EtOAc. The layers were separated. The product was extracted with three portions of EtOAc. The combined organic layer was washed with brine, was then dried ($Na_2SO_4$), and was then concentrated under diminished pressure. The residue was applied to a silica gel column; eluting with 100:0→0:100 Hex-EtOAc afforded secondary amine 1.

Procedure A3

To a stirred suspension at 23° C. containing the amine (1.00 equiv.) and magnesium sulfate (0.25 equiv.) in DCM (0.10 M) was added ethyl 2-oxoacetate (50% w/w solution in toluene, 1.00 equiv.). The suspension was stirred at 23° C. for 1 hr, was then filtered, and was then concentrated under diminished pressure. The residue was dissolved into ethyl acetate (0.10 M), and the resulting solution was treated with 10% Pd/C (0.05 equiv.) under an atmosphere of hydrogen (1 atm) at 23° C. for 2 hr. Celite was added to trap Pd/C; the resulting suspension was stirred at 23° C. for 5 min, and was then filtered; the collected filtrate was concentrated under diminished pressure to secondary amine 1.

Procedure A4

A suspension containing the amine (1.00 equiv.) in THF (0.10 M) was treated with sodium bicarbonate (4.00 equiv.). Then, ethyl 2-bromoacetate (1.20 equiv.) was added, and the reaction mixture was stirred at 23° C. for 18 hr. The reaction mixture was diluted with TBME, was filtered, and the collected filtrate was concentrated under diminished pressure. The residue was applied to a silica gel column; eluting with 100:0-85:15 DCM-MeOH afforded secondary amine 1.

General Procedure B to Prepare Amide 3

A solution containing the appropriate 2-((tert-butoxycarbonyl)amino)-2-(aryl)acetic acid 1.00 equiv.) 2 and the appropriate secondary amine 1 (1.00 equiv.) in DMF (0.20 M) was treated with HATU (1.10 equiv.) and DIPEA (1.10 equiv.) at 23° C. for 5.0 h. The reaction mixture was partitioned between EtOAc and water. The product was extracted with three portions of EtOAc. The combined organic layer was washed with two portions of water, then with brine, was then dried ($Na_2SO_4$), and was then concentrated under diminished pressure. The obtained oil was applied to a silica gel column; eluting with 80:20→40:60 Hex-EtOAc afforded amide 3.

General Procedure C to Prepare Amine 4

General Procedure C1

A solution containing the N-Boc-protected amine 3 (1.00 equiv.) in DCM (0.10 M) was treated with trifluoroacetic acid (10.0 equiv.) at 23° C. for 1.5 h. The reaction mixture was concentrated under diminished pressure, then the residue was taken up in toluene, and the resulting mixture was concentrated under diminished pressure. This process was repeated twice to afford amine 4 as the TFA salt.

General Procedure C2

A solution containing the N-Boc-protected amine 3 (1.00 equiv.) in dioxane (0.20 M) was treated with hydrochloric acid (4 M solution in dioxane, 10.0 equiv.) at 23° C. for 16 h. The reaction mixture was concentrated under diminished pressure, then the residue was taken up in toluene, and the resulting mixture was concentrated under diminished pressure. This process was repeated twice to afford amine 4 as the HCl salt.

General Procedure D to Prepare Chlorosulfonyl 6

A mixture containing 1,2-dihydroquinolin-2-one 5 (1.00 equiv.) in chlorosulfonic acid (6.50 equiv.) was stirred at 90° C. for 3 h. The reaction mixture was allowed to cool down to room temperature, and was then poured carefully into 50 mL of crushed ice, leading to the formation of a precipitate. The solid was collected by filtration, was washed with small portions of cold water, and was then dried over $P_2O_5$ under diminished pressure to afford 2-oxo-1,2-dihydroquinoline-6-sulfonyl chloride 6.

General Procedure E to Prepare the Sulfonamide 7

Amine 4 was dissolved into DMF (0.10 M), was then treated with DIPEA (2.00 equiv.), and was then treated with sulfonyl chloride 6 (1.20 equiv.) at 23° C. for 16 h. The reaction mixture was partitioned between water and EtOAc. The layers were separated, then the product was extracted with three portions of EtOAc. The combined organic layer was washed with brine, was then dried ($Na_2SO_4$), and was then concentrated under diminished pressure. The crude product was purified by HPLC to afford sulfonamide 7.

General Procedure F to Prepare Acid 8

A solution containing ester 7 (1.00 equiv.) in 2:1 THF-ethanol (0.15 M) was treated with 4 M aqueous sodium hydroxide (10.0 equiv.) at 23° C. for 17 hr. The reaction mixture was treated with 1 M aqueous hydrochloric acid (15.0 equiv.) and was partitioned with chloroform. The layers were separated; the aqueous layer was extracted with three portions of chloroform. The combined organic layer was washed with brine, was then dried (sodium sulfate), and was then concentrated under diminished pressure to afford acid 8.

General Procedure G to Carry Out the Chiral Separation of Racemic Final Products When necessary, the two enantiomers were separated by chiral HPLC using one of the following methods:

General Procedure G1

Column: CHIRALPAK IG, 5×50 cm, 20 uM; Mobile Phase: ACN/IPA/Diethylamine 85:15:0.08; Flow Rate: 30.0 mL/min.

General Procedure G2

Column: CHIRALPAK IA (5×50 cm, 20 uM); Mobile Phase: Hex/EtOH/MeOH 40:30:30; Flow Rate: 35 mL/min.

General Procedure H to Prepare Amide 9

A solution containing acid 8 (1.00 equiv.) and the appropriate amine (1.10 equiv.) in DCM (0.05 M) was treated with EDC (1.10 equiv.) and TEA (1.20 equiv.) at 23° C. for 5 hr. The reaction mixture was partitioned between 0.1 M aqueous HCl and DCM. The layers were separated; the aqueous layer was extracted with one portion of DCM. The combined organic layer was washed with brine, was then dried ($Na_2SO_4$), and was then concentrated under diminished pressure. The crude residue was purified by HPLC to afford amide 9.

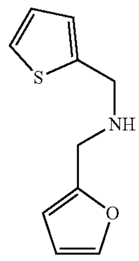 [SMILES: c1coc(CNCc2cccs2)c1]

1-(furan-2-yl)-N-(thiophen-2-ylmethyl)methanamine

A mixture containing furan-2-ylmethanamine (1.00 mL, 11.32 mmol) and thiophene-2-carbaldehyde (1.06 mL, 11.32 mmol) in EtOH (22.6 mL) was heated in the microwave reactor at 120° C. for 0.5 h. The reaction solution was transferred to a round-bottomed flask, and was then treated with sodium borohydride (0.856 g, 22.63 mmol) at 90° C. for 3 h, then at 23° C. for 16 h. The reaction mixture was concentrated under diminished pressure, and the residue was partitioned between 50 mL of DCM and 50 mL of water. The product was extracted with two 25-mL portions of DCM. The combined organic layer was washed with 50 mL of brine, was then dried ($Na_2SO_4$), and was then concentrated under diminished pressure. The crude residue was applied to a silica gel column (100 g); eluting with 90:10→50:50 Hex-EtOAc afforded 1-(furan-2-yl)-N-(thiophen-2-ylmethyl)methanamine as a clear light pale yellow oil; yield: 1.87 g (86%).

LC-MS (Method A): t=1.77 min.

$^1$H NMR (400 MHz, $CDCl_3$) δ 7.38 (dd, J=1.9, 0.8 Hz, 1H), 7.22 (dd, J=4.8, 1.4 Hz, 1H), 6.98-6.92 (m, 2H), 6.32 (dd, J=3.2, 1.9 Hz, 1H), 6.22-6.18 (m, 1H), 3.99 (d, J=0.7 Hz, 2H), 3.82 (s, 2H), 1.98 (s, 2H).

$^{13}$C NMR (101 MHz, $CDCl_3$) δ 153.5, 143.5, 142.1, 126.8, 125.4, 124.7, 110.3, 107.5, 47.2, 45.0.

HRMS (ESI) m/z 194.0635 (M+H)+($C_{10}H_{12}NOS$ requires 194.0634).

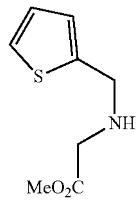 [SMILES: COC(=O)CNCc1cccs1]

Methyl (thiophen-2-ylmethyl)glycinate

A 100 mL round bottom flask was charged with glycine methyl ester hydrochloride (750 mg, 6 mmol) and a stir bar. MeOH (24 mL, 0.25 M) and $E_{t3}N$ (840 μL, 6 mmol) were added via syringe, followed by thiophene 2-carboxaldehyde (620 μL, 7.2 mmol). Reaction was stirred 1.5 h at rt, and the presence of imine was confirmed using ESI/MS. The solution was chilled to 0-5° C. using an ice bath, and sodium borohydride (450 mg, 12 mmol) was slowly added to the reaction mixture in portions. The ice bath was removed, and the reaction was allowed to warm to rt over 30 minutes. MeOH was then removed under reduced pressure, and the reaction mixture was partitioned between EtOAc (10 mL) and $H_2O$ (10 mL). The $H_2O$ layer was removed, and EtOAc washed with $H_2O$ (2×10 mL) and brine (10 mL). The reaction was dried, filtered, and concentrated under reduced pressure. The residue was purified using flash silica chromatography, eluting with 5-50% EtOAc/Hexanes to yield 308 mg (28%) of methyl (thiophen-2-ylmethyl)glycinate as a clear oil.

$^1$H NMR (500 MHz, $CDCl_3$) δ 7.24 (dt, J=4.9, 1.2 Hz, 1H), 7.05-6.88 (m, 2H), 4.04 (q, J=1.3 Hz, 2H), 3.86-3.65 (m, 3H), 3.56-3.41 (m, 2H), 2.25-1.96 (m, 1H).

$^{13}$C NMR (126 MHz, $CDCl_3$) δ 172.71, 143.08, 126.65, 125.34, 124.77, 51.82, 49.47, 47.75.

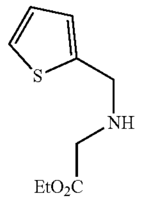

1-Ethyl (thiophen-2-ylmethyl)glycinate

A solution containing thiophen-2-ylmethanamine (2.00 mL, 19.49 mmol), ethyl 2-oxoacetate (50% w/w solution in toluene) (5.95 mL, 29.2 mmol) and acetic acid (0.056 mL, 0.975 mmol) in ethanol (130 mL) was stirred at 23° C. for 2.0 hr. Then, sodium cyanoborohydride (3.67 g, 58.5 mmol) was added, and the resulting solution was stirred at 60° C. for 1.5 hr. The reaction mixture was allowed to cool down to room temperature and was then concentrated under diminished pressure. The residue was partitioned between 50 mL of water and 50 mL of EtOAc. The layers were separated. The product was extracted with three 50-mL portions of EtOAc. The combined organic layer was washed with 50 mL of brine, was then dried ($Na_2SO_4$), and was then concentrated under diminished pressure. The residue was applied to a silica gel column (80 g); eluting with 100:0→0:100 Hex-EtOAc afforded ethyl (thiophen-2-ylmethyl)glycinate (2.70 g, 13.55 mmol, 69.5% yield) as a dark yellow light oil.

$^1$H NMR (400 MHz, $CDCl_3$) δ 7.23 (dd, J=4.7, 1.6 Hz, 1H), 6.97-6.91 (m, 2H), 4.19 (q, J=7.1 Hz, 2H), 4.03 (s, 2H), 3.44 (s, 2H), 1.99 (s, 1H), 1.28 (t, J=7.2 Hz, 3H).

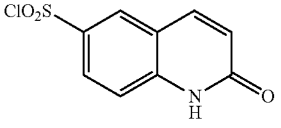 [SMILES: O=c1ccc2cc(S(=O)(=O)Cl)ccc2[nH]1]

2-oxo-1,2-dihydroquinoline-6-sulfonyl Chloride

A mixture containing 1,2-dihydroquinolin-2-one (1.30 g, 8.96 mmol) in chlorosulfonic acid (3.90 ml, 58.7 mmol) was stirred at 90° C. for 3 h. The reaction mixture was allowed to cool down to room temperature, and was then poured carefully into 50 mL of crushed ice, leading to the formation of a precipitate. The solid was collected by filtration, was washed with small portions of cold water, and was then dried to afford 2-oxo-1,2-dihydroquinoline-6-sulfonyl chloride as a light brown solid; yield: 1.52 g (70%).

$^1H$ NMR (400 MHz, DMSO-$d_6$) δ 11.81 (s, 1H), 7.96 (d, J=9.4 Hz, 1H), 7.89 (d, J=1.9 Hz, 1H), 7.70 (dd, J=8.5, 1.9 Hz, 1H), 7.23 (d, J=8.5 Hz, 1H), 6.49 (d, J=9.5 Hz, 1H).

$^{13}C$ NMR (100 MHz, DMSO-$d_6$) δ 162.4, 142.5, 141.1, 139.2, 128.5, 125.3, 122.4, 118.5, 115.0.

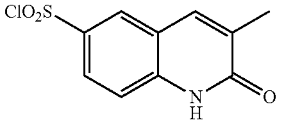 [SMILES: Cc1cc2cc(S(=O)(=O)Cl)ccc2[nH]c1=O]

3-methyl-2-oxo-1,2-dihydroquinoline-6-sulfonyl Chloride

A mixture containing N-(2-formylphenyl)propionamide (500 mg, 2.82 mmol) and cesium carbonate (4.597 g, 14.11 mmol) in DMF (Volume: 28.200 mL) was stirred at 60° C. for 22 h. The reaction mixture was diluted with 50 mL of EtOAc. The suspension was stirred vigorously at 23° C. for 5 min, and was then filtered through a pad of celite. The collected clear yellow filtrate was washed with three 25-mL portions of water. The product was extracted with two 25-mL portions of EtOAc. The combined organic layer was washed with 25 mL of sat. aqueous $NH_4Cl$, was then dried ($Na_2SO_4$), and was then concentrated under diminished pressure. The residue was applied to a silica gel column (50 g); eluting with 60:40→20:80 Hex-EtOAc afforded the product contaminated with a small amount of an unidentified by-product. The solid was recrystallized from EtOAc to afford 3-methylquinolin-2(1H)-one (280 mg, 1.759 mmol, 62.3% yield) as a white solid.

$^1H$ NMR (400 MHz, DMSO-$d_6$) δ 11.72 (s, 1H), 7.78-7.73 (m, 1H), 7.56 (dd, J=7.8, 1.4 Hz, 1H), 7.42 (ddd, J=8.5, 7.2, 1.4 Hz, 1H), 7.27 (ddd, J=8.2, 1.2, 0.6 Hz, 1H), 7.14 (ddd, J=7.8, 7.2, 1.2 Hz, 1H), 2.08 (d, J=1.2 Hz, 3H).

A mixture containing 3-methylquinolin-2(1H)-one (0.280 g, 1.759 mmol) in chlorosulfonic acid (0.766 mL, 11.52 mmol) was stirred at 90° C. for 3 h. The mixture was then poured carefully into 5 mL of crushed ice, leading to the formation of a white precipitate. The solid was collected by filtration, was washed with small portions of cold water, and was then dried under diminished pressure to afford 3-methyl-2-oxo-1,2-dihydroquinoline-6-sulfonyl chloride (0.403 g, 1.564 mmol, 89% yield) as a white solid.

$^1H$ NMR (400 MHz, DMSO-$d_6$) δ 11.80 (s, 1H), 7.84-7.79 (m, 2H), 7.64 (dd, J=8.5, 1.9 Hz, 1H), 7.22 (d, J=8.5 Hz, 1H), 2.08 (d, J=1.2 Hz, 3H).

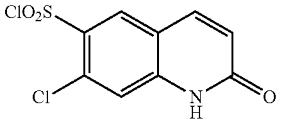 [SMILES: O=c1ccc2cc(S(=O)(=O)Cl)c(Cl)cc2[nH]1]

7-chloro-2-oxo-1,2-dihydroquinoline-6-sulfonyl Chloride

The reaction was carried out in two 500-mg batches. A suspension containing 7-chloroquinolin-2(1H)-one (0.500 g, 2.78 mmol) in chlorosulfonic acid (1.305 ml, 19.49 mmol) was heated in the microwave reactor at 175° C. for 45 min. The reaction mixture obtained in both vials was allowed to cool down to room temperature, and was then poured into crushed ice (approx. 20 mL). The precipitate was collected by filtration, and was then dried under diminished pressure over $P_2O_5$ to afford the crude product as a light brown powder. The crude product was applied to a silica gel column (Isco, 40 g, solid deposit); eluting with 100:0→0:100 DCM-EtOAc afforded 7-chloro-2-oxo-1,2-dihydroquinoline-6-sulfonyl chloride (0.210 g, 0.755 mmol, 27.1% yield) as a white solid.

$^1H$ NMR (400 MHz, DMSO-$d_6$) δ 11.79 (s, 1H), 8.15 (s, 1H), 7.96 (dt, J=9.5, 0.6 Hz, 1H), 7.28 (t, J=0.5 Hz, 1H), 6.48 (d, J=9.5 Hz, 1H).

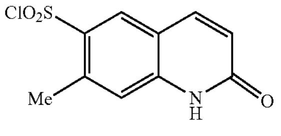 [SMILES: Cc1cc2[nH]c(=O)ccc2cc1S(=O)(=O)Cl]

7-methyl-2-oxo-1,2-dihydroquinoline-6-sulfonyl Chloride

A mixture containing 7-methylquinolin-2(1H)-one (0.080 g, 0.503 mmol) in chlorosulfonic acid (2.00 g, 17.2 mmol) was stirred at 65° C. for 3 h. The mixture was then poured carefully into 5 mL of crushed ice, leading to the formation of a white precipitate. The solid was collected by filtration, was washed with small portions of cold water, and was then dried under diminished pressure to afford 7-methyl-2-oxo-1,2-dihydroquinoline-6-sulfonyl chloride (0.050 g, 0.503 mmol, 39% yield) as a brown solid.

$^1H$ NMR (400 MHz, DMSO-$d_6$) δ 11.66 (s, 1H), 7.98 (s, 1H), 7.90 (d, J=9.4 Hz, 1H), 7.04 (s, 1H), 6.40 (d, J=9.5 Hz, 1H), 2.58 (s, 3H).

The exemplary compounds provided below were synthesized according to exemplary Scheme 1 and Examples 3A and 3B above.

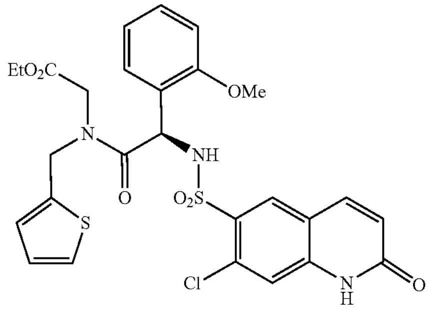 [SMILES: COc1ccccc1[C@@H](NS(=O)(=O)c1cc2ccc(=O)[nH]c2cc1Cl)C(=O)N(CC(=O)O)Cc1cccs1]

4-Ethyl (R)—N-(2-((7-chloro-2-oxo-1,2-dihydroquinoline)-6-sulfonamido)-2-(2-methoxyphenyl)acetyl)-N-(thiophen-2-ylmethyl)glycinate A solution containing ethyl (R)—N-(2-((tert-butoxycarbonyl)amino)-2-(2-methoxyphenyl)acetyl)-N-(thiophen-2-ylmethyl)glycinate (0.500 g, 1.081 mmol) in dioxane (5.20 mL) was treated with 4 M hydrochloric acid in dioxane (5.40 mL, 21.6 mmol) at 23° C. for 23 hr. The reaction mixture was concentrated under diminished pressure. The residue was co-evaporated with 5 mL of hexanes, then with two 5-mL portions of DCM. The resulting residue was dissolved into DMF (10.3 mL), and was then treated at 0-5° C. with DIPEA (0.415 mL, 2.378 mmol) and with 7-chloro-2-oxo-1,2-dihydroquinoline-6-sulfonyl chloride (0.340 g, 1.223 mmol). The cooling was removed, and the reaction mixture (clear brown solution) was stirred at 23° C. for 1 hr. The reaction mixture was concentrated under diminished pressure. The residue was partitioned between 20 mL of water and 20 mL of EtOAc. The layers were separated; the aqueous layer was extracted with three 20 mL portions of EtOAc. The combined organic layer was washed with 20 mL of brine, was then dried (sodium sulfate), and was then concentrated under diminished pressure. The residue was applied to a silica gel column (Isco gold, 40 g); eluting with 100:0-85:15 DCM-MeOH to afford the product, along with an unidentified impurity. The fractions containing the product were pooled; the resulting solution was concentrated under diminished pressure. The residue was applied to a silica gel column (Isco gold, 24 g); eluting with 100:0-0:100 DCM-EtOAc afforded 4-Ethyl (R)—N-(2-((7-chloro-2-oxo-1,2-dihydroquinoline)-6-sulfonamido)-2-(2-methoxyphenyl)acetyl)-N-(thiophen-2-ylmethyl)glycinate.

LC-MS (Method A): t=5.04 min; 605 $[M+H]^+$ $^1$H NMR (600 MHz, DMSO-$d_6$) δ 12.00 (t, J=2.3 Hz, 2H), 8.22 (d, J=9.0 Hz, 1H), 8.13-8.10 (m, 2H), 8.09 (s, 1H), 7.97 (dd, J=9.6, 6.6 Hz, 2H), 7.43 (dd, J=5.1, 1.2 Hz, 1H), 7.34 (dd, J=5.1, 1.3 Hz, 1H), 7.25 (ddd, J=18.2, 7.6, 1.7 Hz, 2H), 7.19-7.15 (m, 3H), 7.10 (ddd, J=8.2, 7.4, 1.7 Hz, 1H), 6.94 (dd, J=5.1, 3.4 Hz, 1H), 6.91 (dd, J=3.4, 1.2 Hz, 1H), 6.89-6.83 (m, 3H), 6.79 (td, J=7.5, 1.1 Hz, 1H), 6.72 (dd, J=8.4, 1.1 Hz, 1H), 6.65 (dd, J=8.5, 1.0 Hz, 1H), 6.58 (dt, J=9.6, 2.2 Hz, 2H), 5.75 (d, J=9.1 Hz, 1H), 5.48 (d, J=8.9 Hz, 1H), 4.67 (d, J=15.1 Hz, 1H), 4.49 (s, 2H), 4.45 (d, J=15.1 Hz, 1H), 4.03-3.91 (m, 4H), 3.85-3.76 (m, 4H), 3.50 (s, 3H), 3.44 (s, 3H), 1.09 (t, J=7.1 Hz, 3H), 1.04 (t, J=7.1 Hz, 3H).

$^{13}$C NMR (151 MHz, DMSO_$d_6$) δ 177.82, 172.07, 171.91, 171.27, 171.07, 164.86, 158.14, 157.91, 144.67, 142.91, 142.89, 141.87, 141.54, 135.10, 134.98, 134.04, 133.73, 133.68, 132.94, 132.81, 131.98, 131.97, 130.35, 129.95, 129.89, 129.42, 129.39, 126.24, 126.22, 126.19, 125.92, 123.61, 123.56, 119.91, 119.87, 113.65, 113.41, 63.87, 63.53, 58.50, 58.44, 53.62, 53.35, 50.40, 50.14, 48.58, 48.01, 43.50, 43.10, 17.04, 16.88.

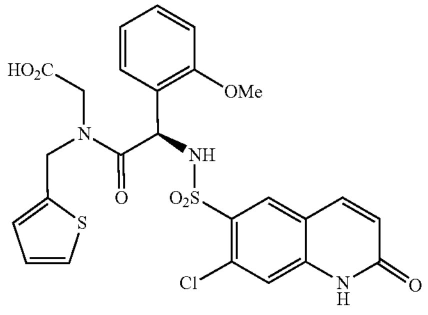

5-(R)—N-(2-((7-chloro-2-oxo-1,2-dihydroquinoline)-6-sulfonamido)-2-(2-methoxyphenyl)acetyl)-N-(thiophen-2-ylmethyl)glycine A solution containing ethyl (R)—N-(2-((7-chloro-2-oxo-1,2-dihydroquinoline)-6-sulfonamido)-2-(2-methoxyphenyl)acetyl)-N-(thiophen-2-ylmethyl)glycinate (0.160 g, 0.265 mmol) in 2:1 THF (1.24 mL)-ethanol (0.620 mL) was treated with 4 M aqueous sodium hydroxide (0.662 mL, 2.65 mmol) at 23° C. for 17 hr. The reaction mixture was treated with 1 M aqueous hydrochloric acid (3.97 mL, 3.97 mmol) and was partitioned with 10 mL of chloroform. The layers were separated; the aqueous layer was extracted with three 10 mL portions of chloroform. The combined organic layer was washed with 10 mL of brine, was then dried (sodium sulfate), and was then concentrated under diminished pressure to afford (R)—N-(2-((7-chloro-2-oxo-1,2-dihydroquinoline)-6-sulfonamido)-2-(2-methoxyphenyl)acetyl)-N-(thiophen-2-ylmethyl)glycine (0.125 g, 0.217 mmol, 82% yield) as a white solid.

LC-MS (Method A): t=4.63 min; 576 $[M+H]^+$ $^1$H NMR (400 MHz, DMSO-$d_6$) δ 11.96 (s, 1H), 8.13-8.02 (m, 2H), 7.94 (d, J=9.7 Hz, 1H), 7.37 (ddd, J=36.5, 5.1, 1.3 Hz, 1H), 7.26 (ddd, J=13.1, 7.7, 1.7 Hz, 1H), 7.17 (d, J=6.7 Hz, 1H), 7.15-7.04 (m, 1H), 6.93 (dd, J=5.1, 3.5 Hz, 0.5×1H), 6.89 (dd, J=3.4, 1.3 Hz, 0.5×1H), 6.87-6.84 (m, 1H), 6.79 (dtd, J=18.5, 7.6, 1.1 Hz, 1H), 6.70-6.62 (m, 1H), 6.57 (dt, J=9.6, 1.6 Hz, 1H), 5.75 (d, J=9.0 Hz, 0.5×1H), 5.54 (d, J=9.0 Hz, 0.5×1H), 4.52 (d, J=17.1 Hz, 2H), 3.90-3.66 (m, 2H), 3.51 (s, 0.5×3H), 3.44 (s, 0.5×3H).

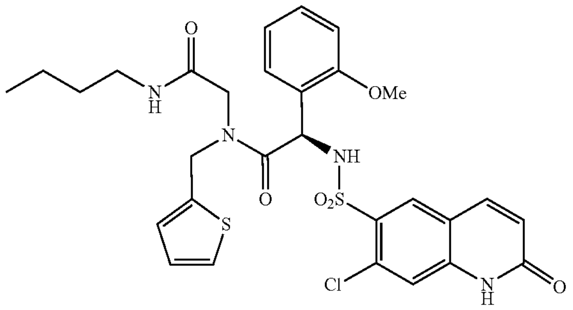 [SMILES: CCCCNC(=O)CN(Cc1cccs1)C(=O)[C@H](NS(=O)(=O)c1cc2ccc(=O)[nH]c2cc1Cl)c1ccccc1OC]

(R)—N-(2-(butylamino)-2-oxoethyl)-2-((7-chloro-2-oxo-1,2-dihydroquinoline)-6-sulfonamido)-2-(2-methoxyphenyl)-N-(thiophen-2-ylmethyl)acetamide LC-MS (Method A): t=4.95 min; 632 $[M+H]^+$

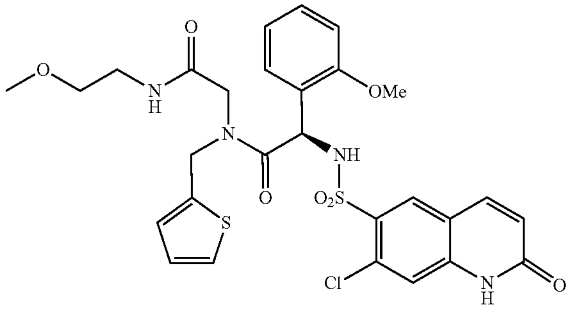 [SMILES: COCCNC(=O)CN(Cc1cccs1)C(=O)[C@H](NS(=O)(=O)c1cc2ccc(=O)[nH]c2cc1Cl)c1ccccc1OC]

(R)-2-((7-chloro-2-oxo-1,2-dihydroquinoline)-6-sulfonamido)-N-(2-((2-methoxyethyl)amino)-2-oxoethyl)-2-(2-methoxyphenyl)-N-(thiophen-2-ylmethyl)acetamide LC-MS (Method A): t=4.34 min; 634 $[M+H]^+$

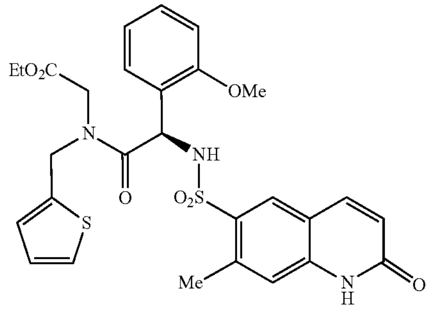

Ethyl (R)—N-(2-(2-methoxyphenyl)-2-((7-methyl-2-oxo-1,2-dihydroquinoline)-6-sulfonamido)acetyl)-N-(thiophen-2-ylmethyl)glycinate LC-MS (Method A): t=4.95 min; 584 $[M+H]^+$ Table 2 below provides data on X-ray data collection and refinement statistics for crystal structures of exemplary OGT inhibitor compound complexes.

REFERENCES 1. (a) Hart, G. W.; Slawson, C.; Ramirez-Correa, G.; Lagerlof, O., Cross Talk Between O-GlcNAcylation and Phosphorylation: Roles in Signaling, Transcription, and Chronic Disease. *Annu. Rev. Biochem.* 2011, 80, 825; (b) Hanover, J. A.; Krause, M. W.; Love, D. C., linking metabolism to epigenetics through O-GlcNAcylation. *Nat. Rev. Mol. Cell Biol.* 2012, 13, 312.
2. (a) Slawson, C.; Hart, G. W., O-GlcNAc signalling: implications for cancer cell biology. *Nat. Rev. Cancer* 2011, 11, 678; (b) Yang, X.; Qian, K., Protein O-GlcNAcylation: emerging mechanisms and functions. *Nat. Rev. Mol. Cell Biol.* 2017, 18, 452.
3. (a) Gloster, T. M.; Zandberg, W. F.; Heinonen, J. E.; Shen, D. L.; Deng, L., et al., Hijacking a biosynthetic pathway yields a glycosyltransferase inhibitor within cells. *Nat. Chem. Biol.* 2011, 7, 174; (b) Ortiz-Meoz, R. F.; Jiang, J.; Lazarus, M. B.; Orman, M.; Janetzko, J., et al., A Small Molecule that Inhibits OGT Activity in Cells. *ACS Chem. Biol.* 2015, 10, 1392; (c) Hu, C. W.; Worth, M.; Fan, D.; Li, B.; Li, H., et al., Electrophilic probes for deciphering substrate recognition by O-GlcNAc transferase. *Nat Chem Biol* 2017, 13, 1267.
4. (a) Lazarus, M. B.; Nam, Y.; Jiang, J.; Sliz, P.; Walker, S., Structure of human O-GlcNAc transferase and its complex with a peptide substrate. *Nature* 2011, 469, 564; (b) Lazarus, M. B.; Jiang, J.; Gloster, T. M.; Zandberg, W. F.; Whitworth, G. E., et al., Structural snapshots of the

TABLE 2

X-ray data collection and refinement statistics for crystal structures.

| | OGT:1a:HCF-$1_{11-26}$ complex | OGT:ent-1a:HCF-$1_{11-26}$ complex | OGT:2a:HCF-$1_{11-26}$ complex | OGT:3a:HCF-$1_{11-26}$ complex | OGT:4a:HCF-$1_{11-26}$ complex |
|---|---|---|---|---|---|
| Data collection | | | | | |
| Space Group | P6122 | P6122 | P6122 | P6122 | P3221 |
| Cell dimensions | | | | | |
| a, b, c (Å) | 98.79 98.79 365.91 | 98.61 98.61 365.11 | 98.18 98.18 365.10 | 98.63 98.63 365.20 | 100.30 100.30 130.30 |
| a, b, g (°) | 90.00 90.00 120.00 | 90.00 90.00 120.00 | 90.00 90.00 120.00 | 90.00 90.00 120.00 | 90.00 90.00 120.00 |
| Resolution (Å) | 55.61-2.00 (2.04-2.00) | 91.28-2.10 (2.15-2.10) | 85.03-2.00 (2.04-2.00) | 77.37-2.00 (2.04-2.00) | 50.15-2.75 (2.90-2.75) |
| $R_{sym}$ or $R_{merge}$ | 0.119 (0.976) | 0.190 (1.230) | 0.150 (1.251) | 0.177 (1.058) | 0.211 (1.539) |
| I/sI | 7.1 (1.3) | 6.2 (1.4) | 6.7 (1.1) | 4.9 (1.4) | 6.1 (1.3) |
| CC(1/2) | 0.995 (0.547) | 0.992 (0.571) | 0.995 (0.469) | 0.990 (0.489) | 0.994 (0.248) |
| Completeness (%) | 99.4 (95.2) | 100.0 (99.8) | 99.3 (97.5) | 98.7 (98.6) | 99.8 (99.8) |
| Redundancy | 4.7 (3.8) | 7.7 (6.6) | 5.6 (4.2) | 4.9 (5.1) | 7.3 (6.7) |
| Average mosaicity | 0.39 | 0.25 | 0.31 | 0.55 | 0.49 |
| Refinement | | | | | |
| Resolution (Å) | 55.61-2.00 | 85.40-2.10 | 85.03-2.00 | 77.37-2.00 | 50.15-2.75 |
| No. refelections | 72030 | 62340 | 70760 | 70836 | 20180 |
| $R_{work}/R_{free}$ | 0.1800/0.2104 | 0.1853/0.2180 | 0.1858/0.2117 | 0.1908/0.2204 | 0.1900/0.2403 |
| No. atoms | | | | | |
| Protein | 5626 | 5616 | 5616 | 5620 | 5519 |
| Ligand/ion | 37 | 37 | 42 | 43 | 38 |
| Water | 393 | 298 | 350 | 401 | 40 |
| B-factors | | | | | |
| Protein | 36.97 | 37.96 | 35.69 | 34.29 | 73.62 |
| Ligand/ion | 28.36 | 54.15 | 28.84 | 50.18 | 48.34 |
| Water | 38.64 | 36.21 | 37.39 | 35.81 | 53.26 |
| R.m.s deviations | | | | | |
| Bond lengths (Å) | 0.007 | 0.008 | 0.003 | 0.004 | 0.002 |
| Bond Angles (°) | 0.73 | 0.808 | 0.54 | 0.603 | 0.422 |

* Values in parenthesis are for highest-resolution shell reaction coordinate for O-GlcNAc transferase. *Nat. Chem. Biol.* 2012, 8, 966; (c) Lazarus, M. B.; Jiang, J.; Kapuria, V.; Bhuiyan, T.; Janetzko, J., et al., HCF-1 is cleaved in the active site of O-GlcNAc transferase. *Science* 2013, 342, 1235; (d) Schimpl, M.; Zheng, X.; Borodkin, V. S.; Blair, D. E.; Ferenbach, A. T., et al., O-GlcNAc transferase invokes nucleotide sugar pyrophosphate participation in catalysis. *Nat. Chem. Biol.* 2012, 8, 969.

5. (a) Lubas, W. A.; Hanover, J. A., Functional Expression of O-linked GlcNAc Transferase: DOMAIN STRUCTURE AND SUBSTRATE SPECIFICITY. *J. Biol. Chem.* 2000, 275, 10983; (b) Iyer, S. P. N.; Hart, G. W., Roles of the Tetratricopeptide Repeat Domain in O-GlcNAc Transferase Targeting and Protein Substrate Specificity. *J. Biol. Chem.* 2003, 278, 24608; (c) Jinek, M.; Rehwinkel, J.; Lazarus, B. D.; Izaurralde, E.; Hanover, J. A., et al., The superhelical TPR-repeat domain of O-linked GlcNAc transferase exhibits structural similarities to importin [alpha]. *Nat. Struct. Mol. Biol.* 2004, 11, 1001; (d) Rafie, K.; Raimi, O.; Ferenbach, A. T.; Borodkin, V. S.; Kapuria, V., et al., Recognition of a glycosylation substrate by the O-GlcNAc transferase TPR repeats. *Open Biol.* 2017, 7; (e) Levine, Z. G.; Fan, C.; Melicher, M. S.; Orman, M.; Benjamin, T., et al., O-GlcNAc Transferase Recognizes Protein Substrates Using an Asparagine Ladder in the Tetratricopeptide Repeat (TPR) Superhelix. *J. Am. Chem. Soc.* 2018, 140, 3510.
6. Gross, B. J.; Kraybill, B. C.; Walker, S., Discovery of O-GlcNAc transferase inhibitors. *J. Am. Chem. Soc.* 2005, 127, 14588.
7. (a) Capotosti, F.; Guernier, S.; Lammers, F.; Waridel, P.; Cai, Y., et al., O-GlcNAc Transferase Catalyzes Site-Specific Proteolysis of HCF-1. *Cell* 2011, 144, 376; (b) Janetzko, J.; Trauger, S. A.; Lazarus, M. B.; Walker, S., How the glycosyltransferase OGT catalyzes amide bond cleavage. *Nat. Chem. Biol.* 2016, 12, 899.
8. Itkonen, H. M.; Minner, S.; Guldvik, I. J.; Sandmann, M. J.; Tsourlakis, M. C., et al., O-GlcNAc Transferase Integrates Metabolic Pathways to Regulate the Stability of c-MYC in Human Prostate Cancer Cells. *Cancer Res.* 2013, 73, 5277.
9. Park, S.-K.; Zhou, X.; Pendleton, K. E.; Hunter, O. V.; Kohler, J. J., et al., A Conserved Splicing Silencer Dynamically Regulates O-GlcNAc Transferase Intron Retention and O-GlcNAc Homeostasis. *Cell Rep.* 2017, 20, 1088.
10. (a) Boutz, P. L.; Bhutkar, A.; Sharp, P. A., Detained introns are a novel, widespread class of post-transcriptionally spliced introns. *Genes Dev.* 2015, 29, 63; (b) Pendleton, K. E.; Park, S.-K.; Hunter, O. V.; Bresson, S. M.; Conrad, N. K., Balance between MAT2A intron detention and splicing is determined cotranscriptionally. *RNA* 2018, 24, 778.
11. Ruan, H.-B.; Ma, Y.; Torres, S.; Zhang, B.; Feriod, C., et al., Calcium-dependent O-GlcNAc signaling drives liver autophagy in adaptation to starvation. *Genes Dev.* 2017, 31, 1655.
12. Bond, M. R.; Hanover, J. A., A little sugar goes a long way: The cell biology of O-GlcNAc. *J. Cell Biol.* 2015, 208, 869.
13. Halgren, T. A., Identifying and characterizing binding sites and assessing druggability. *J. Chem. Inf. Model* 2009, 49, 377.
14. Schrödinger Release 2018-1: Maestro, Schrödinger, LLC, New York, NY, 2018
15. Schrödinger Release 2018-1: MacroModel, Schrödinger, LLC, New York, NY, 2018
16. Harder, E.; Damm, W.; Maple, J.; Wu, C.; Reboul, M.; Xiang, J. Y.; Wang, L.; Lupyan, D.; Dahlgren, M. K.; Knight, J. L.; Kaus, J. W.; Cerutti, D. S.; Krilov, G.; Jorgensen, W. L.; Abel, R.; Friesner, R. A., OPLS3: A force field providing broad coverage of drug-like small molecules and proteins. *J. Chem. Theory Comput.* 2016, 12, 281.
17. Lee, C.; Yang, W.; Parr, R. G., Development of the Colle-Salvetti correlation-energy formula into a functional of the electron density. *Phys. Rev. B* 1988, 37, 785.
18. Marenich, A. V.; Cramer, C. J.; Truhlar, D. G., Universal solvation model based on solute electron density and on a continuum model of the solvent defined by the bulk dielectric constant and atomic surface tensions. *J. Phys. Chem. B.* 2009, 113, 6378.
19. Gaussian 09, Revision A.02, M. J. Frisch, G. W. Trucks, H. B. Schlegel, G. E. Scuseria, M. A. Robb, J. R. Cheeseman, G. Scalmani, V. Barone, G. A. Petersson, H. Nakatsuji, X. Li, M. Caricato, A. Marenich, J. Bloino, B. G. Janesko, R. Gomperts, B. Mennucci, H. P. Hratchian, J. V. Ortiz, A. F. Izmaylov, J. L. Sonnenberg, D. Williams-Young, F. Ding, F. Lipparini, F. Egidi, J. Goings, B. Peng, A. Petrone, T. Henderson, D. Ranasinghe, V. G. Zakrzewski, J. Gao, N. Rega, G. Zheng, W. Liang, M. Hada, M. Ehara, K. Toyota, R. Fukuda, J. Hasegawa, M. Ishida, T. Nakajima, Y. Honda, O. Kitao, H. Nakai, T. Vreven, K. Throssell, J. A. Montgomery, Jr., J. E. Peralta, F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, J. M. Millam, M. Klene, C. Adamo, R. Cammi, J. W. Ochterski, R. L. Martin, K. Morokuma, O. Farkas, J. B. Foresman, and D. J. Fox, Gaussian, Inc., Wallingford CT, 2016.
20. Lazarus, M. B.; Nam, Y.; Jiang, J.; Sliz, P.; Walker, S., Structure of human O-GlcNAc transferase and its complex with a peptide substrate. *Nature* 2011, 469, 564.
21. Evans, P., Scaling and assessment of data quality. *Acta Crystallogr., Sect. D* 2006, 62, 72.
22. Evans, P. R.; Murshudov, G. N., How good are my data and what is the resolution? *Acta Crystallogr., Sect. D: Biol. Crystallogr.* 2013, 69, 1204.
23. Winn, M. D.; Ballard, C. C.; Cowtan, K. D.; Dodson, E. J.; Emsley, P.; Evans, P. R.; Keegan, R. M.; Krissinel, E. B.; Leslie, A. G. W.; McCoy, A.; McNicholas, S. J.; Murshudov, G. N.; Pannu, N. S.; Potterton, E. A.; Powell, H. R.; Read, R. J.; Vagin, A.; Wilson, K. S., Overview of the CCP4 suite and current developments. *Acta Crystallogr., Sect. D: Biol. Crystallogr.* 2011, 67, 235.
24. Lazarus, M. B.; Jiang, J.; Kapuria, V.; Bhuiyan, T.; Janetzko, J.; Zandberg, W. F.; Vocadlo, D. J.; Herr, W.; Walker, S., HCF-1 is cleaved in the active site of O-GlcNAc transferase. *Science* 2013, 342, 1235.
25. Adams, P. D.; Afonine, P. V.; Bunkoczi, G.; Chen, V. B.; Davis, I. W.; Echols, N.; Headd, J. J.; Hung, L.-W.; Kapral, G. J.; Grosse-Kunstleve, R. W.; McCoy, A. J.; Moriarty, N. W.; Oeffner, R.; Read, R. J.; Richardson, D. C.; Richardson, J. S.; Terwilliger, T. C.; Zwart, P. H., PHENIX: a comprehensive Python-based system for macromolecular structure solution. *Acta Crystallogr., Sect. D* 2010, 66, 213.
26. (a) Painter, J.; Merritt, E. A., Optimal description of a protein structure in terms of multiple groups undergoing TLS motion. *Acta Crystallogr., Sect. D* 2006, 62, 439; (b)

Painter, J.; Merritt, E. A., TLSMD web server for the generation of multi-group TLS models. *J. Appl. Crystallogr.* 2006, 39, 109.
27. Emsley, P.; Lohkamp, B.; Scott, W. G.; Cowtan, K., Features and development of Coot. *Acta Crystallogr., Sect. D* 2010, 66, 486.
28. Moriarty, N. W.; Grosse-Kunstleve, R. W.; Adams, P. D., electronic Ligand Builder and Optimization Workbench (eLBOW): a tool for ligand coordinate and restraint generation. *Acta Crystallogr., Sect. D* 2009, 65, 1074.
29. The PyMOL Molecular Graphics System, Version 2.0 Schrödinger, LLC, www.pymol.org, 2018.
30. Morin, A.; Eisenbraun, B.; Key, J.; Sanschagrin, P. C.; Timony, M. A.; Ottaviano, M.; Sliz, P., Collaboration gets the most out of software. *eLife* 2013, 2, e01456.
31. Wienken, C. J.; Baaske, P.; Rothbauer, U.; Braun, D.; Duhr, S., Protein-binding assays in biological liquids using microscale thermophoresis. *Nat. Commun.* 2010, 1, 100.
32. Navarrete-Perea, J.; Yu, Q.; Gygi, S. P.; Paulo, J. A., Streamlined Tandem Mass Tag (SL-TMT) protocol: An efficient strategy for quantitative (phospho)proteome profiling using tandem mass tag-synchronous precursor selection-MS3. *J. Proteome Res.* 2018, 17, 2226.
33. (a) Ting, L.; Rad, R.; Gygi, S. P.; Haas, W., MS3 eliminates ratio distortion in isobaric multiplexed quantitative proteomics. *Nat. Methods* 2011, 8, 937; (b) McAlister, G. C.; Nusinow, D. P.; Jedrychowski, M. P.; Wuhr, M.; Huttlin, E. L.; Erickson, B. K.; Rad, R.; Haas, W.; Gygi, S. P., MultiNotch MS3 enables accurate, sensitive, and multiplexed detection of differential expression across cancer cell line proteomes. *Anal. Chem.* 2014, 86, 7150.
34. Paulo, J. A.; O'Connell, J. D.; Gygi, S. P., A Triple Knockout (TKO) proteomics standard for diagnosing ion interference in isobaric labeling experiments. *J. Am. Soc. Mass Spectrom.* 2016, 27, 1620.
35. Huttlin, E. L.; Jedrychowski, M. P.; Elias, J. E.; Goswami, T.; Rad, R.; Beausoleil, S. A.; Villén, J.; Haas, W.; Sowa, M. E.; Gygi, S. P., A tissue-specific atlas of mouse protein phosphorylation and expression. *Cell* 2010, 143, 1174.
36. Beausoleil, S. A.; Villén, J.; Gerber, S. A.; Rush, J.; Gygi, S. P., A probability-based approach for high-throughput protein phosphorylation analysis and site localization. *Nat. Biotechnol.* 2006, 24, 1285.
37. (a) Elias, J. E.; Gygi, S. P., Target-decoy search strategy for mass spectrometry-based proteomics. In *Proteome Bioinformatics*, Hubbard, S. J.; Jones, A. R., Eds. Humana Press: Totowa, NJ, 2010; pp 55; (b) Elias, J. E.; Gygi, S. P., Target-decoy search strategy for increased confidence in large-scale protein identifications by mass spectrometry. *Nat. Methods* 2007, 4, 207.
38. McAlister, G. C.; Huttlin, E. L.; Haas, W.; Ting, L.; Jedrychowski, M. P.; Rogers, J. C.; Kuhn, K.; Pike, I.; Grothe, R. A.; Blethrow, J. D.; Gygi, S. P., Increasing the multiplexing capacity of TMTs using reporter ion isotopologues with isobaric masses. *Anal. Chem.* 2012, 84, 7469.
39. Pangborn, A. B.; Giardello, M. A.; Grubbs, R. H.; Rosen, R. K.; Timmers, F. J., Safe and convenient procedure for solvent purification. *Organometallics* 1996, 15, 1518.
40. Ortiz-Meoz, R. F.; Jiang, J.; Lazarus, M. B.; Orman, M.; Janetzko, J.; Fan, C.; Duveau, D. Y.; Tan, Z. W.; Thomas, C. J.; Walker, S., A small molecule that inhibits OGT activity in cells. *ACS Chem. Biol.* 2015, 10, 1392.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects described herein, is/are referred to as comprising particular elements and/or features, certain embodiments described herein or aspects described herein consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments described herein, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment described herein can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A compound of Formula (I-A):

(I-A)

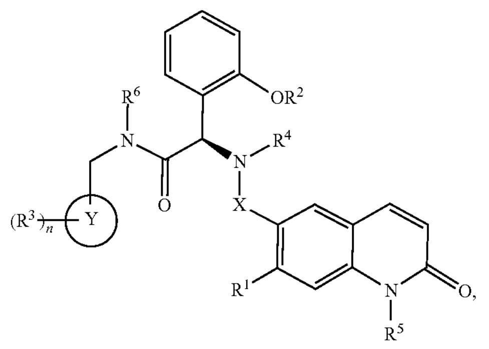

or a pharmaceutically acceptable salt, solvate, hydrate, polymorph, co-crystal, tautomer, stereoisomer, isotopically labeled compound, or prodrug thereof, wherein X is —$SO_2$—, —SO—, or —C(═O)—;

Ring Y is 5-membered heterocyclyl or 5-membered heteroaryl with 1-2 heteroatoms selected from the group consisting of N and S;

$R^1$ is chloro;

$R^2$ is unsubstituted methyl;

$R^3$ is halogen, —CN, —SCN, —$NO_2$, —$N_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —$OR^a$, —$N(R^b)_2$, or —$SR^a$;

each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl;

$R^4$ is hydrogen, optionally substituted alkyl, or a nitrogen protecting group;

$R^5$ is hydrogen, optionally substituted alkyl, or a nitrogen protecting group;

$R^6$ is hydrogen, optionally substituted alkyl, or a nitrogen protecting group; and n is 0, 1, 2, 3, 4, or 5.

2. The compound of claim 1, wherein Ring Y is thiophenyl, isothiazolyl, or thiazolyl.

3. The compound of claim 1, wherein $R^6$ is optionally substituted $C_{1-6}$ alkyl.

4. The compound of claim 3, wherein $R^6$ is of the formula: —$(CH_2)_xC(═O)OR^{4b}$ or —$(CH_2)_xC(═O)N(R^{4c})_2$, wherein:

x is 1, 2, 3, 4, 5, or 6;

$R^{4b}$ is hydrogen or optionally substituted $C_{1-6}$ alkyl; and each instance of $R^{4c}$ is independently hydrogen or optionally substituted $C_{1-6}$ alkyl.

5. The compound of claim 4, wherein $R^6$ is of the formula:

—$(CH_2)C(═O)OH$, —$(CH_2)C(═O)OMe$, —$(CH_2)C(═O)OEt$, —$(CH_2)C(═O)NH(Me)$,

—$(CH_2)C(═O)NH(Et)$, —$(CH_2)C(═O)NH$(n-propyl), or —$(CH_2)C(═O)NH(CH_2)_2OMe$.

6. The compound of claim 1, wherein $R^4$ is hydrogen.

7. The compound of claim 1, wherein $R^5$ is hydrogen.

8. The compound of claim 1, wherein the compound is of the formula:

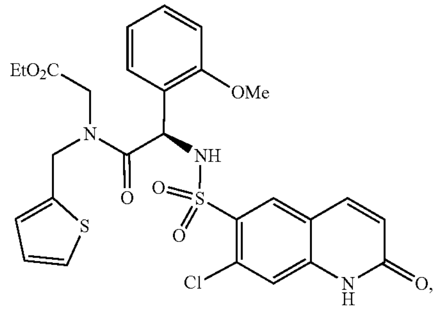

-continued

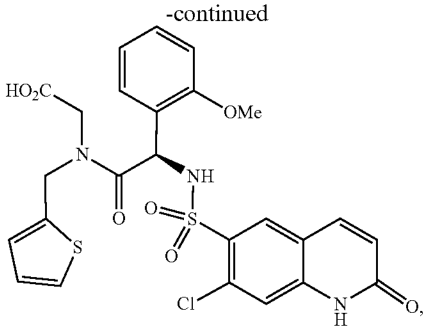

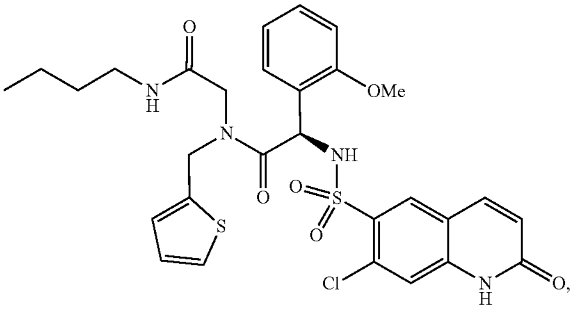

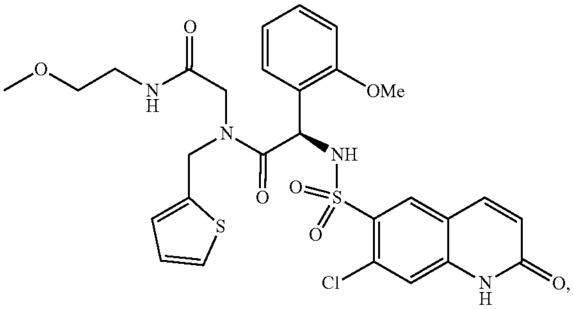

or a pharmaceutically acceptable salt, solvate, hydrate, polymorph, co-crystal, tautomer, stereoisomer, isotopically labeled compound, or prodrug thereof.

9. The compound of claim 1, or a pharmaceutically acceptable salt thereof.

10. A pharmaceutical composition comprising a compound of claim 1, or a pharmaceutically acceptable salt, solvate, hydrate, polymorph, co-crystal, tautomer, stereoisomer, isotopically labeled compound, or prodrug thereof, and a pharmaceutically acceptable excipient.

11. A method for treating an O-linked N-acetylglucosamine transferase (OGT)-associated disease or condition in a subject in need of such treatment, the method comprising administering to the subject a therapeutically effective amount of a compound of claim 1, or a pharmaceutically acceptable salt, solvate, hydrate, polymorph, co-crystal, tautomer, stereoisomer, isotopically labeled compound, or prodrug thereof.

12. A method for inhibiting OGT activity in a biological sample, the method comprising contacting the biological sample with an effective amount of a compound of claim 1, or a pharmaceutically acceptable salt, solvate, hydrate, polymorph, co-crystal, tautomer, stereoisomer, isotopically labeled compound, or prodrug thereof.

* * * * *

SEQUENCE LISTING

<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 1

Thr His Glu Thr Gly Thr Thr Asn Thr Ala Thr Thr Ala Thr Ser Asn
1 5 10 15